US011111243B2

(12) United States Patent
Yu et al.

(10) Patent No.: US 11,111,243 B2
(45) Date of Patent: Sep. 7, 2021

(54) AZAINDOLE COMPOUNDS AS HISTONE METHYLTRANSFERASE INHIBITORS

(71) Applicant: GLOBAL BLOOD THERAPEUTICS, INC., South San Francisco, CA (US)

(72) Inventors: Chul Yu, San Ramon, CA (US); Ming Yu, Foster City, CA (US); Manuel Zancanella, San Mateo, CA (US); Zhe Li, San Diego, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/002,408

(22) Filed: Jun. 7, 2018

(65) Prior Publication Data

US 2018/0354947 A1 Dec. 13, 2018

Related U.S. Application Data

(60) Provisional application No. 62/517,410, filed on Jun. 9, 2017.

(51) Int. Cl.
*C07D 471/04* (2006.01)
*A61P 7/00* (2006.01)
*C07D 519/00* (2006.01)
*C07D 487/04* (2006.01)

(52) U.S. Cl.
CPC .............. *C07D 471/04* (2013.01); *A61P 7/00* (2018.01); *C07D 487/04* (2013.01); *C07D 519/00* (2013.01)

(58) Field of Classification Search
CPC .................................................... C07D 471/04
USPC ........................................... 546/81; 514/292
See application file for complete search history.

(56) References Cited

U.S. PATENT DOCUMENTS

| 4,107,288 | A | 8/1978 | Oppenheim et al. |
| 5,145,684 | A | 9/1992 | Liversidge et al. |
| 8,932,557 | B2 * | 1/2015 | Chen ............... C07B 59/002 424/1.65 |
| 2002/0099068 | A1 | 7/2002 | Ritzeler et al. |
| 2011/0142796 | A1 | 6/2011 | Connors et al. |
| 2011/0275762 | A1 | 11/2011 | Cmijanovic et al. |
| 2012/0228819 | A1 | 8/2012 | Arndt et al. |
| 2012/0244110 | A1 | 9/2012 | Chen et al. |
| 2013/0116273 | A1 | 5/2013 | Frederick et al. |
| 2013/0231360 | A1 | 9/2013 | Higgins et al. |
| 2015/0274660 | A1 | 10/2015 | Pliushchev et al. |
| 2017/0002005 | A1 | 1/2017 | Kroth et al. |

FOREIGN PATENT DOCUMENTS

| EP | 2364983 A2 | 9/2011 |
| WO | WO 2008/101682 | 8/2008 |
| WO | WO 2015/192981 | 12/2015 |
| WO | WO 2017/085053 A1 | 5/2017 |

OTHER PUBLICATIONS

Agarwal et al., "G9a inhibition potentiates the anti-tumour activity of Dna double-strand break inducing agents by impairing Dna repair independent of p53 status" Cancer Letters (2016) 280:467475.
Antignano et al., "Methyltransferase G9A regulates T cell differentiation during murine intestinal in ammation," J. Clin. Invest. (2014) 124(5): 1945-55.
Casciello et al., "Functional role of G9a histone methyltransferase in cancer," Front Immunol. (2015) 6:Article 487:1-12.
Charache et al., "Hydroxyurea: Effects on Hemoglobin F Production in Patients With Sickle Cell Anemia" Blood (1992) 79(10):2555-2565.
Clark et al., "Synthetic Uses of the Sequential Ring Positional Reactivity in Pyridin-3-ol and Derivatives" Australian Journal of Chemistry (1981) 34(4):927-932.
Coburn et al., "Picrylamino-substituted Heterocycles V. Pyridines (1,2)," Journal of Heterocyclic Chemistry (1972) 9:1039-1043.
Gennaro, AR., Remington's Pharmaceutical Sciences (2000) 20th Ed., Lippincott Williams & Wilkins, Baltimore, MD, Cover and Table of Contents.
Gennaro, AR., Remington's Pharmaceutical Sciences, (1985) 17th Ed., Mack Publishing Co., Easton, PA, Cover and Table of Contents.
Greene, et al., Protective Groups in Organic Synthesis, (1999) 3rd. Ed., John Wiley & Sons, Cover and Table of Contents.
Imai et al., "Involvement of Histone H3 Lysine 9 (H3K9) Methyltransferase G9a in the Maintenance of HIV-1 Latency and Its Reactivation by BIX01294" J. Biol. Chem. (2010) 285(22):16538-16545.
International Search Report and Written Opinion dated Apr. 5, 2018 for PCT. Application No. PCT/US2017/067855.
Krivega et al., "Inhibition of G9a methyltransferase stimulates fetal hemoglobin production by facilitating LCR/y-globin looping," Blood (2015) 126(5):665-672.
Lanman et al., "Phosphoinositide-3-kinase inhibitors: Evaluation of substituted alcohols as replacements for the piperazine sulfonamide portion of AMG 511" Bioorganic & Medicinal Chemistry Letters (2014) 24(24):5630-5634.
Ling et al., "Lysine methyltransferase G9a methylates the transcription factor MyoD and regulates skeletal muscle differentiation" PNAS (2012) 109(3):841-846.
Liu et al., "Discovery of an in Vivo Chemical Probe of the Lysine Methyltransferases G9a and GLP," J. Med Chem. (2013) 56(21):8931-8942.
Liu, F. et al., "Discovery of a 2,4-Diamino-7-aminoalkoxyquinazoline as a Potent and Selective Inhibitor of Histone Lysine Methyltransferase G9a", Journal of Medicinal Chemistry, (2009), pp. 7950-7953.
Liu, F. et al., "Optimization of Cellular Activity of G9a Inhibitors 7-Aminoalkoxy-quinazolines" Journal of Medicinal Chemistry, (2011), pp. 6139-6150.

(Continued)

*Primary Examiner* — Patricia L Morris
(74) *Attorney, Agent, or Firm* — Alston & Bird LLP

(57) ABSTRACT

The present disclosure provides certain angular tricyclic compounds that are histone methyltransferases G9a and/or GLP inhibitors and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

20 Claims, No Drawings

(56) References Cited

OTHER PUBLICATIONS

Liu, F. et al., "Protein Lysine Methyltransferase G9a Inhibitors: Design Sybthesis and Structure Activity Relationships of 2,4-Diamino-7aminoalkoxy-quinazolines" Journal of Medicinal Chemistry, (2010), pp. 5844-5857.

Merkling et al., "The Epigenetic Regulator G9a Mediates Tolerance to RNA Virus Infection in Drosophila" PLoS Pathog. (2015) 11(4). e1004692.

Renneville et al., "EHMT1 and EHMT2 inhibition induces fetal hemoglobin expression," Blood (2015) 126(16):1930-1939.

Sankaran et al., "The Switch from Fetal to Adult Hemoglobin" Cold Spring Harb Perspect Med. (2013) 3(1): a011643.

Shankar et al., "G9a, a multipotent regulator of gene expression" Epigenetics (2013) 8(1):16-22.

Shinkai et al., "H3K9 methyltransferase G9a and the related molecule GLP" Genes & Dev. (2011) 25(8):781-788.

Sweis et al., "Discovery and Development of Potent and Selective Inhibitors of Histone Methyltransferase G9a" ACS Med Chem Lett. (2014);5(2):205-209.

Wang et al., "Histone H3K9 methyltransferase G9a represses PPARγ expression and adipogenesis" EMBO J. (2013) 32(1):45-59.

Yang et al., "G9a coordinates with the RPA complex to promote DNA damage repair and cell survival" PNAS (2017):1700694114.

You et al., "Cancer Genetics and Epigenetics: Two Sides of the Same Coin'?," Cancer Cell (2012) 22(1):9-20.

Zhang et al., "Down-regulation of G9a triggers DNA damage response and inhibits colorectal cancer cells proliferation" Oncotarget (2015) 6(5): 2917-2927.

Coulthard et al., "XCVI. The Chemotherapy of Derivatives of Harmine and Harmaline. I." Biochemical Journal (1933) 27:727-739.

Novak et al., "Characterization of the 2-(α-Carbolinyl)nitrenium Ion and Its Conjugate Base Produced during the Decomposition of the Model Carcinogen 2-N-(Pivaloyloxy)-2-amino-α-carboline in Aqueous Solution" J. Am. Chem. Soc. (2000) 122(15)3606-3616.

Reniers et al., "Synthesis and evaluation of b-carboline derivatives as potential monoamine oxidase inhibitors" Bioorganic & Medicinal Chemistry (2011) 19 134-144.

Song et al., "β-Carbolines as Specific Inhibitors of Cyclin-Dependent Kinases" Bioorganic & Medicinal Chemistry Letters (2002) 12:1229-1132.

Vedadi et al., "A chemical probe selectively inhibits G9a and GLP methyltransferase activity in cells" Nature Chemical Biology (2011) 7:566-574.

International Search Report and Written Opinion dated Jul. 30, 2018 for PCT Application No. PCT/US2018/036521, filed Jun. 7, 2018.

* cited by examiner

AZAINDOLE COMPOUNDS AS HISTONE METHYLTRANSFERASE INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/517,410, filed Jun. 9, 2017.

FIELD OF THE DISCLOSURE

The present disclosure provides certain azaindole compounds that are histone methyltransferases G9a and/or GLP inhibitors, and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

BACKGROUND

Chromatin modification plays an essential role in transcriptional regulation. These modifications, including DNA methylation, histone acetylation and histone methylation, are important in a variety of biological processes including protein production and cellular differentiation, and are emerging as attractive drug targets in various human diseases. Two particular enzymes associated with histone methylation are G9a and GLP, also known as EHMT2 and EHMT1 (Euchromatic histone-lysine N-methyltransferase 2 and 1). G9a and GLP are the primary enzymes for mono- and dimethylation at Lys 9 of histone H3 (H3K9me1 and H3K9me2), and exist predominantly as a G9a-GLP heteromeric complex that appears to be a functional H3K9 methyltransferase in vivo. Structurally, either G9a or GLP is composed of a catalytic SET domain, a domain containing ankyrin repeats (involved in protein-protein interactions) and nuclear localization signals on the N-terminal region. The SET domain is responsible for the addition of methyl groups on H3, whereas the ankyrin repeats have been observed to represent mono- and dimethyl lysine binding regions. The G9a-GLP complex is thus not only able to both methylate histone tails but also able to recognize this modification, and can function as a scaffold for the recruitment of other target molecules on the chromatin. See Shinkai et al., Genes Dev., 2011; 25(8):781-8; and Shankar et al., Epigenetics, 2013; 8(1):16-22.

Many studies have reported that G9a and GLP play critical roles in various biological processes. Several reports have highlighted its link to a variety of cancers. See Cascielle et al., Front Immunol., 2015 25; 6:487. It is upregulated in hepatocellular carcinoma, B cell acute lymphoblastic leukemia, and lung cancers. In addition, elevated expression of G9a in aggressive lung cancer correlates with poor prognosis, while its knockdown in highly invasive lung cancer cells suppressed metastasis in an in vivo mouse model. In prostate cancer cells (PC3), G9a knockdown caused significant morphological changes and inhibition of cell growth. See Liu et al., J. Med Chem., 2013; 56(21): 8931-42.; and Sweis et al., ACS Med Chem Lett., 2014; 5(2):205-9. Loss of G9a has been demonstrated to impair DNA damage repair and enhance the sensitivity of cancer cells to radiation and chemotherapeutics. See Yang et al., Proc. Natl. Acad. Sci. USA, 2017, doi: 10.1073/pnas.1700694114.

Interestingly, recent studies have also shown that the inhibition of G9a and GLP by either genetic depletion or pharmacological intervention increased fetal hemoglobin (HbF) gene expression in erythroid cells. See Krivega et al., Blood, 2015; 126(5):665-72; and Renneville et al., Blood, 2015; 126(16):1930-9. Inducing fetal globin gene would be potentially therapeutically beneficial for the disease of hemoglobinopathies, including beta-thalassemia where the production of normal (β-globin, a component of adult hemoglobin, is impaired. Similarly, induction of HbF would potentially be beneficial by diluting the concentration of hemoglobin S (HbS) molecules, thereby reducing polymerization of HbS. See Sankaran et al., Cold Spring Harb Perspect Med., 2013; 3(1): a011643. Moreover, G9a or GLP inhibitions may potentiate other clinically used therapies, such as hydroxyurea or HDAC inhibitors. These agents may act, at least in part, by increasing γ-globin gene expression through different mechanisms. See Charache et al., Blood, 1992; 79(10):2555-65. Thus, there is a need for the development of small molecules that are capable of inhibiting the activity of G9a and/or GLP. The compounds of the present disclosure fulfill this and related needs.

SUMMARY

In one aspect provided is a compound of Formula (I):

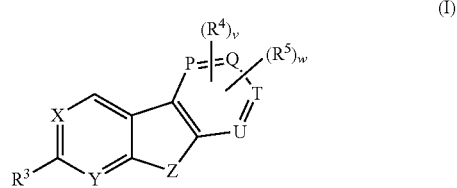

(I)

wherein:
X can be N (nitrogen) or $CR^1$;
Y can be N (nitrogen) or $CR^2$;
P, Q, T, and U can be independently CH, C (carbon) (when $R^4$ or $R^5$ is attached), or N (nitrogen); provided that at least one and not more than two of P, Q, T and U are N (nitrogen);
Z can be O (oxygen), S (sulfur), or $NR^6$, wherein $R^6$ can be hydrogen, alkyl, or cycloalkyl;
$R^1$ can be hydrogen, alkyl, alkoxy, halo, haloalkyl, haloalkoxy, or cycloalkyl;
$R^2$ can be hydrogen, alkyl, alkoxy, halo, haloalkyl, haloalkoxy, or cycloalkyl;
$R^3$ can be —W-alkylene-$R^7$, wherein:
  W can be bond, NH, O (oxygen), or S (sulfur);
  alkylene can be optionally substituted with $R^8$, wherein $R^8$ can be halo, haloalkyl, haloalkoxy, hydroxy, or alkoxy, and one $CH_2$ in the alkylene can be optionally replaced with NH or O (oxygen); and
  $R^7$ can be —$NR^aR^b$, wherein $R^a$ and $R^b$ can be independently hydrogen, alkyl, or haloalkyl; or $R^a$ and $R^b$ can be together with the nitrogen to which they are attached form heterocycloamino, bridged heterocycloamino, or spiroheterocycloamino, wherein the heterocycloamino, the bridged heterocycloamino and the spiroheterocycloamino are optionally substituted with one or two substituents independently selected from alkyl, halo, haloalkyl, hydroxy, alkoxy, and haloalkoxy; or $R^7$ can be heterocyclyl that is attached to the alkylene at a ring carbon atom and can be optionally substituted with one or two substituents independently selected from alkyl, halo, haloalkyl, hydroxy, alkoxy and haloalkoxy;

$R^4$ and $R^5$ can be independently alkyl, alkenyl, alkynyl, cycloalkyl, cycloalkenyl, halo, hydroxy, haloalkoxy, alkoxy, cyano, $NH_2$, $NR^cR^d$, alkoxyalkylamino, hydroxyalkylamino, aminoalkylamino, hydroxyalkyl, alkoxyalkyl, alkylthio, alkoxyalkyloxy, phenyl, heteroaryl, heteroaryloxy, heterocyclyl, heterocyclyloxy, heterocyclylamino, 5-8 membered bridged heterocycloamino or spiroheterocycloamino, wherein the phenyl, the cycloalkyl, the heteroaryl, and the heterocyclyl either alone or as part of another group are optionally substituted with one, two, or three substituents independently selected from alkyl, halo, haloalkyl, haloalkoxy, hydroxy, hydroxyalkyl, alkoxy, $NH_2$, alkylamino, dialkylamino, carboxy, carboxyalkyl, and alkoxycarbonyl, and wherein the alkyl of $R^4$ and $R^5$ is optionally substituted with cycloalkyl, and the alkenyl and the alkynyl of $R^4$ and $R^5$ are independently optionally substituted with hydroxy or cycloalkyl;

$R^c$ is hydrogen, alkyl, cycloalkyl, or heteocyclyl;

$R^d$ is alkyl, cycloalkyl, or heteocyclyl; or $R^c$ and $R^d$ together with the nitrogen to which they are attached form a 4- to 7-membered heterocycloamino; and v and w are independently 0 or 1;

or a pharmaceutically acceptable salt thereof.

In a second aspect, this disclosure is directed to a pharmaceutical composition comprising a compound of Formula (I) (or any of the embodiments thereof described herein), or a pharmaceutically acceptable salt thereof; and a pharmaceutically acceptable excipient.

In a third aspect, this disclosure is directed to a method of treating a disease treatable by inhibition of G9a and/or GLP in a subject in need thereof, comprising administering to the subject a therapeutically effective amount of a compound of Formula (I) (or any of the embodiments thereof described herein), or a pharmaceutically acceptable salt thereof; or a pharmaceutical composition comprising a compound of Formula (I) (or any of the embodiments thereof described herein), or a pharmaceutically acceptable salt thereof, in a therapeutically effective amount, and a pharmaceutically acceptable excipient. In one embodiment, the disease can be a hemoglobinopathy, such as beta-thalassemia and sickle cell disease See Krivega et al., Blood, 2015; 126(5):665-72; and Renneville et al., Blood. 2015 Oct. 15; 126(16):1930-9. In a second embodiment, the disease can be a cancer or tumor, for example, a cancer or tumor where G9a or GLP can be overexpressed. See Cascielle et al., Front Immunol, 2015; 6:487. In a third embodiment, treating a cancer and/or tumor comprises increasing tumor free survival and/or reducing tumor mass and/or slowing tumor growth. In a fourth embodiment, the disease can be a cancer predisposition syndrome, such as Cowden syndrome. See You et al., Cancer Cell, 2012; 22(1):9-20. In a fifth embodiment, the disease can be an inflammatory and/or autoimmune disease, such as treating intestinal inflammation. See Antignano et al., J Clin Invest, 2014; 124(5):1945-55. In a sixth embodiment, the disease can be a metabolic disease, such as diabetes and/or obesity, such as diabetes and obesity See Wang et al., EMBO J., 2013; 32(1):45-59. In a seventh embodiment, the disease can be related to skeletal muscle development and regeneration. See Ling et al., Proc Natl Acad Sci USA., 2012; 109(3):841-6. In an eighth embodiment, the disease can be a viral disease, such as HIV-1 (human immunodeficiency virus 1) and HBV (Hepatitis B Virus). See Imai et al., J Biol Chem., 2010; 285(22):16538-45; and Merkling et al., PLoS Pathog., 2015; 11(4): e1004692. The compounds and compositions described herein can be administered with one or more additional therapeutic agents including, but not limited to, anticancer agents and antiviral agents. See, e.g., Front Immunol., 2015; 6:487; Agarwal et al., Cancer Lett. 2016:467 and Zhang et al., Oncotarget 2015, 6(5):2917.

In a fourth aspect provided is the use of a compound of Formula (I) (or any of the embodiments thereof described herein), or a pharmaceutically acceptable salt thereof, in the treatment of the diseases provided in the third aspect herein.

In a fifth aspect, this disclosure is directed to a method of inhibiting G9a and/or GLP, comprising contacting a cell with a therapeutically effective amount of a compound of Formula (I) (or any of the embodiments thereof described herein), or a pharmaceutically acceptable salt thereof. In some embodiments, the cell suffers from one or more of the diseases provided in the third aspect herein.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl (isopropyl), n-butyl, sec-butyl, iso-butyl, tert-butyl, pentyl (straight-chained or branched), hexyl (straight-chained or branched), and the like.

"Alkylene" means a linear saturated divalent hydrocarbon radical of one to six carbon atoms or a branched saturated divalent hydrocarbon radical of three to six carbon atoms unless otherwise stated, e.g., methylene, ethylene, propylene, 1-methylpropylene, 2-methylpropylene, butylene, pentylene, and the like.

"Alkenyl" means a linear hydrocarbon radical of two to six carbon atoms or a branched hydrocarbon radial of 3 to 6 carbon atoms that includes one or two double bonds, ethenyl, propenyl (straight-changed or branched), allenyl, butenyl (straight-changed or branched), pentenyl (straight-changed or branched) and hexenyl (straight-changed or branched).

"Alkynyl" means a linear hydrocarbon radical of two to six carbon atoms or a branched hydrocarbon radial of 3 to 6 carbon atoms that includes one or two triple bonds, ethynyl, propynyl (straight-changed or branched), butynyl (straight-changed or branched), pentynyl (straight-changed or branched) and hexynyl (straight-changed or branched).

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means alkyl as defined above which is substituted with one or two alkoxy groups as defined above, e.g., methoxyethyl, ethoxyethyl, methoxypropyl, and the like.

"Alkoxyalkylamino" means —NHR radical where R is alkoxyalkyl as defined above, e.g., methoxyethylamino, 1-, 2- or 3-methoxypropylamino, and the like.

"Alkoxyalkyloxy" means —OR radical where R is alkoxyalkyl as defined above, e.g., methoxyethyloxy, ethoxyethyloxy, and the like.

"Hydroxyalkylamino" means —NHR radical where R is hydroxyalkyl as defined herein, e.g., hydroxyethylamino, 1-, 2- or 3-hydroxypropylamino, and the like.

"Alkylcarbonyl" or "Acyl" means a —COR radical where R is alkyl as defined above, e.g., methylcarbonyl, ethylcarbonyl, and the like.

"Aminoalkyl" means a -(alkylene)-NR'R" radical where R' and R" are independently hydrogen or alkyl as defined above.

"Aminoalkylamino" means —NHR radical where R is aminoalkyl as defined above, e.g., aminoethylamino, methylaminoethylamino, dimethylaminoethylamino, diethylaminoethylamino, and the like.

"Alkylamino" means a —NHR' radical where R' is alkyl as defined above.

"Alkylthio" means a —SR' radical where R' is alkyl as defined above.

"Bridged heterocycloamino" means a saturated heterocycloamino radical as defined herein of 5 to 8 ring atoms wherein two non-adjacent carbon atoms or non-adjacent carbon and nitrogen atom are linked with alkylene chain as defined herein.

"Cycloalkyl" means a cyclic saturated monovalent hydrocarbon radical of three to ten carbon atoms, unless stated otherwise, e.g., cyclopropyl, cyclobutyl, cyclopentyl, or cyclohexyl, and the like.

"Cycloalkenyl" means a cyclic nonaromatic hydrocarbon radical of three to ten carbon atoms containing one or two double bonds, unless stated otherwise, e.g., cyclopropenyl, cyclobutenyl, cyclopentenyl, cyclohexenyl, and the like.

"Carboxy" means a —C(=O)OH group.

"Carboxyalkyl" means an alkyl radical as defined above that is substituted with a carboxy group.

"Dialkylamino" means an —NRR' radical where R and R' are alkyl as defined above.

"Halo" or "halogen" means fluoro, chloro, bromo, or iodo, preferably fluoro or chloro.

"Haloalkyl" means an alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, and —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined herein, e.g., —OCF$_3$, —OCH$_2$Cl, —OCHF$_2$, —OCH$_2$CF$_3$, and —OCF$_2$CF$_3$, —OCHF$_2$, and the like. When the haloalkyl of a haloalkoxy is an alkyl is substituted with only fluoro, it is referred to as a fluoroalkoxy.

"Hydroxyalkyl" means alkyl as defined above which is substituted with one or two hydroxy groups as defined above, e.g., hydroxyethyl, hydroxyethyl, 1,3-dihydroxypropyl, and the like.

"Heterocyclyl" means a saturated or unsaturated, nonaromatic, monovalent monocyclic group of 3 to 8 ring atoms in which one or two ring atoms are heteroatom independently selected from N, O, and S(O)$_n$, where n is an integer from 0 to 2, and the remaining ring atoms are C, unless stated otherwise. Additionally, one or two ring carbon atoms in the heterocyclyl ring can optionally be replaced by a —C(=O)— group. More specifically the term heterocyclyl includes, but is not limited to, pyrrolidino, piperidino, homopiperidino, 2-oxopyrrolidinyl, 2-oxopiperidinyl, morpholino, piperazino, dihydropyranyl, thiomorpholino, and the like. When the heterocyclyl ring is unsaturated, it can contain one or two ring double bonds provided that the ring is not aromatic. When the heterocyclyl group contains at least one nitrogen atom (e.g., pyrrolidino, piperidino, homopiperidino, morpholino, piperazino, thiomorpholino, and the like), the heterocyclyl ring can also be referred to herein as "heterocycloamino" and is a subset of the heterocyclyl group.

"Heterocyclyloxy" means —OR radical where R is heterocyclyl as defined above, e.g., pyrrolidinyloxy, tetrahydrofuranyloxy, and the like.

"Heterocyclylamino" means —NHR radical where R is heterocyclyl as defined above, e.g., pyrrolidinylamino, tetrahydrofuranylamino, piperidinylamino, and the like.

"Heteroaryl" means a monovalent monocyclic or bicyclic aromatic radical of 5 to 10 ring atoms, unless otherwise stated, where one or more, (in one embodiment, one, two, or three), ring atoms are heteroatom independently selected from N, O, and S, and the remaining ring atoms are carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. When the heteroaryl ring contains 5- or 6 ring atoms, it is also referred to herein as 5- or 6-membered heteroaryl.

"Heteroaryloxy" means —OR radical where R is heteroaryl as defined above, e.g., pyridinyloxy, furanyloxy, and the like.

"Oxo" means =(O) group. As would be readily apparent to one of skill in the art, "carbonyl" refers to an oxo radical attached to a carbon atom, i.e., —C(=O)—.

"Spiroheterocycloamino" means a saturated bicyclic ring having 7 to 10 ring atoms in which one, two, or three ring atoms are heteroatom selected from N, N-oxide, O, and S(O)$_n$, where n is an integer from 0 to 2, the remaining ring atoms being C, provided that at least one ring atom is N, and the rings are connected through only one atom. The connecting atom is also called the spiroatom, and is most often a quaternary carbon ("spiro carbon").

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting group. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diastereomeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt. and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

It is to be understood that where compounds disclosed herein have unfilled valencies, then the valencies are to be filled with hydrogen.

Also provided herein are isotopologues (isotopically labeled analogues) of the compounds described herein. Substitution with isotopes such as deuterium may afford certain therapeutic advantages resulting from greater metabolic stability, such as, for example, increased in vivo half-life or reduced dosage requirements. In some embodiments, at any position of a compound described herein, or a pharmaceutically acceptable salt thereof, that has a hydrogen, the hydrogen atom can be replaced with hydrogen-2 (deuterium) or hydrogen-3 (tritium). For example, one or more of $R^1$, $R^2$, $R^a$, $R^b$ and/or $R^4$ can include one or more deuteriums (such as 1, 2 or 3 deuteriums).

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees and apes, and, in particular, humans. In some embodiments, the subject can be human. In some embodiments, the subject can be a child and/or an infant, for example, a child or infant with a fever. In other embodiments, the subject can be an adult.

"Treating" or "treatment" of a disease includes:

(1) preventing the disease, i.e., causing the clinical symptoms of the disease not to develop in a subject that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure, or a pharmaceutically acceptable salt thereof, that, when administered to a subject for treating a disease, is sufficient to effect such treatment for the disease. The "therapeutically effective amount" will vary depending on the compound, the disease and its severity and the age, weight, etc., of the subject to be treated.

EMBODIMENTS

In further embodiments 1-61 below, the present disclosure includes:

1. In embodiment 1, the compounds of Formula (I), or a pharmaceutically acceptable salt thereof, are as defined in the Summary. With embodiment 1, in a group of compounds, or a pharmaceutically acceptable salt thereof, Z is $NR^6$. With embodiment 1, in another group of compounds, or a pharmaceutically acceptable salt thereof, $R^6$ is H when Z is $NR^6$. With embodiment 1, in yet another group of compounds, or a pharmaceutically acceptable salt thereof, $R^6$ is alkyl, such as methyl or ethyl when Z is $NR^6$. With embodiment 1, in yet another group of compounds, or a pharmaceutically acceptable salt thereof, $R^6$ is cycloalkyl when Z is $NR^6$. With embodiment 1, in yet another group of compounds, or a pharmaceutically acceptable salt thereof, $R^6$ is cyclopropyl when Z is $NR^6$.

2. In embodiment 2, the compounds of embodiment 1 and the group of compounds contained therein, or a pharmaceutically acceptable salt thereof, are those wherein X is $CR^1$ and Y is $CR^2$ where $R^1$ is hydrogen, alkyl, alkoxy, halo, haloalkyl, haloalkoxy, or cycloalkyl and $R^2$ is hydrogen, alkyl, alkoxy, halo, haloalkyl, haloalkoxy, or cycloalkyl.

Within embodiment 2, in a group of compounds, or a pharmaceutically acceptable salt thereof, X is $CR^1$ and Y is $CR^2$, where $R^1$ is hydrogen. Within embodiment 2, in a group of compounds, or a pharmaceutically acceptable salt thereof, X is $CR^1$ and Y is $CR^2$, where $R^2$ is hydrogen. Within embodiment 2, in another group of compounds, or a pharmaceutically acceptable salt thereof, X is $CR^1$ and Y is $CR^2$, where $R^1$ and $R^2$ are each hydrogen. Within embodiment 2, in another group of compounds, or a pharmaceutically acceptable salt thereof, X is $CR^1$, where $R^1$ is alkyl (e.g., methyl, ethyl, n-propyl or iso-propyl), and Y is $CR^2$. Within embodiment 2, in another group of compounds, or a pharmaceutically acceptable salt thereof, X is $CR^1$, where $R^1$ is alkoxy (such as methoxy, ethoxy, n-propoxy and iso-propoxy), and Y is $CR^2$. Within embodiment 2, in another group of compounds, or a pharmaceutically acceptable salt thereof, X is $CR^1$, where $R^1$ is halo (such as fluoro, or chloro), and Y is $CR^2$. Within embodiment 2, in another group of compounds, or a pharmaceutically acceptable salt thereof, X is $CR^1$, where $R^1$ is haloalkyl (e.g., $CF_3$), and Y is $CR^2$. Within embodiment 2, in another group of compounds, or a pharmaceutically acceptable salt thereof, X is $CR^1$, where $R^1$ is haloalkoxy (e.g., $OCF_3$), and Y is $CR^2$. Within embodiment 2, in another group of compounds, or a pharmaceutically acceptable salt thereof, X is $CR^1$, where $R^1$ is cycloalkyl (such as cyclopropyl), and Y is $CR^2$. Within the groups in embodiment 2, in a group of compounds, X is $CR^1$ and Y is CH. Within the groups in embodiment 2, in a group of compounds, $R^1$ is methoxy. Within embodiment 2, in another group of compounds, or a pharmaceutically acceptable salt thereof, X is $CR^1$, where $R^1$ is alkoxy (such as methoxy, ethoxy, n-propoxy and iso-propoxy), and Y is $CR^2$, where $R^2$ is hydrogen. Within embodiment 2, in another group of compounds, or a pharmaceutically acceptable salt thereof, X is $CR^1$, where $R^1$ is methoxy, and Y is $CR^2$, where $R^2$ is hydrogen. Within embodiment 2, in another group of compounds, or a pharmaceutically acceptable salt thereof, X is $CR^1$ and Y is $CR^2$, where $R^2$ is alkoxy (e.g., methoxy, ethoxy, n-propoxy or iso-propoxy). Within embodiment 2, in another group of compounds, or a pharmaceutically acceptable salt thereof, X is $CR^1$ and Y is $CR^2$, where $R^1$ is hydrogen and $R^2$ is alkoxy (e.g., methoxy, ethoxy, n-propoxy or iso-propoxy). Within embodiment 2, in another group of compounds, or a pharmaceutically acceptable salt thereof, X is $CR^1$, where $R^1$ is alkyl and Y is $CR^2$. Within embodiment 2, in another group of compounds, or a pharmaceutically acceptable salt thereof, X is $CR^1$, where $R^1$ is alkyl (e.g., methyl, ethyl, n-propyl or iso-propyl), and Y is $CR^2$, where $R^2$ is hydrogen.

3. In embodiment 3, the compounds of embodiment 1, or a pharmaceutically acceptable salt thereof, are those wherein X is $CR^1$ and Y is N. Within embodiment 3, in a group of compounds, or a pharmaceutically acceptable salt thereof, X is $CR^1$, where $R^1$ is hydrogen, and Y is N. Within embodiment 3, in another group of compounds, or a pharmaceutically acceptable salt thereof, X is $CR^1$, where $R^1$ is alkyl (e.g., methyl, ethyl, n-propyl or iso-propyl), and Y is N. Within embodiment 3, in a group of compounds, or a pharmaceutically acceptable salt thereof, X is $CR^1$, where $R^1$ is alkoxy (for example, methoxy, ethoxy, n-propoxy or iso-propoxy), and Y is N. Within embodiment 3, in another group of compounds, or a pharmaceutically acceptable salt thereof, X is $CR^1$, where $R^1$ is halo (such as fluoro, or chloro), and Y is N. Within embodiment 3, in another group of compounds, or a pharmaceutically acceptable salt thereof, X is $CR^1$, where $R^1$ is haloalkyl (e.g., $CF_3$), and Y is N. Within embodiment 3, in another group of compounds, or a pharmaceutically acceptable salt thereof, X is $CR^1$, where $R^1$ is haloalkoxy (e.g., $OCF_3$), and Y is N. Within embodiment 3, in another group of compounds, or a pharmaceutically acceptable salt thereof, X is $CR^1$, where $R^1$ is cycloalkyl (such as cyclopropyl), and Y is N.

4. In embodiment 4, the compounds of embodiment 1, 2 or 3, or a pharmaceutically acceptable salt thereof, are those wherein Q is N, and P, T, and U are CH or C (when $R^4$ or $R^5$ is attached). Within embodiment 4, in a group of compounds, or a pharmaceutically acceptable salt thereof, P is $CR^4$. Within the groups in embodiment 4, in another group of compounds, P is $CR^4$ and T is $CR^5$. Within the groups in embodiment 4, in another group of compounds, P is $CR^4$ and T is CH. Within the groups in embodiment 4, in another group of compounds, P is $CR^4$ and U is $CR^5$. Within the groups in embodiment 4, in another group of compounds, P is $CR^4$ and U is CH.

5. In embodiment 5, the compounds of embodiment 1, 2 or 3, or a pharmaceutically acceptable salt thereof, are those wherein Q and U are each N, and P and T are each CH or C (when $R^4$ or $R^5$ is attached). Within the groups in embodiment 5, in another group of compounds, P is $CR^4$ and T is $CR^5$. Within the groups in embodiment 5, in another group of compounds, P is $CR^4$ and T is CH.

6. In embodiment 6, the compounds of embodiment 1, 2 or 3, or a pharmaceutically acceptable salt thereof, are those wherein P is N (nitrogen); and Q, T, and U are each CH.

7. In embodiment 7, the compounds of embodiment 1, 2 or 3, or a pharmaceutically acceptable salt thereof, are those wherein P, Q and U are each CH; and T is N (nitrogen).

8. In embodiment 8, the compounds of embodiment 1, 2 or 3, or a pharmaceutically acceptable salt thereof, are those wherein P and T are each N (nitrogen); and Q and U are each CH.

9. In embodiment 9, the compounds of embodiment 1, 2 or 3, or a pharmaceutically acceptable salt thereof, are those wherein P is C (wherein $R^4$ is attached); Q is N (nitrogen); and T and U are each CH.

10. In embodiment 10, the compounds of embodiment 1, 2 or 3, or a pharmaceutically acceptable salt thereof, are those wherein P, T and U are each CH; and Q is N (nitrogen).

11. In embodiment 11, the compounds of embodiment 1, 2 or 3, or a pharmaceutically acceptable salt thereof, are those wherein P, Q and T are each CH; and U is N (nitrogen).

12. In embodiment 12, the compounds of embodiment 1, 2 or 3, or a pharmaceutically acceptable salt thereof, are those wherein P and U are each CH; T is C (wherein $R^5$ is attached) and Q is N (nitrogen).

13. In embodiment 13, the compounds of embodiment 1, 2 or 3, or a pharmaceutically acceptable salt thereof, are those wherein P is C (wherein $R^4$ is attached); Q is N (nitrogen); T is C (wherein $R^5$ is attached); and U is CH.

14. In embodiment 14, the compounds of embodiment 1, 2 or 3, or a pharmaceutically acceptable salt thereof, are those wherein P and T are each CH; Q and U is N (nitrogen).

15. In embodiment 15, the compounds of embodiment 1, 2 or 3, or a pharmaceutically acceptable salt thereof, are those wherein P and Q are each CH; T is C (wherein $R^5$ is attached); and U is N (nitrogen).

16. In embodiment 16, the compounds of embodiment 1, 2 or 3, or a pharmaceutically acceptable salt thereof, are those wherein P is C (wherein $R^4$ is attached); Q is N (nitrogen); T is CH; and U is C (wherein $R^5$ is attached).

17. In embodiment 17, the compounds of embodiment 1, 2 or 3, or a pharmaceutically acceptable salt thereof, are those wherein P is C (wherein $R^4$ is attached); Q is N (nitrogen); T is CH; and U is N (nitrogen).

18. In embodiment 18, the compounds of embodiment 1, 2 or 3, or a pharmaceutically acceptable salt thereof, are those wherein P is C (wherein $R^4$ is attached); Q is N (nitrogen); T is $CR^5$ (wherein $R^5$ is attached); and U is N (nitrogen).

19. In embodiment 19, the compounds of embodiment 1, 2 or 3, or a pharmaceutically acceptable salt thereof, are those wherein Q is N (nitrogen); and P, T, and U are independently CH or C (when $R^4$ or $R^5$ is attached).

20. In embodiment 20, the compounds of embodiment 1, 2 or 3, or a pharmaceutically acceptable salt thereof, are those wherein Q is N (nitrogen); and P, T, and U are independently CH or C (when $R^4$ or $R^5$ is attached). Within embodiment 20, in a group of compounds, or a pharmaceutically acceptable salt thereof, P is $CR^4$. Within embodiment 20, in a group of compounds, or a pharmaceutically acceptable salt thereof, T is CH. Within embodiment 20, in another group of compounds, or a pharmaceutically acceptable salt thereof, T is $CR^5$. Within embodiment 20, in a group of compounds, or a pharmaceutically acceptable salt thereof, U is CH. Within embodiment 20, in another group of compounds, or a pharmaceutically acceptable salt thereof, U is $CR^5$. Within embodiment 20, in another group of compounds, or a pharmaceutically acceptable salt thereof, T and U are each CH.

21. In embodiment 21, the compounds of any one of embodiments 1 to 20 and groups contained therein, or a pharmaceutically acceptable salt thereof, are those wherein $R^3$ is —W-alkylene-$R^7$, where W is bond.

22. In embodiment 22, the compounds of any one of embodiments 1 to 20 and groups contained therein, or a pharmaceutically acceptable salt thereof, are those wherein $R^3$ is —W-alkylene-$R^7$, where W is NH.

23. In embodiment 23, the compounds of any one of embodiments 1 to 20 and groups contained therein, or a pharmaceutically acceptable salt thereof, are those wherein $R^3$ is —W-alkylene-$R^7$, where W is O (oxygen).

24. In embodiment 24, the compounds of any one of embodiments 1 to 20 and groups contained therein, or a pharmaceutically acceptable salt thereof, are those wherein $R^3$ is —W-alkylene-$R^7$, where W is S (sulfur).

25. In embodiment 25, the compounds of any one of embodiments 21 to 24 and groups contained therein, or a pharmaceutically acceptable salt thereof, are those wherein the alkylene is an unsubstituted alkylene (such as an unsubstituted $C_{1-4}$ alkylene).

26. In embodiment 26, the compounds of any one of embodiments 21 to 24 and groups contained therein, or a pharmaceutically acceptable salt thereof, are those wherein the alkylene is a substituted alkylene substituted with $R^8$, wherein $R^8$ is halo (such as fluoro or chloro), haloalkyl (e.g., —$CH_2Cl$, —$CF_3$, —$CHF_2$, —$CH_2CF_3$, and —$CF_2CF_3$), haloalkoxy (such as —$OCF_3$, —$OCH_2Cl$, —$OCHF_2$, —$OCH_2CF_3$, and —$OCF_2CF_3$), hydroxy, or alkoxy (for example, methoxy, ethoxy, n-propoxy or iso-propoxy), and/or one $CH_2$ in the alkylene is optionally replaced with NH or O (oxygen). Within embodiment 26, in a group of compounds, or a pharmaceutically acceptable salt thereof, wherein the one $CH_2$ in the alkylene being replaced is the $CH_2$ after the first $CH_2$ in the alkylene after W. For example, replacement of the $CH_2$ after the first $CH_2$ in the alkylene after W with an oxygen wherein the alkylene initially is 3 carbons in length prior to replacement (i.e., the second $CH_2$ in the initial alkylene after W) would result in a radical having the formula —$CH_2O$—$CH_2$—*, wherein the * indicates the point of attachment to $R^7$. Within embodiment 26, in a group of compounds, or a pharmaceutically acceptable salt thereof, wherein the one $CH_2$ in the alkylene being replaced is the $CH_2$ after the second $CH_2$ in the alkylene after W. An example of replacing the $CH_2$ after the second $CH_2$ in the alkylene after W is —$CH_2CH_2O$—$CH_2$—*, wherein the replacement is with an oxygen, the initial alkylene is 4 carbons in length prior to replacement and the * indicates the point of attachment to $R^7$.

27. In embodiment 27, the compounds of embodiment 21, 23, 25 or 26 and groups contained therein, or a pharmaceutically acceptable salt thereof, are those wherein —W-alkylene- in $R^3$ is —$(CH_2)_2$—*, —$(CH_2)_3$—*, —$(CH_2)_4$—*, —$CH_2CH(CH_3)CH_2$—*, *—$CH_2CH(CH_3)CH_2$—, —O—$(CH_2)$—*, —O—$(CH_2)_2$—*, —O—$(CH_2)_2$—O—$(CH_2)_2$—*, —O—$(CH_2)_3$—*, —$OCH_2CH(F)CH_2$—*, —$OCH_2CH(OH)CH_2$—*, —$OCH_2CH(OCH_3)CH_2$—*, or —$OCH_2CH(OCF_3)CH_2$—*, wherein the * indicates the point of attachment to $R^7$. Within embodiment 27, in a group of compounds, or a pharmaceutically acceptable salt thereof, wherein —W-alkylene- is —$(CH_2)_2$—*, —$(CH_2)_3$—*, —$(CH_2)_4$—*, —$CH_2CH(CH_3)CH_2$—*, —O—$(CH_2)_2$—*, or —O—$(CH_2)_3$—*, wherein the * indicates the point of attachment to $R^7$. Within embodiment 27, in a group of compounds, or a pharmaceutically acceptable salt thereof, wherein —W-alkylene- is —O—$(CH_2)_3$—*, wherein the * indicates the point of attachment to $R^7$.

28. In embodiment 28, the compounds of any one of embodiments 21 to 27 and groups contained therein, or a pharmaceutically acceptable salt thereof, are those wherein $R^7$ is —$NR^aR^b$, where $R^a$ and $R^b$ are independently hydrogen, alkyl, or haloalkyl. Within embodiment 28, in a group of compounds, or a pharmaceutically acceptable salt thereof, $R^7$ is —$NR^aR^b$, where —$NR^aR^b$ is $NH_2$, methylamino, ethylamino, dimethylamino, diethylamino, diisopropylamino or (ethyl)(methyl)amino.

29. In embodiment 29, the compounds of any one of embodiments 21 to 27 and groups contained therein, or a pharmaceutically acceptable salt thereof, are those wherein $R^7$ is —$NR^aR^b$, where $R^a$ and $R^b$ together with the nitrogen to which they are attached form heterocycloamino, bridged heterocycloamino, or spiroheterocycloamino, wherein the heterocycloamino, the bridged heterocycloamino and the spiroheterocycloamino are optionally substituted with one or two substituents independently selected from alkyl, halo, haloalkyl, hydroxy, alkoxy, and haloalkoxy. Within embodiment 29, in a group of compounds, or a pharmaceutically acceptable salt thereof, the heterocycloamino can be unsubstituted. Within embodiment 29, in another group of compounds, or a pharmaceutically acceptable salt thereof, the heterocycloamino can be substituted with one or two substituents independently selected from alkyl (such as methyl, ethyl, n-propyl or iso-propyl), halo (e.g., as fluoro or chloro), haloalkyl (e.g., —$CH_2Cl$, —$CF_3$, —$CHF_2$, —$CH_2CF_3$, and —$CF_2CF_3$), hydroxy, alkoxy (for example, methoxy, ethoxy, n-propoxy or iso-propoxy) and haloalkoxy (such as —$OCF_3$, —$OCH_2Cl$, —$OCHF_2$, —$OCH_2CF_3$, and —$OCF_2CF_3$). Within embodiment 29, in a group of compounds, or a pharmaceutically acceptable salt thereof, the heterocycloamino can be azetidin-1-yl, pyrrolidin-1-yl, piperidin-1-yl, piperazin-1-yl, morpholin-4-yl, thiomorpholin-4-yl or 3-azabicyclo[3.1.1]heptan-3-yl, each heterocycloamino optionally substituted with one or two substituents independently selected from alkyl, halo, haloalkyl, hydroxy, alkoxy, and haloalkoxy, such as methyl, hydroxy, methoxy, and fluoro. Within embodiment 29, in a group of compounds, or a pharmaceutically acceptable salt thereof, $R^7$ is —$NR^aR^b$, where $R^a$ and $R^b$ together with the nitrogen to which they are attached form pyrrolidin-1-yl, 3(S)-fluoropyrrolidin-1-yl, 3(R)-fluoropyrrolidin-1-yl, 2-methylpyrrolidin-1-yl, 3,5-dimethylpyrrolidin-1-yl, or 3,3-dimethylpyrrolidin-1-yl. Within embodiment 29, in other group of compounds, or a pharmaceutically acceptable salt thereof, $R^7$ is —$NR^aR^b$, where $R^a$ and $R^b$ together with the nitrogen to which they are attached form pyrrolidin-1-yl.

30. In embodiment 30, the compounds of any one of embodiments 21 to 27 and groups contained therein, or a pharmaceutically acceptable salt thereof, are those wherein $R^7$ is heterocyclyl that is attached to the alkylene at a ring carbon atom and is optionally substituted with one or two substituents independently selected from alkyl, halo, haloalkyl, hydroxy, alkoxy and haloalkoxy. Within embodiment 30, in a group of compounds, or a pharmaceutically acceptable salt thereof, wherein $R^7$ is a nitrogen-containing heterocyclyl. For example, the heterocyclyl for $R^7$ can be pyrrolidino, piperidino, homopiperidino, 2-oxopyrrolidinyl, 2-oxopiperidinyl, morpholino, piperazino, dihydropyranyl, or thiomorpholino. Within embodiment 30, in a group of compounds, or a pharmaceutically acceptable salt thereof, wherein $R^7$ is an unsubstituted heterocyclyl, such as an unsubstituted nitrogen-containing heterocyclyl. Within embodiment 30, in another group of compounds, or a pharmaceutically acceptable salt thereof, wherein $R^7$ is a substituted heterocyclyl, such as a substituted nitrogen-containing heterocyclyl, where the heterocyclyl is one or two substituents independently selected from alkyl (such as methyl, ethyl, n-propyl or iso-propyl), halo (e.g., as fluoro or chloro), haloalkyl (e.g., —$CH_2Cl$, —$CF_3$, —$CHF_2$, —$CH_2CF_3$, and —$CF_2CF_3$), hydroxy, alkoxy (for example, methoxy, ethoxy, n-propoxy or iso-propoxy) and haloalkoxy (such as —$OCF_3$, —$OCH_2Cl$, —$OCHF_2$, —$OCH_2CF_3$, and —$OCF_2CF_3$). Within embodiment 30, in a group of compounds, or a pharmaceutically acceptable salt thereof, wherein $R^7$ is piperidin-3-yl optionally substituted with alkyl.

31. In embodiment 31, the compounds of any one of embodiments 1 to 20 and groups contained therein, or a pharmaceutically acceptable salt thereof, are those wherein $R^3$ is —O—$(CH_2)_3$-pyrrolidin-1-yl, —O—$(CH_2)_3$-piperidin-1-yl, —O—$(CH_2)$-piperidin-3-yl, or —O—$(CH_2)_3$-morpholin-4-yl, wherein pyrrolidin-1-yl, piperidin-1-yl, piperidin-3-yl and morpholin-4-yl are each optionally substituted with one or two substituents independently selected from methyl, hydroxy, methoxy, and fluoro. 32. In embodiment 32, the compounds of any one of embodiments 1 to 24 and groups contained therein, or a pharmaceutically acceptable salt thereof, are those wherein —W-alkylene- in $R^3$ is —$(CH_2)$—O—$(CH_2)_2$—*, or —$(CH_2)_2$—O—$(CH_2)_2$—*, wherein the * indicates the point of attachment to —$NR^aR^b$. Within embodiment 32, in a group of compounds, or a pharmaceutically acceptable salt thereof, $R^7$ is —$NR^aR^b$, where —$NR^aR^b$ is $NH_2$, methylamino, ethylamino, dimethylamino, or diethylamino. Within embodiment 32, in another group of compounds, or a pharmaceutically acceptable salt thereof, $R^7$ is —$NR^aR^b$, where —$NR^aR^b$ together with the nitrogen to which they are attached form heterocycloamino wherein the heterocycloamino is optionally substituted with one or two substituents independently selected from alkyl, halo, haloalkyl, hydroxy, alkoxy and haloalkoxy. Within embodiment 32, in another group of compounds, or a pharmaceutically acceptable salt thereof, $R^7$ is —$NR^aR^b$, where —$NR^aR^b$ together with the nitrogen to which they are attached form a saturated heterocycloamino (such as azetidin-1-yl, pyrrolidin-1-yl, piperidin-1-yl, morpholin-4-yl, or thiomorpholin-4-yl), optionally substituted with one or two substituents independently selected from methyl, hydroxy, methoxy, and fluoro.

Within embodiment 32, in another group of compounds, or a pharmaceutically acceptable salt thereof, $R^3$ is —$(CH_2)$—O—$(CH_2)_2$-pyrrolidin-1-yl, —$(CH_2)$—O—$(CH_2)_2$-piperidin-1-yl, or —$(CH_2)$—O—$(CH_2)_2$-morpholin-4-yl, wherein the pyrrolidin-1-yl, the piperidin-1-yl, and the morpholin-4-yl are each optionally substituted with one or two substituents independently selected from methyl, hydroxy, methoxy, and fluoro. Within embodiment 32, in yet another group of compounds, or a pharmaceutically acceptable salt thereof, $R^3$ is —$(CH_2)$—O—$(CH_2)_2$—$NR^aR^b$, where $NR^aR^b$ is pyrrolidin-1-yl, 3-hydroxy-3-methylpyrrolidin-1-yl, 3-hydroxy-3-methylazetidin-1-yl, 3-fluoroazetidinyl, 3-fluoropyrrolidinyl, 3(R)-fluoropyrrolidinyl, 3(S)-fluoropyrrolidinyl, 3,5-dimethylpyrrodin-1-yl, or 3,3-dimethylpyrrodin-1-yl, preferably pyrrolidin-1-yl.

33. In embodiment 33, the compounds of any one of embodiments 1 to 32 and groups contained therein, or a pharmaceutically acceptable salt thereof, are those wherein w is 0.

34. In embodiment 34, the compounds of any one of embodiments 1 to 32 and groups contained therein, or a pharmaceutically acceptable salt thereof, are those wherein w is 1. With embodiment 34, in a group of compounds, or a pharmaceutically acceptable salt thereof, are those wherein $R^5$ is $NH_2$, halo, alkyl, hydroxy, alkoxy, cycloalkyl, or hydroxyalkyl. Within embodiment 34, in a group of compounds, or a pharmaceutically acceptable salt thereof, $R^5$ is hydroxy, $NH_2$, fluoro, chloro, methyl, ethyl, hydroxy, methoxy, cyclopropyl, cyclopentyl, or hydroxymethyl. Within embodiment 34, in another group of compounds, or a pharmaceutically acceptable salt thereof, $R^5$ is $NH_2$. Within embodiment 34, in another group of compounds, or a pharmaceutically acceptable salt thereof, $R^5$ is alkyl (such as a $C_{1-6}$ alkyl). Within embodiment 34, in a group of compounds, or a pharmaceutically acceptable salt thereof, $R^5$ is methyl. Within embodiment 34, in another group of compounds, or a pharmaceutically acceptable salt thereof, $R^5$ is cycloalkyl (for example a $C_{3-6}$ alkyl). Within embodiment 34, in a group of compounds, or a pharmaceutically acceptable salt thereof, $R^5$ is cyclopropyl. Within embodiment 34, in another group of compounds, or a pharmaceutically acceptable salt thereof, $R^5$ is halo (e.g., a fluoro or chloro). Within embodiment 34, in another group of compounds, or a pharmaceutically acceptable salt thereof, $R^5$ is hydroxy or hydroxyalkyl (hydroxy($C_{1-4}$ alkyl)). Within embodiment 34, in a group of compounds, or a pharmaceutically acceptable salt thereof, $R^5$ is hydroxymethyl. Within embodiment 34, in another group of compounds, or a pharmaceutically acceptable salt thereof, $R^5$ is alkoxy (such as a $C_{1-6}$ alkoxy). Within embodiment 34, in a group of compounds, or a pharmaceutically acceptable salt thereof, $R^5$ is methoxy.

35. In embodiment 35, the compounds of any one of embodiments 1 to 34 and groups contained therein, or a pharmaceutically acceptable salt thereof, are those wherein v is 0. Within embodiment 35, in a group of compounds, or a pharmaceutically acceptable salt thereof, w is 0. Within embodiment 35, in a group of compounds, or a pharmaceutically acceptable salt thereof, w is 1. When w is 1, in a group or compounds, or a pharmaceutically acceptable salt thereof, $R^5$ can be selected from any of the groups of compounds, or a pharmaceutically acceptable salt thereof, provided within embodiment 34.

36. In embodiment 36, the compounds of any one of embodiments 1 to 34 and groups contained therein, or a pharmaceutically acceptable salt thereof, are those wherein v is 1. Within embodiment 36, in a group of compounds, or a pharmaceutically acceptable salt thereof, w is 0. Within embodiment 36, in a group of compounds, or a pharmaceutically acceptable salt thereof, w is 1. When w is 1, in a group or compounds, or a pharmaceutically acceptable salt thereof, $R^5$ can be selected from any of the groups of compounds, or a pharmaceutically acceptable salt thereof, provided within embodiment 34.

37. In embodiment 37, the compounds of embodiment 36 and groups contained therein, or a pharmaceutically acceptable salt thereof, are those wherein $R^4$ is hydroxy.

38. In embodiment 38, the compounds of embodiment 36 and groups contained therein, or a pharmaceutically acceptable salt thereof, are those wherein $R^4$ is alkyl, cycloalkyl, cycloalkenyl, halo, haloalkoxy, alkoxy, cyano, $NH_2$, $NR^cR^d$, alkoxyalkylamino, hydroxyalkylamino, aminoalkylamino, hydroxyalkyl, alkoxyalkyl, alkylthio, alkoxyalkyloxy, phenyl, heteroaryl, heteroaryloxy, heterocyclyl, heterocyclyloxy, 5-8 membered bridged heterocycloamino or spiroheterocycloamino, wherein the phenyl, the heteroaryl, and the heterocyclyl either alone or a part of another group are optionally substituted with one, two, or three substituents independently selected from alkyl, halo, haloalkyl, haloalkoxy, hydroxy, alkoxy, $NH_2$, alkylamino, dialkylamino, carboxy, carboxyalkyl, and alkoxycarbonyl, and wherein the alkyl of $R^4$ is optionally substituted with unsubstituted cycloalkyl; $R^c$ is hydrogen, alkyl, cycloalkyl, or heteocyclyl; and $R^d$ is alkyl, cycloalkyl, or heteocyclyl; or $R^c$ and $R^d$ together with the nitrogen to which they are attached form a 4- to 7-membered heterocycloamino. Within embodiment 38, in another group of compounds, or a pharmaceutically acceptable salt thereof, $R^4$ is alkyl or cycloalkyl. Within embodiment 38, in another group of compounds, or a pharmaceutically acceptable salt thereof, $R^4$ is $NH_2$, $NR^cR^d$, alkoxyalkylamino, hydroxyalkylamino or aminoalkylamino. Within embodiment 38, in another group of compounds, or a pharmaceutically acceptable salt thereof, $R^4$ is heteroaryl, heterocyclyl, 5-8 membered bridged heterocycloamino or spiroheterocycloamino, wherein the heteroaryl and the heterocyclyl either alone or as part of another group are optionally substituted with one, two, or three substituents independently selected from alkyl, halo, haloalkyl, haloalkoxy, hydroxy, alkoxy, $NH_2$, alkylamino, dialkylamino, carboxy, carboxyalkyl, and alkoxycarbonyl. Within embodiment 38, in another group of compounds, or a pharmaceutically acceptable salt thereof, $R^4$ is methyl, ethyl, n-propyl, isopropyl, tert-butyl, ethynyl, fluoro, chloro, cyclopropyl, 1-methylcyclopropyl, cyclobutyl, cyclopentyl, cyclopent-1-en-1-yl, 2-cyclopropylethynyl, 2-cyclopropylethenyl, 2-cyclopropylethyl, pyrrolidin-1-yl, 3-hydroxypyrrolidin-1-yl, 2-isopropylpyrrolidin-1-yl, 2,2-dimethylpyrrolidin-1-yl, 2-isopropylpyrrolidin-1-yl, 2-(carboxymethyl)pyrrolidin-1-yl, 2-carboxypyrrolidin-1-yl, pyridin-2-yl, pyridin-3-yl, pyridin-4-yl, piperidin-1-yl, piperdin-2-yl, piperdin-3-yl, piperdin-4-yl, 4-hydroxypiperidin-1-yl, morpholin-4-yl, oxetan-3-yl, oxetan-2-yl, oxan-2-yl, oxan-3-yl oxan-4-yl, tetrahydropyran-4-yl, 1,2,3,6-tetrahydropyridin-4-yl, 3,6-dihydro-2H-pyran-4-yl, tetrahydrofuran-3-yl, azetidine-1-yl, 3-hydroxyazetidin-1-yl, pyrrolidin-3-yloxy, 1-methylpyrrolidin-3-yloxy, oxan-4-yloxy, pyrrolidin-3-yloxy, 2-ethoxyeth-1-yl, 3-methoxyprop-1-yl, methylamino, ethylamino, n-propylamino, n-butylamino, isopropylamino, isobutylamino, tertbutylamino, cyclopropylamino, cyclobutylamino, cyclopentylamino, cyclohexylamino, cycloheptylamino, (cyclopropylmethyl)amino, (cyclobutylmethyl)amino, (cyclopentylmethyl)amino, (cyclohexylmethyl)amino, dimethylamino, diethylamino, dimethylamino, di-(n-propyl) amino, di-(isopropyl)amino, di-(n-butyl)amino, di-(isobutyl)amino, di-(tertbutyl)amino, (methyl)(ethyl)amino, 2-ethoxyethylamino, 3-methoxyprop-2-ylamino, thiazol-2-yl, thiazol-4-yl, thiazol-5-yl, pyrazol-1-yl, pyrazol-3-yl, pyrazol-4-yl, imidazole-1-yl, imidazole-2-yl, imidazole-4-yl, imidazole-5-yl, oxazol-5-yl, oxazol-2-yl, oxazol-4-yl, 1,2,4-triazol-5-yl, 1,2,4-triazol-3-yl, 1,2,4-triazol-1-yl, hydroxymethyl, 4-difluoromethoxyphenyl, 3-difluoromethoxyphenyl, 2-difluoromethoxypyridin-4-yl, 6-difluoromethoxypyridin-3-yl, 4-methylaminopyridin-2-yl, 2-methylaminopyridin-4-yl, 6-methylamino-pyridin-2-yl, 4-difluoromethylphenyl, 2-hydroxyprop-2-yl, 4-(2-hydroxypropyl)phenyl, 4-(2-hydroxypropan-2-yl)phenyl, 2-(carboxymethyl)phenyl, 2-carboxyphenyl, 2-methoxyethoxy, methoxy, ethoxy, n-propoxy, isopropoxy, n-butoxy, iso-butoxy and tert-butoxy, hydroxy, methylsulfenyl, 3-hydroxy-3-methylbut-1-yn-1-yl, 3-hydroxy-3-methylbut-1-en-1-yl, 3-hydroxy-3-methylbutyl, 2-hydroxypropan-2-yl, 1-azaspiro[3,4]octan-1-yl, 4-azaspiro[2,4]heptan-4-yl, 5-azaspiro[3,4]octan-5-yl, 1-azaspiro[3,3]heptan-1-yl, 2-oxa-5-azaspiro[3,4]octan-5-yl, 6-oxa-1-azaspiro[3,3]heptan-1-yl, 6-oxa-1-azaspiro[3,4]octan-1-yl, 7-oxa-1-azaspiro[4,4]nonan-1-yl, 8-oxa-3-azabicyclo[3.2.1]octan-3-yl, or 7,7-dioxido-7-thia-1-azaspiro[4.4]nonan-1-yl. Within embodiment 38, in another group of compounds, or a pharmaceutically acceptable salt thereof, $R^4$ is methyl, ethyl, n-propyl, isopropyl, or tert-butyl. Within embodiment 38, in another group of compounds, or a pharmaceutically acceptable salt thereof, $R^4$ is methyl, ethyl, n-propyl, or isopropyl. Within embodiment 38, in another group of compounds, or a pharmaceutically acceptable salt thereof, $R^4$ is cyclopropyl, 1-methylcyclopropyl, cyclobutyl, or cyclopentyl. Within embodiment 38, in another group of compounds, or a pharmaceutically acceptable salt thereof, $R^4$ is cyclopropyl. Within embodiment 38, in another group of compounds, or a pharmaceutically acceptable salt thereof, $R^4$ is pyrrolidin-1-yl, 3-hydroxypyrrolidin-1-yl, 2-isopropylpyrrolidin-1-yl, 2,2-dimethylpyrrolidin-1-yl, 2-isopropylpyrrolidin-1-yl, 2-(carboxymethyl)pyrrolidin-1-yl, 2-carboxypyrrolidin-1-yl, pyridin-2-yl, pyridin-3-yl, pyridin-4-yl, piperidin-1-yl, piperdin-2-yl, piperdin-3-yl, piperdin-4-yl, 4-hydroxypiperidin-1-yl, morpholin-4-yl, oxetan-3-yl, oxetan-2-yl, oxan-2-yl, oxan-3-yl oxan-4-yl, tetrahydropyran-4-yl, 1,2,3,6-tetrahydropyridin-4-yl, 3,6-dihydro-2H-pyran-4-yl, tetrahydrofuran-3-yl, azetidine-1-yl, 3-hydroxyazetidin-1-yl, thiazol-2-yl, thiazol-4-yl, thiazol-5-yl, pyrazol-1-yl, pyrazol-3-yl, pyrazol-4-yl, imidazole-1-yl, imidazole-2-yl, imidazole-4-yl, imidazole-5-yl, oxazol-5-yl, oxazol-2-yl, oxazol-4-yl, 1,2,4-triazol-5-yl, 1,2,4-triazol-3-yl, 1,2,4-triazol-1-yl, hydroxymethyl, 4-difluoromethoxyphenyl, 3-difluoromethoxyphenyl, 2-difluoromethoxypyridin-4-yl, 6-difluoromethoxypyridin-3-yl, 4-methylaminopyridin-2-yl, 2-methylaminopyridin-4-yl, or 6-methylamino-pyridin-2-yl. Within embodiment 38, in another group of compounds, or a pharmaceutically acceptable salt thereof, $R^4$ is pyrrolidin-1-yl, 3-hydroxypyrrolidin-1-yl, 2-isopropylpyrrolidin-1-yl, 2,2-dimethylpyrrolidin-1-yl, 2-isopropylpyrrolidin-1-yl, 2-(carboxymethyl)pyrrolidin-1-yl, or 2-carboxypyrrolidin-1-yl. Within embodiment 38, in another group of compounds, or a pharmaceutically acceptable salt thereof, $R^4$ is pyrrolidin-1-yl. Within embodiment 38, in another group of compounds, or a pharmaceutically acceptable salt thereof, $R^4$ is 1-azaspiro[3,4]octan-1-yl, 4-azaspiro[2,4]heptan-4-yl, 5-azaspiro[3,4]octan-5-yl, 1-azaspiro[3,3]heptan-1-yl, 2-oxa-5-azaspiro[3,4]octan-5-yl, 6-oxa-1-azaspiro[3,3]heptan-1-yl, 6-oxa-1-azaspiro[3,4]octan-1-yl, 7-oxa-1-azaspiro[4,4]nonan-1-yl, 8-oxa-3-azabicyclo[3.2.1]octan-3-yl, or 7,7-dioxido-7-thia-1-azaspiro[4.4]nonan-1-yl. Within embodiment 38, in another group of compounds, or a pharmaceutically acceptable salt thereof, $R^4$ is methylamino, ethylamino, n-propylamino, n-butylamino, isopropylamino, isobutylamino, tertbutylamino, cyclopropylamino, cyclobutylamino, cyclopentylamino, cyclohexylamino, cycloheptylamino, (cyclopropylmethyl)amino, (cyclobutylmethyl)amino, (cyclopentylmethyl)amino, (cyclohexylmethyl)amino, dimethylamino, diethylamino, dimethylamino, di-(n-propyl)amino, di-(isopropyl)amino, di-(n-butyl)amino, di-(isobutyl)amino, di-(tertbutyl)amino, or (methyl)(ethyl)amino.

39. In embodiment 39, the compounds of embodiment 1, or a pharmaceutically acceptable salt thereof, are those wherein Z is $R^6$, wherein $R^6$ is hydrogen; X is $CR^1$; Y is $CR^2$, P is CH or $CR^4$; Q is N; T is CH or $CR^5$; U is CH or N; $R^1$ and $R^2$ are independently hydrogen or methoxy; $R^3$ is —O—$(CH_2)_2$—$R^7$, —O—$(CH_2)_3$—$R^7$ or —O—$(CH_2)_4$—$R^7$; $R^7$ is —$NR^aR^b$, wherein $R^a$ and $R^b$ are independently methyl, ethyl, n-propyl or isopropyl, or —$NR^aR^b$ together with the nitrogen to which they are attached form a 4-membered heterocycloamino or a 5-membered heterocycloamino wherein each heterocycloamino is optionally substituted with one or two substituents independently selected from alkyl, halo, haloalkyl, hydroxy, alkoxy and haloalkoxy; $R^4$ is methyl, ethyl, n-propyl, isopropyl, cyclopropyl, cyclobutyl, cyclopentyl, heterocyclyl, $NH_2$, or $NR^cR^d$, wherein the cyclopropyl, the cyclobutyl, and the cyclopentyl are optionally substituted with one, two, or three substituents independently selected from alkyl, halo, haloalkyl, haloalkoxy, hydroxy, alkoxy, $NH_2$, alkylamino, dialkylamino, carboxy, carboxyalkyl, and alkoxycarbonyl; $R^5$ is $NH_2$; $R^c$ is hydrogen, alkyl, cycloalkyl, or heteocyclyl; and $R^d$ is alkyl, cycloalkyl or heterocyclyl; or $R^c$ and $R^d$ together with the nitrogen to which they are attached form a 4- to 7-membered heterocycloamino. Within embodiment 39, when X is $CR^1$; Y is $CR^2$, P is CH or $CR^4$; Q is N; T is CH or $CR^5$; and U is CH or N, the compound of Formula (I) has the following structure (hereinafter referred to as a "compound of Formula (Ia), or a pharmaceutically acceptable salt thereof"):

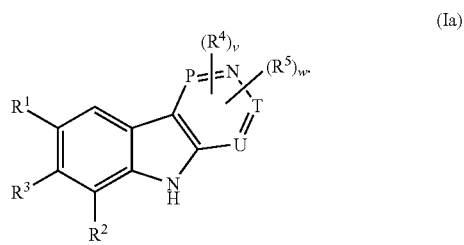

(Ia)

Within embodiment 39, in a group of compounds, or a pharmaceutically acceptable salt thereof, $R^1$ is methoxy and $R^2$ is hydrogen. Within embodiment 39, in another group of compounds, or a pharmaceutically acceptable salt thereof, $R^1$ is hydrogen and $R^2$ is methoxy. Within embodiment 39, in a group of compounds, or a pharmaceutically acceptable salt thereof, $R^3$ is —O—$(CH_2)_2$—$R^7$. Within embodiment 39, in another group of compounds, or a pharmaceutically acceptable salt thereof, $R^3$ is —O—$(CH_2)_3$—$R^7$. Within embodiment 39, in another group of compounds, or a pharmaceutically acceptable salt thereof, $R^3$ is —O—$(CH_2)_4$—$R^7$. Within embodiment 39, in a group of compounds, or a pharmaceutically acceptable salt thereof, $R^7$ is —$NR^aR^b$, where $R^a$ and $R^b$ are independently methyl, ethyl, n-propyl or isopropyl. Within embodiment 39, in a group of compounds, or a pharmaceutically acceptable salt thereof, $R^7$ is —$NR^aR^b$, where $R^a$ and $R^b$ are independently methyl, ethyl, n-propyl or isopropyl. Within embodiment 39, in a group of compounds, or a pharmaceutically acceptable salt thereof, $R^a$ and $R^b$ are each methyl. Within embodiment 39, in another group of compounds, or a pharmaceutically acceptable salt thereof, $R^7$ is —$NR^aR^b$, wherein —$NR^aR^b$ together with the nitrogen to which they are attached form a 4-membered heterocycloamino or a 5-membered heterocycloamino wherein each heterocycloamino is optionally substituted with one or two substituents independently selected from alkyl, halo, haloalkyl, hydroxy, alkoxy and haloalkoxy. Within embodiment 39, in a group of compounds, or a pharmaceutically acceptable salt thereof, $NR^aR^b$ together with the nitrogen to which they are attached form pyrrolidin-1-yl. Within embodiment 39, in another group of compounds, or a pharmaceutically acceptable salt thereof, $NR^aR^b$ together with the nitrogen to which they are attached form azetidin-1-yl. Within embodiment 39, in a group of compounds, or a pharmaceutically acceptable salt thereof, v is 0 and w is 0. Within embodiment 39, in another group of compounds, or a pharmaceutically acceptable salt thereof, v is 1 and w is 0. Within embodiment 39, in a group of compounds, or a pharmaceutically acceptable salt thereof, v is 0 and w is 1. Within embodiment 39, in another group of compounds, or a pharmaceutically acceptable salt thereof, v is 1 and w is 1. Within embodiment 39, in a group of compounds, or a pharmaceutically acceptable salt thereof, P is CH. Within embodiment 39, in a group of compounds, or a pharmaceutically acceptable salt thereof, P is $CR^4$, wherein $R^4$ is methyl, ethyl, n-propyl, or isopropyl. Within embodiment 39, in a group of compounds, or a pharmaceutically acceptable salt thereof, P is $CR^4$, wherein $R^4$ is cyclopropyl, cyclobutyl, or cyclopentyl, wherein the cyclopropyl, the cyclobutyl, or the cyclopentyl are optionally substituted with one, two, or three substituents independently selected from alkyl (such as $C_{1-4}$ alkyl), halo (such as F), haloalkyl (such as $CF_3$), haloalkoxy (such as $OCF_3$), hydroxy, alkoxy (such as $C_{1-4}$ alkoxy), $NH_2$, alkylamino (such as $C_{1-4}$ alkylamino), dialkylamino (for example, a dialkylamino wherein each alkyl is independently a $C_{1-4}$ alkyl), carboxy, carboxyalkyl (such as $C_{2-5}$ carboxyalkyl), and alkoxycarbonyl (such as $C_{2-5}$ alkoxycarbonyl). Within embodiment 39, in a group of compounds, or a pharmaceutically acceptable salt thereof, P is $CR^4$, wherein $R^4$ is a 4- to 6-membered heterocyclyl (such as oxetanyl, tetrahydrofuranyl, or tetrahydropyranyl). Within embodiment 39, in another group of compounds, or a pharmaceutically acceptable salt thereof, P is $CR^4$, wherein $R^4$ is $NH_2$ or $NR^cR^d$, wherein $R^c$ is hydrogen, alkyl, cycloalkyl, or heteocyclyl; and $R^d$ is alkyl, cycloalkyl, or heteocyclyl. Within embodiment 39, in a group of compounds, or a pharmaceutically acceptable salt thereof, P is $CR^4$, wherein $R^4$ is $NR^cR^d$, wherein $R^c$ and $R^d$ together with the nitrogen to which they are attached form a 4- to 6-membered heterocycloamino (e.g., azetidinyl, pyrrolidinyl, piperidinyl, piperazinyl, or morpholinyl). Within embodiment 39, in a group of compounds, or a pharmaceutically acceptable salt thereof, T is CH. Within embodiment 39, in another group of compounds, or a pharmaceutically acceptable salt thereof, T is $CR^5$, wherein $R^5$ is $NH_2$. Within embodiment 39, in a group of compounds, or a pharmaceutically acceptable salt thereof, U is CH. Within embodiment 39, in a group of compounds, or a pharmaceutically acceptable salt thereof, U is N. Any combination of X, Y, $R^1$, $R^2$, $R^3$, $R^4$ (including $R^c$ and $R^d$), $R^5$, $R^7$ (including $R^a$ and $R^b$), T, and U as defined in embodiment 39 is encompassed by this disclosure. 40. In embodiment 40, the compounds of embodiment 1, or a pharmaceutically acceptable salt thereof, are those wherein the compound of Formula (I) has the structure of Formula (Ib), or a pharmaceutically acceptable salt thereof:

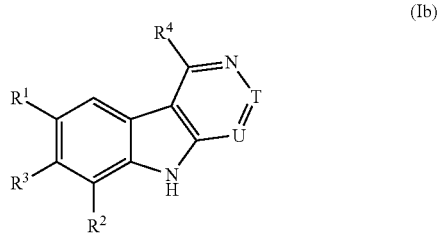

wherein $R^1$, $R^2$, $R^3$, $R^4$ (including $R^c$ and $R^d$), $R^5$, $R^7$ (including $R^a$ and $R^b$), T, and U are as defined in the Summary. Within embodiment 40, in a group of compounds, or a pharmaceutically acceptable salt thereof, $R^1$ is methoxy and $R^2$ is hydrogen. Within embodiment 40, in another group of compounds, or a pharmaceutically acceptable salt thereof, $R^1$ is hydrogen and $R^2$ is methoxy. Within embodiment 40, in a group of compounds, or a pharmaceutically acceptable salt thereof, $R^3$ is —O—$(CH_2)_2$—$R^7$. Within embodiment 40, in another group of compounds, or a pharmaceutically acceptable salt thereof, $R^3$ is —O—$(CH_2)_3$—$R^7$. Within embodiment 40, in another group of compounds, or a pharmaceutically acceptable salt thereof, $R^3$ is —O—$(CH_2)_4$—$R^7$. Within embodiment 40, in a group of compounds, or a pharmaceutically acceptable salt thereof, $R^7$ is —$NR^aR^b$, where $R^a$ and $R^b$ are independently methyl, ethyl, n-propyl or isopropyl. Within embodiment 40, in a group of compounds, or a pharmaceutically acceptable salt thereof, $R^a$ and $R^b$ are each methyl. Within embodiment 40, in another group of compounds, or a pharmaceutically acceptable salt thereof, $R^7$ is —$NR^aR^b$, wherein —$NR^aR^b$ together with the nitrogen to which they are attached form a 4-membered heterocycloamino or a 5-membered heterocycloamino wherein each heterocycloamino is optionally substituted with one or two substituents independently selected from alkyl, halo, haloalkyl, hydroxy, alkoxy and haloalkoxy. Within embodiment 40, in a group of compounds, or a pharmaceutically acceptable salt thereof, $NR^aR^b$ together with the nitrogen to which they are attached form pyrrolidin-1-yl. Within embodiment 40, in another group of compounds, or a pharmaceutically acceptable salt thereof, $NR^aR^b$ together with the nitrogen to which they are attached form azetidin-1-yl. Within embodiment 37, in a group of compounds, or a pharmaceutically acceptable salt thereof, $R^4$ is methyl, ethyl, n-propyl, or isopropyl. Within embodiment 40, in a group of compounds, or a pharmaceutically acceptable salt thereof, $R^4$ is cyclopropyl, cyclobutyl, or cyclopentyl wherein the cyclopropyl, the cyclobutyl, or the cyclopentyl are optionally substituted with one, two, or three substituents independently selected from alkyl (such as $C_{1-4}$ alkyl), halo (such as F), haloalkyl (such as $CF_3$), haloalkoxy (such as $OCF_3$), hydroxy, alkoxy (such as $C_{1-4}$ alkoxy), $NH_2$, alkylamino (such as $C_{1-4}$ alkylamino), dialkylamino (for example, a dialkylamino wherein each alkyl is independently a $C_{1-4}$ alkyl), carboxy, carboxyalkyl (such as $C_{2-5}$ carboxyalkyl), and alkoxycarbonyl (such as $C_{2-5}$ alkoxycarbonyl). Within embodiment 40, in a group of compounds, or a pharmaceutically acceptable salt thereof, $R^4$ is a 4- to 6-membered heterocyclyl (such as oxetanyl, tetrahydrofuranyl, or tetrahydropyranyl). Within embodiment 40, in another group of compounds, or a pharmaceutically acceptable salt thereof, $R^4$ is $NH_2$ or $NR^cR^d$, wherein $R^c$ is hydrogen, alkyl, cycloalkyl or heterocyclyl, and $R^d$ is alkyl, cycloalkyl or heterocyclyl. Within embodiment 40, in a group of compounds, or a pharmaceutically acceptable salt thereof, $R^4$ is $NR^cR^d$, wherein $R^c$ and $R^d$ together with the nitrogen to which they are attached form a 4- to 6-membered heterocycloamino (e.g., azetidinyl, pyrrolidinyl, piperidinyl, piperazinyl, or morpholinyl). Within embodiment 40, in a group of compounds, or a pharmaceutically acceptable salt thereof, T is CH. Within embodiment 40, in another group of compounds, or a pharmaceutically acceptable salt thereof, T is $CR^5$, wherein $R^5$ is $NH_2$. Within embodiment 40, in a group of compounds, or a pharmaceutically acceptable salt thereof, U is CH. Within embodiment 40, in another group of compounds, or a pharmaceutically acceptable salt thereof, U is N. Any combination of $R^1$, $R^2$, $R^3$, $R^4$ (including $R^c$ and $R^d$), $R^5$, $R^7$ (including $R^a$ and $R^b$), T, and U as defined in embodiment 40 is encompassed by this disclosure.

41. In embodiment 41, the compounds of embodiment 1, or a pharmaceutically acceptable salt thereof, are those wherein the compound of Formula (I) has the structure of Formula (Ic), or a pharmaceutically acceptable salt thereof:

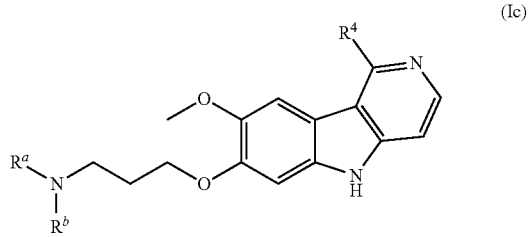

wherein $R^a$, $R^b$, and $R^4$ (including $R^c$ and $R^d$) are as defined in the Summary. Within embodiment 41, in a group of compounds, or a pharmaceutically acceptable salt thereof, $R^a$ and $R^b$ are independently methyl, ethyl, n-propyl or isopropyl. Within embodiment 41, in a group of compounds, or a pharmaceutically acceptable salt thereof, $R^a$ and $R^b$ are each methyl. Within embodiment 41, in a group of compounds, or a pharmaceutically acceptable salt thereof, —$NR^aR^b$ together with the nitrogen to which they are attached form a 4-membered heterocycloamino or a 5-membered heterocycloamino wherein each heterocycloamino is optionally substituted with one or two substituents independently selected from alkyl, halo, haloalkyl, hydroxy, alkoxy and haloalkoxy. Within embodiment 41, in a group of compounds, or a pharmaceutically acceptable salt thereof, $NR^aR^b$ together with the nitrogen to which they are attached form pyrrolidin-1-yl. Within embodiment 41, in a group of compounds, or a pharmaceutically acceptable salt thereof, $R^4$ is methyl, ethyl, n-propyl, or isopropyl. Within embodiment 41, in a group of compounds, or a pharmaceutically acceptable salt thereof, $R^4$ is cyclopropyl, cyclobutyl, or cyclopentyl wherein the cyclopropyl, the cyclobutyl, or the cyclopentyl are optionally substituted with one, two, or three substituents independently selected from alkyl (such as $C_{1-4}$ alkyl), halo (such as F), haloalkyl (such as $CF_3$), haloalkoxy (such as $OCF_3$), hydroxy, alkoxy (such as $C_{1-4}$ alkoxy), $NH_2$, alkylamino (such as $C_{1-4}$ alkylamino), dialkylamino (for example, a dialkylamino wherein each alkyl is independently a $C_{1-4}$ alkyl), carboxy, carboxyalkyl (such as $C_{2-5}$ carboxyalkyl), and alkoxycarbonyl (such as $C_{2-5}$ alkoxycarbonyl). Within embodiment 41, in a group of compounds, or a pharmaceutically acceptable salt thereof, $R^4$ is methyl, ethyl, n-propyl, isopropyl, or cyclopropyl. Within embodiment 41, in a group of compounds, or a pharmaceutically acceptable salt thereof, $R^a$ and $R^b$ are each methyl; and $R^4$ is methyl, ethyl, n-propyl, isopropyl, or cyclopropyl. Within embodiment 41, in a group of compounds, or a pharmaceutically acceptable salt thereof, $R^4$ is a 4- to 6-membered heterocyclyl (such as oxetanyl, tetrahydrofuranyl, or tetrahydropyranyl). Within embodiment 41, in another group of compounds, or a pharmaceutically acceptable salt thereof, $R^4$ is $NH_2$ or $NR^cR^d$, wherein $R^c$ is hydrogen, alkyl, cycloalkyl or heterocyclyl, and $R^d$ is alkyl, cycloalkyl or heterocyclyl. Within embodiment 41, in a group of compounds, or a pharmaceutically acceptable salt thereof, $R^4$ is $NR^cR^d$, wherein $R^c$ and $R^d$ together with the nitrogen to which they are attached form a 4- to 6-membered heterocycloamino (e.g., azetidinyl, pyrrolidinyl, piperidinyl, piperazinyl, or morpholinyl). Any combination of $R^4$ (including $R^c$ and $R^d$), $R^a$, and $R^b$ as defined in embodiment 41 is encompassed by this disclosure.

42. In embodiment 42, the compounds of embodiment 1, or a pharmaceutically acceptable salt thereof, are those wherein the compound, or a pharmaceutically acceptable salt thereof, is selected from compound numbers: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 1a, 2a, 3a, 4a, 5a, 6a, 7a, 8a, 9a, 10a, 11a, 12a, 13a, 14a, 15a, 16a, 17a, 18a, 19a, 20a, 21a, 22a, 23a, 24a, 25a, 26a, 27a, 28a, 29a, 30a, 31a, 32a, 33a, 34a, 35a, 36a, 37a, 38a, 39a, 40a, 41a, 42a, 43a, 44a, 45a, 46a, 47a, 48a, 49a, 50a, 51a, 52a, 53a, 54a, 55a, 56a, 57a, 58a, 59a, 60a, 61a, 62a, 63a, 64a, 65a, 66a and 67a as shown in Table 1 or Table 2, or a parent compound of the salt as shown in Table 1, or a pharmaceutically acceptable salt of the parent compound.

43. In embodiment 43, the compounds of embodiment 1, or a pharmaceutically acceptable salt thereof, are those wherein the compound, or a pharmaceutically acceptable salt thereof, is selected from compound numbers: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101 and 102, as shown in Table 1, or a parent compound of a salt as shown in Table 1, or a pharmaceutically acceptable salt of the parent compound.

44. In embodiment 44, the compounds of embodiment 1, or a pharmaceutically acceptable salt thereof, are those wherein the compound, or a pharmaceutically acceptable salt thereof, is selected from compound numbers: 1a, 2a, 3a, 4a, 5a, 6a, 7a, 8a, 9a, 10a, 11a, 12a, 13a, 14a, 15a, 16a, 17a, 18a, 19a, 20a, 21a, 22a, 23a, 24a, 25a, 26a, 27a, 28a, 29a, 30a, 31a, 32a, 33a, 34a, 35a, 36a, 37a, 38a, 39a, 40a, 41a, 42a, 43a, 44a, 45a, 46a, 47a, 48a, 49a, 50a, 51a, 52a, 53a, 54a, 55a, 56a, 57a, 58a, 59a, 60a, 61a, 62a, 63a, 64a, 65a, 66a and 67a.

45. Embodiment 45 provides a pharmaceutical composition comprising a compound of any one of embodiments 1-44, or a pharmaceutically acceptable salt thereof, and a pharmaceutically acceptable excipient.

46. Embodiment 46 provides a method of inhibiting the activity of G9a comprising contacting a cell that contains G9a with an effective amount of a compound of any one of embodiments 1-44, or a pharmaceutically acceptable salt thereof, and thereby inhibiting the activity of the G9a. Within embodiment 46, in a group of methods, the method can be conducted in vitro. Within embodiment 46, in another group of methods, the cell can be in a subject, and the subject is suffering from a disease treatable by inhibiting G9a.

47. Embodiment 47 provides a method of inhibiting the activity of GLP comprising contacting a cell that contains GLP with an effective amount of a compound of any one of embodiments 1-44, or a pharmaceutically acceptable salt thereof, and thereby inhibiting the activity of GLP. Within embodiment 47, in a group of methods, the method can be conducted in vitro. Within embodiment 47, in another group of methods, the cell can be in a subject, and the subject is suffering from a disease treatable by inhibiting GLP.

48. Embodiment 48 provides a method of increasing fetal hemoglobin (HbF) protein levels comprising contacting a cell characterized as having impaired production of β-globin with an effective amount of a compound of any one of embodiments 1-44, or a pharmaceutically acceptable salt thereof, and thereby increasing fetal hemoglobin (HbF) protein levels.

49. Embodiment 49 provides a method of reducing the concentration of hemoglobin S molecules comprising contacting a cell characterized as having a hemoglobin S mutation with an effective amount of a compound of any one of embodiments 1-44, or a pharmaceutically acceptable salt thereof, and thereby reducing the concentration of hemoglobin S molecules. Embodiment 49 also provides a method of inhibiting the polymerization of hemoglobin S molecules comprising contacting a cell characterized as having a hemoglobin S mutation with an effective amount of a compound of any one of embodiments 1-44, or a pharmaceutically acceptable salt thereof, and thereby inhibiting the polymerization of hemoglobin S molecules. Those skilled in the art understand that hemoglobin S can polymerize under hypoxic conditions to form hemoglobin polymers that result in the red blood cell (RBC) losing its deformability properties and taking on a sickle-like shape. See, for example, Rees et al., Lancet 2010, 376, 2018-2031. As used herein, "inhibiting the polymerization of hemoglobin S molecules" refers to inhibiting the formation of such hemoglobin polymers.

50. Embodiment 50 provides a method of inhibiting G9a activity in a subject comprising administering to the subject suffering from a disease that is treatable by fetal hemoglobin an effective amount of a compound of any one of embodiments 1-44, or a pharmaceutically acceptable salt thereof.

51. Embodiment 51 provides a method of inhibiting GLP activity in a subject comprising administering to the subject suffering from a disease that is treatable by fetal hemoglobin an effective amount of a compound of any one of embodiments 1-44, or a pharmaceutically acceptable salt thereof.

52. Embodiment 52 provides a method for treating a disease comprising administrating to a subject suffering from the disease treatable by fetal hemoglobin an effective amount of a compound of any one of embodiments 1-44, or a pharmaceutically acceptable salt thereof.

53. Embodiment 53 provides method for treating a disease characterized by impaired production of β-globin comprising administrating to a subject suffering from the disease characterized by impaired production of β-globin an effective amount of a compound of any one of embodiments 1-44, or a pharmaceutically acceptable salt thereof. Within embodiment 53, in a group of compounds, or a pharmaceutically acceptable salt thereof, the disease is beta-thalassemia.

54. Embodiment 54 provides a method for treating a disease characterized by increased concentration of polymerized hemoglobin S molecules comprising administrating to a subject suffering from the disease characterized by increased concentration of polymerized hemoglobin S molecules an effective amount of a compound of any one of embodiments 1-44, or a pharmaceutically acceptable salt thereof. Within embodiment 54, in a group of compounds, or a pharmaceutically acceptable salt thereof, the disease is sickle cell disease.

55. Embodiment 55 provides a method of ameliorating or treating a hemoglobinopathy, comprising administering an effective amount of a compound of any one of embodiments 1-44, or a pharmaceutically acceptable salt thereof, or the pharmaceutical composition of embodiment 45 to a subject in need thereof. Within embodiment 55, in a group of compounds, or a pharmaceutically acceptable salt thereof, the hemoglobinopathy is sickle cell disease. Within embodiment 55, in a group of compounds, or a pharmaceutically acceptable salt thereof, the hemoglobinopathy is beta-thalassemia.

56. Embodiment 56 provides a use of an effective amount of a compound of any one of embodiments 1-44, or a pharmaceutically acceptable salt thereof, in the preparation of a medicament for inhibiting the activity of G9a in a cell that contains G9a.

57. Embodiment 57 provides a use of an effective amount of a compound of any one of embodiments 1-44, or a pharmaceutically acceptable salt thereof, in the preparation of a medicament for inhibiting the activity of GLP in a cell that contains GLP.

58. Embodiment 58 provides a use of an effective amount of a compound of any one of embodiments 1-44, or a pharmaceutically acceptable salt thereof, in the preparation of a medicament for increasing fetal hemoglobin (HbF) protein levels in a cell characterized as having impaired production of β-globin.

59. Embodiment 59 provides a use of an effective amount of a compound of any one of embodiments 1-44, or a pharmaceutically acceptable salt thereof, in the preparation of a medicament for reducing the concentration of hemoglobin S molecules in a cell characterized as having a hemoglobin S mutation. Embodiment 59 also provides a use of an effective amount of a compound of any one of embodiments 1-44, or a pharmaceutically acceptable salt thereof, in the preparation of a medicament for inhibiting the polymerization of hemoglobin S molecules in a cell characterized as having a hemoglobin S mutation.

60. Embodiment 60 provides a use of an effective amount of a compound of any one of embodiments 1-44, or a pharmaceutically acceptable salt thereof, in the preparation of a medicament for treating a disease treatable by fetal hemoglobin.

61. Embodiment 61 provides a use of an effective amount of a compound of any one of embodiments 1-44, or a pharmaceutically acceptable salt thereof, in the preparation of a medicament for treating a disease treatable by fetal hemoglobin.

62. Embodiment 62 provides a use of an effective amount of a compound of any one of embodiments 1-44, or a pharmaceutically acceptable salt thereof, in the preparation of a medicament for treating a disease characterized by impaired production of β-globin. Within embodiment 62, in a group of compounds, or a pharmaceutically acceptable salt thereof, the disease is beta-thalassemia.

63. Embodiment 63 provides a use of an effective amount of a compound of any one of embodiments 1-44, or a pharmaceutically acceptable salt thereof, in the preparation of a medicament for treating a disease characterized by increased concentration of polymerized hemoglobin S molecules. Within embodiment 63, in a group of compounds, or a pharmaceutically acceptable salt thereof, the disease is sickle cell disease.

64. Embodiment 64 provides a use of an effective amount of a compound of any one of embodiments 1-44, or a pharmaceutically acceptable salt thereof, in the preparation of a medicament for ameliorating or treating a hemoglobinopathy. Within embodiment 64, in a group of compounds, or a pharmaceutically acceptable salt thereof, the hemoglobinopathy is sickle cell disease. Within embodiment 64, in a group of compounds, or a pharmaceutically acceptable salt thereof, the hemoglobinopathy is beta-thalassemia.

Representative compounds of Formula (I), or salts thereof, are disclosed in Tables 1 and 2 below. Although Tables 1 and 2 may show a specific salt of a compound of Formula (I), those skilled in the art will be able to recognize the parent compound (wherein the "parent compound" is a compound without a salt moiety present), and other salts, such as pharmaceutically acceptable salts, of those compounds in Tables 1 and 2.

TABLE 1

| Compound # | Structure of Parent Compound | Name | MS Found |
|---|---|---|---|
| 1 |  | 1-[3-({6-methoxy-5H-pyrido[3,2-b]indol-7-yl}oxy)propyl]pyrrolidine | 326.5 |
| 2 |  | 1-[3-({8-methoxy-5H-pyrido[3,2-b]indol-7-yl}oxy)propyl]pyrrolidine | 326.5 |

TABLE 1-continued

| Compound # | Structure of Parent Compound | Name | MS Found |
|---|---|---|---|
| 3 | | 1-[3-({6-methoxy-9H-pyrido[3,4-b]indol-7-yl)oxy)propyl]pyrrolidine | 326 |
| 4 | | 1-[3-({8-methoxy-5H-pyrimido[5,4-b]indol-7-yl}oxy)propyl]pyrrolidine | 327 |
| 5 | | 1-[3-({8-methoxy-1-methyl-5H-pyrido[4,3-b]indol-7-yl}oxy)propyl]pyrrolidine | 340 |
| 6 | | 1-[3-({8-methoxy-5H-pyrido[4,3-b]indol-7-yl}oxy)propyl]pyrrolidine | 326.2 |
| 7 | | 1-[3-({6-methoxy-9H-pyrido[2,3-b]indol-7-yl}oxy)propyl]pyrrolidine | 326 |
| 8 | | 8-methoxy-7-[3-(pyrrolidin-1-yl)propoxy]-5H-pyrido[4,3-b]indol-3-amine | 341.4 |
| 9 | | 1-[3-({1-fluoro-8-methoxy-5H-pyrido[4,3-b]indol-7-yl}oxy)propyl]pyrrolidine | 344 |

TABLE 1-continued

| Compound # | Structure of Parent Compound | Name | MS Found |
|---|---|---|---|
| 10 | | 8-methoxy-1-methyl-7-[3-(pyrrolidin-1-yl)propoxy]-5H-pyrido[4,3-b]indol-3-amine | 355 |
| 11 | | (3S)-1-{8-methoxy-7-[3-(pyrrolidin-1-yl)propoxy]-5H-pyrido[4,3-b]indol-1-yl}pyrrolidin-3-ol | 411.5 |
| 12 | | 1-[3-({1-cyclopropyl-8-methoxy-5H-pyrido[4,3-b]indol-7-yl}oxy)propyl]pyrrolidine | 366 |
| 13 | | (3R)-1-{8-methoxy-7-[3-(pyrrolidin-1-yl)propoxy]-5H-pyrido[4,3-b]indol-1-yl}pyrrolidin-3-ol | 411 |
| 14 | | 8-methoxy-N-[(2S)-1-methoxypropan-2-yl]-7-[3-(pyrrolidin-1-yl)propoxy]-5H-pyrido[4,3-b]indol-1-amine | 413 |

TABLE 1-continued

| Compound # | Structure of Parent Compound | Name | MS Found |
|---|---|---|---|
| 15 | | 1-{8-methoxy-7-[3-(pyrrolidin-1-yl)propoxy]-5H-pyrido[4,3-b]indol-1-yl}pyrrolidine | 395 |
| 16 | | 1-{8-methoxy-7-[3-(pyrrolidin-1-yl)propoxy]-5H-pyrido[4,3-b]indol-1-yl}piperidin-4-ol | 425 |
| 17 | | 4-{8-methoxy-7-[3-(pyrrolidin-1-yl)propoxy]-5H-pyrido[4,3-b]indol-1-yl}morpholine | 411 |
| 18 | | 1-{8-methoxy-7-[3-(pyrrolidin-1-yl)propoxy]-5H-pyrido[4,3-b]indol-1-yl}azelidin-3-ol | 397 |
| 19 | | 3-{8-methoxy-7-[3-(pyrrolidin-1-yl)propoxy]-5H-pyrido[4,3-b]indol-1-yl}-8-oxa-3-azabicyclo[3.2.1]octane | 437.1 |

TABLE 1-continued

| Compound # | Name | MS Found |
|---|---|---|
| 20 | N-(2-ethoxyethyl)-8-methoxy-7-[3-(pyrrolidin-1-yl)propoxy]-5H-pyrido[4,3-b]indol-1-amine | 413.4 |
| 21 | 1-[3-({8-methoxy-1-propyl-5H-pyrido[4,3-b]indol-7-yl}oxy)-propyl]pyrrolidine | 368.1 |
| 22 | 1-[3-({6-methoxy-9H-pyrimido-[4,5-b]indol-7-yl}oxy)propyl]-pyrrolidine | 326.8 |
| 23 | 8-methoxy-1-(pyridin-4-yl)-7-(3-(pyrrolidin-1-yl)propoxy)-5H-pyrido[4,3-b]indole | 403.3 |
| 24 | 8-methoxy-1-(pyridin-3-yl)-7-(3-(pyrrolidin-1-yl)propoxy)-5H-pyrido[4,3-b]indole | 403.3 |
| 25 | 8-methoxy-1-(pyridin-2-yl)-7-(3-(pyrrolidin-1-yl)propoxy)-5H-pyrido[4,3-b]indole | 403.3 |

TABLE 1-continued

| Compound # | Structure of Parent Compound | Name | MS Found |
|---|---|---|---|
| 26 | | 1-[3-({6-methoxy-5H-pyrido[3,2-b]indol-7-yl}oxy)propyl]pyrrolidine hydrochloride | 326.5 |
| 27 | | 1-[3-({8-methoxy-5H-pyrido[3,2-b]indol-7-yl}oxy)propyl]pyrrolidine hydrochloride | 326.5 |
| 28 | | 1-[3-({6-methoxy-9H-pyrido[3,4-b]indol-7-yl}oxy)propyl]pyrrolidine hydrochloride | 326.0 |
| 29 | | 1-[3-({8-methoxy-1-methyl-5H-pyrido[4,3-b]indol-7-yl}oxy)propyl]pyrrolidine hydrochloride | 340.0 |
| 30 | | 1-[3-({6-methoxy-9H-pyrido[2,3-b]indol-7-yl}oxy)propyl]pyrrolidine hydrochloride | 326.0 |
| 31 | | 1-[3-({8-methoxy-5H-pyrido[4,3-b]indol-7-yl}oxy)propyl]pyrrolidine hydrochloride | 326.2 |
| 32 | | 8-methoxy-7-[3-(pyrrolidin-1-yl)propoxy]-5H-pyrido[4,3-b]indol-3-amine hydrochloride | 341.4 |

TABLE 1-continued

| Compound # | Name | MS Found |
|---|---|---|
| 33 | 6-methoxy-7-[3-(pyrrolidin-1-yl)propoxy]-9H-pyrido[2,3-b]indol-2-amine hydrochloride | 340.9 |
| 34 | 1-[3-({1-fluoro-8-methoxy-5H-pyrido[4,3-b]indol-7-yl}oxy)propyl]pyrrolidine hydrochloride | 344.0 |
| 35 | 8-methoxy-1-methyl-7-[3-(pyrrolidin-1-yl)propoxy]-5H-pyrido[4,3-b]indol-3-amine hydrochloride | 355.0 |
| 36 | (3S)-1-{8-methoxy-7-[3-(pyrrolidin-1-yl)propoxy]-5H-pyrido[4,3-b]indol-1-yl}pyrrolidin-3-ol hydrochloride | 411.5 |
| 37 | (3R)-1-{8-methoxy-7-[3-(pyrrolidin-1-yl)propoxy]-5H-pyrido[4,3-b]indol-1-yl}pyrrolidin-3-ol | 411.0 |
| 38 | 8-methoxy-N-[(2S)-1-methoxypropan-2-yl]-7-[3-(pyrrolidin-1-yl)propoxy]-5H-pyrido[4,3-b]indol-1-amine | 413.1 |

TABLE 1-continued

| Compound # | Structure of Parent Compound | Name | MS Found |
|---|---|---|---|
| 39 | | 1-{8-methoxy-7-[3-(pyrrolidin-1-yl)propoxy]-5H-pyrido[4,3-b]indol-1-yl}pyrrolidine | 395.0 |
| 40 | | 1-{8-methoxy-7-[3-(pyrrolidin-1-yl)propoxy)-5H-pyrido[4,3-b]indol-1-yl}piperidin-4-ol | 425.0 |
| 41 | | 4-{8-methoxy-7-[3-(pyrrolidin-1-yl)propoxy]-5H-pyrido[4,3-b]indol-1-yl}morpholine | 411.0 |
| 42 | | 1-{8-methoxy-7-[3-(pyrrolidin-1-yl)propoxy]-5H-pyrido[4,3-b]indol-1-yl}azelidin-3-ol | 397.0 |
| 43 | | 1-[3-({1-cyclopropyl-8-methoxy-5H-pyrido[4,3-b]indol-7-yl}oxy)propyl]pyrrolidine | 366.0 |

TABLE 1-continued

| Compound # | Structure of Parent Compound | Name | MS Found |
|---|---|---|---|
| 44 | 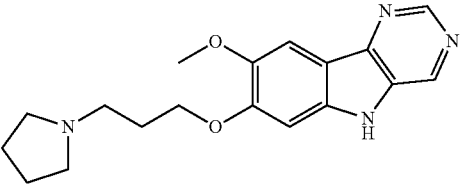 [SMILES: COc1cc2c(cc1OCCCN1CCCC1)[nH]c1cncnc12] | 1-[3-({8-methoxy-5H-pyrimido[5,4-b]indol-7-yl}oxy)propyl]pyrrolidine | 327.0 |
| 45 | 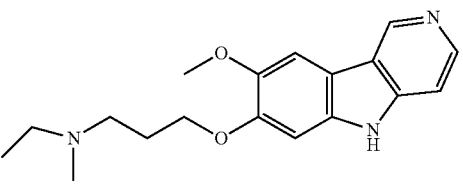 [SMILES: CCN(C)CCCOc1cc2[nH]c3ccncc3c2cc1OC] | ethyl[3-({8-methoxy-5H-pyrido[4,3-b]indol-7-yl}oxy)propyl]methylamine hydrochloride | 314.3 |
| 46 | 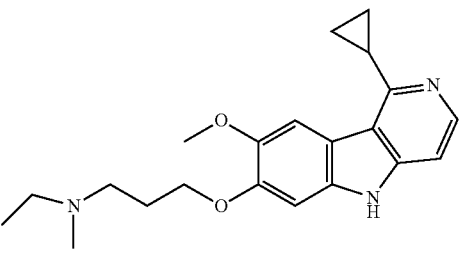 [SMILES: CCN(C)CCCOc1cc2[nH]c3ccnc(C4CC4)c3c2cc1OC] | [3-({1-cyclopropyl-8-methoxy-5H-pyrido[4,3-b]indol-7-yl}oxy)propyl](ethyl)methylamine hydrochloride | 353.8 |
| 47 | 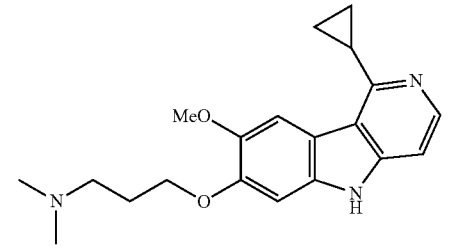 [SMILES: COc1cc2c(cc1OCCCN(C)C)[nH]c1ccnc(C3CC3)c12] | [3-({1-cyclopropyl-8-methoxy-5H-pyrido[4,3-b]indol-7-yl}oxy)propyl]dimethylamine hydrochloride | 340.2 |
| 48 | 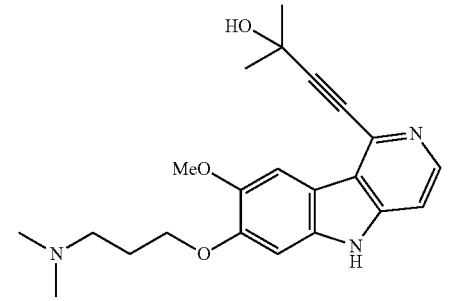 [SMILES: COc1cc2c(cc1OCCCN(C)C)[nH]c1ccnc(C#CC(C)(C)O)c12] | 4-{7-[3-(dimethylamino)propoxy]-8-methoxy-5H-pyrido[4,3-b]indol-1-yl}-2-methylbut-3-yn-2-ol hydrochloride | 382.1 |
| 49 | 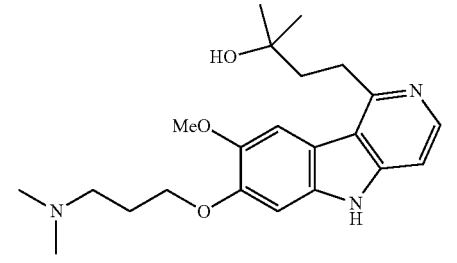 [SMILES: COc1cc2c(cc1OCCCN(C)C)[nH]c1ccnc(CCC(C)(C)O)c12] | 4-{7-[3-(dimethylamino)propoxy]-8-methoxy-5H-pyrido[4,3-b]indol-1-yl}-2-methylbutan-2-ol hydrochloride | 386.0 |

TABLE 1-continued

| Compound # | Structure of Parent Compound | Name | MS Found |
|---|---|---|---|
| 50 | | 4-{7-[3-(dimethylamino)propoxy]-8-methoxy-5H-pyrido[4,3-b]indol-1-yl}but-3-yn-2-ol hydrochloride | 368.0 |
| 51 | | (3-{[1-(2-cyclopropylethynyl)-8-methoxy-5H-pyrido[4,3-b]indol-7-yl]oxy}propyl)dimethylamine hydrochloride | 364.2 |
| 52 | | 3-((1-(2-cyclopropylethyl)-8-methoxy-5H-pyrido[4,3-b]indol-7-yl)oxy)-N,N-dimethylpropan-1-amine hydrochloride | 368.2 |
| 53 | | {2-[2-({1-cyclopropyl-8-methoxy-5H-pyrido[4,3-b]indol-7-yl}oxy)ethoxy]ethyl}dimethylamine hydrochloride | 370.4 |
| 55 | | [3-({8-methoxy-1-propyl-5H-pyrido[4,3-b]indol-7-yl}oxy)propyl]dimethylamine hydrochloride | 342.2 |

TABLE 1-continued

| Compound # | Name | MS Found |
|---|---|---|
| 56 | [3-({1-cyclopentyl-8-methoxy-5H-pyrido[4,3-b]indol-7-yl}oxy)propyl]dimethylamine hydrochloride | 368.1 |
| 57 | (3-{[1-(2-ethoxyethyl)-8-methoxy-5H-pyrido[4,3-b]indol-7-yl]oxy}propyl)dimethylamine hydrochloride | 372.2 |
| 58 | (3-{[8-methoxy-1-(3-methoxypropyl)-5H-pyrido[4,3-b]indol-7-yl]oxy}propyl)dimethylamine hydrochloride | 372.2 |
| 59 | [3-({1-ethynyl-8-methoxy-5H-pyrido[4,3-b]indol-7-yl}oxy)propyl]dimethylamine hydrochloride | 324.0 |
| 60 | 1-[3-({1-cyclopropyl-8-methoxy-5H-pyrido[4,3-b]indol-7-yl}oxy)propyl]-2-methylpyrrolidine hydrochloride | 380.4 |
| 61 | [3-({1-cyclopropyl-8-methoxy-5H-pyrido[4,3-b]indol-7-yl}oxy)propyl]bis(propan-2-yl)amine hydrochloride | 396.4 |

TABLE 1-continued

| Compound # | Structure of Parent Compound | Name | MS Found |
|---|---|---|---|
| 62 | | (3R)-1-[3-({1-cyclopropyl-8-methoxy-5H-pyrido[4,3-b]indol-7-yl}oxy)propyl]-3-fluoropyrrolidine hydrochloride | 384.4 |
| 63 | | (3S)-1-[3-({1-cyclopropyl-8-methoxy-5H-pyrido[4,3-b]indol-7-yl}oxy)propyl]-3-fluoropyrrolidine hydrochloride | 384.4 |
| 64 | | 1-(3-{[1-(3,6-dihydro-2H-pyran-4-yl)-8-methoxy-5H-pyrido[4,3-b]indol-7-yl]oxy}propyl)pyrrolidine hydrochloride | 408.4 |
| 65 | | 1-(3-{[8-methoxy-1-(oxan-4-yl)-5H-pyrido[4,3-b]indol-7-yl]oxy}propyl)pyrrolidine hydrochloride | 410.5 |
| 66 | | 4-{8-methoxy-7-[3-(pyrrolidin-1-yl)propoxy]-5H-pyrido[4,3-b]indol-1-yl}-1,2,3,6-tetrahydropyridine bishydrochloride | 407.3 |

TABLE 1-continued

| Compound # | Structure of Parent Compound | Name | MS Found |
|---|---|---|---|
| 67 | | (3-{[8-methoxy-1-(propan-2-yl)-5H-pyrido[4,3-b]indol-7-yl]oxy}propyl)dimethylamine hydrochloride | 342.4 |
| 68 | | (3-{[8-methoxy-1-(oxan-4-yl)-5H-pyrido[4,3-b]indol-7-yl]oxy}propyl)dimethylamine hydrochloride | 384.4 |
| 69 | | [3-({1-cyclobutyl-8-methoxy-5H-pyrido[4,3-b]indol-7-yl}oxy)propyl]dimethylamine hydrochloride | 354.4 |
| 70 | | [2-({8-methoxy-5H-pyrido[4,3-b]indol-7-yl}oxy)ethyl]dimethylamine hydrochloride | 286.4 |
| 71 | | 1-[2-({8-methoxy-5H-pyrido[4,3-b]indol-7-yl}oxy)ethyl]pyrrolidine hydrochloride | 312.3 |
| 72 | | 1-[3-({8-methoxy-5H-pyrido[4,3-b]indol-7-yl}oxy)propyl]azetidine hydrochloride | 312.3 |

TABLE 1-continued

| Compound # | Structure of Parent Compound | Name | MS Found |
|---|---|---|---|
| 73 | | 1-(3-{[8-methoxy-1-(oxan-4-yloxy)-5H-pyrido[4,3-b]indol-7-yl]oxy}propyl)pyrrolidine trifluoroacetate | 426.2 |
| 74 | | 3-({8-methoxy-7-[3-(pyrrolidin-1-yl)propoxy]-5H-pyrido[4,3-b]indol-1-yl}oxy)pyrrolidine bis(2,2,2-trifluoroacetate) | 411.2 |
| 75 | | 1-(3-{[8-methoxy-1-(propan-2-yloxy)-5H-pyrido[4,3-b]indol-7-yl]oxy}propyl)pyrrolidine trifluoroacetate | 384.2 |
| 76 | | 1-{8-methoxy-7-[3-(pyrrolidin-1-yl)propoxy]-5H-pyrido[4,3-b]indol-1-yl}-1H-imidazole trifluoroacetate | 392.2 |
| 77 | | 1-[8-methoxy-7-[3-(pyrrolidin-1-yl)propoxy]-5H-pyrido[4,3-b]indol-1-yl]-1H-pyrazole trifluoroacetate | 384.2 |

TABLE 1-continued

| Compound # | Structure of Parent Compound | Name | MS Found |
|---|---|---|---|
| 78 | | 5-{8-methoxy-7-[3-(pyrrolidin-1-yl)propoxy]-5H-pyrido[4,3-b]indol-1-yl}-1,3-thiazole trifluoroacetate | 409.1 |
| 79 | | {8-methoxy-7-[3-(pyrrolidin-1-yl)propoxy]-5H-pyrido[4,3-b]indol-3-yl}methanol trifluoroacetate | 356.2 |
| 80 | | 8-methoxy-7-(3-(pyrrolidin-1-yl)propoxy)-5H-pyrido[4,3-b]indol-3-ol formate | 342.2 |
| 81 | | 4-[8-methoxy-7-[3-(pyrrolidin-1-yl)propoxy]-5H-pyrido[4,3-b]indol-1-yl]-1H-pyrazole hydrochloride | 392.2 |
| 82 | | 8-methoxy-7-[3-(pyrrolidin-1-yl)propoxy]-5H-pyrido[4,3-b]indol-1-yl]methanol trifluoroacetate | 356.2 |
| 83 | | 3-[8-methoxy-7-[3-(pyrrolidin-1-yl)propoxy]-5H-pyrido[4,3-b]indol-1-yl]-4H-1,2,4-triazole formate | 393.2 |

TABLE 1-continued

| Compound # | Structure of Parent Compound | Name | MS Found |
|---|---|---|---|
| 84 | | 1-(1H-imidazol-5-yl)-8-methoxy-7-(3-(pyrrolidin-1-yl)propoxy)-5H-pyrido[4,3-b]indole trifluoroacetate | 392.2 |
| 85 | | N,N-diethyl-8-methoxy-7-[3-(pyrrolidin-1-yl)propoxy]-5H-pyrido[4,3-b]indol-1-amine bis formate | 392.2 |
| 86 | | 1-{4-chloro-8-methoxy-7-[3-(pyrrolidin-1-yl)propoxy]-5H-pyrido[4,3-b]indol-1-yl}pyrrolidine hydrochloride | 429.2 |
| 87 | | 3-[({8-methoxy-5H-pyrido[4,3-b]indol-7-yl}oxy)methyl]piperidine hydrochloride | 429.2 |
| 88 | | [3-({8-methoxy-5H-pyrido[4,3-b]indol-7-yl}oxy)propyl]dimethylamine hydrochloride | 300.1 |
| 89 | | 1-{8-methoxy-4-methyl-7-[3-(pyrrolidin-1-yl)propoxy]-5H-pyrido[4,3-b]indol-1-yl}pyrrolidine hydrochloride | 408.9 |

TABLE 1-continued

| Compound # | Structure of Parent Compound | Name | MS Found |
|---|---|---|---|
| 90 | | [3-({8-methoxy-1-methyl-5H-pyrido[4,3-b]indol-7-yl}oxy)propyl]dimethylamine hydrochloride | 314.5 |
| 91 | | [3-({1-ethyl-8-methoxy-5H-pyrido[4,3-b]indol-7-yl}oxy)propyl]dimethylamine hydrochloride | 328.1 |
| 92 | | (3-{[8-methoxy-1-(pyrrolidin-1-yl)-5H-pyrido[4,3-b]indol-7-yl]oxy}propyl)dimethylamine hydrochloride | 369.0 |
| 93 | | 7-[3-(dimethylamino)propoxy]-8-methoxy-N,N-dimethyl-5H-pyrido[4,3-b]indol-1-amine hydrochloride | 343.3 |
| 94 | | 1-[3-({8-methoxy-5-methyl-5H-pyrido[4,3-b]indol-7-yl}oxy)propyl]pyrrolidine hydrochloride | 340.1 |
| 95 | | (3-{[8-methoxy-1-(methylsulfanyl)-5H-pyrido[4,3-b]indol-7-yl]oxy}propyl)dimethylamine hydrochloride | 346.2 |

TABLE 1-continued

| Compound # | Name | MS Found |
|---|---|---|
| 96 | 1-(3-{[8-methoxy-1-(2-methoxyethoxy)-5H-pyrido[4,3-b]indol-7-yl]oxy}propyl)pyrrolidine trifluoroacetate | 400.2 |
| 97 | 8-methoxy-7-(3-(pyrrolidin-1-yl)propoxy)-5H-pyrido[4,3-b]indol-1-ol trifluoroacetate | 342.2 |
| 98 | 3-[3-({8-methoxy-5H-pyrido[4,3-b]indol-7-yl}oxy)propyl]-3-azabicyclo[3.1.1]heptane hydrochloride | 352.3 |
| 99 | 1-[3-({8-methoxy-3-methyl-5H-pyrido[4,3-b]indol-7-yl}oxy)propyl]pyrrolidine hydrochloride | 340.3 |
| 100 | 1-[3-({1,8-dimethoxy-5H-pyrido[4,3-b]indol-7-yl}oxy)propyl]pyrrolidine hydrochloride | 356.4 |
| 101 | 1-[3-({3-cyclopropyl-8-methoxy-5H-pyrido[4,3-b]indol-7-yl}oxy)propyl]pyrrolidine hydrochloride | 366.4 |

TABLE 1-continued

| Compound # | Structure of Parent Compound | Name | MS Found |
|---|---|---|---|
| 102 | | [3-({1-cyclopropyl-8-methoxy-5H-pyrido[4,3-b]indol-7-yl}oxy)propyl]diethylamine hydrochloride | 368.4 |

Additional compounds of Formula (I) are those disclosed in Table 2 below.

TABLE 2

| Compound # | Structure of Parent Compound | Name |
|---|---|---|
| 1a | | 1-{4,8-dimethoxy-7-[3-(pyrrolidin-1-yl)propoxy]-5H-pyrido[4,3-b]indol-1-yl}pyrrolidine |
| 2a | | 1-{4-cyclopropyl-8-methoxy-7-[3-(pyrrolidin-1-yl)propoxy]-5H-pyrido[4,3-b]indol-1-yl}pyrrolidine |
| 3a | | 12-methoxy-11-[3-(pyrrolidin-1-yl)propoxy]-3-(pyrrolidin-3-yloxy)-8-oxa-4-azatricyclo[7.4.0.0$^{2,7}$]trideca-1(13),2(7),3,5,9,11-hexaene |

TABLE 2-continued

| Compound # | Structure of Parent Compound | Name |
|---|---|---|
| 4a | | 1-(3-{[8-methoxy-5-methyl-1-(pyrrolidin-3-yloxy)-5H-pyrido[4,3-b]indol-7-yl]oxy}propyl)pyrrolidine |
| 5a | | 3-({8-methoxy-7-[3-(pyrrolidin-1-yl)propoxy]-5H-pyrido[4,3-b]indol-1-yl}oxy)-1-methylpyrrolidine |
| 6a | | 3-[({8-methoxy-5H-pyrido[4,3-b]indol-7-yl}oxy)methyl]-1-methylpiperidine |
| 7a | | 1-[3-({8-ethyl-5H-pyrido[4,3-b]indol-7-yl}oxy)propyl]-pyrrolidine |
| 8a | | 6-[3-({1-cyclopropyl-8-methoxy-5H-pyrido[4,3-b]indol-7-yl}oxy)propyl]-2-oxa-6-azaspiro[3.3]heptane |
| 9a | | [3-({1-cyclopropyl-8-methoxy-5H-pyrido[4,3-b]indol-7-yl}oxy)propyl](methyl)(2,2,2-trifluoroethyl)amine |

TABLE 2-continued

| Compound # | Structure of Parent Compound | Name |
|---|---|---|
| 10a | | 1-[3-({1-cyclopropyl-8-methoxy-5H-pyrido[4,3-b]indol-7-yl}oxy)propyl]-2,5-dimethylpyrrolidine |
| 11a | | 1-[3-({1-cyclopropyl-8-methoxy-5H-pyrido[4,3-b]indol-7-yl}oxy)propyl]piperidine |
| 12a | | 1-[3-({1-cyclopropyl-8-methoxy-5H-pyrido[4,3-b]indol-7-yl}oxy)propyl]-3-fluoroazetidine |
| 13a | | 1-(3-{[8-methoxy-1-(propan-2-yl)-5H-pyrido[4,3-b]indol-7-yl]oxy}propyl)pyrrolidine |
| 14a | | 1-(3-{[8-methoxy-1-(oxetan-3-yl)-5H-pyrido[4,3-b]indol-7-yl]oxy}propyl)pyrrolidine |
| 15a | | 1-(3-{[8-methoxy-1-(oxetan-2-yl)-5H-pyrido[4,3-b]indol-7-yl]oxy}propyl)pyrrolidine |
| 16a | | 1-(3-{[8-methoxy-1-(1-methylcyclopropyl)-5H-pyrido[4,3-b]indol-7-yl]oxy}propyl)pyrrolidine |

TABLE 2-continued

| Compound # | Structure of Parent Compound | Name |
|---|---|---|
| 17a | | 1-[3-({1-tert-butyl-8-methoxy-5H-pyrido[4,3-b]indol-7-yl}oxy)propyl]pyrrolidine |
| 18a | | 1-(3-{[8-methoxy-1-(oxolan-3-yl)-5H-pyrido[4,3-b]indol-7-yl]oxy}propyl)pyrrolidine |
| 19a | | 5-[8-methoxy-7-[3-(pyrrolidin-1-yl)propoxy]-5H-pyrido[4,3-b]indol-1-yl}-1,3-oxazole |
| 20a | | 2-{8-methoxy-7-[3-(pyrrolidin-1-yl)propoxy]-5H-pyrido[4,3-b]indol-1-yl}-1,3-thiazole |
| 21a | | 2-{8-methoxy-7-[3-(pyrrolidin-1-yl)propoxy]-5H-pyrido[4,3-b]indol-1-yl}-1,3-oxazole |
| 22a | | 4-{8-methoxy-7-[3-(pyrrolidin-1-yl)propoxy]-5H-pyrido[4,3-b]indol-1-yl}-4H-1,2,4-triazole |

TABLE 2-continued

| Compound # | Structure of Parent Compound | Name |
|---|---|---|
| 23a | | 1-[3-({6-methoxy-4-methyl-9H-pyrimido[4,5-b]indol-7-yl}oxy)propyl]pyrrolidine |
| 24a | | 1-[3-({4-cyclopropyl-6-methoxy-9H-pyrimido[4,5-b]indol-7-yl}oxy)propyl]pyrrolidine |
| 25a | | 1-{6-methoxy-7-[3-(pyrrolidin-1-yl)propoxy]-9H-pyrimido[4,5-b]indol-4-yl}pyrrolidine |
| 26a | | 1-(3-{[1-(cyclopent-1-en-1-yl)-8-methoxy-5H-pyrido[4,3-b]indol-7-yl]oxy}propyl)pyrrolidine |
| 27a | | 1-({1-cyclopentyl-8-methoxy-5H-pyrido[4,3-b]indol-7-yl}oxy)-3-(pyrrolidin-1-yl)propan-2-ol |
| 28a | | 1-({8-methoxy-1-methyl-5H-pyrido[4,3-b]indol-7-yl}oxy)-3-(pyrrolidin-1-yl)propan-2-ol |
| 29a | | 1-({1-cyclopropyl-8-methoxy-5H-pyrido[4,3-b]indol-7-yl}oxy)-3-(pyrrolidin-1-yl)propan-2-ol |

TABLE 2-continued

| Compound # | Structure of Parent Compound | Name |
|---|---|---|
| 30a | | 1-[3-({1-cyclopentyl-8-methoxy-5H-pyrido[4,3-b]indol-7-yl}oxy)-2-methoxypropyl]pyrrolidine |
| 31a | | 1-[2-methoxy-3-({8-methoxy-1-methyl-5H-pyrido[4,3-b]indol-7-yl}oxy)propyl]pyrrolidine |
| 32a | | 1-[3-({1-cyclopropyl-8-methoxy-5H-pyrido[4,3-b]indol-7-yl}oxy)-2-methoxypropyl]pyrrolidine |
| 33a | | 1-[3-({1-[4-(difluoromethoxy)phenyl]-8-methoxy-5H-pyrido[4,3-b]indol-7-yl}oxy)propyl]pyrrolidine |
| 34a | | 1-[3-({1-[3-(difluoromethoxy)phenyl]-8-methoxy-5H-pyrido[4,3-b]indol-7-yl}oxy)propyl]pyrrolidine |
| 35a | | 2-(difluoromethoxy)-4-{8-methoxy-7-[3-(pyrrolidin-1-yl)propoxy]-5H-pyrido[4,3-b]indol-1-yl}pyridine |

TABLE 2-continued

| Compound # | Structure of Parent Compound | Name |
|---|---|---|
| 36a | | 2-(difluoromethoxy)-5-{8-methoxy-7-[3-(pyrrolidin-1-yl)propoxy]-5H-pyrido[4,3-b]indol-1-yl}pyridine |
| 37a | | 1-[3-({1-[4-(difluoromethyl)phenyl]-8-methoxy-5H-pyrido[4,3-b]indol-7-yl}oxy)propyl]pyrrolidine |
| 38a | | 2-{8-methoxy-7-[3-(pyrrolidin-1-yl)propoxy]-5H-pyrido[4,3-b]indol-1-yl}propan-2-ol |
| 39a | | 4-{8-methoxy-7-[3-(pyrrolidin-1-yl)propoxy]-5H-pyrido[4,3-b]indol-1-yl}-4-azaspiro[2.4]heptane |
| 40a | | 5-{8-methoxy-7-[3-(pyrrolidin-1-yl)propoxy]-5H-pyrido[4,3-b]indol-1-yl}-5-azaspiro[3.4]octane |

TABLE 2-continued

| Compound # | Structure of Parent Compound | Name |
|---|---|---|
| 41a | | 5-{8-methoxy-7-[3-(pyrrolidin-1-yl)propoxy]-5H-pyrido[4,3-b]indol-1-yl}-2-oxa-5-azaspiro[3.4]octane |
| 42a | | 1-{8-methoxy-7-[3-(pyrrolidin-1-yl)propoxy]-5H-pyrido[4,3-b]indol-1-yl}-2,2-dimethylpyrrolidine |
| 43a | | 1-{8-methoxy-7-[3-(pyrrolidin-1-yl)propoxy]-5H-pyrido[4,3-b]indol-1-yl}-2-(propan-2-yl)pyrrolidine |
| 44a | | 1-{8-methoxy-7-[3-(pyrrolidin-1-yl)propoxy]-5H-pyrido[4,3-b]indol-1-yl}-6-oxa-1-azaspiro[3.3]heptane |
| 45a | | 1-{8-methoxy-7-[3-(pyrrolidin-1-yl)propoxy]-5H-pyrido[4,3-b]indol-1-yl}-1-azaspiro[3.3]heptane |
| 46a | | 1-{8-methoxy-7-[3-(pyrrolidin-1-yl)propoxy]-5H-pyrido[4,3-b]indol-1-yl}-6-oxa-1-azaspiro[3.4]octane |

TABLE 2-continued

| Compound # | Structure of Parent Compound | Name |
|---|---|---|
| 47a | | 1-{8-methoxy-7-[3-(pyrrolidin-1-yl)propoxy]-5H-pyrido[4,3-b]indol-1-yl}-1-azaspiro[3.4]octane |
| 48a | | 1-{8-methoxy-7-[3-(pyrrolidin-1-yl)propoxy]-5H-pyrido[4,3-b]indol-1-yl}-7-oxa-1-azaspiro[4.4]nonane |
| 49a | | 1-{8-methoxy-7-[3-(pyrrolidin-1-yl)propoxy]-5H-pyrido[4,3-b]indol-1-yl}-7$\lambda^6$-thia-1-azaspiro[4.4]nonane-7,7-dione |
| 50a | | 1-[3-({4-cyclopentyl-6-methoxy-9H-pyrimido[4,5-b]indol-7-yl}oxy)propyl]pyrrolidine |
| 51a | | {2-[2-({6-methoxy-9H-pyrimido[4,5-b]indol-7-yl}oxy)ethoxy]ethyl}dimethylamine |
| 52a | | 1-(3-{[4-(azetidin-1-yl)-6-methoxy-9H-pyrimido[4,5-b]indol-7-yl]oxy}propyl)pyrrolidine |
| 53a | | {2-[2-({8-methoxy-1-methyl-5H-pyrido[4,3-b]indol-7-yl}oxy)ethoxy]ethyl}dimethylamine |

TABLE 2-continued

| Compound # | Structure of Parent Compound | Name |
|---|---|---|
| 54a | | [2-(2-{[8-methoxy-1-(pyrrolidin-1-yl)-5H-pyrido[4,3-b]indol-7-yl]oxy}ethoxy)ethyl]dimethylamine |
| 55a | | {2-[2-({1-cyclopentyl-8-methoxy-5H-pyrido[4,3-b]indol-7-yl}oxy)ethoxy]ethyl}dimethylamine |
| 56a | | 6-{8-methoxy-7-[3-(pyrrolidin-1-yl)propoxy]-5H-pyrido[4,3-b]indol-1-yl}-N-methylpyridin-2-amine |
| 57a | | 4-{8-methoxy-7-[3-(pyrrolidin-1-yl)propoxy]-5H-pyrido[4,3-b]indol-1-yl}-N-methylpyridin-2-amine |
| 58a | | 1-{[8-methoxy-1-(pyrrolidin-1-yl)-5H-pyrido[4,3-b]indol-7-yl]oxy}-3-(pyrrolidin-1-yl)propan-2-ol |
| 59a | | 1-{8-methoxy-7-[2-methoxy-3-(pyrrolidin-1-yl)propoxy]-5H-pyrido[4,3-b]indol-1-yl}pyrrolidine |

TABLE 2-continued

| Compound # | Structure of Parent Compound | Name |
|---|---|---|
| 60a | | 1-{8-methoxy-7-[3-(pyrrolidin-1-yl)propoxy]-5H-pyrido[4,3-b]indol-1-yl}pyrrolidine-2-carboxylic acid |
| 61a | | 2-(1-{8-methoxy-7-[3-(pyrrolidin-1-yl)propoxy]-5H-pyrido[4,3-b]indol-1-yl}pyrrolidin-2-yl)acetic acid |
| 62a | | 2-{8-methoxy-7-[3-(pyrrolidin-1-yl)propoxy]-5H-pyrido[4,3-b]indol-1-yl}benzoic acid |
| 63a | | 2-(2-{8-methoxy-7-[3-(pyrrolidin-1-yl)propoxy]-5H-pyrido[4,3-b]indol-1-yl}phenyl)acetic acid |

TABLE 2-continued

| Compound # | Structure of Parent Compound | Name |
| --- | --- | --- |
| 64a | | 2-(4-{8-methoxy-7-[3-(pyrrolidin-1-yl)propoxy]-5H-pyrido[4,3-b]indol-1-yl}phenyl)propan-2-ol |
| 65a | | 8-methoxy-7-((2-(pyrrolidin-1-yl)ethoxy)methyl-5H-pyrido[4,3-b]indole |
| 66a | | 8-methoxy-1-methyl-7-((2-(pyrrolidin-1-yl)ethoxy)methyl-5H-pyrido[4,3-b]indole |
| 67a | | 8-methoxy-3-methyl-7-((2-(pyrrolidin-1-yl)ethoxy)methyl)-5H-pyrido[4,3-b]indole |

General Synthetic Scheme

Compounds of this disclosure can be made by the methods depicted in the reaction schemes shown below.

The starting materials and reagents used in preparing these compounds are either available from commercial suppliers such as Sigma-Aldrich Chemical Co., (Milwaukee, Wis.), Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials, the intermediates, and the final products of the reaction(s) may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) where Z is $NR^6$ and X, Y, P, Q, T, U, $R^1$, $R^2$, $R^3$, $R^4$, $R^5$, v and w are as defined in the Summary, can be prepared by the following procedure described in Scheme 1 below.

Scheme 1

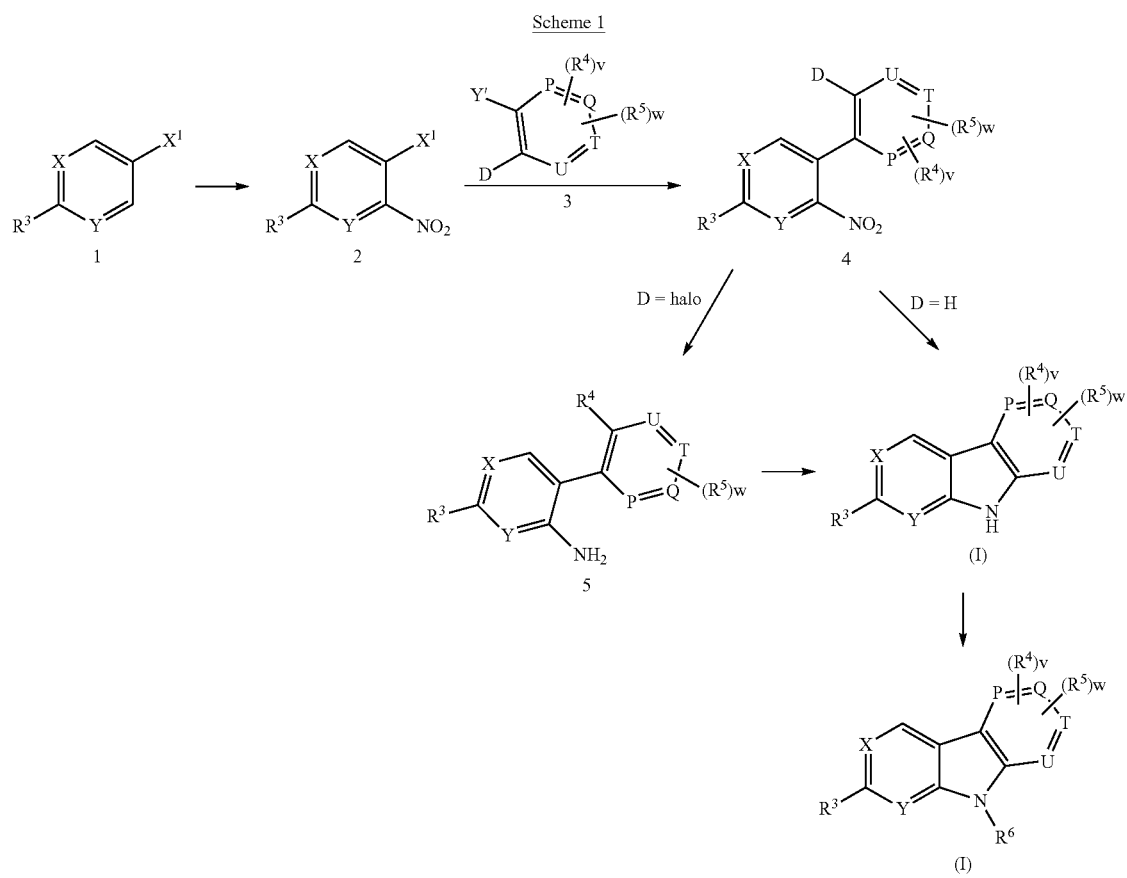

Treatment of a compound of formula 1 where $X^1$ is halo (such as chloro, bromo, or iodo, preferably bromo), and $R^1$, $R^2$, and $R^3$ are as defined in the Summary or a precursor group thereof, with nitric acid in sulfuric or acetic acid provides a compound of formula 2. Compounds of formula 1 are either commercially available or they can be prepared by methods well known in the art. For example, compounds of formula 1 where $R^3$ is —W-alkylene-$R^7$, wherein W is NH, O, or S; alkylene is optionally substituted with $R^8$ (wherein $R^8$ is halo, haloalkyl, haloalkoxy, hydroxy, or alkoxy) and one $CH_2$ in the alkylene chain is optionally replaced with NH or O, and $R^7$ is —$NR^aR^b$ wherein $R^a$ and $R^b$ are as defined in the Summary can be prepared by reacting commercially available starting materials such as 4-bromo-2-methoxyphenol, 4-bromo-2-methylphenol, 4-bromo-2-ethylphenol, 4-bromo-2-methoxyaniline, 4-bromo-2-methoxybenzenethiol, 3-bromo-6-hydroxy-2-methylpyridine, 5-bromo-2-fluoroanisole, 4-bromo-1-iodo-2-methoxybenzene, 1-benzyloxy-4-bromo-2-methoxybenzene, 5-(benzyloxy)-2-bromo-4-methoxyphenol, 4-iodo-2-methoxyphenol, or 4-chloro-2-methylbenzamine with an amine of formula LG-(alkylene)-$NR^aR^b$, wherein $R^a$ and $R^b$ are as defined in the Summary or a suitable amino protecting group and LG is a suitable leaving group, such as halo under suitable alkylating reaction conditions, e.g., by reacting a compound of formula 1 with the above amine in the presence of a base, such as potassium carbonate, cesium carbonate, diethylamine, and the like, and in a suitable organic solvent, such as dimethylformamide, tetrahydrofuran, and the like. Amines of formula LG-(alkylene)-$NR^aR^b$ such as 1-(3-chloropropropyl)pyrrolidine, 1-(3-chloropropyl)dimethylamine, and 2-(2-chloroethoxy)ethyl]dimethylamine are commercially available.

Treatment of a compound of formula 2 with a compound of formula 3 where P, Q, T, U are as defined in the Summary, and $R^4$ and $R^5$ are as defined in the Summary, or a precursor group thereof, D is H or halo, and Y' is a boronic acid or boronic ester under Suzuki coupling reaction conditions provides a compound of formula 4. Compounds of formula 3 are either commercially available or they can be prepared from corresponding halides of formula 3 where Y' is halo by methods well known in the art. Compounds of formula 3 where Y' is boronic acid or ester, or Y' is halo, such as pyridine-3-boronic acid, pyridine-3-boronic acid pinacol ester, 2-fluoropyridine-3-boronic acid, 2-methoxypyridine-3-boronic acid, 2-chloropyridine-3-boronic acid, 2-fluoropyridine-3-boronic acid, pinacol ester, 2-bromopyridine-3-boronic acid, 2-methylpyridine-3-boronic acid, 2-(t-butoxycarbonylamino)pyridine-3-boronic acid, 2-cyanopyridine-3-boronic acid pinacol ester, 2-ethyl-3-pyridinylboronic acid, 2-morpholinopyridine-3-boronic acid, 2-(4-tert-butoxycarbonylpiperazinyl)pyridine-3-boronic acid pinacol ester, 2-phenyl-3-(tetramethyl-1,3,2-dioxaborolan-2-yl)pyridine, 2-(dimethylamino)pyridin-3-ylboronic acid, N,N-dimethyl-2-((3-(4,4,5,5-tetramethyl-1,3,2-dioxaborolan-2-yl)pyridin-2-yl)oxy)ethanamine, 2-(4-methyl-1H-pyrazol-1-yl)-3-(4,4,5,5-tetramethyl-1,3,2-dioxaborolan-2-yl)pyridine, 4-fluoropyridine-3-boronic acid, 4-fluoro-3-(tetramethyl-1,3,2-dioxaborolan-2-yl)pyridine-2-carbaldehyde, 2-chloro-6-methylpyridine-3-boronic acid, (2-chloro-6-aminopyridin-3-yl)boronic acid, 5-chloro-2-fluoropyridine-3-boronic acid, 3-bromo-2-methylpyridine, 3-bromopyridine, 3-bromo-2-hydroxymethylpyridine, 3-bromo-2-cyclopropylpyridine, 2-(3-bromo-pyridin-2-yl)-propan-2-ol, 3-bromo-2-propylpyridine, and 3-bromo-2-(tert-butyl)pyridine are commercially available.

It will be also readily recognized by a person skilled in the art that compounds of formula 2 where X' is halo can be converted to corresponding boronic acid or ester and reaction with a compound of formula 3 where Y' is halo provides a compound of formula 4. Compound of formula 4 where D is hydrogen can be converted to a compound of Formula (I) under Cadogan reaction condition. See, for example, Majgier-Baranowska et al., Tetrahedron Letters 53 (2012) 4785-4788; and Karimi et al., Tetrahedron Letters 58 (2017) 2223-2227 (particularly Scheme 3b). Alternatively, the nitro group in a compound of formula 4 can be first reduced to amino group to provide a compound of formula 5 that has an amino which can then be converted to a compound of Formula (I) under aryl cyclization reaction conditions.

A compound of Formula (I) can be converted to other compounds of Formula (I). For example, compounds of Formula (I) where $R^6$ is alkyl or cycloalkyl can be prepared by reacting a corresponding compounds of Formula (I) where $R^6$ is hydrogen with an alkyl or a cycloalkyl halide, respectively, under alkylation reaction condition. Alkyl halides and cycloalkyl halides, such as iodomethane, iodoethane, 2-iodo-propane, 1-bromobutane, and cyclopropyl bromide, are commercially available.

Compounds of Formula (I), where $R^4$ and/or $R^5$ is halo, can be displaced with $NR^cR^d$, alkoxyalkylamino, heterocyclylamino, spiroheterocycloamino, 5-membered NH-containing heteroaryl, phenyl, heteroarylbornic acid, heteroarylboronic ester or an alcohol for example, methylamine, ethylamine, n-propylamine, isopropylamine, dimethylamine, diethylamine, tert-butylamine, azetidine, pyrrolidine, 3-amino-azetidine, 3-hydroxypyrrolidine, imidazole, pyrazole, morpholine, N-methyl-morpholine, 4-hydroxy-piperidine, piperidine, 2-ethoxyethylamine, 4-azaspiro[2.4]heptane, 2-oxa-5-azaspiro[3.4]octane, 2-isopropylpyrrolidine, and 7-oxa-1-azaspiro[4.4]nonane, in the presence of a base to provide a compound of Formula (I) where $R^4$ and/or $R^5$ is alkoxy, $NH_2$, $NR^cR^d$, alkoxyalkyloxy, phenyl, heteroaryl, heteroaryloxy, heterocyclyloxy, heterocyclylamino, 5-8 membered bridged heterocycloamino, or spiroheterocycloamino, wherein the phenyl, the heteroaryl, and the heterocyclyl either alone or a part of another group are optionally substituted with one, two, or three substituents independently selected from alkyl, halo, haloalkyl, haloalkoxy, hydroxy, hydroxyalkyl, alkoxy, $NH_2$, alkylamino, dialkylamino, carboxy, carboxyalkyl, and alkoxycarbonyl, wherein the alkyl, the alkenyl and the alkynyl are optionally substituted with hydroxy and cycloalkyl.

Alternatively, compounds of Formula (I) where Z is $NR^6$ and X, Y, P, Q, T, U, $R^1$, $R^2$, $R^3$, $R^4$, $R^5$, v and w are as defined in the Summary, can be prepared by the following procedure described in Scheme 2 below.

Scheme 2

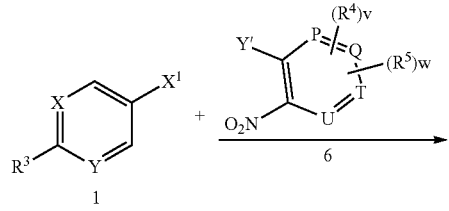

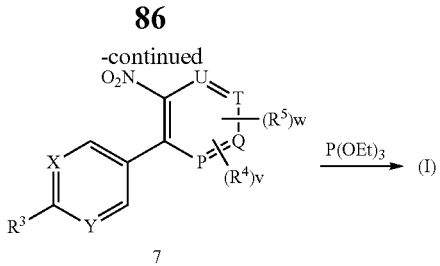

Alternatively, a compound of formula 1 as defined in Scheme 1 above can be reacted with a compound of formula 6 that includes a nitro where P, Q, T and U are as defined in the Summary and $R^4$ and $R^5$ are as defined in the Summary or a precursor group thereof, and Y' is a boronic acid or boronic ester under Suzuki coupling reaction conditions provides a compound of formula 7. Compound 7 is then reduced to a compound of Formula (I) as described in Scheme 1 above.

Testing

The G9a inhibitory activity of the compounds of the present disclosure can be tested using the in vitro assay described in Biological Examples 1 below. The ability of the compounds of the disclosure to stimulated fetal hemoglobin can be tested using the in vitro assay described in Biological Example 2 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg subject body weight per day, which can be administered in single or multiple doses. A suitable dosage level may be from about 0.1 to about 250 mg/kg per day or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, or 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents and/or anti-cancer therapies. In some embodiments, the anti-cancer therapies can be surgery and/or radiation therapy. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of docetaxel (Taxol™), such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, cabozantinib, or crizotinib; VEGFR inhibitor such as sunitinib, sorafenib, regorafinib, lenvatinib, vandetanib, cabozantinib, or axitinib; EGFR inhibitor such as afatinib, brivanib, carbozatinib, erlotinib, gefitinib, neratinib, or lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, or TG100-115; MTOR inhibitor such as rapamycin (sirolimus), temsirolimus, everolimus, XL388, XL765, AZD2013, PF04691502, PKI-587, BEZ235, or GDC0349; MEK inhibitor such as AZD6244, trametinib, PD184352, pimasertinib, GDC-0973, or AZD8330; and proteasome inhibitor such as carfilzomib, MLN9708, delanzomib, or bortezomib.

Other anti-cancer agents that can be employed in combination with a compound of this disclosure include Adriamycin; Dactinomycin; Bleomycin; Vinblastine; Cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a compound of the disclosure such as 20-epi-analogues of 1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid diethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan, etc.), nitrosoureas (e.g., carmustine, lomusitne, etc.), or triazenes (decarbazine, etc.). Examples of antimetabolites include but are not limited to folic acid analog (e.g., methotrexate), pyrimidine analogs (e.g., cytarabine, etc.), or purine analogs (e.g., mercaptopurine, thioguanine, pentostatin, etc.).

Examples of natural products useful in combination with a compound of this disclosure include but are not limited to vinca alkaloids (e.g., vincristine, etc.), epipodophyllotoxins (e.g., etoposide, etc.), antibiotics (e.g., daunorubicin, doxorubicin, bleomycin, etc.), enzymes (e.g., L-asparaginase, etc.), or biological response modifiers (e.g., interferon alpha, etc.).

Examples of alkylating agents that can be employed in combination a compound of this disclosure include, but are not limited to, nitrogen mustards (e.g., mechloroethamine, cyclophosphamide, chlorambucil, melphalan, etc.), ethylenimine and methylmelamines (e.g., hexamethylmelamine, thiotepa, etc.), alkyl sulfonates (e.g., busulfan, etc.), nitrosoureas (e.g., carmustine, lomusitne, semustine, streptozocin, etc.), or triazenes (decarbazine, etc.). Examples of antimetabolites include, but are not limited to folic acid analog (e.g., methotrexate, etc.), pyrimidine analogs (e.g., fluorouracil, floxuridine, cytarabine, etc.), or purine analogs (e.g., mercaptopurine, thioguanine, pentostatin, etc.).

Examples of hormones and antagonists useful in combination a compound of this disclosure include, but are not limited to, adrenocorticosteroids (e.g., prednisone, etc.), progestins (e.g., hydroxyprogesterone caproate, megestrol acetate, and medroxyprogesterone acetate, etc.), estrogens (e.g., diethylstilbestrol, and ethinyl estradiol, etc.), antiestrogen (e.g., tamoxifen, etc.), androgens (e.g., testosterone propionate, fluoxymesterone, etc.), antiandrogen (e.g., flutamide, etc.), and gonadotropin releasing hormone analog (e.g., leuprolide, etc.). Other agents that can be used in the methods and compositions described herein for the treatment or prevention of cancer include platinum coordination complexes (e.g., cisplatin, carboblatin, etc.), anthracenedione (e.g., mitoxantrone, etc.), substituted urea (e.g., hydroxyurea, etc.), methyl hydrazine derivative (e.g., procarbazine, etc.) and adrenocortical suppressant (e.g., mitotane, aminoglutethimide, etc.).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8 and Spongistatin 9), Cemadotin hydrochloride (also known as LU-103793 and NSC-D-669356), Epothilones (such as Epothilone A, Epothilone B, Epothilone C (also known as desoxyepothilone A or dEpoA)), Epothilone D (also referred to as KOS-862, dEpoB and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone, Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358

(Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes) and SSR-250411 (Sanofi).

EXAMPLES

The following preparations of compounds of Formula (I) (Examples) and intermediates (References) are given to enable those skilled in the art to more clearly understand and to practice the present disclosure. They should not be considered as limiting the scope of the disclosure, but merely as being illustrative and representative thereof.

Reference 1

Synthesis of 1-(benzyloxy)-4-bromo-2-methoxy-5-nitrobenzene

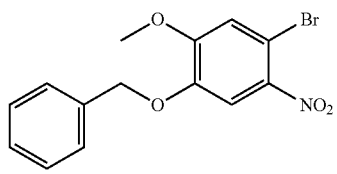 [SMILES: COc1cc(Br)c([N+](=O)[O-])cc1OCc1ccccc1]

Step 1

4-Bromo-2-methoxyphenol (5.0 g, 24.6 mmol), benzyl bromide (3.2 mL, 27.1 mmol), and potassium carbonate (6.8 g, 49.3 mmol) were added to acetonitrile (123 mL), and the reaction mixture was heated to 80° C. for 6 h. The reaction was cooled to room temperature and diluted with water, and extracted with ethyl acetate. The combined organics were dried with MgSO$_4$, filtered, and concentrated under reduced pressure to afford 1-(benzyloxy)-4-bromo-2-methoxybenzene (7.2 g, 100%) as a crude oil.

Step 2

Nitric acid (5.0 mL) was added to a solution of 1-(benzyloxy)-4-bromo-2-methoxybenzene (7.2 g, 24.6 mmol) in acetic acid (40.0 mL) at 0° C. The reaction mixture was stirred for 16 h at room temperature. The reaction mixture was concentrated under reduced pressure to remove bulk acetic acid. Water was added, and the reaction mixture was cooled to 0° C. which resulted in precipitation. The precipitates were filtered, washed solid with water, and dried under reduced pressure to afford 1-(benzyloxy)-4-bromo-2-methoxy-5-nitrobenzene (8.30 g; 99%) as a yellow solid.

Reference 2

Synthesis of 1-[3-(4-bromo-2-methoxyphenoxy) propyl]pyrrolidine

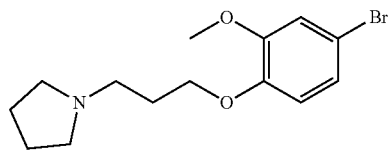 [SMILES: COc1cc(Br)ccc1OCCCN1CCCC1]

A mixture of 4-bromo-2-methoxyphenol (1.6 g, 7.88 mmol), 1-(3-chloro-propyl)pyrrolidine hydrochloride (1.9 g, 9.46 mmol), and potassium carbonate (3.3 g, 23.64 mmol) in DMF (39.4 mL) was heated at 100° C. for 16 h. The reaction mixture was diluted reaction with water, and the aqueous layer with washed with ethyl acetate. The combined organics were dried with MgSO$_4$, filtered, concentrated under reduced pressure, and purified by silica gel using 10% MeOH in DCM to afford 1-[3-(4-bromo-2-methoxyphenoxy)-propyl]pyrrolidine (1.3 g, 53%) as a brown oil.

Reference 3

Synthesis of 1-(3-(4-bromo-2-methoxy-5-nitrophenoxy)propyl)pyrrolidine

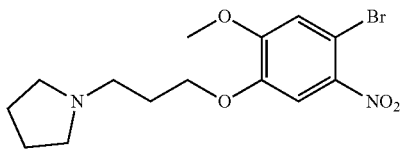 [SMILES: COc1cc(Br)c([N+](=O)[O-])cc1OCCCN1CCCC1]

1-[3-(4-Bromo-2-methoxyphenoxy)propyl]pyrrolidine (17.0 g, 54.10 mmol) in acetic acid (150.0 mL) was stirred, and then HNO$_3$ (65%/wt. %, 30.00 mL) was added dropwise at 0° C. The resulting reaction mixture was stirred for 2 h at room temperature. Ice water (500 mL) was added, and the mixture stirred for 1 h at room temperature, which resulted in the formation of a precipitate. The solids were collected by filtration. The resulting filter cake was washed with water (2×30 mL) and dried under reduced pressure to afford 1-(3-(4-bromo-2-methoxy-5-nitrophenoxy)propyl)pyrrolidine as a yellow solid (10.6 g, 55%).

Reference 4

Synthesis of 1-{3-[4-(4,4-dimethyl-1,3,2-dioxaborolan-2-yl)-2-methoxy-5-nitrophenoxy]-propyl}pyrrolidine

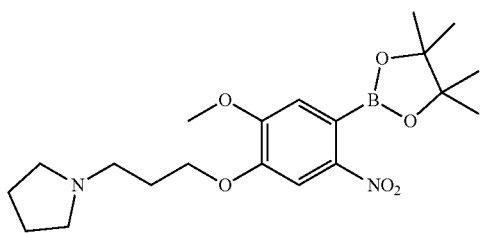 [SMILES: COc1cc(B2OC(C)(C)C(C)(C)O2)c([N+](=O)[O-])cc1OCCCN1CCCC1]

A mixture of 1-[3-(4-bromo-2-methoxy-5-nitrophenoxy)propyl]pyrrolidine (8.0 g, 22.27 mmol), bis(pinacolato)diboron (8.51 g, 33.51 mmol), potassium acetate (4.4 g, 44.63 mmol), and Pd(dppf)$_2$Cl$_2$ DCM (1.63 g, 2.23 mmol) in 1,4-dioxanes (200 mL) was stirred and heated for 3 h at 110° C. under N2. The mixture was concentrated under reduced pressure. The resulting residue was purified by silica gel column using 10% MeOH in DCM to afford 1-{3-[4-(4,4-dimethyl-1,3,2-dioxaborolan-2-yl)-2-methoxy-5-nitrophenoxy]propyl}pyrrolidine (6.1 g, 67%) as a gray solid.

Reference 5

Synthesis of tert-butyl 7-(benzyloxy)-1-chloro-8-methoxy-5H-pyrido[4,3-b]indole-5-carboxylate

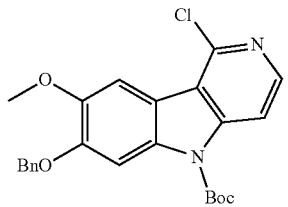 [SMILES: COc1cc2c3c(Cl)nccc3n(C(=O)OC(C)(C)C)c2cc1OCc1ccccc1]

Step 1

In a 20 mL microwave vial, Pd(dppf)$_2$Cl$_2$.DCM (63 mg, 0.08 mmol) was added to a solution of 1-(benzyloxy)-4-bromo-2-methoxy-5-nitrobenzene (870 g, 2.57 mol), 2-chloro-3-pyridinylboronic acid (526 mg, 3.34 mmol), and 2M potassium acetate (3.3 mL, 6.69 mmol) in DMF (9 mL). In the microwave, the reaction was heated to 130° C. for 1 h. The reaction mixture was diluted with ethyl acetate and filtered thru a plug of Celite. Water was added to the filtrate. Ethyl acetate was used to wash the aqueous layer. The combined organics were dried with MgSO$_4$, filtered, and concentrated under reduced pressure. The resulting residue was purified by silica gel column using 0% to 50% ethyl acetate in hexanes to afford 3-[4-(benzyloxy)-5-methoxy-2-nitrophenyl]-2-chloropyridine (560 mg, 59%) as a yellow oil.

Step 2

3-[4-(Benzyloxy)-5-methoxy-2-nitrophenyl]-2-chloropyridine (1.50 g, 4.05 mmol) in triethyl phosphite (8.0 mL) was stirred and heated for 24 h at 130° C. The reaction mixture was cooled to room temperature. The reaction mixture was concentrated under reduced pressure to afford 7-(benzyloxy)-1-chloro-8-methoxy-5H-pyrido[4,3-b]indole (1.37 g, 99%) as a crude orange solid.

Step 3

Di-tert-butyl dicarbonate (1.32 g, 6.07 mmol) was added to a mixture containing 7-(benzyloxy)-1-chloro-8-methoxy-5H-pyrido[4,3-b]indole (1.37 g, 4.04 mmol), Hunig's base (1.0 mL, 6.07 mmol), and DMAP (0.10 g, 0.80 mmol) in 1,4-dioxane (11 mL). The reaction mixture was stirred for 15 minutes, and then concentrated under reduced pressure. The resulting residue was triturated with 10% DCM in hexanes to afford the titled compound, tert-butyl 7-(benzyloxy)-1-chloro-8-methoxy-5H-pyrido[4,3-b]indole-5-carboxylate (0.62 g; 34.93%), as a white solid. MS (ESI, pos. ion) m/z: 439.0 (M+1).

Reference 6

Synthesis of 7-(benzyloxy)-4-chloro-1-fluoro-8-methoxy-5H-pyrido[4,3-b]indole

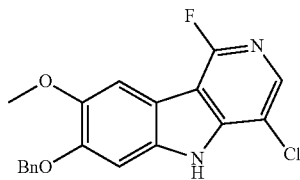 [SMILES: COc1cc2c(cc1OCc1ccccc1)[nH]c1c(Cl)cnc(F)c12]

The title compound was prepared as described in Reference 5, by substituting 2-chloro-3-pyridinylboronic acid with (5-chloro-2-fluoropyridin-3-yl)boronic acid. MS (ESI, pos. ion) m/z: 357.0 (M+1).

Reference 7 tert-butyl 7-hydroxy-8-methoxy-5H-pyrido[4,3-b]indole-5-carboxylate

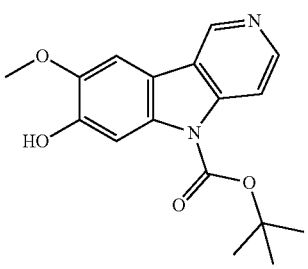 [SMILES: COc1cc2c3cnccc3n(C(=O)OC(C)(C)C)c2cc1O]

Combined tert-butyl 7-(benzyloxy)-1-chloro-8-methoxy-5H-pyrido[4,3-b]indole-5-carboxylate (290.00 mg; 0.66 mmol; 1.00 eq.) and 10% palladium on carbon (70.32 mg; 0.07 mmol; 0.10 eq.) in methanol (20 mL) and DCM (10 mL). Stirred in the presence of hydrogen gas (1 atm) via balloon. The reaction was heated to 40° C. for 1 hour. Afterwards the reaction mixture was filtered thru a plug of Celite and the filtrate was concentrated to afford tert-butyl 7-hydroxy-8-methoxy-5H-pyrido[4,3-b]indole-5-carboxylate (207.69 mg; 100.00%) as a white solid. MS (ESI, pos. ion) m/z: 357.0 (M-56).

Reference 8 tert-butyl 1-cyclopropyl-7-hydroxy-8-methoxy-5H-pyrido[4,3-b]indole-5-carboxylate

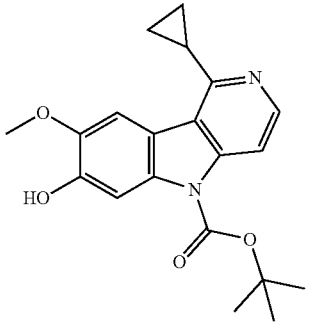 [SMILES: COc1cc2c3c(C4CC4)nccc3n(C(=O)OC(C)(C)C)c2cc1O]

Step 1

A mixture of tert-butyl 7-(benzyloxy)-1-chloro-8-methoxy-5H-pyrido[4,3-b]indole-5-carboxylate (10.00 g; 22.78 mmol; 1.00 eq.), cyclopropylboronic acid (6.85 g; 79.74 mmol; 3.50 eq.), tricyclohexylphosphane (638.93 mg; 2.28 mmol; 0.10 eq.) and potassium phosphate, tribasic (9.67 g; 45.57 mmol; 2.00 eq.) in toluene (113.92 mL) and water (5.70 mL) was purged with nitrogen for 10 minutes. palladium acetate (511.52 mg; 2.28 mmol; 0.10 eq.) was then added and the mixture was heated to 100 C in a sealed flask for 4 hours. The mixture was diluted with EtOAc and washed with water and brine. The organic layer was dried over MgSO$_4$, filtered and concentrated. The resulting residue was purified by column chromatography eluting with 0-50% EtOAc in heptane to obtain tert-butyl 7-(benzyloxy)-1-cyclopropyl-8-methoxy-5H-pyrido[4,3-b]indole-5-carboxylate (8.85 g; 87%) as an off-white solid. 1H NMR (400 MHz, DMSO-d6) δ 8.32 (d, J=5.7 Hz, 1H), 8.00 (s, 1H), 7.88 (d, J=5.7 Hz, 1H), 7.83 (s, 1H), 7.50-7.45 (m, 2H), 7.42-7.36 (m, 2H), 7.36-7.29 (m, 1H), 5.19 (s, 2H), 3.90 (s, 3H), 2.79 (p, J=6.5 Hz, 1H), 1.66 (s, 9H), 1.15-1.08 (m, 4H).

Step 2

A flask charged with mixture of tert-butyl 7-(benzyloxy)-1-cyclopropyl-8-methoxy-5H-pyrido[4,3-b]indole-5-carboxylate (9.02 g; 20.29 mmol; 1.00 eq.) in ethanol (902.00 mL) and the flask was purged with N2 for 10 min. Palladium hydroxide (0.57 g; 4.06 mmol; 0.20 eq.) was added to the reaction mix and the system purged with nitrogen and then hydrogen. The mixture was left stirring under hydrogen gas via balloon for 2 hours. The reaction mixture was filtered over celite and the filtrate concentrated to dryness to afford tert-butyl 1-cyclopropyl-7-hydroxy-8-methoxy-5H-pyrido[4,3-b]indole-5-carboxylate (5.72 g; 79%). 1H NMR (400 MHz, DMSO-d6) δ 9.64 (s, 1H), 8.28 (d, J=5.7 Hz, 1H), 7.85-7.78 (m, 2H), 7.76 (s, 1H), 3.89 (s, 3H), 2.81-2.68 (m, 1H), 1.67 (s, 9H), 1.13-1.06 (m, 4H).

Reference 9 tert-butyl 1-chloro-7-hydroxy-8-methoxy-5H-pyrido[4,3-b]indole-5-carboxylate

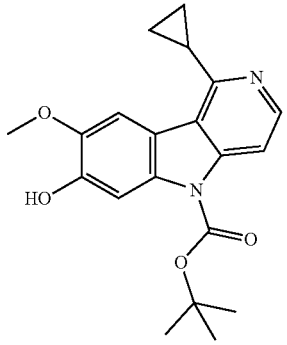 [SMILES: COc1cc2c3c(C4CC4)nccc3n(C(=O)OC(C)(C)C)c2cc1O]

A mixture of tert-butyl 7-(benzyloxy)-1-chloro-8-methoxy-5H-pyrido[4,3-b]indole-5-carboxylate (401 mg, 0.91 mmol) and Pd(OH)$_2$ (101 mg) in THF (25 mL) was purged with N2 for 10 min, followed by treatment under hydrogen gas via balloon for 10 minutes. The resulting mixture was allowed to stir at room temperature under hydrogen atmosphere for 8 minutes. The reaction mixture was filtered through a small pad of celite and rinsed with MeOH. The resulting filtrate were combined and the organic solvents were removed under reduced pressure to provide crude product of tert-butyl 1-chloro-7-hydroxy-8-methoxy-5H-pyrido[4,3-b]indole-5-carboxylate (260 mg, 80%).

Reference 10

4-chloro-1-fluoro-7,8-dimethoxy-5H-pyrido[4,3-b]indole

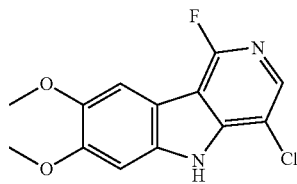 [SMILES: COc1cc2[nH]c3c(Cl)cnc(F)c3c2cc1OC]

Step 1

A mixture of 1-bromo-4,5-dimethoxy-2-nitrobenzene (3.4 g; 12.97 mmol; 1.00 eq.), (5-chloro-2-fluoropyridin-3-yl)boronic acid (4.6 g; 25.95 mmol; 2.00 eq.), Pd(dppf)$_2$Cl$_2$.DCM (529.76 mg; 0.65 mmol; 0.05 eq.), and Potassium Carbonate (4.5 g; 32.44 mmol; 2.50 eq.) in 1,4-dioxane (90 mL) was heated to 100° C. for 4 hours. Let the reaction cool to rt. The reaction mixture was diluted with water. The aqueous layer was extracted with ethyl acetate. The combined organics were dried with MgSO$_4$, filtered, and concentrated under reduced pressure. The resulting residue was purified by silica gel using 0% to 50% ethyl acetate in hexanes to afford 5-chloro-3-(4,5-dimethoxy-2-nitrophenyl)-2-fluoropyridine (3.3 g; 81%). MS (ESI, pos. ion) m/z: 313.0 (M+1).

Step 2

A mixture of 5-chloro-3-(4,5-dimethoxy-2-nitrophenyl)-2-fluoropyridine (3.3 g; 10.5 mmol; 1.00 eq.) in triethyl phosphite (35 mL; 0.30 mol/L; 10.55 mmol; 1.00 eq.) was heated to 120° C. for 16 hours. The mixture was cooled to room temperature and concentrated under reduced pressure. The resulting residue was triturated with 33% DCM in heptanes, filtered, and dried under hi-vac to afford the title compound (1.7 g; 57%) MS (ESI, pos. ion) m/z: 313.0 (M+1).

Reference 11

3-(4-bromo-2-methoxy-5-nitrophenoxy)-N,N-dimethylpropan-1-amine

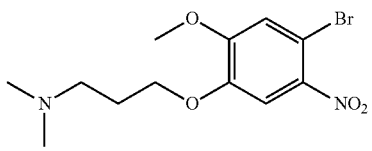 [SMILES: COc1cc(Br)c([N+](=O)[O-])cc1OCCCN(C)C]

To a solution of [3-(4-bromo-2-methoxyphenoxy)propyl]dimethylamine (22.38 g; 77.66 mmol; 1.00 eq.) in glacial acetic acid (194.15 mL) was added 15.8N nitric acid (22.38 mL). The reaction was stirred at room temperature for 18 hours. Yellow precipitation formed in the reaction mixture. Removed bulk acetic acid under reduced pressure using a water bath at 40° C. Diluted with water. Slowly added 2M NaOH until pH ~4. Due to large volume of water, solid NaOH was added and stirred until pH ~9. Let the heterogeneous mixture stir for 30 minutes and filtered. The solid was washed with water during filtration. The title compound (22.60 g; 87.34%) was obtained as a light yellow solid after drying under hi-vac. $^1$H NMR (400 MHz, Acetonitrile-d3) δ 7.59 (s, 1H), 7.27 (s, 1H), 4.09 (t, J=6.5 Hz, 2H), 3.91 (s, 3H), 2.38 (t, J=7.0 Hz, 2H), 2.18 (s, 6H), 1.94-1.87 (m, 2H). MS (ESI, pos. ion) m/z: 332.9 (M+1).

Example 1

Synthesis of 1-[3-({6-methoxy-5H-pyrido[3,2-b]indol-7-yl}oxy)propyl]pyrrolidine

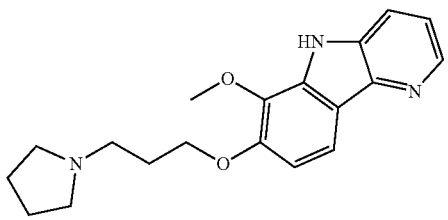 [SMILES: COc1c(OCCCN2CCCC2)ccc2c1[nH]c1cccnc12]

Step 1

In a 20 mL microwave vial, a mixture of 4-bromo-2-methoxyphenol (1.50 g, 7.39 mmol), bis(pinacolato)diboron (2.44 g, 9.6 mmol), potassium acetate (2.18 g, 22.2 mmol), and Pd(dppf)$_2$Cl$_2$.DCM (150.83 mg, 0.2 mmol) in 1,4-dioxane (8.0 mL) was heated to 130° C. for 1 h in a microwave reactor. The reaction mixture was filtered thru a plug of Celite and concentrated under reduced pressure to afford 2-methoxy-4-(4,4,5,5-tetramethyl-1,3,2-dioxaborolan-2-yl)phenol (1.84 g, 100%) as a crude oil.

Step 2

In a 20 mL microwave vial, a mixture of 2-methoxy-4-(4,4,5,5-tetramethyl-1,3,2-dioxaborolan-2-yl)phenol (1.84 g, 8.1 mmol), 2-bromo-3-nitropyridine (1 65 g, 8.1 mmol), potassium acetate (2.18 g, 22.2 mmol), and Pd(dppf)$_2$Cl$_2$.DCM (181.00 mg, 0.2 mmol) in DMF (8.0 mL) was heated to 130° C. for 30 minutes in a microwave reactor. The reaction mixture was filtered thru a plug of Celite and concentrated under reduced pressure. The resulting residue was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford 2-methoxy-4-(3-nitropyridin-2-yl)phenol (0.40 g, 22%) as a white solid.

Step 3

A mixture of 2-methoxy-4-(3-nitropyridin-2-yl)phenol (0.40 g, 1.6 mol), 1-(3-chloropropyl)pyrrolidine hydrochloride (0.30 g, 1.6 mmol), and potassium carbonate (0.68 g, 4.9 mmol) in DMF (10.0 mL) was heated to 100° C. for 16 h. The reaction mixture was cooled to room temperature, diluted with water and extracted with ethyl acetate. The combined organics were dried with MgSO$_4$, filtered, and concentrated under reduced pressure. The resulting residue was purified by silica gel column using 0% to 10% MeOH in DCM to afford 2-{3-methoxy-4-[3-(pyrrolidin-1-yl)propoxy]phenyl}-3-nitropyridine (0.31 g, 53%).

Step 4

A mixture of 2-{3-methoxy-4-[3-(pyrrolidin-1-yl)propoxy]phenyl}-3-nitropyridine (0.10 g, 0.3 mmol) and triethyl phosphite (2.0 mL) was stirred and heated to 120° C. for 24 h. The resulting residue was cooled to room temperature and concentrated under reduced pressure. The resulting residue was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min). The more polar compound is 1-[3-({8-methoxy-5H-pyrido[3,2-b]indol-7-yl}oxy)propyl]pyrrolidine (7.0 mg, 7%) MS (ESI, pos. ion) m/z: 326.5 (M+1). The less polar compound is 1-[3-({6-methoxy-5H-pyrido[3,2-b]indol-7-yl}oxy)propyl]pyrrolidine (18.0 mg, 17%) MS (ESI, pos. ion) m/z: 326.5 (M+1).

Example 2

Synthesis of 1-[3-({6-methoxy-9H-pyrido[3,4-b]indol-7-yl}oxy)propyl]pyrrolidine

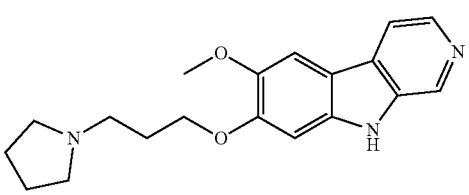 [SMILES: COc1cc2c(cc1OCCCN1CCCC1)[nH]c1cnccc12]

Step 1

In a 5 mL microwave vial, a mixture of 1-(benzyloxy)-4-bromo-2-methoxy-5-nitrobenzene (0.40 g, 1.2 mmol), 4-pyridinylboronic acid (0.22 g; 1.8 mmol), 2M potassium carbonate (1.77 mL, 3.6 mmol), and Pd(dppf)$_2$Cl$_2$.DCM (24.2 mg, 0.03 mmol) in DMF (2.0 mL) was heated to 130° C. for 30 minutes in a microwave reactor. The reaction mixture was filtered thru a plug of Celite. The filtrate was diluted with water and extracted with ethyl acetate. The combined organics were dried with MgSO$_4$, filtered, and concentrated under reduced pressure. The resulting residue was purified by silica gel column using 0% to 50% ethyl acetate in hexanes to afford 4-[4-(benzyloxy)-5-methoxy-2-nitrophenyl]pyridine (0.30 g; 75%).

Step 2

A mixture of 4-[4-(benzyloxy)-5-methoxy-2-nitrophenyl]pyridine (0.3 g, 0.9 mmol) and triethyl phosphite (2.0 mL) was heated to 130° C. for 24 h. The reaction was cooled to room temperature and concentrated under reduced pressure. The resulting residue was purified by silica gel column using 0% to 75% ethyl acetate in hexanes to afford 7-(benzyloxy)-6-methoxy-9H-pyrido[3,4-b]indole (110.00 mg, 41%).

Step 3

Di-tert-butyl dicarbonate (95 mg, 0.43 mmol) was added to a solution of 7-(benzyloxy)-6-methoxy-9H-pyrido[3,4-b]indole (110 mg, 0.36 mmol) and DMAP (9 mg; 0.07 mmol) in 1,4-dioxane (4.0 mL). The reaction mixture was stirred at room temperature for 1 h and concentrated under reduced pressure. The resulting residue was purified by silica gel column using 0% to 45% ethyl acetate in hexanes to afford tert-butyl 7-(benzyloxy)-6-methoxy-9H-pyrido[3,4-b]indole-9-carboxylate (70.00 mg; 48%).

Step 4

A mixture of tert-butyl 7-(benzyloxy)-6-methoxy-9H-pyrido[3,4-b]indole-9-carboxylate (70 mg, 0.17 mmol) and 10% palladium on carbon (18 mg, 0.02 mmol) in methanol (2.0 mL) was stirred at room temperature in 1 atm of H$_2$ via balloon. The reaction mixture was stirred for 1 h and filtered thru plug of Celite. The filtrate was concentrated under reduced pressure to afford tert-butyl 7-hydroxy-6-methoxy-9H-pyrido[3,4-b]indole-9-carboxylate (54 mg, 99%).

Step 5

A mixture of tert-butyl 7-hydroxy-6-methoxy-9H-pyrido[3,4-b]indole-9-carboxylate (54 mg, 0.2 mmol), 1-(3-chloropropyl)pyrrolidine hydrochloride (47 mg, 0.3 mmol), and potassium carbonate (71 mg, 0.5 mmol) in DMF (3.0 mL) was heated to 100° C. for 16 h. The reaction mixture was diluted with water and extracted with ethyl acetate. The combined organics were dried with MgSO$_4$, filtered and concentrated under reduced pressure. The resulting crude was treated with 1M HCl (1.0 mL) and stirred for 1 h. The aqueous mixture was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford the titled compound, 1-[3-({6-methoxy-9H-pyrido[3,4-b]indol-7-yl}oxy)propyl]pyrrolidine (10 mg, 18%). MS (ESI, pos. ion) m/z: 326.0 (M+1).

Example 3

Synthesis of 1-[3-({8-methoxy-1-methyl-5H-pyrido[4,3-b]indol-7-yl}oxy)propyl]pyrrolidine

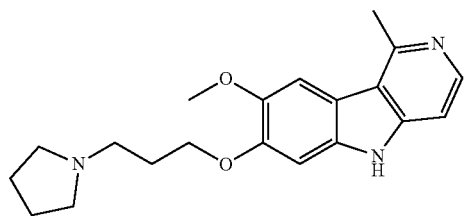 [SMILES: COc1cc2c(cc1OCCCN1CCCC1)[nH]c1ccnc(C)c12]

The title compound was prepared as described in Example 2, by substituting 4-pyridinylboronic acid with (2-methylpyridin-3-yl)boronic acid. MS (ESI, pos. ion) m/z: 340.0 (M+1).

Example 4

Synthesis of 1-[3-({8-methoxy-5H-pyrido[4,3-b]indol-7-yl}oxy)propyl]pyrrolidine and 1-[3-({6-methoxy-9H-pyrido[2,3-b]indol-7-yl}oxy)propyl]pyrrolidine

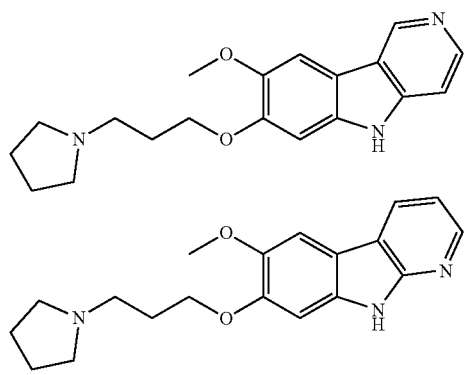

Step 1

In a 5 mL microwave vial, a mixture of 1-(benzyloxy)-4-bromo-2-methoxy-5-nitrobenzene (0.62 g, 1.83 mmol), 3-pyridinylboronic acid (0.34 g; 2.75 mmol), Pd(dppf)$_2$Cl$_2$.DCM (37 mg; 0.05 mmol), and 2M potassium carbonate (2.8 mL, 5.50 mmol) in DMF (2.00 mL) was heated to 130° C. for 30 minutes in a microwave reactor. The reaction mixture was diluted ethyl acetate and filtered thru a plug of Celite. Water was added to the filtrate, and the layers were separated. The aqueous layer was washed with ethyl acetate. The combined organics were dried with MgSO$_4$, filtered, and concentrated under reduced pressure. The resulting residue was purified by silica gel using 0% to 50% ethyl acetate in hexanes to afford 3-(4-(benzyloxy)-5-methoxy-2-nitrophenyl)pyridine (0.31 g; 50%) as a dark oil.

Step 2

Trifluoroacetic acid (2 mL) was added to 3-(4-(benzyloxy)-5-methoxy-2-nitrophenyl)pyridine (0.31 g, 0.91 mmol) and stirred for 16 h at room temperature. The reaction mixture was concentrated under reduced pressure. The resulting reside was purified by silica column using 0% to 80% ethyl acetate in hexanes to afford 2-methoxy-5-nitro-4-(pyridin-3-yl)phenol (0.1 g, 45%).

Step 3

A mixture of 2-methoxy-5-nitro-4-(pyridin-3-yl)phenol (0.1 g, 0.41 mmol), 1-(3-chloropropyl)pyrrolidine hydrochloride (92 mg, 0.61 mmol) and potassium carbonate (0.17 g, 1.22 mmol) in DMF (2.0 mL) was heated to 100° C. for 18 h. The reaction mixture was cooled to room temperature. The reaction mixture was diluted with water. The aqueous solution was extracted with ethyl acetate. The combined organics were dried with MgSO$_4$, filtered, and concentrated under reduced pressure. The resulting residue was purified by silica gel column using 0% to 10% MeOH in DCM to afford 3-{5-methoxy-2-nitro-4-[3-(pyrrolidin-1-yl)propoxy]phenyl}pyridine (0.1 g, 69%).

Step 4

A mixture of 3-{5-methoxy-2-nitro-4-[3-(pyrrolidin-1-yl)propoxy]phenyl}pyridine (0.1 g, 0.28 mmol) and triethyl phosphite (2.0 mL) was heated to 120° C. for 24 h. The reaction mixture was cooled to room temperature. The resulting residue was concentrated under reduced pressure and purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford the more polar regio-isomer, 1-[3-({8-methoxy-5H-pyrido[4,3-b]indol-7-yl}oxy)propyl]-pyrrolidine (8.0 mg, 3%), MS (ESI, pos. ion) m/z: 326.2 (M+1) and less polar region-isomer, 1-[3-({6-methoxy-9H-pyrido[2,3-b]indol-7-yl}oxy)propyl]pyrrolidine (18.0 mg; 10%), MS (ESI, pos. ion) m/z: 326.0 (M+1).

Example 5

Synthesis of 8-methoxy-7-[3-(pyrrolidin-1-yl)propoxy]-5H-pyrido[4,3-b]indol-3-amine

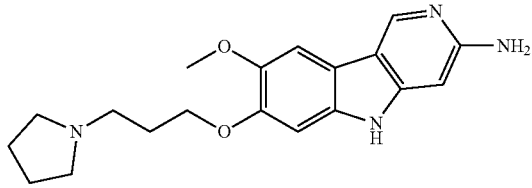 [SMILES: COc1cc2c(cc1OCCCN1CCCC1)[nH]c1cc(N)ncc12]

Step 1

In a 5 mL microwave vial, a mixture of 5-(4,4,5,5-tetramethyl-1,3,2-dioxaborolan-2-yl)-2-pyridinylamine (0.3 g, 1.36 mmol), 1-[3-(4-bromo-2-methoxy-5-nitrophenoxy)propyl]pyrrolidine (0.5 g, 1.36 mmol), Pd(dppf)$_2$Cl$_2$.DCM (33 mg, 0.04 mmol), and 2M potassium carbonate (1.4 mL, 2.73 mmol) in DMF (2.7 mL) was heated to 120° C. for 1 h in a microwave reactor. The reaction mixture was diluted with water. The aqueous layer was extracted with ethyl acetate. The combined organics were dried with MgSO$_4$, filtered, and concentrated under reduced pressure. The resulting residue was purified by silica gel column using 0% to 10% MeOH in DCM to afford 5-{5-methoxy-2-nitro-4-[3-(pyrrolidin-1-yl)propoxy]phenyl}pyridin-2-amine (0.33 g, 65%) as a brown oil.

Step 2

Di-tert-butyl dicarbonate (316.45 mg; 1.45 mmol) was added to a mixture of 5-{5-methoxy-2-nitro-4-[3-(pyrrolidin-1-yl)propoxy]phenyl}pyridin-2-amine (180.00 mg; 0.48 mmol) and N,N-dimethylaminopyridine (11.81 mg; 0.10 mmol) in acetonitrile (5 mL). The reaction mixture was heated to 50° C. for 1 h. The reaction mixture was cooled to room temperature. The reaction mixture was concentrated under reduced pressure. The resulting residue was purified by silica gel column using 0% to 10% MeOH in DCM to afford tert-butyl N-[(tert-butoxy)carbonyl]-N-(5-{5-methoxy-2-nitro-4-[3-(pyrrolidin-1-yl)propoxy]phenyl}pyridin-2-yl)carbamate (0.16 g, 57%).

Step 3

A mixture of tert-butyl N-[(tert-butoxy)carbonyl]-N-(5-{5-methoxy-2-nitro-4-[3-(pyrrolidin-1-yl)propoxy]phenyl}pyridin-2-yl)carbamate (0.16 g, 0.28 mmol) and triethyl phosphite (3.0 mL) was heated to 120° C. for 24 h. The reaction mixture was cooled to room temperature and concentrated under reduced pressure. 1M HCl (3 mL) was added to the resulting residue and heated to 50° C. for 1 h.

The solution was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford the more polar regio-isomer 8-methoxy-7-[3-(pyrrolidin-1-yl)propoxy]-5H-pyrido[4,3-b]indol-3-amine (20.0 mg, 21%). MS (ESI, pos. ion) m/z: 341.4 (M+1).

Example 6

Synthesis of 1-[3-({1-fluoro-8-methoxy-5H-pyrido[4,3-b]indol-7-yl}oxy)propyl]pyrrolidine

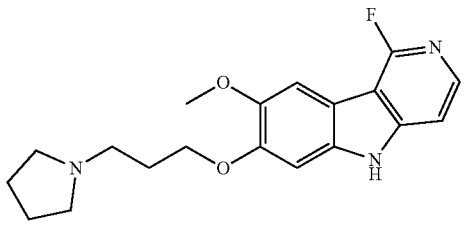 [SMILES: COc1cc2c(cc1OCCCN1CCCC1)[nH]c1ccnc(F)c12]

The title compound was prepared as described in Example 5, by substituting 5-(4,4,5,5-tetramethyl-1,3,2-dioxaborolan-2-yl)-2-pyridinylamine with (2-fluoropyridin-3-yl)boronic acid. MS (ESI, pos. ion) m/z: 344.0 (M+1).

Example 7

Synthesis of 8-methoxy-1-methyl-7-[3-(pyrrolidin-1-yl)propoxy]-5H-pyrido[4,3-b]indol-3-amine

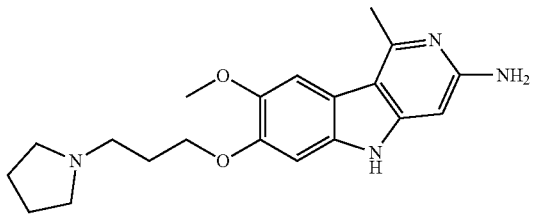 [SMILES: COc1cc2c(cc1OCCCN1CCCC1)[nH]c1cc(N)nc(C)c12]

Step 1

Di-tert-butyl dicarbonate (2.6 g, 11.76 mmol) was added to a mixture of 5-bromo-6-methylpyridin-2-amine (1.1 g, 5.88 mmol) and DMAP (0.14 g, 1.18 mmol) in THF (20.0 mL). The reaction mixture was heated to 50° C. for 1 h. The reaction mixture was cooled to room temperature. The reaction mixture was concentrated under reduced pressure. The resulting residue was purified by silica gel using 0% to 30% ethyl acetate in hexanes to afford tert-butyl N-(5-bromo-6-methylpyridin-2-yl)-N-[(tert-butoxy)carbonyl]carbamate (2.1 g, 92%).

Step 2

In a 20 mL microwave vial, a mixture of tert-butyl N-(5-bromo-6-methylpyridin-2-yl)-N-[(tert-butoxy)carbonyl]carbamate (1.4 g, 3.62 mmol), bis(pinacolato)diboron (1.4 g, 5.42 mmol), Pd(dppf)$_2$Cl$_2$.DCM (74 mg, 0.09 mmol), and potassium carbonate (2.0 g, 14.46 mmol) in 1,4-dioxanes (12.0 mL) was heated to 130° C. for 7 h. The reaction mixture was diluted with water. The aqueous layer was extracted with ethyl acetate. The combined organics were dried with MgSO$_4$, filtered, and concentrated under reduced pressure. The resulting residue was purified by silica gel column using 0% to 50% ethyl acetate in hexanes to afford tert-butyl N-[(tert-butoxy)carbonyl]-N-[6-methyl-5-(tetramethyl-1,3,2-dioxaborolan-2-yl)pyridin-2-yl]carbamate (1.5 g, 95%).

Step 3

In a 5 mL microwave vial, a mixture of tert-butyl N-[(tert-butoxy)carbonyl]-N-[6-methyl-5-(tetramethyl-1,3,2-dioxaborolan-2-yl)pyridin-2-yl]carbamate (0.40 g, 0.92 mmol), 1-[3-(4-bromo-2-methoxy-5-nitrophenoxy)propyl]pyrrolidine (0.33 g, 0.92 mmol), Pd(dppf)$_2$Cl$_2$.DCM (23 mg, 0.03 mmol), and 2M potassium carbonate (0.90 mL, 1.84 mmol) in NMP (2.5 mL) was heated to 130° C. for 30 minutes in a microwave reactor. The reaction mixture was diluted with water. The aqueous layer was extracted with ethyl acetate. The combined organics were dried with MgSO$_4$, filtered, and concentrated under reduced pressure. The resulting residue was purified by silica gel column using 0% to 10% MeOH in DCM to afford tert-butyl N-[(tert-butoxy)carbonyl]-N-(5-{5-methoxy-2-nitro-4-[3-(pyrrolidin-1-yl)propoxy]phenyl}-6-methylpyridin-2-yl)carbamate (0.35 g, 65%).

Step 4

A mixture of tert-butyl N-[(tert-butoxy)carbonyl]-N-(5-{5-methoxy-2-nitro-4-[3-(pyrrolidin-1-yl)propoxy]phenyl}-6-methylpyridin-2-yl)carbamate (0.35 g, 0.60 mmol) and triethyl phosphite (6 mL) was heated to 120° C. for 24 h. The reaction mixture was concentrated under reduced pressure. 1M hydrochloric acid (3.00 mL) solution was added to the resulting residue and stirred for 3 h. The aqueous solution was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford the titled compound 8-methoxy-1-methyl-7-[3-(pyrrolidin-1-yl)propoxy]-5H-pyrido[4,3-b]indol-3-amine (8 mg, 4%). MS (ESI, pos. ion) m/z: 355.0 (M+1).

Example 8

Synthesis of (3S)-1-{8-methoxy-7-[3-(pyrrolidin-1-yl)propoxy]-5H-pyrido[4,3-b]indol-1-yl}pyrrolidin-3-ol

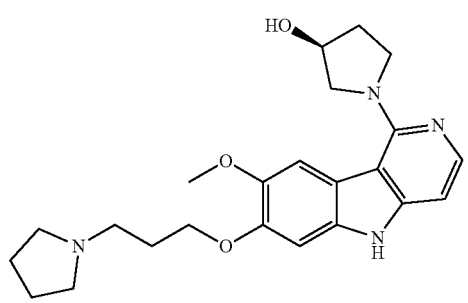 [SMILES: COc1cc2c(cc1OCCCN1CCCC1)[nH]c1ccnc(N3CC[C@H](O)C3)c12]

Step 1

In a 20 mL microwave vial, a mixture of Brettphos G1 (25 mg, 0.03 mmol), tert-butyl 7-(benzyloxy)-1-chloro-8-methoxy-5H-pyrido[4,3-b]indole-5-carboxylate (270 mg, 0.62 mmol), (3S)-3-pyrrolidinol (161 mg, 1.85 mmol), and potassium tert-butoxide (207 mg, 1.85 mmol) in NMP (6.0 mL) was heated to 140° C. for 1.5 h in a microwave reactor. The reaction mixture was diluted with water. The aqueous layer was extracted with ethyl acetate. The combined organics were dried with MgSO$_4$, filtered, and concentrated under reduced pressure. The resulting residue was purified by silica gel column using 0% to 80% ethyl acetate in hexanes to afford (3S)-1-[7-(benzyloxy)-8-methoxy-5H-pyrido[4,3-b]indol-1-yl]pyrrolidin-3-ol (239 mg, 99%).

Step 2

Di-tert-butyl dicarbonate (269 mg, 1.23 mmol) was added to a mixture of (3S)-1-[7-(benzyloxy)-8-methoxy-5H-pyrido[4,3-b]indol-1-yl]pyrrolidin-3-ol (239 mg, 0.62 mmol), DMAP (15 mg, 0.12 mmol), and Hunig's base (0.21 mL, 1.23 mmol) in acetonitrile (3 mL). The reaction mixture was stirred for 2 h at room temperature and concentrated under reduced pressure. The resulting residue was purified by silica gel column using 0% to 30% ethyl acetate in hexanes to afford tert-butyl 7-(benzyloxy)-1-[(3S)-3-{[(tert-butoxy)carbonyl]oxy}pyrrolidin-1-yl]-8-methoxy-5H-pyrido[4,3-b]indole-5-carboxylate (363 mg, 99%).

Step 3

A mixture of tert-butyl 7-(benzyloxy)-1-[(3S)-3-{[(tert-butoxy)carbonyl]oxy}pyrrolidin-1-yl]-8-methoxy-5H-pyrido[4,3-b]indole-5-carboxylate (363.00 mg, 0.62 mmol) and 10% wt palladium on carbon (33 mg, 0.03 mmol) in methanol (10 mL) was stirred under hydrogen gas pressure via balloon for 1 h. The reaction mixture was filtered thru a plug of Celite and concentrated under reduced pressure to afford tert-butyl 1-[(3S)-3-{[(tert-butoxy)carbonyl]oxy}pyrrolidin-1-yl]-7-hydroxy-8-methoxy-5H-pyrido[4,3-b]indole-5-carboxylate (300 mg, 97%).

Step 4

A mixture of tert-butyl 1-[(3S)-3-{[(tert-butoxy)carbonyl]oxy}pyrrolidin-1-yl]-7-hydroxy-8-methoxy-5H-pyrido[4,3-b]indole-5-carboxylate (300 mg, 0.60 mmol), 1-(3-chloropropyl)pyrrolidine hydrochloride (240 mg, 1.20 mol), and potassium carbonate (331 mg, 2.40 mol) in DMF (6 mL) was heated to 100° C. for 16 h. The reaction mixture was cooled to room temperature, filtered, and concentrated under reduced pressure. 1M HCl (5 mL) was added to the resulting residue and heated to 50° C. for 1 h. The aqueous solution was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford the titled compound (3S)-1-{8-methoxy-7-[3-(pyrrolidin-1-yl)propoxy]-5H-pyrido[4,3-b]indol-1-yl}pyrrolidin-3-ol (110 mg, 38%).

Example 9

Synthesis of (3R)-1-{8-methoxy-7-[3-(pyrrolidin-1-yl)propoxy]-5H-pyrido[4,3-b]indol-1-yl}pyrrolidin-3-ol

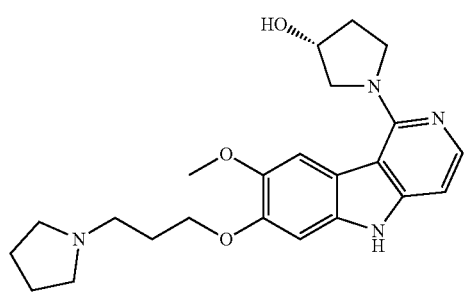 [SMILES: COc1cc2c(cc1OCCCN1CCCC1)[nH]c1ccnc(N3CC[C@@H](O)C3)c12]

The title compound was prepared as described in Example 8, by substituting (3S)-3-pyrrolidinol with (3R)-3-pyrrolidinol. MS (ESI, pos. ion) m/z: 411.0 (M+1).

Example 10

Synthesis of 8-methoxy-N-[(2S)-1-methoxypropan-2-yl]-7-[3-(pyrrolidin-1-yl)propoxy]-5H-pyrido[4,3-b]indol-1-amine

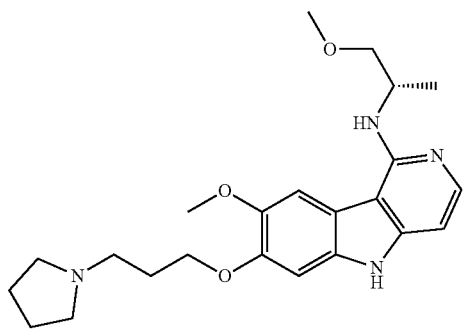 [SMILES: COC[C@H](C)Nc1nccc2[nH]c3cc(OCCCN4CCCC4)c(OC)cc3c12]

The title compound was prepared as described in Example 8, by substituting (3S)-3-pyrrolidinol with (2S)-1-methoxypropan-2-amine. MS (ESI, pos. ion) m/z: 413.0 (M+1).

Example 11

Synthesis of 1-{8-methoxy-7-[3-(pyrrolidin-1-yl)propoxy]-5H-pyrido[4,3-b]indol-1-yl}pyrrolidine

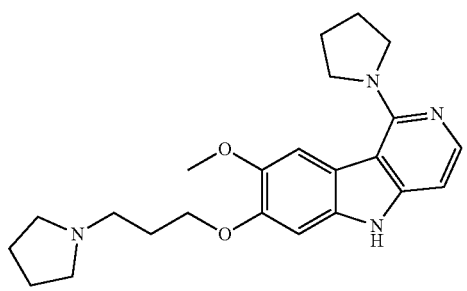 [SMILES: COc1cc2c(cc1OCCCN1CCCC1)[nH]c1ccnc(N3CCCC3)c12]

The title compound was prepared as described in Example 8, by substituting (3S)-3-pyrrolidinol with pyrolidine. MS (ESI, pos. ion) m/z: 395.0 (M+1).

Example 12

Synthesis of 1-{8-methoxy-7-[3-(pyrrolidin-1-yl)propoxy]-5H-pyrido[4,3-b]indol-1-yl}piperidin-4-ol

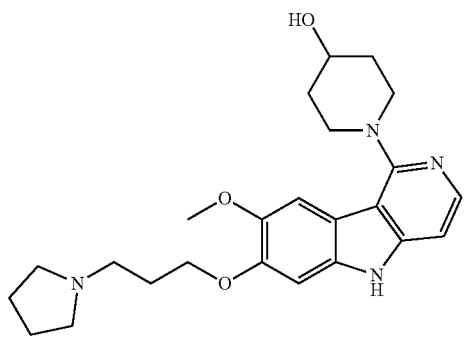 [SMILES: COc1cc2c(cc1OCCCN1CCCC1)[nH]c1ccnc(N3CCC(O)CC3)c12]

The title compound was prepared as described in Example 8, but substituted (3S)-3-pyrrolidinol with 4-hydroxypiperidine. MS (ESI, pos. ion) m/z: 425.0 (M+1).

Example 13

Synthesis of 4-{8-methoxy-7-[3-(pyrrolidin-1-yl)propoxy]-5H-pyrido[4,3-b]indol-1-yl}morpholine

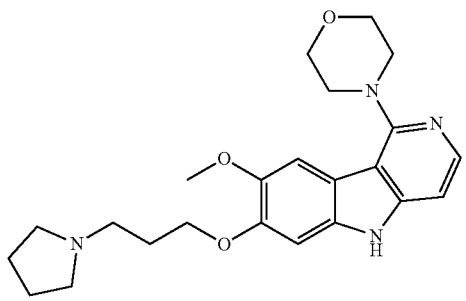 [SMILES: COc1cc2c(cc1OCCCN1CCCC1)[nH]c1ccnc(N3CCOCC3)c12]

The title compound was prepared as described in Example 8, by substituting (3S)-3-pyrrolidinol with morpholine. MS (ESI, pos. ion) m/z: 411.0 (M+1).

Example 14

Synthesis of 1-{8-methoxy-7-[3-(pyrrolidin-1-yl)propoxy]-5H-pyrido[4,3-b]indol-1-yl}azetidin-3-ol

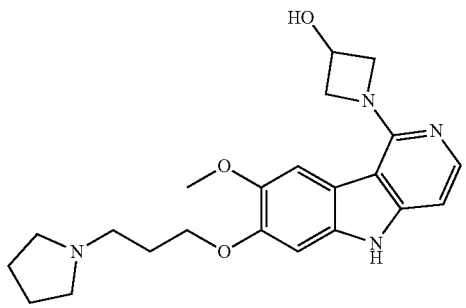 [SMILES: COc1cc2c(cc1OCCCN1CCCC1)[nH]c1ccnc(N3CC(O)C3)c12]

The title compound was prepared as described in Example 8, by substituting (3S)-3-pyrrolidinol with 3-hydroxyazetidine. MS (ESI, pos. ion) m/z: 397.0.0 (M+1).

Example 15

Synthesis of 3-{8-methoxy-7-[3-(pyrrolidin-1-yl)propoxy]-5H-pyrido[4,3-b]indol-1-yl}-8-oxa-3-azabicyclo[3.2.1]octane

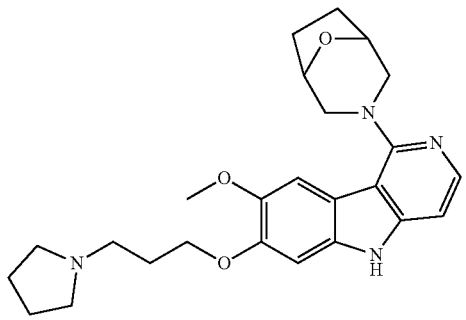 [SMILES: COc1cc2c(cc1OCCCN1CCCC1)[nH]c1ccnc(N3CC4CCC(C3)O4)c12]

The title compound was prepared as described in Example 8, by substituting (3S)-3-pyrrolidinol with 8-oxa-3-azabicyclo[3.2.1]octane. MS (ESI, pos. ion) m/z: 437.1 (M+1).

Example 16

Synthesis of N-(2-ethoxyethyl)-8-methoxy-7-[3-(pyrrolidin-1-yl)propoxy]-5H-pyrido[4,3-b]indol-1-amine

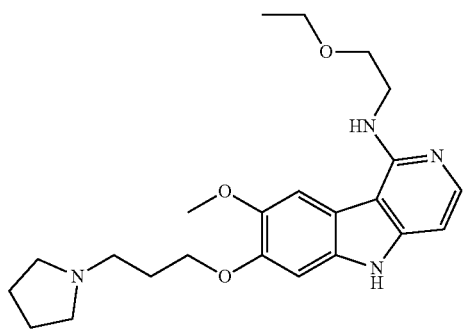 [SMILES: CCOCCNc1nccc2[nH]c3cc(OCCCN4CCCC4)c(OC)cc3c12]

Step 1

In a 20 mL microwave vial, a mixture of 7-(benzyloxy)-4-chloro-1-fluoro-8-methoxy-5H-pyrido[4,3-b]indole (600 mg, 1.68 mmol), 2-ethoxyethylamine (450 mg, 5.05 mmol), and Hunig's base (0.29 mL, 1.68 mmol) in NMP (6 mL) was heated to 120° C. for 5 h in a microwave reactor. The reaction mixture was concentrated under reduced pressure. The resulting residue was purified by silica gel column using 0% to 50% ethyl acetate in hexanes to afford 7-(benzyloxy)-4-chloro-N-(2-ethoxyethyl)-8-methoxy-5H-pyrido[4,3-b]indol-1-amine (320 mg; 44%).

Step 2

Di-tert-butyl dicarbonate (522 mg, 2.39 mmol) was added to a mixture of 7-(benzyloxy)-4-chloro-N-(2-ethoxyethyl)-8-methoxy-5H-pyrido[4,3-b]indol-1-amine (340 mg, 0.80 mmol) and DMAP (20 mg, 0.16 mmol) in acetonitrile (4 mL). The reaction mixture was heated to 45° C. for 1 h. The reaction mixture was cooled to room temperature and concentrated under reduced pressure. The resulting residue was purified by silica gel column using 0% to 30% ethyl acetate in hexanes to afford tert-butyl 7-(benzyloxy)-1-{[(tert-butoxy)carbonyl](2-ethoxyethyl)amino}-4-chloro-8-methoxy-5H-pyrido[4,3-b]indole-5-carboxylate (150 mg, 30%).

Step 3

A mixture of tert-butyl 7-(benzyloxy)-1-{[(tert-butoxy)carbonyl](2-ethoxyethyl)amino}-4-chloro-8-methoxy-5H-pyrido[4,3-b]indole-5-carboxylate (150 mg, 0.24 mmol) and 10% wt palladium on carbon (25 mg, 0.02 mmol) in methanol (2.40 mL) was stirred under hydrogen gas via balloon for 1 h. The reaction mixture was filtered thru a plug of Celite and concentrated under reduced pressure to afford tert-butyl 1-{[(tert-butoxy)carbonyl](2-ethoxyethyl)amino}-7-hydroxy-8-methoxy-5H-pyrido[4,3-b]indole-5-carboxylate (120 mg, 99%).

Step 4

A mixture of tert-butyl 1-{[(tert-butoxy)carbonyl](2-ethoxyethyl)amino}-7-hydroxy-8-methoxy-5H-pyrido[4,3-b]indole-5-carboxylate (120 mg, 0.24 mmol), 1-(3-chloropropyl)pyrrolidine hydrochloride (88 mg, 0.48 mmol), and potassium carbonate (132 mg, 0.96 mmol) in DMF (2.4 mL) was heated to 100° C. for 16 h. The reaction mixture was diluted with water. The aqueous layer was extracted with ethyl acetate. The combined organics were dried with MgSO$_4$, filtered, and concentrated under reduced pressure. The resulting residue was purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to afford N-(2-ethoxyethyl)-8-methoxy-7-[3-(pyrrolidin-1-yl)propoxy]-5H-pyrido[4,3-b]indol-1-amine (65 mg, 56%). MS (ESI, pos. ion) m/z: 413.4 (M+1).

Example 17

Synthesis of 1-[3-({1-cyclopropyl-8-methoxy-5H-pyrido[4,3-b]indol-7-yl}oxy)propyl]pyrrolidine

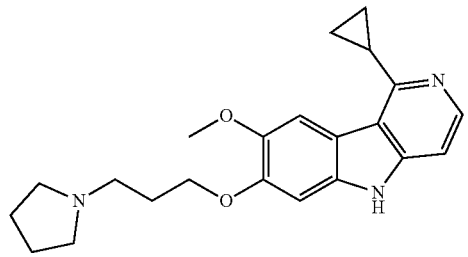 [SMILES: COc1cc2c(cc1OCCCN1CCCC1)[nH]c1ccnc(C3CC3)c12]

The title compound was prepared as described in Example 7, modifying Step 1 as follows. MS (ESI, pos. ion) m/z: 366.0.0 (M+1).

Step 1

A mixture of tert-butyl 7-(benzyloxy)-1-chloro-8-methoxy-5H-pyrido[4,3-b]indole-5-carboxylate (100 g, 0.23 mol), cyclopropylboronic acid (69 g, 0.80 mol), tricyclohexylphosphane (6 mg, 0.02 mmol), and potassium phosphate tribasic (97 mg, 0.46 mmol) in toluene (1.1 mL) and water (0.06 mL) was purged with nitrogen for 10 minutes. Palladium acetate (5.1 mg; 0.02 mmol) was then added, and the sealed vial was heated to 100° C. for 5 h. The mixture was diluted with ethyl acetate and washed with water and brine. The organic layer was dried over MgSO$_4$, filtered and concentrated under reduced pressure. The resulting residue was purified by silica gel column eluting with 0-60% ethyl acetate in hexanes to obtain tert-butyl 7-(benzyloxy)-1-cyclopropyl-8-methoxy-5H-pyrido[4,3-b]indole-5-carboxylate (90 mg, 88%) as an off-white solid.

Example 18

Synthesis of 1-[3-({8-methoxy-5H-pyrimido[5,4-b]indol-7-yl}oxy)propyl]pyrrolidine

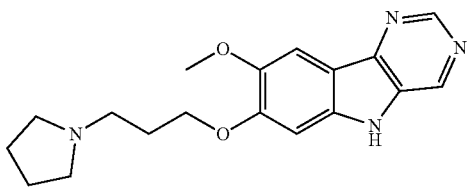 [SMILES: COc1cc2c(cc1OCCCN1CCCC1)[nH]c1cncnc12]

Step 1

A mixture of 1-{3-[2-methoxy-5-nitro-4-(tetramethyl-1,3,2-dioxaborolan-2-yl)phenoxy]propyl}pyrrolidine (500 mg, 1.23 mmol), 4,5-dichloropyrimidine (220 mg, 1.48 mmol), Pd(amphos)Cl$_2$ (59 mg, 0.08 mmol), and 2M sodium carbonate (1.23 mL, 2.46 mmol) in 1,4-dioxane (5 mL) was purged with N2 for 6 min. The resulting mixture was sealed and left stirring at 90° C. for 45 minutes. The resulting mixture was cooled to room temperature, diluted with water and extracted with ethyl acetate. The combined organic layers were washed with water. After removal of the organic solvents under reduced pressure, the residue was purified by flash chromatography on silica gel column eluted with 0-100% solvent A in CH$_2$Cl$_2$ (solvent A: 0.2% NH$_4$OH/10% MeOH/88.9% CH$_2$Cl$_2$) to provide 5-chloro-4-{5-methoxy-2-nitro-4-[3-(pyrrolidin-1-yl)propoxy]phenyl}-pyrimidine as a brown solid (422 mg, 87%).

Step 2

A mixture of 5-chloro-4-{5-methoxy-2-nitro-4-[3-(pyrrolidin-1-yl)propoxy]phenyl}-pyrimidine (420 mg, 1.07 mmol) in ethyl acetate (5 mL) was added into a vial charged with anhydrous SnCl$_2$ (439 mg, 2.3 mmol). This mixture was left stirring at 95° C. for 2 h. To the mixture was added additional anhydrous SnCl$_2$ (200 mg, 1.04 mmol) and ethyl acetate (2.5 mL). The resulting mixture was sealed and allowed to stir at 65° C. for 24 h. The crude solution was cooled to room temperature, treated with water and then 20% aqueous NaOH. The mixture was extracted with a mixture solvent of 25% $^i$PrOH/75% chloroform thrice. After removal of the organic solvents under reduced pressure, the residue was purified by flash chromatography on silica gel column eluted with 0-100% solvent A in solvent B (solvent A: 0.2% NH$_4$OH/10% MeOH/88.9% CH$_2$Cl$_2$; solvent B: 1% NH$_4$OH/99% MeOH) to provide 2-(5-chloropyrimidin-4-yl)-4-methoxy-5-[3-(pyrrolidin-1-yl)propoxy]aniline (150 mg, 39%) as a brown syrup.

Step 3

A mixture of 2-(5-chloropyrimidin-4-yl)-4-methoxy-5-[3-(pyrrolidin-1-yl)propoxy]aniline (120 mg, 0.33 mmol), potassium tert-butoxide (371 mg, 3.31 mmol), and Brettphos G1 (34 mg, 0.04 mmol) in 1,4-dioxane (10 mL) was purged with N2 for 5 minutes. The resulting mixture was sealed and allowed to stir at 90° C. for 45 minutes. The crude mixture was cooled to room temperature and treated with water. After removal of the volatiles under reduced pressure, the residue was dissolved in DMSO (6 mL) filtered through a small pad of celite, and purified by prep-HPLC (Prep-C18, Phenomenex Luna column, 21.2×250 mm; gradient elution of 0-60% MeCN in water over a 16 min period, where water contains 0.1% HCl, flow rate: 20 mL/min) to provide the title compound (1-[3-({8-methoxy-5H-pyrimido[5,4-b]indol-7-yl}oxy)propyl]pyrrolidine (34 mg, 32%). MS (ESI, pos. ion) m/z: 327.0.0 (M+1).

Example 19

3-{8-methoxy-7-[3-(pyrrolidin-1-yl)propoxy]-5H-pyrido[4,3-b]indol-1-yl}-8-oxa-3-azabicyclo[3.2.1]octane

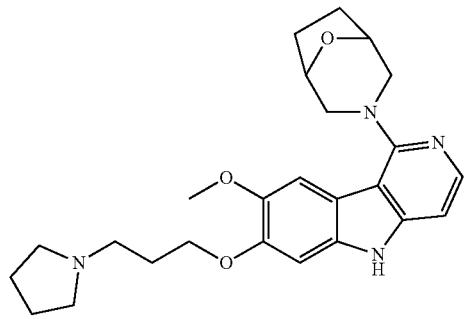 [SMILES: COc1cc2c(cc1OCCCN1CCCC1)[nH]c1ccnc(N3CC4CCC(C3)O4)c12]

The title compound was prepared as described in Example 36, Steps 1-4, but substituting (3S)-3-pyrrolidinol with 8-oxa-3-azabicyclo[3.2.1]octane. MS (ESI, pos. ion) m/z: 437.1 (M+1).

Example 20

N-(2-ethoxyethyl)-8-methoxy-7-[3-(pyrrolidin-1-yl)propoxy]-5H-pyrido[4,3-b]indol-1-amine

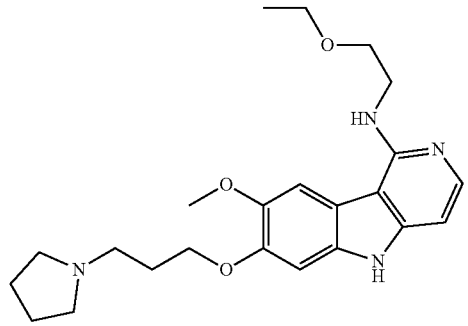 [SMILES: CCOCCNc1nccc2[nH]c3cc(OCCCN4CCCC4)c(OC)cc3c12]

Step 1

Combined 7-(benzyloxy)-4-chloro-1-fluoro-8-methoxy-5H-pyrido[4,3-b]indole (600 mg, 1.68 mmol), 2-ethoxyethylamine (450 mg, 5.05 mmol), and Hunig's base (0.29 mL, 1.68 mmol) in NMP (6 mL) in a microwave vial. Heated the reaction to 120° C. for 5 hours in the microwave. Concentrated under reduced pressure and purified resulting residue by silica gel column using 0% to 50% ethyl acetate in hexanes to afford 7-(benzyloxy)-4-chloro-N-(2-ethoxyethyl)-8-methoxy-5H-pyrido[4,3-b]indol-1-amine (320 mg; 44%).

Step 2

Di-tert-butyl dicarbonate (522 mg, 2.39 mmol) was added to a solution containing 7-(benzyloxy)-4-chloro-N-(2-ethoxyethyl)-8-methoxy-5H-pyrido[4,3-b]indol-1-amine (340 mg, 0.80 mmol) and DMAP (20 mg, 0.16 mmol) in acetonitrile (4 mL). Heated the reaction to 45° C. for 1 hour. Concentrated and purified by silica gel column using 0% to 30% ethyl acetate in hexanes to afford tert-butyl 7-(benzyloxy)-1-{[(tert-butoxy)carbonyl] (2-ethoxyethyl)amino}-4-chloro-8-methoxy-5H-pyrido[4,3-b]indole-5-carboxylate (150 mg, 30%).

Step 3

Combined tert-butyl 7-(benzyloxy)-1-{[(tert-butoxy)carbonyl] (2-ethoxyethyl)amino}-4-chloro-8-methoxy-5H-pyrido[4,3-b]indole-5-carboxylate (150 mg, 0.24 mmol) and 10% wt palladium on carbon (25 mg, 0.02 mmol) in methanol (2.40 mL). Stirred under hydrogen gas via balloon for 1 hour. Filtered thru a plug of Celite and concentrated under reduced pressure to afford tert-butyl 1-{[(tert-butoxy)carbonyl] (2-ethoxyethyl)amino}-7-hydroxy-8-methoxy-5H-pyrido[4,3-b]indole-5-carboxylate (120 mg, 99%).

Step 4

Combined tert-butyl 1-{[(tert-butoxy)carbonyl](2-ethoxyethyl)amino}-7-hydroxy-8-methoxy-5H-pyrido[4,3-b]indole-5-carboxylate (120 g, 0.24 mol), 1-(3-chloropropyl)pyrrolidine hydrochloride (88 mg, 0.48 mmol), and potassium carbonate (132 mg, 0.96 mmol) in DMF (2.4 mL). Heated the reaction to 100° C. for 16 hours. Diluted reaction with water. Washed aqueous layer with ethyl acetate. Combined organics, dried with $MgSO_4$, filtered, and concentrated under reduced pressure. Purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the title compound (65 mg, 56%). $^1$H NMR (400 MHz, Methanol-d4) δ 7.91 (s, 1H), 7.67 (d, J=7.0 Hz, 1H), 7.26 (s, 1H), 7.11 (d, J=7.0 Hz, 1H), 4.28 (t, J=5.5 Hz, 2H), 4.03 (s, 3H), 3.92-3.76 (m, 4H), 3.58 (q, J=7.0 Hz, 2H), 3.50 (t, J=7.0 Hz, 2H), 3.16 (dt, J=10.0, 7.5 Hz, 2H), 2.34 (dq, J=12.6, 6.5, 6.0 Hz, 2H), 2.26-2.14 (m, 2H), 2.13-1.98 (m, 2H), 1.16 (t, J=7.0 Hz, 3H). MS (ESI, pos. ion) m/z: 413.4 (M+1).

Example 21

1-[3-({8-methoxy-1-propyl-5H-pyrido[4,3-b]indol-7-yl}oxy)propyl]pyrrolidine hydrochloride

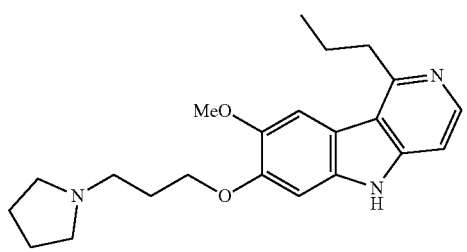 [SMILES: CCCc1nccc2[nH]c3cc(OCCCN4CCCC4)c(OC)cc3c12]

Step 1

A flask charged with a mixture of tert-butyl 7-(benzyloxy)-1-cyclopropyl-8-methoxy-5H-pyrido[4,3-b]indole-5-carboxylate, Reference 8, step 1 (1.77 g; 3.98 mmol; 1.00 eq.) and palladium on carbon (0.88 g; 0.83 mmol; 0.21 eq.) in MeOH (60 mL) was purged with N2 for 10 min, followed by hydrogen gas via balloon for 22 hours. The reaction mixture was filtered through a small pad of celite and rinsed with MeOH. The organic solutions were combined. After removal of the organic solvents under reduced pressure, the resulting residue was purified by flash chromatography on silica gel column eluted with 0-100% EtOAc in Hexanes to provide tert-butyl 7-hydroxy-8-methoxy-1-propyl-5H-pyrido[4,3-b]indole-5-carboxylate as white solid (0.52 g) and tert-butyl 1-cyclopropyl-7-hydroxy-8-methoxy-5H-pyrido[4,3-b]indole-5-carboxylate as white solid (0.78).

Step 2

To a vial charged with tert-butyl 7-hydroxy-8-methoxy-1-propyl-5H-pyrido[4,3-b]indole-5-carboxylate (44.00 mg; 0.14 mmol; 1.00 eq.) was added a solution of (tributylphosphoranylidene)acetonitrile (130.76 mg; 0.54 mmol) in $CH_2Cl_2$ (0.5 mL). The mixture was allowed to stir at 60° C. with N2 line to blow off the solvents completely. To the resulting residue was added 3-(pyrrolidin-1-yl)propan-1-ol (58.18 mg; 0.45 mmol; 1.50 eq.) in $CH_2Cl_2$ (0.3 mL). After removal of the solvent under N2 line, the vial was sealed and the residue was allowed to be heated at 60° C. for 1 hour. The mixture was purified by flash chromatography on silica gel column eluted with 0-100% solvent A (solvent A: 0.3% $NH_4OH$/10% MeOH/89.7% $CH_2Cl_2$) in $CH_2Cl_2$ to provide tert-butyl 8-methoxy-1-propyl-7-[3-(pyrrolidin-1-yl)propoxy]-5H-pyrido[4,3-b]indole-5-carboxylate as a colorless solid (38 mg, 63%). MS (ESI, pos. ion) m/z: 468.2 (M+1).

Step 3

A mixture of tert-butyl 8-methoxy-1-propyl-7-[3-(pyrrolidin-1-yl)propoxy]-5H-pyrido[4,3-b]indole-5-carboxylate (38 mg, 0.08 mmol) in TFA (2.0 mL) was allowed to stir at 90° C. for 20 min. The resulting mixture was allowed to cool to room temperature and the residue was purified by Prep HPLC (Waters XSelect CSH C18 column, 19×150 mm; gradient elution of 0-40% $CH_3CN$ in water 0.1% formic acid over a 20 min period, flow rate 28 ml/min) to provide the title compound (11 mg, 28%). $^1$H NMR (400 MHz, DMSO-$d_6$) δ 13.09 (s, 1H), 10.76 (s, 1H), 8.35 (d, J=6.7 Hz, 1H), 7.78 (d, J=6.7 Hz, 1H), 7.58 (s, 1H), 7.32 (s, 1H), 4.21 (t, J=6.1 Hz, 2H), 3.91 (s, 3H), 3.58-3.44 (m, 4H), 3.27 (s, 2H), 3.00 (s, 2H), 2.23 (dq, J=12.7, 6.4 Hz, 2H), 1.98 (d, J=7.7 Hz, 2H), 1.87 (h, J=7.2 Hz, 4H), 0.99 (t, J=7.3 Hz, 3H). MS (ESI, pos. ion) m/z: 368.1 (M+1).

Example 22

1-[3-({6-methoxy-9H-pyrimido[4,5-b]indol-7-yl}oxy)propyl]pyrrolidine hydrochloride

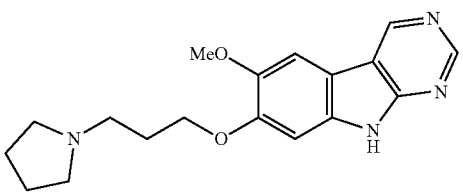 [SMILES: COc1cc2c(cc1OCCCN1CCCC1)[nH]c1ncncc12]

Step 1

To a mixture of 1-(benzyloxy)-4-bromo-2-methoxy-5-nitrobenzene, Reference 1 (2.0 g; 5.91 mmol; 1.00 eq.), 5-pyrimidinylboronic acid (1.1 mg; 8.87 mmol; 1.50 eq.), Pd(dppf)$_2$Cl$_2$—$CH_2Cl_2$ (483.00 mg; 0.59 mmol; 0.10 eq.) and cesium carbonate (3.85 mg; 11.83 mmol; 2.00 eq.) in DMF (12 mL) was added saturated aqueous $NaHCO_3$ (5 mL). The mixture was purged with N2 for 5 min, sealed and allowed to stir at 120° C. under N2 for 30 min. The resulting reaction mixture was allowed to cool to rt, diluted with water and extracted with 25% $^i$PrOH/chloroform thrice. The organic solutions were combined. After removal of the volatiles under reduced pressure, the residue was purified by flash chromatography on silica gel column eluted 0-100% solvent A (solvent A: 0.3% NH₄OH/10% MeOH/89.7% CH₂Cl₂) in CH₂Cl₂ to provide 5-[4-(benzyloxy)-5-methoxy-2-nitrophenyl]pyrimidine (2.05 g) as colorless syrup. MS (ESI, pos. ion) m/z: 338.2 (M+1).

Step 2

To a vial charged with 5-[4-(benzyloxy)-5-methoxy-2-nitrophenyl]pyrimidine (1.20 g, 3.56 mmol, 1.00 eq.) was added triethyl phosphite (5 mL). This mixture was sealed and allowed to stir at 120° C. for 30 h. After removal of the volatiles under reduced pressure, the residue was subjected to 25 g silica gel column for purification using 0-100% solvent A (solvent A: 0.3% NH₄OH/10% MeOH/89.7% CH₂Cl₂) in CH₂Cl₂ to provide 7-(benzyloxy)-6-methoxy-9H-pyrimido[4,5-b]indole as brown syrup (387 mg, 35%). MS (ESI, pos. ion) m/z: 306.1 (M+1).

Step 3

A mixture of 7-(benzyloxy)-6-methoxy-9H-pyrimido[4,5-b]indole (0.370 g, 1.21 mmol, 1.00 eq.), di-tert-butyl carbonate (310 mg, 1.82 mmol, 1.5 eq.), N,N-dimethylpyridin-4-amine (145 mg, 1.21 mmol, 1.0 eq.) in CH₂Cl₂ (4 mL) and Et₃N (1 mL) was allowed to stir at rt for 12 hr. After removal of the volatiles under reduced pressure, the residue was subjected to 10 g silica gel column for purification using 0-50% solvent A (solvent A: 0.3% NH₄OH/10% MeOH/89.7% CH₂Cl₂) in CH₂Cl₂ to provide tert-butyl 7-(benzyloxy)-6-methoxy-9H-pyrimido[4,5-b]indole-9-carboxylate as colorless solid (284 mg, 58%). MS (ESI, pos. ion) m/z: 306.0 (M-100+1).

Step 4

A suspension of tert-butyl 7-(benzyloxy)-6-methoxy-9H-pyrimido[4,5-b]indole-9-carboxylate (283.00 mg; 0.70 mmol) and Pd/C (80 mg) in MeOH (10 mL) was purged with N2 followed with H₂ for 5 mins respectively. The mixture was allowed to stir at rt for 3.0 h. The solid was filtered off through a small pad of celite and washed with MeOH thrice. The organic solutions were combined. Removal of the volatiles under reduced pressure provide tert-butyl 7-hydroxy-6-methoxy-9H-pyrimido[4,5-b]indole-9-carboxylate as a crude solid (185 mg, 85%). MS (ESI, pos. ion) m/z: 215.8 (M-100+1).

Step 5

The title compound was made from tert-butyl 7-hydroxy-6-methoxy-9H-pyrimido[4,5-b]indole-9-carboxylate following a synthetic sequence similar as described for Example 21. The crude product was purified with preparative HPLC (Prep-C18, Waters SunFire column, 19×150 mm; gradient elution of 0-40% CH₃CN in water over a 20 min period, where both solvents contain 0.1% HCl) to provide the title compound. ¹H NMR (400 MHz, DMSO-d₆) δ 13.53 (br, 1H), 10.85 (br, 1H), 9.60 (s, 1H), 9.18 (s, 1H), 8.01 (s, 1H), 7.21 (s, 1H), 4.21 (t, J=6.1 Hz, 2H), 3.86 (s, 3H), 3.55 (m, 2H), 3.28 (m, 2H), 2.99 (dq, J=10.3, 7.3 Hz, 2H), 2.23 (dq, J=12.7, 6.3 Hz, 2H), 2.04-1.77 (m, 4H); MS (ESI, pos. ion) m/z: 326.8 (M+1).

Example 23

4-{8-methoxy-7-[3-(pyrrolidin-1-yl)propoxy]-5H-pyrido[4,3-b]indol-1-yl}pyridine bishydrochloride

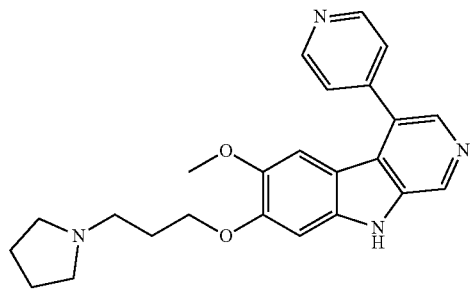 [SMILES: COc1cc2c(cc1OCCCN1CCCC1)[nH]c1cncc(-c3ccncc3)c12]

The title compound was prepared as described in Example 24, Steps 1-4, but substituting 4-pyridinylboronic acid with 3-pyridinylboronic acid. ¹H NMR (400 MHz, DMSO-d6) δ 13.58 (s, 1H), 11.06 (s, 1H), 9.10-9.04 (m, 2H), 8.58 (d, J=6.6 Hz, 1H), 8.16-8.10 (m, 2H), 8.01 (d, J=6.6 Hz, 1H), 7.34 (s, 1H), 6.88 (s, 1H), 4.21-4.19 (m, 2H), 3.60 (s, 3H), 3.56-3.48 (m, 2H), 3.29-3.21 (m, 2H), 3.01-2.91 (m, 2H), 2.26-2.18 (m, 2H), 1.99-1.81 (m, 4H). MS (ESI, pos. ion) m/z: 403.3 (M+1).

Example 24

3-{8-methoxy-7-[3-(pyrrolidin-1-yl)propoxy]-5H-pyrido[4,3-b]indol-1-yl}pyridine bishydrochloride

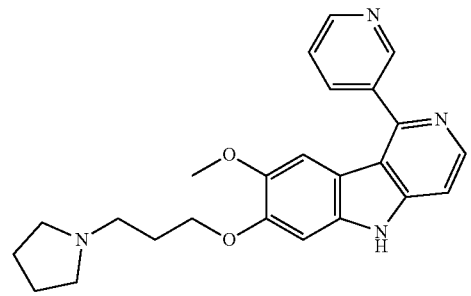 [SMILES: COc1cc2c(cc1OCCCN1CCCC1)[nH]c1ccnc(-c3cccnc3)c12]

Step 1

Tert-butyl 7-(benzyloxy)-1-chloro-8-methoxy-5H-pyrido[4,3-b]indole-5-carboxylate, Reference 5 (0.10 g; 0.23 mmol; 1.00 eq.) and 3-pyridinylboronic acid (33.61 mg; 0.27 mmol; 1.20 eq.) were suspended in 1,2-dimethoxyethane (3.5 mL). The mixture was purged with argon gas. Water (0.6 mL) and sodium carbonate solution (0.46 mL; 2.50 mol/L; 1.14 mmol; 5.00 eq.) were added next. Tetrakis(triphenylphosphane)palladium (13.16 mg; 0.01 mmol; 0.05 eq.) was then added and the reaction vessel was sealed and stirred in a heat block at 100° C. After 6 h, the reaction was cooled and found to be an ~4:1 mixture of des-Boc:N-Boc product. The reaction mixture was partitioned into ethyl acetate, water and sodium bicarbonate solution. The phases were separated, the aqueous phase was extracted 2× more with ethyl acetate, and the combined organic phases were dried over magnesium sulfate. After evaporation the mixture was purified by silica gel chromatography (10-80% ethyl acetate/dichloromethane, then 0-10% methanol/dichloromethane) to give a residue of tert-butyl 7-(benzyloxy)-8-methoxy-1-(pyridin-3-yl)-5H-pyrido[4,3-b]indole-5-carboxylate (40 mg, 14%) MS (ESI, pos. ion) m/z: 482.3 (M+1). and a solid of 3-[7-(benzyloxy)-8-methoxy-5H-pyrido[4,3-b]indol-1-yl]pyridine (210 mg, 85%). MS (ESI, pos. ion) m/z: 482.3 (M+1).

Step 2

3-[7-(benzyloxy)-8-methoxy-5H-pyrido[4,3-b]indol-1-yl]pyridine (0.21 g; 0.56 mmol; 1.00 eq.) was suspended in 1,4-dioxane (6 mL). Hunig's base (0.20 mL; 1.13 mmol; 2.00 eq.), di-tert-butyl dicarbonate (0.18 g; 0.85 mmol; 1.50 eq.) in 1,4-dioxane (1 mL) and N,N-dimethylaminopyridine (6.89 mg; 0.06 mmol; 0.10 eq.) were added and the reaction was stirred at 30° C. for 16 h. The solution was then partitioned into ethyl acetate, water and sodium bicarbonate solution. The phases were separated. The aqueous phase was extracted with ethyl acetate. The combined organic phases were washed with sodium chloride solution and dried over magnesium sulfate. After evaporation the residue was purified by silica gel chromatography (10%-80% ethyl acetate/dichloromethane) to give a film of tert-butyl 7-(benzyloxy)-8-methoxy-1-(pyridin-3-yl)-5H-pyrido[4,3-b]indole-5-carboxylate (266 mg, 98%). MS (ESI, pos. ion) m/z: 482.3 (M+1).

Step 3

Tert-butyl 7-(benzyloxy)-8-methoxy-1-(pyridin-3-yl)-5H-pyrido[4,3-b]indole-5-carboxylate (308.00 mg; 0.64 mmol; 1.00 eq.) was dissolved in ethanol (7 mL). 10% Palladium on carbon (10.21 mg; 0.01 mmol; 0.01 eq.) (Aldrich 10%) was carefully added and the reaction vessel was then charged with an $H_2$ balloon. After 1.5 h, more palladium on carbon (10.21 mg; 0.01 mmol; 0.01 eq.) was added and the reaction stirred for 14 h. Over the next 9 h, two more portions or palladium on carbon were added (85 mg total) and the reaction was allowed to stir for 14 h more. The mixture was then purged with nitrogen gas, filtered through Celite, rinsed through with methanol and evaporated to a foamy residue of tert-butyl 7-hydroxy-8-methoxy-1-(pyridin-3-yl)-5H-pyrido[4,3-b]indole-5-carboxylate (226 mg, 95%). MS (ESI, pos. ion) m/z: 392.2 (M+1).

Step 4

Tert-butyl 7-hydroxy-8-methoxy-1-(pyridin-3-yl)-5H-pyrido[4,3-b]indole-5-carboxylate (226.00 mg; 0.58 mmol; 1.00 eq.) was dissolved in N,N-dimethylformamide (6 mL). 1-(3-Chloropropyl)pyrrolidin-1-ium chloride (159.45 mg; 0.87 mmol; 1.50 eq.) and potassium carbonate (278.88 mg; 2.02 mmol; 3.50 eq.) were added and the reaction was then stirred in a heat block at 98° C. After 13 h, The mixture was partitioned into ethyl acetate, water and sodium bicarbonate solution. The phases were separated, the aqueous phase was extracted 3× more with ethyl acetate, the combined organic phases washed with sodium chloride solution and dried over magnesium sulfate. After evaporation the residue was dissolved in dichloromethane (6 mL) and trifluoroacetic acid (2.90 mL; 0.20 mol/L; 0.58 mmol; 1.00 eq.) was added slowly. The reaction was evaporated to dryness after 1.5 h and then toluene (20 mL) was added. The residue was triturated, and the solvent was evaporated. The residue was purified by reverse phase chromatography (Phenomenex Luna C18, 21×250 mm, 0-50% acetonitrile/0.1% aqueous HCl gradient over 10 minutes, flow rate 28 ml/min) to give a yellow solid of 3-{8-methoxy-7-[3-(pyrrolidin-1-yl)propoxy]-5H-pyrido[4,3-b]indol-1-yl}pyridine bishydrochloride (102 mg, 37%). $^1$H NMR (400 MHz, DMSO-d6) δ 15.46 (s, 1H), 13.56 (s, 1H), 11.07 (s, 1H), 9.19 (d, J=2.2 Hz, 1H), 9.02 (dd, J=5.0, 1.6 Hz, 1H), 8.60 (d, J=6.7 Hz, 1H), 8.53 (dt, J=8.0, 2.0 Hz, 1H), 8.02 (d, J=6.6 Hz, 1H), 7.92 (dd, J=7.9, 5.0 Hz, 1H), 7.37 (s, 1H), 6.83 (s, 1H), 4.23 (t, J=6.2 Hz, 2H), 3.62-3.52 (m, 5H), 3.32-3.24 (m, 2H), 3.05-2.96 (m, 2H), 2.29-2.21 (m, 2H), 2.04-1.84 (m, 4H). MS (ESI, pos. ion) m/z: 403.3 (M+1).

Example 25

2-{8-methoxy-7-[3-(pyrrolidin-1-yl)propoxy]-5H-pyrido[4,3-b]indol-1-yl}pyridine bishydrochloride

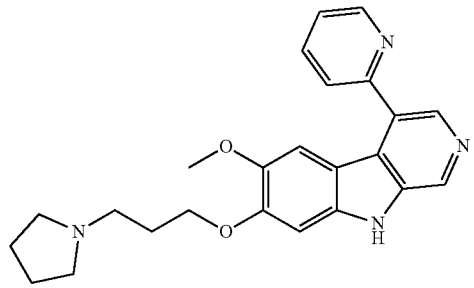 [SMILES: COc1cc2c(cc1OCCCN1CCCC1)[nH]c1cncc(-c3ccccn3)c12]

Step 1

Tert-butyl 7-(benzyloxy)-1-chloro-8-methoxy-5H-pyrido[4,3-b]indole-5-carboxylate (0.25 g; 0.57 mmol; 1.00 eq.) (intermediate-) was suspended in 1,4-dioxane (7 mL) The mixture was purged with argon gas. 2-(Tributylstannyl)pyridine (0.20 mL; 0.63 mmol; 1.10 eq.) and then tetrakis(triphenylphosphane) palladium (65.82 mg; 0.06 mmol; 0.10 eq.) were added and the reaction was sealed and stirred in a heat block at 105° C. After 3.5 h, the reaction was cooled and found to have a mixture of 5:1 N-Boc product and des-Boc product. The reaction was then filtered through Celite, rinsed through with ethyl acetate and evaporated. The residue was purified by silica gel chromatography (10-67% ethyl acetate/dichloromethane, then 0-10% methanol/dichloromethane) to give a solid of tert-butyl 7-(benzyloxy)-8-methoxy-1-(pyridin-2-yl)-5H-pyrido[4,3-b]indole-5-carboxylate (~0.25 g). MS (ESI, pos. ion) m/z: 482.2 (M+1).

Step 2

Tert-butyl 7-(benzyloxy)-8-methoxy-1-(pyridin-2-yl)-5H-pyrido[4,3-b]indole-5-carboxylate (308.00 mg; 0.64 mmol; 1.00 eq.) was suspended in ethanol (7 mL). 10% Palladium on carbon (10.21 mg; 0.01 mmol; 0.01 eq.) (Aldrich 10%) was added carefully and the reaction vessel was charged with an $H_2$ balloon. After 30 m, more palladium on carbon (10.21 mg; 0.01 mmol; 0.01 eq.) was added and the reaction stirred for 14 h. Over the next 6 d, seven more portions of palladium on carbon were added (485 mg total) and the reaction was stirred further for 21 h. The reaction was then purged with nitrogen gas, filtered through Celite, rinsed through with methanol and ethanol, and evaporated. The crude was purified by silica gel chromatography (0-10% methanol/dichloromethane) to separate over-reduced products. Tert-butyl 7-hydroxy-8-methoxy-1-(pyridin-2-yl)-5H-pyrido[4,3-b]indole-5-carboxylate (146 mg, 58%) was isolated as a glassy residue.

Step 3

Tert-butyl 7-hydroxy-8-methoxy-1-(pyridin-2-yl)-5H-pyrido[4,3-b]indole-5-carboxylate (146.00 mg; 0.37 mmol; 1.00 eq.) was dissolved in N,N-dimethylformamide (4 mL). 1-(3-chloropropyl)pyrrolidin-1-ium chloride (103.01 mg; 0.56 mmol; 1.50 eq.) and potassium carbonate (180.16 mg; 1.31 mmol; 3.50 eq.) were added and the mixture was stirred in a heat block at 98° C. After 5.5 h, the reaction was cooled and partitioned into ethyl acetate, water and sodium bicarbonate solution. The phases were separated, the aqueous phase was extracted 3× more with ethyl acetate, the combined organic phases were washed with sodium chloride solution and dried over magnesium sulfate. Solvent was evaporated and the residue was dissolved in dichloromethane (4 mL). Trifluoroacetic acid (1.85 mL; 0.20 mol/L; 0.37 mmol; 0.99 eq.) was added slowly and the solution was stirred for 3 h. The reaction was evaporated to dryness and then toluene (20 mL) was added. The residue was triturated, solvent was evaporated and then purified by reverse phase chromatography (Waters XSelect CSH C18 column, 19×250 mm, 0-65% acetonitrile/0.1% aqueous HCl gradient over 10 minutes, flow rate 28 ml/min) to give an orange solid of 2-{8-methoxy-7-[3-(pyrrolidin-1-yl)propoxy]-5H-pyrido[4,3-b]indol-1-yl}pyridine bishydrochloride (77 mg, 43%). $^1$H NMR (400 MHz, DMSO-d6) δ 13.43 (s, 1H), 10.86 (s, 1H), 9.08-9.03 (m, 1H), 8.57 (d, J=6.7 Hz, 1H), 8.32-8.23 (m, 2H), 8.03 (d, J=6.6 Hz, 1H), 7.83 (ddd, J=6.8, 4.8, 1.9 Hz, 1H), 7.46 (s, 1H), 7.36 (s, 1H), 4.25 (t, J=6.2 Hz, 2H), 3.60-3.55 (m, 2H), 3.33-3.26 (m, 2H), 3.06-2.96 (m, 2H), 2.30-2.21 (m, 2H), 2.06-1.95 (m, 2H), 1.95-1.84 (m, 2H). MS (ESI, pos. ion) m/z: 403.3 (M+1).

Example 26

1-[3-({6-methoxy-5H-pyrido[3,2-b]indol-7-yl}oxy)propyl]pyrrolidine hydrochloride

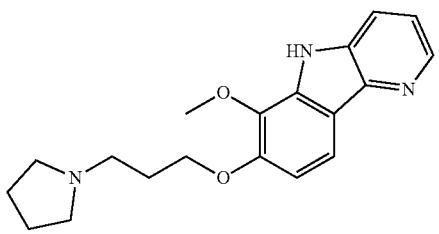 [SMILES: COc1c(OCCCN2CCCC2)ccc2c1[nH]c1cccnc12]

Example 27

1-[3-({8-methoxy-5H-pyrido[3,2-b]indol-7-yl}oxy)propyl]pyrrolidine hydrochloride

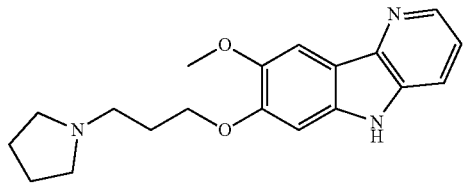 [SMILES: COc1cc2c(cc1OCCCN1CCCC1)[nH]c1cccnc12]

Step 1

4-bromo-2-methoxyphenol (1.50 g, 7.39 mmol), bis(pinacolato)diboron (2.44 g, 9.6 mmol), potassium acetate (2.18 g, 22.2 mmol), and Pd(dppf)$_2$Cl$_2$.DCM (150.83 mg, 0.2 mmol) in 1,4-dioxane (8.0 mL) were combined in a microwave vial. The mixture was heated to 130° C. for 1 hour in a microwave reactor. The mixture was then filtered throughout a plug of Celite and concentrated under reduced pressure to afford 2-methoxy-4-(4,4,5,5-tetramethyl-1,3,2-dioxaborolan-2-yl)phenol (1.84 g, 100%) as a crude oil.

Step 2

2-methoxy-4-(4,4,5,5-tetramethyl-1,3,2-dioxaborolan-2-yl)phenol (1.84 g, 8.1 mmol), 2-bromo-3-nitropyridine (1 65 g, 8.1 mmol), potassium acetate (2.18 g, 22.2 mmol), and Pd(dppf)$_2$Cl$_2$.DCM (181.00 mg, 0.2 mmol) were combined in DMF (8.0 mL) in a microwave vial. The mixture was heated to 130° C. for 30 minutes in a microwave reactor. The mixture was filtered through a plug of Celite, and then concentrated. The residue was purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford 2-methoxy-4-(3-nitropyridin-2-yl)phenol (0.40 g, 22%) as a white solid.

Step 3

2-methoxy-4-(3-nitropyridin-2-yl)phenol (0.40 g, 1.6 mmol), 1-(3-chloropropyl)pyrrolidine hydrochloride (0.30 g, 1.6 mmol) and potassium carbonate (0.68 g, 4.9 mmol) in DMF (10.0 mL) were combined, and then heated to 100° C. for overnight. The mixture was diluted with water, extracted with ethyl acetate, combined organics, dried with MgSO$_4$, filtered, concentrated under reduced pressure and purified by silica gel column using 0% to 10% MeOH in DCM to afford 2-{3-methoxy-4-[3-(pyrrolidin-1-yl)propoxy]phenyl}-3-nitropyridine (0.31 g, 53%).

Step 4

2-{3-methoxy-4-[3-(pyrrolidin-1-yl)propoxy]phenyl}-3-nitropyridine (0.10 g, 0.3 mmol) and triethyl phosphite (2.0 mL) were combined. The mixture was heated to 120° C. for 24 hours. The mixture was concentrated under reduced pressure and purified by prep HPLC (Prep-C18, Phenomenex Luna column, 21.2×250 mm; gradient elution of 0-60% MeCN in water over a 16 min period, where water contains 0.1% HCl, flow rate: 20 mL/min). The more polar compound is 1-[3-({8-methoxy-5H-pyrido[3,2-b]indol-7-yl}oxy)propyl]pyrrolidine (Example 26, 7.0 mg, 7%) MS (ESI, pos. ion) m/z: 326.5 (M+1). The less polar compound is 1-[3-({6-methoxy-5H-pyrido[3,2-b]indol-7-yl}oxy)propyl]pyrrolidine (Example 27, 18.0 mg, 17%) MS (ESI, pos. ion) m/z: 326.5 (M+1).

Example 28

1-[3-({6-methoxy-9H-pyrido[3,4-b]indol-7-yl}oxy)propyl]pyrrolidine hydrochloride

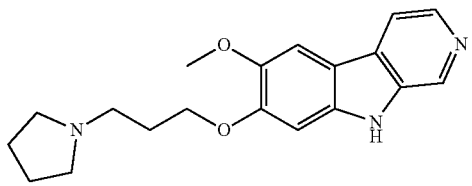 [SMILES: COc1cc2c(cc1OCCCN1CCCC1)[nH]c1cnccc12]

Step 1

1-(benzyloxy)-4-bromo-2-methoxy-5-nitrobenzene (0.40 g, 1.2 mmol), 4-pyridinylboronic acid (0.22 g; 1.8 mmol), 2M potassium carbonate (1.77 mL, 3.6 mmol) and Pd(dppf)$_2$Cl$_2$.DCM (24.2 mg, 0.03 mmol) were combined in DMF (2.0 mL) in a microwave vial. The mixture was heated in the microwave at 130° C. for 30 minutes. The mixture was filtered through a plug of Celite. The mixture was then diluted with water, and extracted with ethyl acetate. The combined organics were dried with MgSO₄, filtered, concentrated under reduced pressure and purified by silica gel column using 0% to 50% ethyl acetate in hexanes to obtain 4-[4-(benzyloxy)-5-methoxy-2-nitrophenyl]pyridine (0.30 g; 75%). MS (ESI, pos. ion) m/z: 337.2 (M+1).
Step 2
4-[4-(benzyloxy)-5-methoxy-2-nitrophenyl]pyridine (0.3 g, 0.9 mmol) and triethyl phosphite (2.0 mL) were combined, and the resulting mixture was heated to 130° C. for 24 hours. The reaction was cooled to room temperature, then concentrated under reduced pressure and purified by silica gel column using 0% to 75% ethyl acetate in hexanes to afford 7-(benzyloxy)-6-methoxy-9H-pyrido[3,4-b]indole (110.00 mg, 41%). MS (ESI, pos. ion) m/z: 305.2 (M+1).
Step 3
7-(benzyloxy)-6-methoxy-9H-pyrido[3,4-b]indole (110 mg, 0.36 mmol), DMAP (9 mg; 0.07 mmol), and di-tert-butyl dicarbonate (95 mg, 0.43 mmol) were combined in 1,4-dioxane (4.0 mL). The reaction stirred at room temperature for 1 hour., then concentrated under reduced pressure and purified by silica gel column using 0% to 45% ethyl acetate in hexanes to afford tert-butyl 7-(benzyloxy)-6-methoxy-9H-pyrido[3,4-b]indole-9-carboxylate (70.00 mg; 48%). MS (ESI, pos. ion) m/z: 348.9 (M-56).
Step 4
Tert-butyl 7-(benzyloxy)-6-methoxy-9H-pyrido[3,4-b]indole-9-carboxylate (70 mg, 0.17 mmol) and 10% palladium on carbon (18 mg, 0.02 mmol) were combined in methanol (2.0 mL). The mixture was stirred at room temperature in 1 atm of H₂ via balloon for 1 hour. The mixture was filtered through a plug of Celite and then concentrated to afford tert-butyl 7-hydroxy-6-methoxy-9H-pyrido[3,4-b]indole-9-carboxylate (54 mg, 99%). MS (ESI, pos. ion) m/z: 258.9 (M-56).
Step 5
Tert-butyl 7-hydroxy-6-methoxy-9H-pyrido[3,4-b]indole-9-carboxylate (54 mg, 0.2 mmol), 1-(3-chloropropyl)pyrrolidine hydrochloride (47 mg, 0.3 mmol), and potassium carbonate (71 mg, 0.5 mmol) were combined in DMF (3.0 mL). The mixture was heated to 100° C. for 16 hours. The mixture was diluted with water, and extracted with ethyl acetate. The combined organics were dried with MgSO₄, filtered and concentrated to afford the crude product. The resulting crude was treated with 1M HCl (1.0 mL), stirred for 1 hour and then purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the title compound (10 mg, 18%). MS (ESI, pos. ion) m/z: 326.0 (M+1).

Example 29

1-[3-({8-methoxy-1-methyl-5H-pyrido[4,3-b]indol-7-yl}oxy)propyl]pyrrolidine hydrochloride

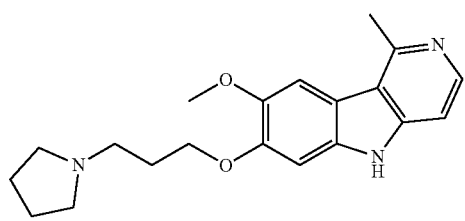 [SMILES: COc1cc2c(cc1OCCCN1CCCC1)[nH]c1ccnc(C)c12]

The title compound was prepared as described in Example 28, Steps 1-5 above, but substituting 4-pyridinylboronic acid with (2-methylpyridin-3-yl)boronic acid. MS (ESI, pos. ion) m/z: 340.0 (M+1).

Example 30

1-[3-({6-methoxy-9H-pyrido[2,3-b]indol-7-yl}oxy)propyl]pyrrolidine hydrochloride

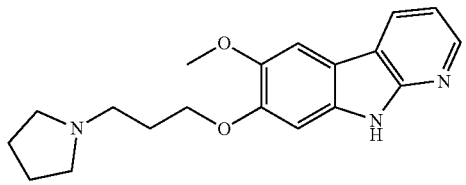 [SMILES: COc1cc2c(cc1OCCCN1CCCC1)[nH]c1ncccc12]

Step 1
1-(benzyloxy)-4-bromo-2-methoxy-5-nitrobenzene (0.62 g, 1.83 mmol), 3-pyridinylboronic acid (0.34 g; 2.75 mmol), Pd(dppf)₂Cl₂.DCM (37 mg; 0.05 mmol) and 2M potassium carbonate (2.8 mL, 5.50 mmol) were combined in DMF (2.00 mL) in a microwave vial. The reaction was heated to 130° C. for 30 minutes in the microwave. The mixture was diluted reaction with ethyl acetate and filtered throughout a plug of Celite. Water was then added, and the layers were separated. The aqueous layer was washed with ethyl acetate. The combined organics were dried with MgSO₄, filtered, concentrated and purified by silica gel using 0% to 50% ethyl acetate in hexanes to afford 3-(4-(benzyloxy)-5-methoxy-2-nitrophenyl)pyridine (0.31 g; 50%) as a dark oil. MS (ESI, pos. ion) m/z: 337.0 (M+1).
Step 2
3-(4-(benzyloxy)-5-methoxy-2-nitrophenyl)pyridine (0.31 g, 0.91 mmol) were combined in TFA for 16 hours. The mixture was concentrated under reduced pressure and purified by silica column using 0% to 80% ethyl acetate in hexanes to afford 2-methoxy-5-nitro-4-(pyridin-3-yl)phenol (0.1 g, 45%).
Step 3
2-methoxy-5-nitro-4-(pyridin-3-yl)phenol (0.1 g, 0.41 mmol), 1-(3-chloropropyl)pyrrolidine hydrochloride (92 mg, 0.61 mmol), and potassium carbonate (0.17 g, 1.22 mmol) were combined in DMF (2.0 mL). The mixture was heated to 100° C. for 18 hours, and then cooled to room temperature. Water was added to the mixture, and the mixture was then extracted with ethyl acetate. The combined organics were dried with MgSO₄, filtered, concentrated, and purified by silica gel column using 0% to 10% MeOH in DCM to afford 3-{5-methoxy-2-nitro-4-[3-(pyrrolidin-1-yl)propoxy]phenyl}pyridine (0.1 g, 69%). MS (ESI, pos. ion) m/z: 358.1 (M+1).
Step 4
3-{5-methoxy-2-nitro-4-[3-(pyrrolidin-1-yl)propoxy]phenyl}pyridine (0.1 g, 0.28 mmol) and triethyl phosphite (2.0 mL) were combined. The mixture was heated to 120° C. for 24 hours. The mixture as then concentrated under reduced pressure and purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the title compound (18.0 mg; 10%) MS (ESI, pos. ion) m/z: 326.0 (M+1).

Example 31

1-[3-({8-methoxy-5H-pyrido[4,3-b]indol-7-yl}oxy)propyl]pyrrolidine hydrochloride

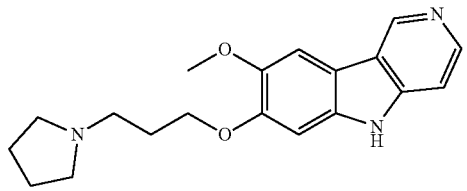 [SMILES: COc1cc2c(cc1OCCCN1CCCC1)[nH]c1ccncc12]

Tert-butyl 7-hydroxy-8-methoxy-5H-pyrido[4,3-b]indole-5-carboxylate, Reference 7 (300 mg; 0.95 mmol; 1.00 eq.), 1-(3-chloropropyl)pyrrolidine hydrochloride (262 mg; 1.43 mmol; 1.50 eq.) and potassium carbonate (395 mg; 2.86 mmol; 3.00 eq.) were combined in DMF (5 mL). The reaction was heated to 100° C. for 16 hours, then cooled to rt. The mixture was filtered through a plug of celite and concentrated. 1M HCl (5 mL) was added, and the mixture was heated to 50° C. for 1 hour. The mixture was concentrated under reduced pressure. The resulting residue was purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the title compound (90 mg; 24%). $^1$H NMR (400 MHz, Methanol-d4) δ 9.43 (d, J=0.8 Hz, 1H), 8.42 (dd, J=6.8, 0.9 Hz, 1H), 7.95 (s, 1H), 7.88 (dd, J=6.8, 0.7 Hz, 1H), 7.33 (s, 1H), 4.32 (t, J=5.5 Hz, 2H), 4.00 (s, 3H), 3.89-3.77 (m, 2H), 3.50 (t, J=7.1 Hz, 2H), 3.16 (ddt, J=10.9, 8.3, 4.6 Hz, 2H), 2.35 (ddd, J=12.7, 6.9, 5.3 Hz, 2H), 2.27-2.15 (m, 2H), 2.14-1.98 (m, 2H). MS (ESI, pos. ion) m/z: 326.2 (M+1).

Example 32

8-methoxy-7-[3-(pyrrolidin-1-yl)propoxy]-5H-pyrido[4,3-b]indol-3-amine hydrochloride

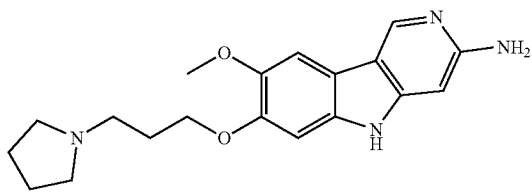 [SMILES: COc1cc2c(cc1OCCCN1CCCC1)[nH]c1cc(N)ncc12]

Example 33

6-methoxy-7-[3-(pyrrolidin-1-yl)propoxy]-9H-pyrido[2,3-b]indol-2-aminehydrochloride

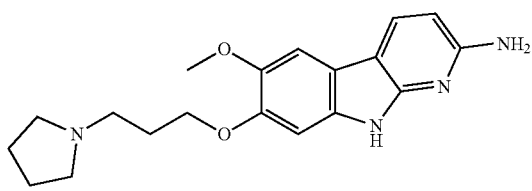 [SMILES: COc1cc2c(cc1OCCCN1CCCC1)[nH]c1nc(N)ccc12]

Step 1

5-(4,4,5,5-tetramethyl-1,3,2-dioxaborolan-2-yl)-2-pyridinylamine (0.3 g, 1.36 mmol), 1-[3-(4-bromo-2-methoxy-5-nitrophenoxy)propyl]pyrrolidine (0.5 g, 1.36 mmol), Pd(dppf)$_2$Cl$_2$.DCM (33 mg, 0.04 mmol), and 2M potassium carbonate (1.4 mL, 2.73 mmol) were combined in DMF (2.7 mL) in a microwave vial. The reaction was heated in a microwave to 120° C. for 1 hour. The mixture was diluted with water. The aqueous layer was washed with ethyl acetate. The combined organics were dried with MgSO$_4$, filtered, concentrated and purified by silica gel column using 0% to 10% MeOH in DCM to afford 5-{5-methoxy-2-nitro-4-[3-(pyrrolidin-1-yl)propoxy]phenyl}pyridin-2-amine (0.33 g, 65%) as a brown oil. MS (ESI, pos. ion) m/z: 373.2 (M+1).

Step 2

5-{5-methoxy-2-nitro-4-[3-(pyrrolidin-1-yl)propoxy]phenyl}pyridin-2-amine (180.00 g; 0.48 mmol; 1.00 eq.), di-tert-butyl dicarbonate (316.45 mg; 1.45 mmol; 3.00 eq.), and N,N-dimethylaminopyridine (11.81 mg; 0.10 mmol; 0.20 eq.) were combined in acetonitrile (4.83 mL). The reaction was heated to 50° C. for 1 hour, and then cooled to room temperature. The mixture was concentrated under reduced pressure and then purified by silica gel column using 0% to 10% MeOH in DCM to afford tert-butyl N-[(tert-butoxy)carbonyl]-N-(5-{5-methoxy-2-nitro-4-[3-(pyrrolidin-1-yl)propoxy]phenyl}pyridin-2-yl)carbamate (0.16 g, 57%).

Step 3

Tert-butyl N-[(tert-butoxy)carbonyl]-N-(5-{5-methoxy-2-nitro-4-[3-(pyrrolidin-1-yl)propoxy]phenyl}pyridin-2-yl)carbamate (0.16 g, 0.28 mmol) and triethyl phosphite (3.0 mL) were combined. The mixture was heated to 120° C. for 24 hours, and then cooled to room temperature. The mixture was concentrated under reduced pressure, and 1M HCl (3 mL) was added to the resulting residue. The aqueous layer was heated to 50° C. for 1 hour and then purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the more polar product 8-methoxy-7-[3-(pyrrolidin-1-yl)propoxy]-5H-pyrido[4,3-b]indol-3-amine hydrochloride (Example 32, 20.0 mg, 21%). $^1$H NMR (400 MHz, Methanol-d4) δ 8.54 (s, 1H), 7.68 (s, 1H), 7.07 (s, 1H), 6.67 (s, 1H), 4.25 (t, J=5.5 Hz, 2H), 3.94 (s, 3H), 3.81 (s, 2H), 3.48 (d, J=7.0 Hz, 2H), 3.14 (s, 2H), 2.36-2.25 (m, 2H), 2.20 (s, 2H), 2.06 (s, 2H). MS (ESI, pos. ion) m/z: 341.4 (M+1) and less polar product 6-methoxy-7-[3-(pyrrolidin-1-yl)propoxy]-9H-pyrido[2,3-b]indol-2-amine hydrochloride (Example 33, 9.0 mgs, 9%). $^1$H NMR (400 MHz, Methanol-d4) δ 8.40 (d, J=8.7 Hz, 1H), 7.57 (s, 1H), 7.15 (s, 1H), 6.58 (d, J=8.8 Hz, 1H), 4.23 (t, J=5.5 Hz, 2H), 3.94 (s, 3H), 3.88-3.75 (m, 2H), 3.48 (t, J=7.0 Hz, 2H), 3.21-3.07 (m, 2H), 2.34-2.24 (m, 2H), 2.19 (dq, J=11.0, 6.2, 4.5 Hz, 2H), 2.08 (ddt, J=13.9, 10.9, 4.7 Hz, 2H). MS (ESI, pos.ion) m/z: 340.9 (M+1).

Example 34

1-[3-({1-fluoro-8-methoxy-5H-pyrido[4,3-b]indol-7-yl}oxy)propyl]pyrrolidine hydrochloride

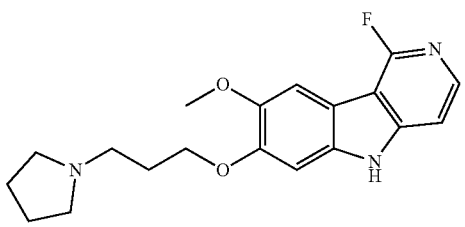 [SMILES: COc1cc2c(cc1OCCCN1CCCC1)[nH]c1ccnc(F)c12]

The title compound was prepared as described in Example 7, Steps 1-3 above, but substituting 5-(4,4,5,5-tetramethyl-1,3,2-dioxaborolan-2-yl)-2-pyridinylamine with (2-fluoropyridin-3-yl)boronic acid. MS (ESI, pos. ion) m/z: 344.0 (M+1).

Example 35

8-methoxy-1-methyl-7-[3-(pyrrolidin-1-yl)propoxy]-5H-pyrido[4,3-b]indol-3-amine hydrochloride

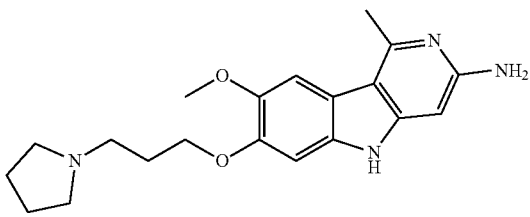 [SMILES: COc1cc2c(cc1OCCCN1CCCC1)[nH]c1cc(N)nc(C)c12]

Step 1

5-bromo-6-methylpyridin-2-amine (1.1 g, 5.88 mmol), di-tert-butyl dicarbonate (2.6 g, 11.76 mmol), and DMAP (0.14 g, 1.18 mmol) were combined in THF (20.0 mL), and the reaction was heated to 50° C. for 1 hour. The mixture was concentrated under reduced pressure and then purified resulting residue by silica gel using 0% to 30% ethyl acetate in hexanes to afford tert-butyl N-(5-bromo-6-methylpyridin-2-yl)-N-[(tert-butoxy)carbonyl]carbamate (2.1 g, 92%). $^1$H NMR (400 MHz, Acetonitrile-d3) δ 7.93 (d, J=8.4 Hz, 1H), 7.10 (dd, J=8.4, 0.7 Hz, 1H), 2.57 (s, 3H), 1.44 (s, 18H).

Step 2

Tert-butyl N-(5-bromo-6-methylpyridin-2-yl)-N-[(tert-butoxy)carbonyl]carbamate (1.4 g, 3.62 mmol), bis(pinacolato)diboron (1.4 g, 5.42 mmol), Pd(dppf)$_2$Cl$_2$.DCM (74 mg, 0.09 mmol), and potassium carbonate (2.0 g, 14.46 mmol) were combined in 1,4-dioxanes (12.0 mL) in a microwave vial. The reaction was heated in the microwave at 130° C. for 7 hours. The mixture was diluted with water. The aqueous layer was washed with ethyl acetate. The combined organics were dried with MgSO$_4$, filtered, concentrated under reduced pressure and purified by silica gel column using 0% to 50% ethyl acetate in hexanes to afford tert-butyl N-[(tert-butoxy)carbonyl]-N-[6-methyl-5-(tetramethyl-1,3,2-dioxaborolan-2-yl)pyridin-2-yl]carbamate (1.5 g, 95%). $^1$H NMR (400 MHz, Acetonitrile-d3) δ 8.00 (d, J=8.4 Hz, 1H), 7.17 (dd, J=8.4, 0.7 Hz, 1H), 2.62 (s, 3H), 1.45 (s, 18H), 1.35 (s, 12H).

Step 3

Tert-butyl N-[(tert-butoxy)carbonyl]-N-[6-methyl-5-(tetramethyl-1,3,2-dioxaborolan-2-yl)pyridin-2-yl]carbamate (0.40 g, 0.92 mol), 1-[3-(4-bromo-2-methoxy-5-nitrophenoxy)propyl]pyrrolidine (0.33 g, 0.92 mmol), Pd(dppf)$_2$Cl$_2$.DCM (23 mg, 0.03 mmol) and 2M potassium carbonate (0.90 mL, 1.84 mmol) were combined in NMP (2.5 mL) in a microwave vial. The reaction was heated to 130° C. for 30 minutes in a microwave. The reaction was diluated with water. Aqueous layer was washed with ethyl acetate The combined organics were dried with MgSO$_4$, filtered, concentrated under reduced pressure and purified resulting residue by silica gel column using 0% to 10% MeOH in DCM to afford tert-butyl N-[(tert-butoxy)carbonyl]-N-(5-{5-methoxy-2-nitro-4-[3-(pyrrolidin-1-yl)propoxy]phenyl}-6-methylpyridin-2-yl)carbamate (0.35 g, 65%). MS (ESI, pos. ion) m/z: 587.6 (M+1).

Step 4

Tert-butyl N-[(tert-butoxy)carbonyl]-N-(5-{5-methoxy-2-nitro-4-[3-(pyrrolidin-1-yl)propoxy]phenyl}-6-methylpyridin-2-yl)carbamate (0.35 g, 0.60 mmol) and triethyl phosphite (6 mL) were combined, and then the reaction was heated to 120° C. for 24 hours. The mixture was concentrated under reduced pressure. 1M HCl (3.00 mL) solution was added. The mixture stirred for 3 hours and then purified by prep HPLC (Prep-C18, Phenomenex Luna column, 21.2× 250 mm; gradient elution of 0-60% MeCN in water over a 16 min period, where water contains 0.1% HCl, flow rate: 20 mL/min) to afford the title compound (8 mg, 4%). MS (ESI, pos. ion) m/z: 355.0 (M+1).

Example 36

(3S)-1-{8-methoxy-7-[3-(pyrrolidin-1-yl)propoxy]-5H-pyrido[4,3-b]indol-1-yl}pyrrolidin-3-ol hydrochloride

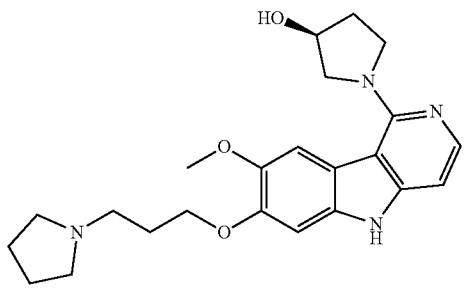 [SMILES: COc1cc2c(cc1OCCCN1CCCC1)[nH]c1ccnc(N3CC[C@H](O)C3)c12]

Step 1

Brettphos G1 (25 mg, 0.03 mmol) was added to a solution containing tert-butyl 7-(benzyloxy)-1-chloro-8-methoxy-5H-pyrido[4,3-b]indol-5-carboxylate (270 mg, 0.62 mmol), (3S)-3-pyrrolidinol (161 mg, 1.85 mmol), and potassium tert-butoxide (207 mg, 1.85 mmol) in NMP (6.0 mL) in a microwave vial. The reaction was heated to 140° C. for 1.5 hours in a microwave. The reaction was diluted with water. The aqueous layer was washed with ethyl acetate. The combined organics were dried with MgSO$_4$, filtered, and concentrated under reduced pressure. The resulting residue was purified by silica gel column using 0% to 80% ethyl acetate in hexanes to afford (3S)-1-[7-(benzyloxy)-8-methoxy-5H-pyrido[4,3-b]indol-1-yl]pyrrolidin-3-ol (239 mg, 99%). MS (ESI, pos. ion) m/z: 390.3 (M+1).

Step 2

(3S)-1-[7-(benzyloxy)-8-methoxy-5H-pyrido[4,3-b]indol-1-yl]pyrrolidin-3-ol (239 mg, 0.62 mmol), di-tert-butyl dicarbonate (269 mg, 1.23 mmol), DMAP (15 mg, 0.12 mmol), and Hunig's base (0.21 mL, 1.23 mmol) were combined in acetonitrile (3 mL). The mixture was stirred for 2 hours at room temperature. The mixture was then concentrated under reduced pressure and purified by silica gel column using 0% to 30% ethyl acetate in hexanes to afford tert-butyl 7-(benzyloxy)-1-[(3S)-3-{[(tert-butoxy)carbonyl]oxy}pyrrolidin-1-yl]-8-methoxy-5H-pyrido[4,3-b]indole-5-carboxylate (363 mg, 99%). MS (ESI, pos. ion) m/z: 590.4 (M+1).

Step 3

Tert-butyl 7-(benzyloxy)-1-[(3S)-3-{[(tert-butoxy)carbonyl]oxy}pyrrolidin-1-yl]-8-methoxy-5H-pyrido[4,3-b]indole-5-carboxylate (363.00 mg, 0.62 mmol), and 10% wt palladium on carbon (33 mg, 0.03 mmol) were combined in methanol (10 mL). The reaction was stirred under hydrogen gas pressure via balloon for 1 hour. The mixture was filtered through a plug of Celite and then concentrated under reduced pressure to afford tert-butyl 1-[(3S)-3-{[(tert-butoxy)carbonyl]oxy}pyrrolidin-1-yl]-7-hydroxy-8-methoxy-5H-pyrido[4,3-b]indole-5-carboxylate (300 mg, 97%). MS (ESI, pos. ion) m/z: 500.4 (M+1).

Step 4

Tert-butyl 1-[(3S)-3-{[(tert-butoxy)carbonyl]oxy}pyrrolidin-1-yl]-7-hydroxy-8-methoxy-5H-pyrido[4,3-b]indole-5-carboxylate (300 mg, 0.60 mmol), 1-(3-chloropropyl)pyrrolidine hydrochloride (240 mg, 1.20 mol) and potassium carbonate (331 mg, 2.40 mol) were combined in DMF (6 mL). The reaction was heated to 100° C. for 16 hours, and then cooled to room temperature. The mixture was filtered and then concentrated under reduced pressure. 1M HCl (5 mL) was added, and then mixture was then heated to 50° C. for 1 hour. The mixture was purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to afford the title compound (110 mg, 38%). $^{1}$H NMR (400 MHz, Methanol-d4) δ 7.67 (d, J=6.9 Hz, 1H), 7.63 (s, 1H), 7.22 (s, 1H), 7.14 (d, J=6.9 Hz, 1H), 4.68 (dq, J=5.3, 3.1, 2.4 Hz, 1H), 4.28 (t, J=5.6 Hz, 2H), 4.22-4.08 (m, 2H), 3.97 (s, 3H), 3.94-3.75 (m, 4H), 3.50 (t, J=7.1 Hz, 2H), 3.22-3.08 (m, 2H), 2.33 (tt, J=12.0, 5.1 Hz, 3H), 2.20 (qt, J=11.0, 4.5 Hz, 3H), 2.07 (td, J=7.3, 3.8 Hz, 2H). MS (ESI, pos. ion) m/z: 411.5 (M+1).

Example 37

(3R)-1-{8-methoxy-7-[3-(pyrrolidin-1-yl)propoxy]-5H-pyrido[4,3-b]indol-1-yl}pyrrolidin-3-ol

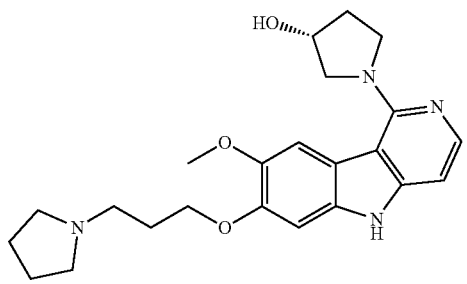 [SMILES: COc1cc2c(cc1OCCCN1CCCC1)[nH]c1ccnc(N3CC[C@@H](O)C3)c12]

The title compound was prepared as described in Example 36, Steps 1-4 above, but substituting (3S)-3-pyrrolidinol with (3R)-3-pyrrolidinol. $^{1}$H NMR (400 MHz, Methanol-d4) δ 7.68 (d, J=6.9 Hz, 1H), 7.65 (s, 1H), 7.24 (s, 1H), 7.15 (d, J=6.9 Hz, 1H), 4.68 (m, 1H), 4.28 (t, J=5.5 Hz, 2H), 4.22-4.08 (m, 2H), 3.97 (s, 3H), 3.95-3.76 (m, 4H), 3.49 (t, J=7.0 Hz, 2H), 3.22-3.09 (m, 2H), 2.33 (h, J=5.3, 4.5 Hz, 3H), 2.21 (q, J=7.5, 6.9 Hz, 3H), 2.07 (dt, J=12.9, 9.1 Hz, 2H). MS (ESI, pos. ion) m/z: 411.0 (M+1).

Example 38

8-methoxy-N-[(2S)-1-methoxypropan-2-yl]-7-[3-(pyrrolidin-1-yl)propoxy]-5H-pyrido[4,3-b]indol-1-amine

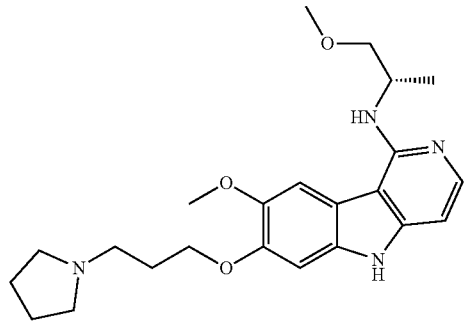 [SMILES: COC[C@H](C)Nc1nccc2[nH]c3cc(OCCCN4CCCC4)c(OC)cc3c12]

The title compound was prepared as described in Example 36, Steps 1-4 above, but substituting (3S)-3-pyrrolidinol with (2S)-1-methoxypropan-2-amine. MS (ESI, pos. ion) m/z: 413.1 (M+1).

Example 39

1-{8-methoxy-7-[3-(pyrrolidin-1-yl)propoxy]-5H-pyrido[4,3-b]indol-1-yl}pyrrolidine

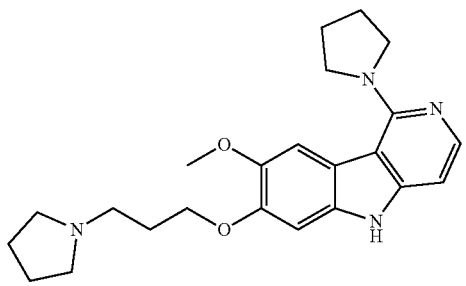 [SMILES: COc1cc2c(cc1OCCCN1CCCC1)[nH]c1ccnc(N3CCCC3)c12]

The title compound was prepared as described in Example 36, Steps 1-4 above, but modifying Step 1 as follows. MS (ESI, pos. ion) m/z: 395.0 (M+1). (Step 1-No Brettphos G1 was used. Substituted original amine, base, and solvent with pyrrolidine, triethylamine and no solvent. The reaction was heated to 120° C. for 3 hours.)

Example 40

1-{8-methoxy-7-[3-(pyrrolidin-1-yl)propoxy]-5H-pyrido[4,3-b]indol-1-yl}piperidin-4-ol

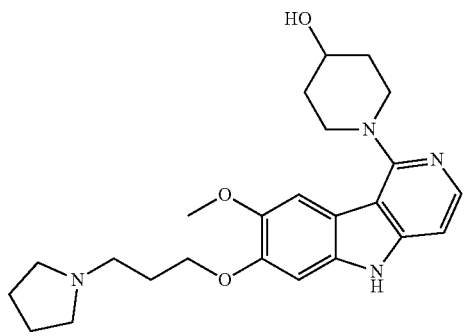 [SMILES: COc1cc2c(cc1OCCCN1CCCC1)[nH]c1ccnc(N3CCC(O)CC3)c12]

The title compound was prepared as described in Example 36, Steps 1-4 above, but modifying Step 1 as follows. MS (ESI, pos. ion) m/z: 425.0 (M+1). (Step 1—No Brettphos G1 was used. Substituted original amine, base, and solvent with 4-hydroxypiperidine, potassium carbonate and DMSO. The reaction was heated to 160° C. for 48 hours.)

Example 41

4-{8-methoxy-7-[3-(pyrrolidin-1-yl)propoxy]-5H-pyrido[4,3-b]indol-1-yl}morpholine

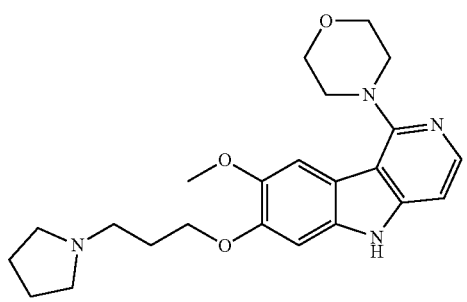 [SMILES: COc1cc2c(cc1OCCCN1CCCC1)[nH]c1ccnc(N3CCOCC3)c12]

The title compound was prepared as described in Example 36, Steps 1-4 above, but modifying Step 1 as follows. MS (ESI, pos. ion) m/z: 411.0 (M+1). (Step 1—No Brettphos G1 was used. Substituted original amine, base, and solvent with morpholine, potassium carbonate and DMSO. The reaction was heated to 120° C. for 3 hours.)

Example 42

1-{8-methoxy-7-[3-(pyrrolidin-1-yl)propoxy]-5H-pyrido[4,3-b]indol-1-yl}azetidin-3-ol

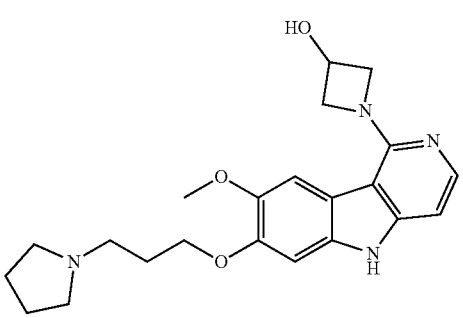 [SMILES: COc1cc2c(cc1OCCCN1CCCC1)[nH]c1ccnc(N3CC(O)C3)c12]

The title compound was prepared as described in Example 36, Steps 1-4 above, but substituting (3S)-3-pyrrolidinol with 3-hydroxyazetidine. MS (ESI, pos. ion) m/z: 397.0.0 (M+1).

Example 43

1-[3-({1-cyclopropyl-8-methoxy-5H-pyrido[4,3-b]indol-7-yl}oxy)propyl]pyrrolidine

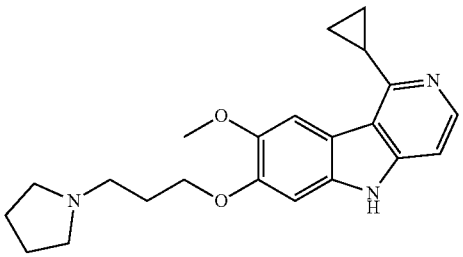 [SMILES: COc1cc2c(cc1OCCCN1CCCC1)[nH]c1ccnc(C3CC3)c12]

The title compound was prepared as described in Example 35, Steps 1-4 above, modifying Step 1 as follows. MS (ESI, pos. ion) m/z: 366.0.0 (M+1).

Step 1

A mixture of tert-butyl 7-(benzyloxy)-1-chloro-8-methoxy-5H-pyrido[4,3-b]indole-5-carboxylate (100 g, 0.23 mol), cyclopropylboronic acid (69 g, 0.80 mol), tricyclohexylphosphane (6 mg, 0.02 mmol) and potassium phosphate tribasic (97 mg, 0.46 mmol) in toluene (1.1 mL) and water (0.06 mL) was sparged with nitrogen for 10 minutes. Palladium acetate (5.1 mg; 0.02 mmol) was then added, and the sealed vial was heated to 100° C. for 5 hours. The mixture was diluted with ethyl acetate and washed with water and brine. The organic layer was dried over MgSO$_4$, filtered and concentrated under reduced pressure. The resulting residue was purified by silica gel column eluting with 0-60% ethyl acetate in hexanes to obtain tert-butyl 7-(benzyloxy)-1-cyclopropyl-8-methoxy-5H-pyrido[4,3-b]indole-5-carboxylate (90 mg, 88%) as an off-white solid.

Example 44

1-[3-({8-methoxy-5H-pyrimido[5,4-b]indol-7-yl}oxy)propyl]pyrrolidine

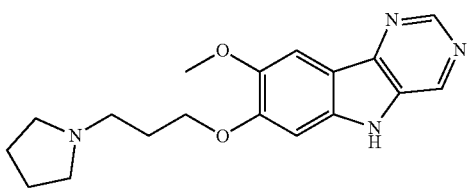 [SMILES: COc1cc2c(cc1OCCCN1CCCC1)[nH]c1cncnc12]

Step 1

1-{3-[2-methoxy-5-nitro-4-(tetramethyl-1,3,2-dioxaborolan-2-yl)phenoxy]propyl}pyrrolidine (500 mg, 1.23 mmol), 4,5-dichloropyrimidine (220 mg, 1.48 mmol), Pd(amphos)Cl₂ (59 mg, 0.08 mmol) and 2M sodium carbonate (1.23 mL, 2.46 mmol) were combined in 1,4-dioxane (5 mL). The mixture was purged with N2 for 6 min, sealed and left stirring at 90° C. for 45 minutes. The mixture was cooled to room temperature, diluted with water and extracted with ethyl acetate. The combined organic layers were washed with water. After removal of the organic solvents under reduced pressure, the residue was purified by flash chromatography on silica gel column eluted with 0-100% solvent A in $CH_2Cl_2$ (solvent A: 0.2% $NH_4OH$/10% MeOH/88.9% $CH_2Cl_2$) to provide the title compound as a brown solid (422 mg, 87%). MS (ESI, pos. ion) m/z: 393.0 (M+1).

Step 2

A mixture of 5-chloro-4-{5-methoxy-2-nitro-4-[3-(pyrrolidin-1-yl)propoxy]phenyl}pyrimidine (420 mg, 1.07 mmol) in ethyl acetate (5 mL) was added into a vial charged with anhydrous $SnCl_2$ (439 mg, 2.3 mmol). This mixture was left stirring at 95° C. for 2 hours. Additional anhydrous $SnCl_2$ (200 mg, 1.04 mmol) and ethyl acetate (2.5 mL) were added. The mixture was sealed and allowed to stir at 65° for 24 hours. The crude solution was cooled to room temperature, treated with water and then 20% aqueous NaOH. The mixture was extracted with a mixture solvent of 25% $^iPrOH$/75% chloroform (3×). After removal of the organic solvents under reduced pressure, the residue was purified by flash chromatography on silica gel column eluted with 0-100% solvent A in solvent B (solvent A: 0.2% $NH_4OH$/10% MeOH/88.9% $CH_2Cl_2$; solvent B: 1% $NH_4OH$/99% MeOH) to provide 2-(5-chloropyrimidin-4-yl)-4-methoxy-5-[3-(pyrrolidin-1-yl)propoxy]aniline (150 mg, 39%) as a brown syrup. MS (ESI, pos. ion) m/z: 363.0.0 (M+1).

Step 3

A mixture of 2-(5-chloropyrimidin-4-yl)-4-methoxy-5-[3-(pyrrolidin-1-yl)propoxy]aniline (120 mg, 0.33 mmol), potassium tert-butoxide (371 mg, 3.31 mmol) and Brettphos G1 (34 mg, 0.04 mmol) in 1,4-dioxane (10 mL) was purged with N2 for 5 minutes. The mixture was sealed and allowed to stir at 90° C. for 45 minutes. The crude mixture was cooled to room temperature and treated with water. After removal of the volatiles under reduced pressure, the residue was dissolved in DMSO (6 mL) and filtered through a small pad of celite and purified by prep HPLC (Prep-C18, Phenomenex Luna column, 21.2×250 mm; gradient elution of 0-60% MeCN in water over a 16 min period, where water contains 0.1% HCl, flow rate: 20 mL/min) to provide the title compound (34 mg, 32%). MS (ESI, pos. ion) m/z: 327.0.0 (M+1).

Example 45 ethyl[3-({8-methoxy-5H-pyrido[4,3-b]indol-7-yl}oxy)propyl]methylamine hydrochloride

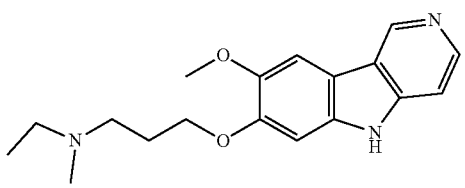 [SMILES: CCN(C)CCCOc1cc2[nH]c3ccncc3c2cc1OC]

Step 1

A mixture of tert-butyl 7-hydroxy-8-methoxy-5H-pyrido[4,3-b]indole-5-carboxylate (200.00 mg; 0.64 mmol; 1.00 eq.), (3-chloropropyl)(ethyl)methylamine hydrochloride (164.25 mg; 0.95 mmol; 1.50 eq.), and potassium carbonate (439.02 mg; 3.18 mmol; 5.00 eq.) in N,N-dimethylformamide (4.00 mL) was heated to 100° C. for 90 minutes. The reaction mixture was cooled to RT and filtered through a plug of Celite. The filtrate was concentrated under reduced pressure to give the crude tert-butyl 7-(3-(ethyl(methyl)amino)propoxy)-8-methoxy-5H-pyrido[4,3-b]indole-5-carboxylate. MS (ESI, pos. ion) m/z: 415.0 (M+1) which also contained some side product resulting from the loss of the Boc protecting group MS (ESI, pos. ion) m/z: 315.0 (M+1). The crude mixture was used in the next step without purification.

Step 2

A 3M solution of hydrogen chloride (4.84 mL), was added to a flask containing crude tert-butyl 7-{3-[ethyl(methyl)amino]propoxy}-8-methoxy-5H-pyrido[4,3-b]indole-5-carboxylate (150.00 mg; 0.36 mmol; 1.00 eq.) and the reaction mix was left stirring overnight at RT. The solvent was removed under vacuum and the residue was dissolved in 1 mL of water and treated with sat solution of $NaHCO_3$ until neutral pH. The solvent was removed under vacuum and the product was taken in DMSO, and purified by prep HPLC prep-HPLC (Prep-C18, Phenomenex Luna column, 21.2×250 mm; gradient elution of 0-30% MeCN in water over a 16 min period, where water contains 0.1% HCl, flow rate: 20 mL/min) to afford the titled compound N-ethyl-3-((8-methoxy-5H-pyrido[4,3-b]indol-7-yl)oxy)-N-methylpropan-1-amine hydrochloride (42 mg, 30%). ¹H NMR (400 MHz, DMSO-d6) δ 14.79 (s, 1H), 12.96 (s, 1H), 10.08 (s, 1H), 9.57 (s, 1H), 8.51 (d, J=6.7 Hz, 1H), 8.05 (s, 1H), 7.90 (d, J=6.7 Hz, 1H), 7.29 (s, 1H), 4.19 (t, J=6.1 Hz, 2H), 3.88 (s, 3H), 3.13 (dddd, J=33.3, 13.0, 8.0, 6.5 Hz, 4H), 2.75 (d, J=4.9 Hz, 3H), 2.21 (t, J=7.4 Hz, 2H), 1.23 (t, J=7.2 Hz, 3H). MS (ESI, pos. ion) m/z: 314.3 (M+1).

Example 46

[3-({1-cyclopropyl-8-methoxy-5H-pyrido[4,3-b]indol-7-yl}oxy)propyl](ethyl)methylamine hydrochloride

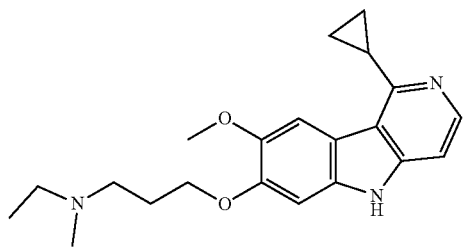 [SMILES: CCN(C)CCCOc1cc2[nH]c3ccnc(C4CC4)c3c2cc1OC]

Step 1

A mixture of tert-butyl 1-cyclopropyl-7-hydroxy-8-methoxy-5H-pyrido[4,3-b]indole-5-carboxylate (105.00 mg; 0.30 mmol; 1.00 eq.), (3-chloropropyl)(ethyl)methylamine hydrochloride (76.48 mg; 0.44 mmol; 1.50 eq.), and potassium carbonate (204.43 mg; 1.48 mmol; 5.00 eq.) in N,N-dimethylformamide (2.10 mL) was heated to 100° C. for 16 hours. The reaction mixture was cooled to RT, filtered through a plug of Celite and concentrated under reduced pressure. The crude was a mixture of tert-butyl 1-cyclopropyl-7-(3-(ethyl(methyl)amino)propoxy)-8-methoxy-5H-pyrido[4,3-b]indole-5-carboxylate MS (ESI, pos. ion) m/z: 454.4 (M+1) which also contained some side product resulting from the loss of the Boc protecting group MS (ESI, pos. ion) m/z: 353.8 (M+1). The crude mixture was used in the next step without purification.

Step 2

A 3M solution of hydrogen chloride (4.84 mL), was added to a flask containing crude tert-butyl 1-cyclopropyl-7-(3-(ethyl(methyl)amino)propoxy)-8-methoxy-5H-pyrido[4,3-b]indole-5-carboxylate (150.00 mg; 0.36 mmol; 1.00 eq.) and the reaction mix was left stirring overnight at RT. The solvent was removed under vacuum and the residue was dissolved in 1 mL of water and treated with sat solution of NaHCO$_3$ until neutral pH. The solvent was removed under vacuum and the product was taken in DMSO, and purified by prep HPLC prep-HPLC (Prep-C18, Phenomenex Luna column, 21.2×250 mm; gradient elution of 0-30% MeCN in water over a 16 min period, where water contains 0.1% HCl, flow rate: 20 mL/min) to afford the title compound (12 mg, 10%). $^1$H NMR (400 MHz, DMSO-d6) δ 14.03 (s, 1H), 13.03 (s, 1H), 10.37-10.14 (m, 1H), 8.21 (dd, J=6.7, 4.4 Hz, 1H), 7.85 (s, 1H), 7.74 (d, J=6.7 Hz, 1H), 7.33 (s, 1H), 4.20 (t, J=6.1 Hz, 2H), 3.91 (s, 3H), 3.22-2.97 (m, 5H), 2.74 (d, J=4.9 Hz, 3H), 2.23 (p, J=6.7 Hz, 2H), 1.43 (dt, J=8.3, 3.2 Hz, 2H), 1.37-1.31 (m, 2H), 1.23 (t, J=7.2 Hz, 3H). MS (ESI, pos. ion) m/z: 353.8 (M+1).

Example 47

[3-({1-cyclopropyl-8-methoxy-5H-pyrido[4,3-b]indol-7-yl}oxy)propyl]dimethylamine hydrochloride

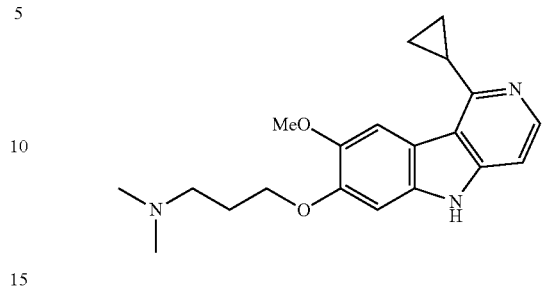

Step 1

A mixture of tert-butyl 1-cyclopropyl-7-hydroxy-8-methoxy-5H-pyrido[4,3-b]indole-5-carboxylate (288.00 mg; 0.81 mmol; 1.00 eq.), N-(3-chloropropyl)-N,N-dimethylamine hydrochloride (138.35 mg; 1.14 mmol; 1.40 eq.) and K$_2$CO$_3$ ((280.36 mg; 2.03 mmol; 2.50 eq.) in DMF (22 mL) was allowed to stir at 100° C. for 6 h. The mixture was then cooled to rt, diluted with water and extracted with iPrOH/CHCl$_3$ (1/3) twice. The combined organic phases were then washed with water (30 mL), brine (20 mL), dried over Na$_2$SO$_4$. After removal of the organic volatiles under reduced pressure, the remaining crude product of tert-butyl 1-cyclopropyl-7-[3-(dimethylamino)propoxy]-8-methoxy-5H-pyrido[4,3-b]indole-5-carboxylate was carried over to the next step.

Step 2.

A solution of the above crude product of tert-butyl 1-cyclopropyl-7-[3-(dimethylamino)propoxy]-8-methoxy-5H-pyrido[4,3-b]indole-5-carboxylate in TFA (2.5 mL) was allowed to stir at 90° C. for 20 min. The resulting mixture was allowed to cool to rt and the residue was subjected to (Waters XSelect CSH C18 column, 19×150 mm, gradient elution of 0-40% CH$_3$CN in water over a 20 min period, flow rate 28 ml/min) to provide the title compound as a TFA salt solid (107 mg, 31%, two steps). $^1$H NMR (400 MHz, Methanol-d4) δ 8.18 (d, J=6.8 Hz, 1H), 7.93 (s, 1H), 7.73 (d, J=6.8 Hz, 1H), 7.36 (s, 1H), 4.33 (t, J=5.6 Hz, 2H), 4.03 (s, 3H), 3.45 (t, J=7.2 Hz, 2H), 3.01 (s, 6H), 3.02-2.91 (m, 1H), 2.41-2.30 (m, 2H), 1.61-1.49 (m, 2H), 1.35-1.23 (m, 2H). MS (ESI, pos. ion) m/z: 340.2 (M+1).

Example 48

4-{7-[3-(dimethylamino)propoxy]-8-methoxy-5H-pyrido[4,3-b]indol-1-yl}-2-methylbut-3-yn-2-ol hydrochloride

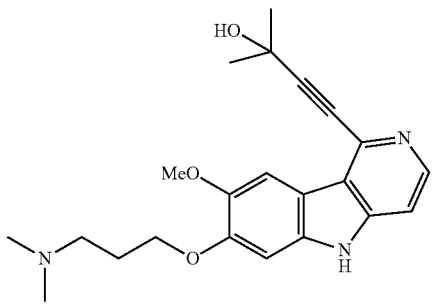 [SMILES: COc1cc2c(cc1OCCCN(C)C)[nH]c1ccnc(C#CC(C)(C)O)c12]

Step 1

Tert-butyl 1-chloro-7-hydroxy-8-methoxy-5H-pyrido[4,3-b]indole-5-carboxylate was converted into tert-butyl 1-chloro-7-[3-(dimethylamino)propoxy]-8-methoxy-5H-pyrido[4,3-b]indole-5-carboxylate following a synthetic sequence as described (Example 47, Step 1).

Step 2

A mixture of 2-methyl-3-butyn-2-ol (146 mg; 1.75 mmol; 6.00 eq.), copper iodide (12 mg; 0.05 mmol; 0.22 eq.), tetrakis(triphenylphosphine) palladium (99 mg; 0.10 mmol; 0.30 eq.) and tert-butyl 1-chloro-7-[3-(dimethylamino)propoxy]-8-methoxy-5H-pyrido[4,3-b]indole-5-carboxylate (125 mg; 0.06 mmol; 1.00 eq.) in DMF/Et$_3$N (1.2 mL/0.5 mL) was purged with N2 for 5 min. The reaction vial was sealed and allowed to stir at 95° C. for 90 minutes. The resulting mixture was allowed to cool to rt, diluted with water, and extracted with 20% $^i$PrOH/chloroform thrice. The combined organic layers were concentrated under reduced pressure, and the remaining residue was purified by flash chromatography on a 10 g silica gel column eluted with 0-100% solvent A (solvent A: 0.3% NH$_4$OH/10% MeOH/89.7% CH$_2$Cl$_2$) in CH$_2$Cl$_2$ to provide tert-butyl 7-[3-(dimethylamino)propoxy]-1-(3-hydroxy-3-methylbut-1-yn-1-yl)-8-methoxy-5H-pyrido[4,3-b]indole-5-carboxylate as a brown syrup (55 mg, 42%).

Step 3

The title compound was synthesized from tert-butyl 7-[3-(dimethylamino)propoxy]-1-(3-hydroxy-3-methylbut-1-yn-1-yl)-8-methoxy-5H-pyrido[4,3-b]indole-5-carboxylate, following a synthetic sequence as described (Example 47, Step 2), as a white solid. $^1$H NMR (400 MHz, Methanol-d4) δ 8.35 (d, J=6.7 Hz, 1H), 8.07 (s, 1H), 7.82 (dd, J=15.2, 6.6 Hz, 1H), 7.36 (s, 1H), 4.33 (td, J=5.6, 2.8 Hz, 2H), 4.03 (d, J=3.2 Hz, 3H), 3.44 (t, J=7.1 Hz, 2H), 3.00 (s, 6H), 2.36 (p, J=6.4 Hz, 2H), 1.75 (s, 6H). MS (ESI, pos. ion) m/z: 382.1 (M+1).

Example 49

4-{7-[3-(dimethylamino)propoxy]-8-methoxy-5H-pyrido[4,3-b]indol-1-yl}-2-methylbutan-2-ol hydrochloride

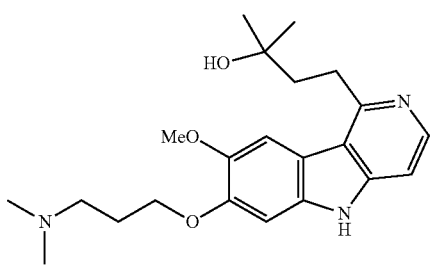 [SMILES: COc1cc2c(cc1OCCCN(C)C)[nH]c1ccnc(CCC(C)(C)O)c12]

A flask charged with a mixture of 4-{7-[3-(dimethylamino)propoxy]-8-methoxy-5H-pyrido[4,3-b]indol-1-yl}-2-methylbut-3-yn-2-ol (Example 48, 35 mg, 0.09 mmol 1.00 eq.) and palladium on carbon (20 mg) in MeOH (1.5 mL) was purged with N2 for 3 min, followed by hydrogen gas via balloon and stirred for 26 hours min. The reaction mixture was filtered through a small pad of celite and rinsed with MeOH thrice. The organic solutions were combined. After removal of the organic solvents under vacuum, the resulting residue was purified by Prep HPLC (Waters XSelect CSH C18 column, 19×150 mm; gradient elution of 0-25% CH$_3$CN in water 0.1% HCl over a 20 min period, flow rate 28 ml/min) to provide the title compound (15 mg, 35%). $^1$H NMR (400 MHz, Methanol-d4) δ 8.25 (d, J=6.6 Hz, 1H), 7.87 (s, 1H), 7.71 (d, J=6.6 Hz, 1H), 7.30 (s, 1H), 4.32 (t, J=5.4 Hz, 2H), 3.99 (s, 3H), 3.57-3.42 (m, 4H), 3.01 (s, 6H), 2.37 (dd, J=8.8, 4.1 Hz, 2H), 1.99-1.90 (m, 2H), 1.36 (s, 6H). MS (ESI, pos. ion) m/z: 386.0 (M+1).

Example 50

4-{7-[3-(dimethylamino)propoxy]-8-methoxy-5H-pyrido[4,3-b]indol-1-yl}but-3-yn-2-ol hydrochloride

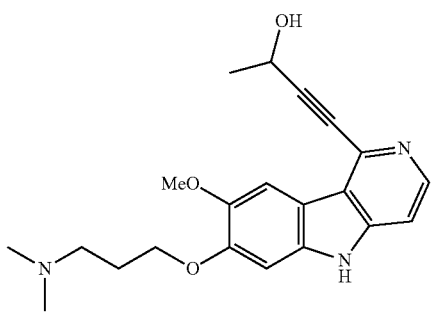 [SMILES: COc1cc2c(cc1OCCCN(C)C)[nH]c1ccnc(C#CC(C)O)c12]

The title compound was synthesized from tert-butyl 1-chloro-7-[3-(dimethylamino)propoxy]-8-methoxy-5H-pyrido[4,3-b]indole-5-carboxylate, following a synthetic sequence as described for Example 48, except that but-3-yn-2-ol was used in the place of 2-methyl-3-butyn-2-ol. $^1$H NMR (400 MHz, Methanol-d4) δ 8.35 (dd, J=6.5, 2.3 Hz, 1H), 8.02 (s, 1H), 7.89-7.80 (m, 1H), 7.36 (d, J=9.7 Hz, 1H), 5.01 (q, J=6.7 Hz, 1H), 4.34 (t, J=5.5 Hz, 2H), 4.01 (s, 3H), 3.45 (t, J=7.1 Hz, 2H), 3.01 (s, 6H), 2.36 (p, J=6.2 Hz, 2H), 1.68 (d, J=6.7 Hz, 3H). MS (ESI, pos. ion) m/z: 368.0 (M+1).

Example 51

(3-{[1-(2-cyclopropylethynyl)-8-methoxy-5H-pyrido[4,3-b]indol-7-yl]oxy}propyl)dimethylamine hydrochloride

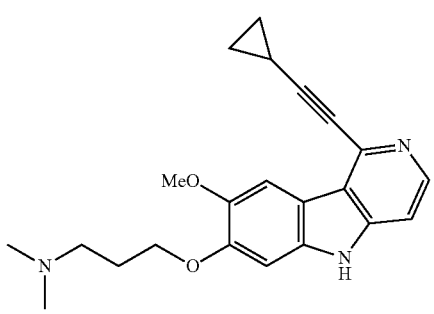 [SMILES: COc1cc2c(cc1OCCCN(C)C)[nH]c1ccnc(C#CC3CC3)c12]

The title compound was synthesized from tert-butyl 1-chloro-7-[3-(dimethylamino)propoxy]-8-methoxy-5H-pyrido[4,3-b]indole-5-carboxylate, following a synthetic sequence as described for Example 48, except that ethynylcyclopropane was used in the place of 2-methyl-3-butyn-2-ol. $^1$H NMR (400 MHz, Methanol-d4) δ 8.29 (d, J=6.7 Hz, 1H), 7.88 (s, 1H), 7.78 (d, J=6.8 Hz, 1H), 7.35 (s, 1H), 4.33 (t, J=5.6 Hz, 2H), 4.03 (s, 3H), 3.45 (t, J=7.2 Hz, 2H), 3.01 (s, 6H), 2.36 (s, 1H), 2.41-2.30 (m, 1H), 1.94 (tt, J=8.2, 5.0 Hz, 1H), 1.34-1.20 (m, 2H), 1.24-1.09 (m, 2H). MS (ESI, pos. ion) m/z: 364.2 (M+1).

Example 52

3-((1-(2-cyclopropylethyl)-8-methoxy-5H-pyrido[4,3-b]indol-7-yl)oxy)-N,N-dimethylpropan-1-amine hydrochloride

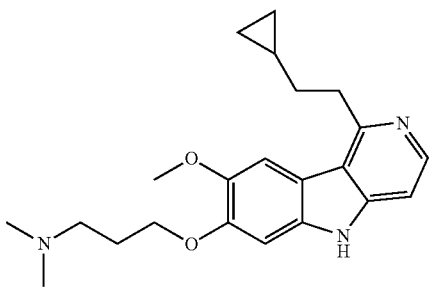 [SMILES: COc1cc2c(cc1OCCCN(C)C)[nH]c1ccnc(CCC3CC3)c12]

A mixture of (3-{[1-(2-cyclopropylethynyl)-8-methoxy-5H-pyrido[4,3-b]indol-7-yl]oxy}propyl)dimethylamine from Example 48 (5.60 mg; 0.02 mmol; 1.00 eq.) was dissolved in in methanol (1.68 mL). The system was purged with nitrogen and palladium on carbon (0.16 mg; 0.00 mmol; 0.10 eq.) was added to the reaction flask. The reaction mix was hydrogenated under atmospheric pressure for 90 minutes using $H_2$ from a balloon. The reaction mix was filtered over Celite and the cake washed with methanol. The combined organics were concentrated to dryness to give the desired 3-((1-(2-cyclopropylethyl)-8-methoxy-5H-pyrido[4,3-b]indol-7-yl)oxy)-N,N-dimethylpropan-1-amine hydrochloride (3.9 mg, 69%). MS (ESI, pos. ion) m/z: 368.2 (M+1).

Example 53

{2-[2-({1-cyclopropyl-8-methoxy-5H-pyrido[4,3-b]indol-7-yl}oxy)ethoxy]ethyl}dimethylamine hydrochloride

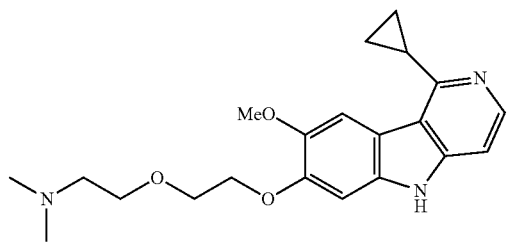 [SMILES: COc1cc2c(cc1OCCOCCN(C)C)[nH]c1ccnc(C3CC3)c12]

Step 1
To a vial charged with tert-butyl 1-cyclopropyl-7-hydroxy-8-methoxy-5H-pyrido[4,3-b]indole-5-carboxylate (48.00 mg; 0.15 mmol; 1.00 eq.) was added a solution of tributylphosphoranylidene)acetonitrile (150.76 mg; 0.59 mmol) in $CH_2Cl_2$ (0.5 mL). The mixture was allowed to stir at 60° C. with N2 line to blow off the solvents completely. To the resulting residue was added 2-[2-(dimethylamino)ethoxy]ethan-1-ol (60.13 mg; 0.45 mmol; 2.50 eq.) in $CH_2Cl_2$ (0.8 mL). After removal of the solvents under N2 line, the vial was sealed and the residue was allowed to be heated at 85° C. for 90 min. The reaction mixture was purified by flash chromatography on silica gel column eluted with 0-100% solvent A (solvent A: 0.3% $NH_4OH$/10% MeOH/89.7% $CH_2Cl_2$) in $CH_2Cl_2$ to provide tert-butyl 1-cyclopropyl-7-{2-[2-(dimethylamino)ethoxy]ethoxy}-8-methoxy-5H-pyrido[4,3-b]indole-5-carboxylate as yellow oil (26 mg, 41%).
Step 2
The title compound was synthesized from tert-butyl 1-cyclopropyl-7-{2-[2-(dimethylamino)ethoxy]ethoxy}-8-methoxy-5H-pyrido[4,3-b]indole-5-carboxylate, following a synthetic sequence as described for Example 21, step 3. $^1$H NMR (400 MHz, Methanol-d4) δ 132.51 (s, 1H), 8.18 (d, J=6.7 Hz, 1H), 7.91 (dd, J=4.8, 1.8 Hz, 1H), 7.73 (d, J=6.8 Hz, 1H), 7.35 (d, J=1.8 Hz, 1H), 4.38-4.31 (m, 2H), 4.05-3.80 (m, 4H), 3.46-3.36 (m, 2H), 2.94 (s, 6H), 2.65 (dd, J=2.2, 1.3 Hz, 1H), 1.65-1.49 (m, 2H), 1.35-1.24 (m, 2H). MS (ESI, pos. ion) m/z: 370.4 (M+1).

Example 54

7-(3-chloropropoxy)-1-cyclopropyl-8-methoxy-5H-pyrido[4,3-b]indole hydrochloride

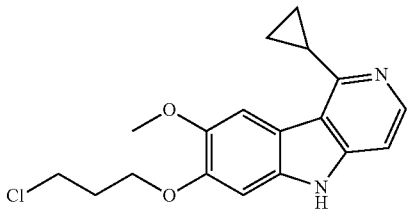 [SMILES: COc1cc2c(cc1OCCCCl)[nH]c1ccnc(C3CC3)c12]

The title compound was isolated as a secondary product from the purification described in step 4 for Example 102 (7.9 mg; 26%); $^1$H NMR (400 MHz, DMSO-$d_6$) δ 13.82 (s, 1H), 12.76 (s, 1H), 8.21 (d, J=6.7 Hz, 1H), 7.85 (s, 1H), 7.72 (d, J=6.7 Hz, 1H), 7.34 (s, 1H), 4.22 (t, J=6.0 Hz, 2H), 3.90 (s, 3H), 3.82 (t, J=6.4 Hz, 2H), 3.00 (td, J=8.6, 4.3 Hz, 1H), 2.24 (p, J=6.2 Hz, 2H), 1.42 (dt, J=6.9, 3.3 Hz, 2H), 1.33-1.27 (m, 2H). MS (ESI, pos. ion) m/z: 331.3 (M+1).

Example 55

[3-({8-methoxy-1-propyl-5H-pyrido[4,3-b]indol-7-yl}oxy)propyl]dimethylamine hydrochloride

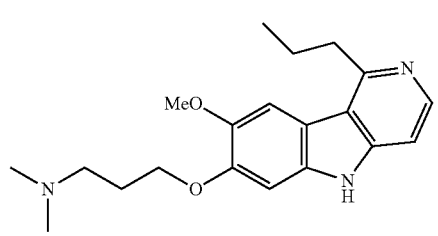 [SMILES: CCCc1nccc2[nH]c3cc(OCCCN(C)C)c(OC)cc3c12]

The title compound was synthesized from tert-butyl 7-hydroxy-8-methoxy-1-propyl-5H-pyrido[4,3-b]indole-5-carboxylate, following a synthetic sequence similar as described for Example 21, except that 3-(dimethylamino)propan-1-ol was used in place of 3-(pyrrolidin-1-yl)propan-1-ol in step 2. ¹H NMR (400 MHz, Methanol-d4) δ 8.29 (d, J=6.8 Hz, 1H), 7.77 (d, J=6.8 Hz, 1H), 7.64 (s, 1H), 7.37 (s, 1H), 4.33 (t, J=5.6 Hz, 2H), 4.03 (s, 3H), 3.51 (dd, J=8.5, 6.9 Hz, 2H), 3.45 (t, J=7.2 Hz, 2H), 3.00 (s, 6H), 2.41-2.29 (m, 2H), 2.00 (h, J=7.4 Hz, 2H), 1.13 (t, J=7.4 Hz, 3H). MS (ESI, pos. ion) m/z: 342.2 (M+1).

Example 56

[3-({1-cyclopentyl-8-methoxy-5H-pyrido[4,3-b]indol-7-yl}oxy)propyl]dimethylamine hydrochloride

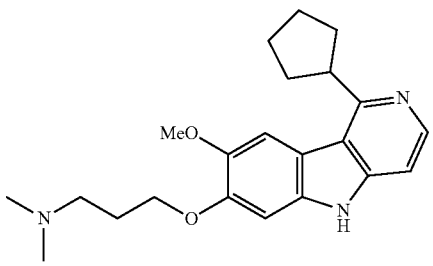 [SMILES: COc1cc2c(cc1OCCCN(C)C)[nH]c1ccnc(C3CCCC3)c12]

Step 1

A mixture of tert-butyl 7-(benzyloxy)-1-chloro-8-methoxy-5H-pyrido[4,3-b]indole-5-carboxylate (650.00 mg; 1.48 mmol; 1.00 eq.), 1-cyclopenten-1-ylboronic acid (580.20 mg; 5.18 mmol; 3.50 eq.), tricyclohexylphosphane (41.53 mg; 0.15 mmol; 0.10 eq.) and potassium phosphate, tribasic (628.72 mg; 2.96 mmol; 2.00 eq.) in toluene (10 mL) and water (0.8 mL) was spurge with nitrogen for 10 minutes. To the mixture was added palladium acetate (33.25 mg; 0.15 mmol; 0.10 eq.). The mixture was allowed to stir under reflux under N2 atmosphere for 2 h. The reaction mixture was allowed to cool to rt, diluted with water and extracted with EtOAc thrice. The combined organic solution was concentrated under reduced pressure. The residue was was purified by flash chromatography on 25 g silica gel column eluted with 0-60% EtOAc in hexanes to provide tert-butyl 7-(benzyloxy)-1-(cyclopent-1-en-1-yl)-8-methoxy-5H-pyrido[4,3-b]indole-5-carboxylate (540 mg, 78%).

Step 2

A flask charged with a mixture of tert-butyl 7-(benzyloxy)-1-(cyclopent-1-en-1-yl)-8-methoxy-5H-pyrido[4,3-b]indole-5-carboxylate (540 mg, 1.45 mmol; 1.00 eq.) and palladium on carbon (0.32 g; 0.31 mmol; 0.21 eq.) in MeOH (24 mL) was purged with N2 for 10 min, followed with H₂ balloon for 8 min. The resulting mixture was allowed to stir at rt under H₂ balloon at for 12 hr. The solid was filtered off through a small pad of celite and rinsed with MeOH. The organic solutions were combined. Removal of the organic solvents under reduced pressure provide the crude product of tert-butyl 1-cyclopentyl-7-hydroxy-8-methoxy-5H-pyrido[4,3-b]indole-5-carboxylate (398 mg, 91%).

Step 3

The title compound was synthesized from the above crude product of tert-butyl 1-cyclopentyl-7-hydroxy-8-methoxy-5H-pyrido[4,3-b]indole-5-carboxylate, following a synthetic sequence as described for Example 47, step 2. ¹H NMR (400 MHz, Methanol-d4) δ 8.26 (d, J=6.8 Hz, 1H), 7.79-7.70 (m, 2H), 7.34 (s, 1H), 4.31 (t, J=5.6 Hz, 2H), 4.03 (s, 3H), 3.44 (t, J=7.2 Hz, 2H), 3.00 (s, 6H), 2.44 (s, 2H), 2.40-2.29 (m, 1H), 2.35 (s, 1H), 2.05-1.95 (m, 7H). MS (ESI, pos. ion) m/z: 368.1 (M+1).

Example 57

(3-{[1-(2-ethoxyethyl)-8-methoxy-5H-pyrido[4,3-b]indol-7-yl]oxy}propyl)dimethylamine hydrochloride

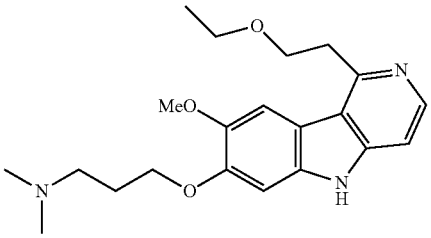 [SMILES: CCOCCc1nccc2[nH]c3cc(OCCCN(C)C)c(OC)cc3c12]

Step 1

A mixture of tert-butyl 7-(benzyloxy)-1-chloro-8-methoxy-5H-pyrido[4,3-b]indole-5-carboxylate (450.00 mg; 1.03 mmol; 1.00 eq.), 2-[(E)-2-ethoxyethenyl]-4,4,5,5-tetramethyl-1,3,2-dioxaborolane (365.53 mg; 1.85 mmol; 1.80 eq.), Pd(dppf)₂Cl₂.DCM (83.73 mg; 0.10 mmol; 0.10 eq.) and Cesium carbonate (1 336.23 mg; 4.10 mmol; 4.00 eq.) in toluene (12 mL) and water (1 mL) was spurge with nitrogen for 10 minutes. The resulting mixture was allowed to reflux under N2 atmosphere for 4 h. The reaction mixture was allowed to cool to rt, diluted with water and extracted with EtOAc thrice. The combined organic solution was concentrated under reduced pressure. The residue was purified by flash chromatography on 25 g silica gel column eluted with 0-60% EtOAc in hexanes to provide tert-butyl 7-(benzyloxy)-1-[(E)-2-ethoxyethenyl]-8-methoxy-5H-pyrido[4,3-b]indole-5-carboxylate as a white solid (393 mg, 81%).

Step 2

A flask charged with a mixture of tert-butyl 7-(benzyloxy)-1-(cyclopent-1-en-1-yl)-8-methoxy-5H-pyrido[4,3-b]indole-5-carboxylate as a white solid (321 mg, 0.68 mmol; 1.00 eq.) and palladium on carbon (139 mg; 0.13 mmol; 0.21 eq.) in MeOH (11 mL) was purged with N2 for 10 min, followed with H₂ balloon for 8 min. The resulting mixture was allowed to stir at rt under H₂ balloon at for 12 hr. The solid was filtered off through a small pad of celite and rinsed with MeOH. The organic solutions were combined. Removal of the organic solvents under reduced pressure provided the crude product of tert-butyl 1-(2-ethoxyethyl)-7-hydroxy-8-methoxy-5H-pyrido[4,3-b]indole-5-carboxylate (209 mg, 81%).

Step 3

The title compound was synthesized from the above crude product of of tert-butyl 1-(2-ethoxyethyl)-7-hydroxy-8-methoxy-5H-pyrido[4,3-b]indole-5-carboxylate, following a synthetic sequence as described for Example 47, step 2. ¹H NMR (400 MHz, Methanol-d4) δ 8.30 (d, J=6.6 Hz, 1H), 7.81-7.69 (m, 2H), 7.36 (s, 1H), 4.33 (t, J=5.3 Hz, 2H), 4.01 (d, J=7.5 Hz, 5H), 3.78 (t, J=5.6 Hz, 2H), 3.46 (q, J=7.0 Hz, 4H), 3.01 (s, 6H), 2.36 (t, J=6.1 Hz, 2H), 1.04 (t, J=6.9 Hz, 3H). MS (ESI, pos. ion) m/z: 372.2 (M+1).

Example 58

(3-{[8-methoxy-1-(3-methoxypropyl)-5H-pyrido[4,3-b]indol-7-yl]oxy}propyl)dimethylamine hydrochloride

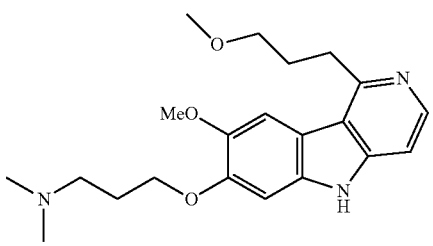 [SMILES: COCCCc1nccc2[nH]c3cc(OCCCN(C)C)c(OC)cc3c12]

Step 1

A mixture of tert-butyl 7-(benzyloxy)-1-chloro-8-methoxy-5H-pyrido[4,3-b]indole-5-carboxylate (150.00 mg; 0.34 mmol; 1.00 eq.), trifluoro[(1E)-3-methoxyprop-1-en-1-yl]-¿4-borane potassium hydride (122.36 mg; 0.68 mmol; 2.00 eq.), palladium acetate (15.35 mg; 0.07 mmol; 0.20 eq.), tricyclohexylphosphine (14.38 mg; 0.05 mmol; 0.15 eq.) and potassium phosphate, tribasic (290.18 mg; 1.37 mmol; 4.00 eq.) in toluene and water (5 mL/1.2 mL) was purged with N2 for 10 min. The mixture was allowed to stir at 110° C. under reflux N2 atmosphere for 70 min. The reaction mixture was allowed to cool to room temperature, diluted with water and extracted with EtOAc thrice. The organic solutions were combined. After removal of the volatiles under reduced pressure, the residue was purified by flash chromatography on silica gel column eluted with 0-50% solvent A (solvent A: 0.3% NH$_4$OH/10% MeOH/89.7% CH$_2$Cl$_2$) in CH$_2$Cl$_2$ to provide tert-butyl 7-(benzyloxy)-8-methoxy-1-[(1E)-3-methoxyprop-1-en-1-yl]-5H-pyrido[4,3-b]indole-5-carboxylate as white solid (112 mgs, 69%).

Step 2

The title product was made from the above product of tert-butyl 7-(benzyloxy)-8-methoxy-1-[(1E)-3-methoxyprop-1-en-1-yl]-5H-pyrido[4,3-b]indole-5-carboxylate, following a synthetic sequence as described for Example 57, steps 2 and 3. $^1$H NMR (400 MHz, Methanol-d$_4$) δ 8.25 (d, J=6.6 Hz, 1H), 7.75-7.64 (m, 2H), 7.27 (s, 1H), 4.30 (t, J=5.5 Hz, 2H), 3.98 (s, 3H), 3.59-3.42 (m, 6H), 3.36 (s, 3H), 3.02 (s, 6H), 2.37 (t, J=6.2 Hz, 2H), 2.14-2.05 (m, 2H). MS (ESI, pos. ion) m/z: 372.2 (M+1).

Example 59

[3-({1-ethynyl-8-methoxy-5H-pyrido[4,3-b]indol-7-yl}oxy)propyl]dimethylamine hydrochloride

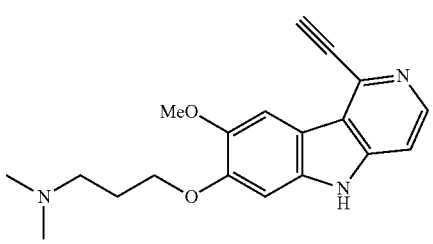 [SMILES: C#Cc1nccc2[nH]c3cc(OCCCN(C)C)c(OC)cc3c12]

Step 1

Tert-butyl 1-chloro-7-[3-(dimethylamino)propoxy]-8-methoxy-5H-pyrido[4,3-b]indole-5-carboxylate was converted to tert-butyl 7-[3-(dimethylamino)propoxy]-8-methoxy-1-[2-(trimethylsilyl)ethynyl]-5H-pyrido[4,3-b]indole-5-carboxylate following a synthetic sequence as described in Example 48, step 3, except that ethynyltrimethylsilane was used in the place of 2-methyl-3-butyn-2-ol, as a white solid.

Step 2

Combined a solution containing tert-butyl 7-[3-(dimethylamino)propoxy]-8-methoxy-1-[2-(trimethylsilyl)ethynyl]-5H-pyrido[4,3-b]indole-5-carboxylate (25 mg, 0.05 mml, 1.0 eq.) in CH$_2$Cl$_2$ (0.8 mL) and TFA (0.3 mL). The reaction mixture was allowed to stir at rt for 30 minutes. The resulting solution was concentrated under reduced pressure. The remaining residue was treated with TBAF (1.0 mL, 1.0 mmol, 1.0 M in THF) and the resulting mixture was allowed to stir at rt for 16 hours. After removal of the organic solvents under reduced pressure the resulting residue was purified on the Prep HPLC (Waters XSelect CSH C18 column, 19×150 mm; gradient elution of 0-45% CH$_3$CN in water 0.1% HCl over a 20 min period, flow rate 28 ml/min) to provide the title compound (4 mg, 20%). $^1$H NMR (400 MHz, Methanol-d4) δ 8.39 (d, Jd=6.6 Hz, 1H), 8.01 (s, 1H), 7.89 (d, J=6.6 Hz, 1H), 7.37 (s, 1H), 5.27 (s, 1H), 4.34 (t, J=5.4 Hz, 2H), 4.00 (s, 3H), 3.44 (t, J=7.1 Hz, 2H), 3.00 (s, 6H), 2.36 (q, J=6.2 Hz, 2H). MS (ESI, pos. ion) m/z: 324.0 (M+1).

Example 60

1-[3-({1-cyclopropyl-8-methoxy-5H-pyrido[4,3-b]indol-7-yl}oxy)propyl]-2-methylpyrrolidine hydrochloride

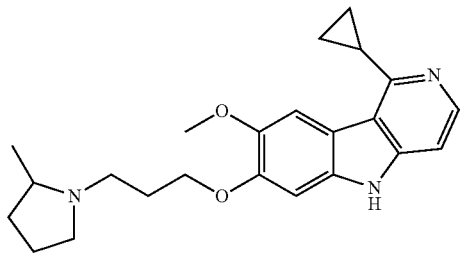 [SMILES: COc1cc2c(cc1OCCCN1CCCC1C)[nH]c1ccnc(C3CC3)c12]

Step 1

A mixture of tert-butyl 7-(benzyloxy)-1-chloro-8-methoxy-5H-pyrido[4,3-b]indole-5-carboxylate (reference 5; 1 000.00 mg; 2.28 mmol; 1.00 eq.), cyclopropylboronic acid (684.98 mg; 7.97 mmol; 3.50 eq.), tricyclohexylphosphane (63.89 mg; 0.23 mmol; 0.10 eq.) and potassium phosphate, tribasic (967.26 mg; 4.56 mmol; 2.00 eq.) in toluene (11.39 mL) and water (0.57 mL) was sparged with nitrogen for 10 minutes. Palladium acetate (51.15 mg; 0.23 mmol; 0.10 eq.) was then added, and the mixture was heated to 100° C. After 3.5 h the mixture was diluted with EtOAc and washed with water and brine. The organic layer was dried over MgSO$_4$, filtered and concentrated. The residue was purified by column chromatography (40 G ISCO Gold) eluting with 0-60% EtOAc in heptane to obtain the desired product as an off-white solid (900 mg; 89% yield).

Step 2

A mixture of tert-butyl 7-(benzyloxy)-1-cyclopropyl-8-methoxy-5H-pyrido[4,3-b]indole-5-carboxylate (700.00 mg; 1.57 mmol; 1.00 eq.) and palladium on carbon (5.03 mg; 0.05 mmol; 0.03 eq.) in methanol (15.75 mL) was stirred under an atmosphere of H$_2$ from a balloon (after evacuating back-filling with H$_2$ three times). After 17 h the mixture was filtered with additional MeOH and concentrated to provide a crude off-white solid which was used in further steps without further purification.

Step 3

A mixture of tert-butyl 1-cyclopropyl-7-hydroxy-8-methoxy-5H-pyrido[4,3-b]indole-5-carboxylate (50.00 mg; 0.14 mmol; 1.00 eq.), 1-chloro-3-iodopropane (0.03 mL; 0.28 mmol; 2.00 eq.) and potassium carbonate (21.42 mg; 0.16 mmol; 1.10 eq.) in acetonitrile (0.71 mL) was heated to 80° C. After 3.5 h the mixture was diluted with EtOAc, washed with brine, dried over MgSO$_4$, filtered and concentrated to provide a yellow oil. The crude material was purified by column chromatography (12 G ISCO Gold) eluting with 0-40% EtOAc/hexanes to obtain a semi-pure colorless oil. This material (40 mg) was used in the following step without further purification.

Step 4

A mixture of tert-butyl 7-(3-chloropropoxy)-1-cyclopropyl-8-methoxy-5H-pyrido[4,3-b]indole-5-carboxylate (40.00 mg; 0.09 mmol; 1.00 eq.), potassium iodide (1.54 mg; 0.01 mmol; 0.10 eq.) and 2-methylpyrrolidine (0.07 mL; 0.60 mmol; 6.50 eq.) in N,N-dimethylformamide (0.46 mL) was heated to 70° C. After 2 h the mixture was cooled to ambient temperature, diluted with 1:1 PhMe/EtOAc, washed with an equal amount of H$_2$O, dried over MgSO$_4$, filtered and concentrated. The crude orange solid was dissolved in DCM (1 mL) and treated with TFA (0.5 mL) at ambient temperature. After 2 h the mixture was concentrated in vacuo. The oily residue was taken up in 1N HCl (~1.0 mL) and purified by Prep HPLC (Phenomenex Luna C18, 21×250 mm, 0-60% acetonitrile/0.1% aqueous HCl gradient over 13 minutes, flow rate 22 ml/min) to provide the title compound. (6 mg; 17%) $^1$H NMR (400 MHz, DMSO-d$_6$) δ 13.79 (s, 1H), 12.84 (s, 1H), 9.65 (s, 1H), 8.21 (d, J=6.6 Hz, 1H), 7.85 (s, 1H), 7.73 (s, 1H), 7.32 (s, 1H), 4.21 (t, J=6.0 Hz, 2H), 3.91 (s, 3H), 3.67-3.63 (m, 1H), 3.50-3.40 (m, 2H), 3.15-307 (m, 2H), 3.03-2.97 (m, 1H), 2.23-2.16 (m, 2H), 1.99-1.87 (m, 2H), 1.65-1.55 (m, 2H), 1.47-1.39 (m, 2H), 1.35 (d, J=6.4 Hz, 3H), 1.31-1.26 (s, 2H); MS (ESI, pos. ion) m/z: 380.4 (M+1).

Example 61

[3-({1-cyclopropyl-8-methoxy-5H-pyrido[4,3-b]indol-7-yl}oxy)propyl]bis(propan-2-yl)amine hydrochloride

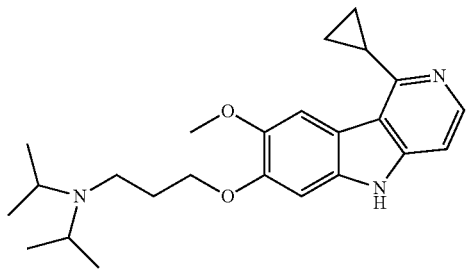 [SMILES: COc1cc2c(cc1OCCCN(C(C)C)C(C)C)[nH]c1ccnc(C3CC3)c12]

The title compound was prepared using the synthetic sequence described for Example 60, changing step 4 as follows. A mixture of 7-(3-chloropropoxy)-1-cyclopropyl-8-methoxy-5H-pyrido[4,3-b]indole (45.00 mg; 0.14 mmol; 1.00 eq.), potassium iodide (2.26 mg; 0.01 mmol; 0.10 eq.) and N,N-diisopropylamine (89.47 mg; 0.88 mmol; 6.50 eq.) in N,N-dimethylformamide (0.68 mL) was heated to 80° C. After overnight the mixture (still showing incomplete conversion) was cooled to ambient temperature, diluted H$_2$O, acidified with 1N HCl and purified via Prep HPLC (Phenomenex Luna C18, 21×250 mm, 0-70% acetonitrile/0.1% aqueous HCl gradient over 13 minutes, flow rate 22 ml/min) to provide [3-({1-cyclopropyl-8-methoxy-5H-pyrido[4,3-b]indol-7-yl}oxy)propyl]bis(propan-2-yl)amine as an off-white solid. $^1$H NMR (400 MHz, DMSO-d$_6$) δ 13.08 (s, 1H), 9.75 (s, 1H), 8.21 (dd, J=6.8, 3.6 Hz, 1H), 7.85 (s, 1H), 7.74 (d, J=6.7 Hz, 1H), 7.31 (s, 1H), 4.22 (t, J=6.0 Hz, 2H), 3.91 (s, 3H), 3.63 (ddd, J=13.1, 8.8, 5.6 Hz, 2H), 3.24 (ddd, J=11.4, 6.9, 4.1 Hz, 2H), 3.06-2.97 (m, 1H), 2.30-2.22 (m, 2H), 1.46-1.40 (m, 2H), 1.37 (dt, J=5.5, 2.9 Hz, 2H), 1.33 (d, J=6.5 Hz, 6H), 1.29 (d, J=6.5 Hz, 6H). MS (ESI, pos. ion) m/z: 396.4 (M+1).

Example 62

(3R)-1-[3-({1-cyclopropyl-8-methoxy-5H-pyrido[4,3-b]indol-7-yl}oxy)propyl]-3-fluoropyrrolidine hydrochloride

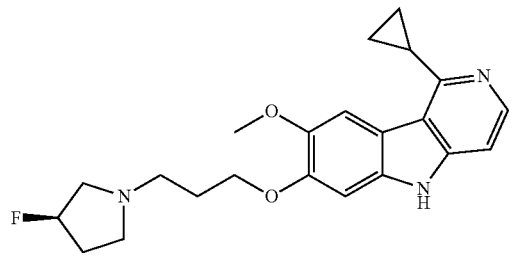 [SMILES: COc1cc2c(cc1OCCCN1CC[C@@H](F)C1)[nH]c1ccnc(C3CC3)c12]

The title compound was prepared using the synthetic sequence described for Example 60, changing step 4 as follows:

A mixture of tert-butyl 7-(3-chloropropoxy)-1-cyclopropyl-8-methoxy-5H-pyrido[4,3-b]indole-5-carboxylate (50.00 mg; 0.12 mmol; 1.00 eq.), potassium iodide (1.93 mg; 0.01 mmol; 0.10 eq.) and (3R)-3-fluoropyrrolidin-1-ium chloride (94.71 mg; 0.75 mmol; 6.50 eq.) in N,N-dimethylformamide (0.58 mL) was heated to 80° C. After 3.5 h the mixture was cooled to ambient temperature, diluted with 1:1 PhMe/EtOAc, washed with H$_2$O, dried over MgSO$_4$, filtered and concentrated.

The crude orange oil was dissolved in DCM (1.2 mL) and treated with TFA (0.6 mL) at ambient temperature. After 4.5 h the mixture was concentrated in vacuo. The oily residue was taken up in 1N HCl (~1.2 mL) and purified by Prep HPLC (Phenomenex Luna C18, 21×250 mm, 0-70% acetonitrile/0.1% aqueous HCl gradient over 13 minutes, flow rate 22 ml/min) to provide (3R)-1-[3-({1-cyclopropyl-8-methoxy-5H-pyrido[4,3-b]indol-7-yl}oxy)propyl]-3-fluoropyrrolidine as a white fluffy powder. $^1$H NMR (400 MHz, DMSO-d6) δ 12.97 (s, 1H), 11.27 (s, 1H), 10.72 (s, 1H), 8.21 (d, J=6.7 Hz, 1H), 7.85 (s, 1H), 7.73 (d, J=6.7 Hz, 1H), 7.32 (s, 1H), 5.46 (d, J=53.4 Hz, 1H), 4.20 (d, J=6.2 Hz, 2H), 3.91 (s, 3H), 3.72 (br s, 1H), 3.40-3.35 (m, 2H), 3.28-3.20

(m, 2H), 3.07-2.94 (m, 1H), 2.24 (t, J=7.4 Hz, 2H), 2.21-2.05 (m, 2H), 1.42 (dt, J=8.3, 3.2 Hz, 2H), 1.34 (dq, J=7.7, 4.8, 4.2 Hz, 2H). MS (ESI, pos. ion) m/z: 384.4 (M+1).

Example 63

(3S)-1-[3-({1-cyclopropyl-8-methoxy-5H-pyrido[4,3-b]indol-7-yl}oxy)propyl]-3-fluoropyrrolidine hydrochloride

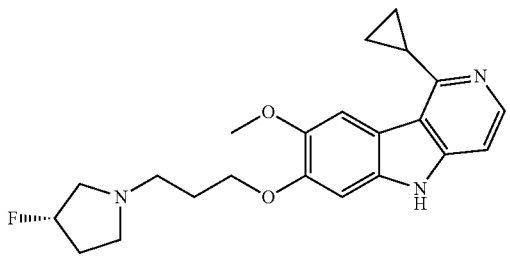 [SMILES: COc1cc2c(cc1OCCCN1CC[C@H](F)C1)[nH]c1ccnc(C3CC3)c12]

The title compound was prepared using the synthetic sequence described for Example 60, changing step 4 as follows:

A mixture of tert-butyl 7-(3-chloropropoxy)-1-cyclopropyl-8-methoxy-5H-pyrido[4,3-b]indole-5-carboxylate (38.00 mg; 0.09 mmol; 1.00 eq.), potassium iodide (1.46 mg; 0.01 mmol; 0.10 eq.), Hunig's base (0.10 mL; 0.57 mmol; 6.50 eq.) and (3S)-3-fluoropyrrolidin-1-ium chloride (71.98 mg; 0.57 mmol; 6.50 eq.) in N,N-dimethylformamide (0.44 mL) was heated to 80° C. After 2 h the mixture was cooled to ambient temperature, diluted with 1:1 PhMe/EtOAc, washed with H₂O, dried over MgSO₄, filtered and concentrated.

The crude orange oil was dissolved in DCM (1.0 mL) and treated with TFA (0.5 mL) at ambient temperature. After 2 h the mixture was concentrated in vacuo. The oily residue was taken up in 1N HCl (~1 mL) and purified by Prep HPLC (Phenomenex Luna C18, 21×250 mm, 0-70% acetonitrile/0.1% aqueous HCl gradient over 13 minutes, flow rate 22 ml/min) to provide title compound. ¹H NMR (400 MHz, DMSO-d₆) δ 13.03 (s, 1H), 11.46 (s, 1H), 10.89 (s, 1H), 8.20 (d, J=6.7 Hz, 1H), 7.85 (s, 1H), 7.73 (d, J=6.7 Hz, 1H), 7.32 (s, 1H), 5.45 (d, J=53.4 Hz, 1H), 4.21 (t, J=6.1 Hz, 2H), 3.91 (s, 3H), 3.72 (s, 1H), 3.40-3.32 (m, 2H), 3.28-3.21 (m, 2H), 3.01 (tt, J=8.5, 5.4 Hz, 1H), 2.35-2.12 (m, 4H), 1.47-1.39 (m, 2H), 1.36 (tt, J=5.3, 2.9 Hz, 2H). MS (ESI, pos. ion) m/z: 384.4 (M+1).

Example 64

1-(3-{[1-(3,6-dihydro-2H-pyran-4-yl)-8-methoxy-5H-pyrido[4,3-b]indol-7-yl]oxy}propyl)pyrrolidine hydrochloride and 1-(3-{[8-methoxy-1-(oxan-4-yl)-5H-pyrido[4,3-b]indol-7-yl]oxy}propyl)pyrrolidine hydrochloride (2:1 Mixture)

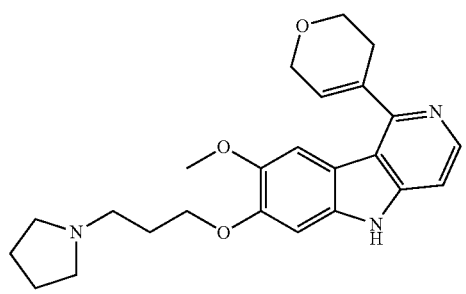

-continued

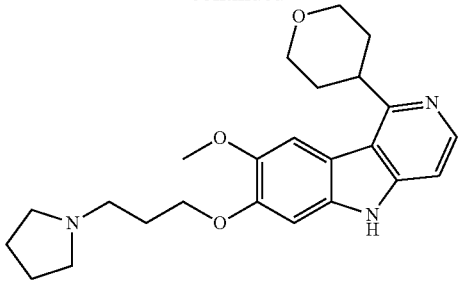

Step 1

A mixture of tert-butyl 7-(benzyloxy)-1-chloro-8-methoxy-5H-pyrido[4,3-b]indole-5-carboxylate (Reference 5; 150.00 mg; 0.34 mmol; 1.00 eq.), 4-(4,4,5,5-tetramethyl-1,3,2-dioxaborolan-2-yl)-3,6-dihydro-2H-pyran (107.69 g; 0.51 mol; 1.50 eq.), 1,1'-bis(diphenylphosphino)ferrocene]dichloropalladium(II) (25.01 mg; 0.03 mmol; 0.10 eq.) and sodium carbonate (108.67 mg; 1.03 mmol; 3.00 eq.) in 1,4-dioxane (1.14 mL) and water (0.34 mL) was heated to 100° C. After 2 hours, the mixture was cooled to ambient temperature, diluted with EtOAc, washed with water and brine, dried over MgSO₄, filtered and concentrated. The residue was purified by column chromatography (12 G ISCO Gold) eluting with 0-80% EtOAc in hexanes to provide tert-butyl 7-(benzyloxy)-1-(3,6-dihydro-2H-pyran-4-yl)-8-methoxy-5H-pyrido[4,3-b]indole-5-carboxylate (76 mg; 46% yield).

Step 2

A mixture of tert-butyl 7-(benzyloxy)-1-(3,6-dihydro-2H-pyran-4-yl)-8-methoxy-5H-pyrido[4,3-b]indole-5-carboxylate (76.00 mg; 0.16 mmol; 1.00 eq.) and palladium on carbon (0.50 mg; 0.00 mmol; 0.03 eq.) in methanol (1.56 mL) was stirred under an atmosphere of H₂ from a balloon. After overnight (still incomplete conversion) more catalyst was added and the mixture was stirred for an additional 7 h. The mixture was then filtered with additional MeOH and concentrated. The crude off-white solid (¹H NMR showed dihydropyran with traces of tetrahydropyran; both masses were detected by LC/MS) was taken on without further purification assuming 100% yield (62 mg, 100% yield).

Step 3

A mixture of tert-butyl 1-(3,6-dihydro-2H-pyran-4-yl)-7-hydroxy-8-methoxy-5H-pyrido[4,3-b]indole-5-carboxylate (62.00 mg; 0.16 mmol; 1.00 eq.) (containing also the reduced tetrahydropyran), 1-(3-chloropropyl)pyrrolidin-1-ium chloride (57.59 mg; 0.31 mmol; 2.00 eq.) and potassium carbonate (86.33 mg; 0.63 mmol; 4.00 eq.) in N,N-dimethylformamide (1.56 mL) was stirred at 100° C. After 7 h the mixture was cooled to ambient temperature, diluted with 1:1 PhMe/EtOAc, washed with water, dried over MgSO₄, filtered and concentrated to provide an orange oil.

The oil was dissolved in 2.0 mL of DCM and treated with 1.0 mL TFA at ambient temperature. After 2 hours, the reaction mixture was concentrated in vacuo. The residue was taken up in 1N HCl (~1.5 mL) and purified by Prep HPLC (Phenomenex Luna C18, 21×250 mm, 0-70% acetonitrile/0.1% aqueous HCl gradient over 13 minutes, flow rate 22 ml/min) to provide 1-(3-{[1-(3,6-dihydro-2H-pyran-4-yl)-8-methoxy-5H-pyrido[4,3-b]indol-7-yl]oxy}propyl)pyrrolidine hydrochloride and 1-(3-{[8-methoxy-1-(oxan-4-yl)-5H-pyrido[4,3-b]indol-7-yl]oxy}propyl)pyrrolidine hydrochloride (2:1 mixture) as a yellow powder. 1H NMR (only major component) (400 MHz, DMSO-d₆) δ 13.13 (s, 1H), 10.71 (s, 1H), 8.39 (d, J=6.7 Hz, 1H), 7.82 (d, J=6.8 Hz, 1H), 7.48 (s, 1H), 7.32 (s, 1H), 6.58 (d, J=2.9 Hz, 1H), 4.41 (q, J=2.8 Hz, 2H), 4.20 (d, J=6.1 Hz, 2H), 4.00 (t, J=5.3 Hz, 2H), 3.84 (s, 3H), 3.60-3.50 (m, 2H), 3.29-3.24 (m, 2H), 3.05-2.95 (m, 2H), 2.69-2.62 (m, 2H), 2.26-2.18 (m, 2H), 2.02-1.94 (m, 2H), 1.92-1.84 (m, 2H). MS (ESI, pos. ion) m/z: 408.4 (M+1).

Example 65

1-(3-{[8-methoxy-1-(oxan-4-yl)-5H-pyrido[4,3-b]indol-7-yl]oxy}propyl)pyrrolidine hydrochloride and 1-(3-{[1-(3,6-dihydro-2H-pyran-4-yl)-8-methoxy-5H-pyrido[4,3-b]indol-7-yl]oxy}propyl)pyrrolidine hydrochloride (4:1 Mixture)

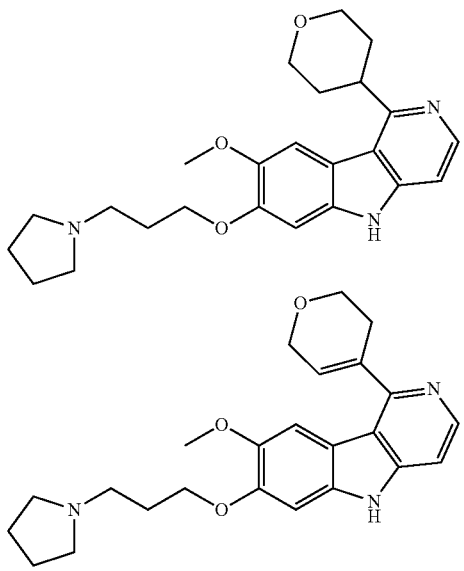

The title compound was prepared using the synthetic procedures described for Example 64 changing step 2 as follows:

A mixture of tert-butyl 7-(benzyloxy)-1-(3,6-dihydro-2H-pyran-4-yl)-8-methoxy-5H-pyrido[4,3-b]indole-5-carboxylate (50.00 mg; 0.10 mmol; 1.00 eq.) and rhodium (5% wt on alumina) (1.06 mg; 0.01 mmol; 0.10 eq.) in methanol (1.03 mL) was stirred under an atmosphere of H₂ from a balloon. After 48 the mixture was filtered with additional MeOH and concentrated. The crude off-white was taken on without further purification assuming 100% yield (40 mg)

After step 3 (as described for Example 64 1-(3-{[8-methoxy-1-(oxan-4-yl)-5H-pyrido[4,3-b]indol-7-yl]oxy}propyl)pyrrolidine hydrochloride and 1-(3-{[1-(3,6-dihydro-2H-pyran-4-yl)-8-methoxy-5H-pyrido[4,3-b]indol-7-yl]oxy}propyl)pyrrolidine hydrochloride and (4:1 mixture) were obtained as a white powder. 1H NMR (only major component) (400 MHz, DMSO-d₆) δ 13.07 (s, 1H), 10.47 (s, 1H), 8.34 (d, J=6.7 Hz, 1H), 7.81 (d, J=7.0 Hz, 1H), 7.64 (s, 1H), 7.33 (s, 1H), 4.22 (t, J=6.1 Hz, 2H), 4.08-4.04 (m, 2H), 3.93 (s, 3H), 3.73 (td, J=11.7, 1.9 Hz, 2H), 3.61-3.52 (m, 2H), 3.28-3.25 (m, 2H), 3.05-2.97 (m, 2H), 2.65-2.62 (m, 1H), 2.26-2.18 (m, 2H), 2.11 (td, J=12.3, 4.2 Hz, 2H), 2.02-1.84 (m, 6H). MS (ESI, pos. ion) m/z: 410.5 (M+1).

Example 66

4-{8-methoxy-7-[3-(pyrrolidin-1-yl)propoxy]-5H-pyrido[4,3-b]indol-1-yl}-1,2,3,6-tetrahydropyridine bishydrochloride

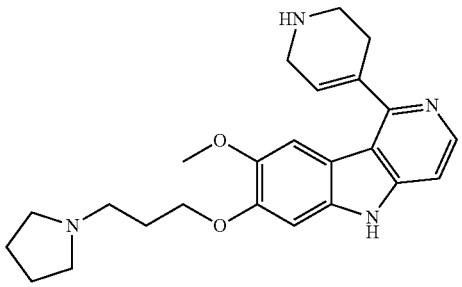 [SMILES: COc1cc2c(cc1OCCCN1CCCC1)[nH]c1ccnc(C3=CCNCC3)c12]

Step 1

A mixture of tert-butyl 7-(benzyloxy)-1-chloro-8-methoxy-5H-pyrido[4,3-b]indole-5-carboxylate (reference 5; 200.00 mg; 0.46 mmol; 1.00 eq.), tert-butyl 4-(4,4,5,5-tetramethyl-1,3,2-dioxaborolan-2-yl)-3,6-dihydro-1(2H)-pyridinecarboxylate (211.35 mg; 0.68 mmol; 1.50 eq.), 1,1'-Bis(diphenylphosphino)ferrocene]dichloropalladium (II) (33.34 mg; 0.05 mmol; 0.10 eq.) and sodium carbonate (144.89 mg; 1.37 mmol; 3.00 eq.) in 1,4-dioxane (1.52 mL) and water (0.46 mL) was heated to 100° C. The mixture was then cooled to ambient temperature, diluted with EtOAc, washed with water and brine, dried over MgSO₄, filtered and concentrated. The residue was purified by column chromatography (24 G ISCO Gold) eluting with 0-100% EtOAc in heptane to provide tert-butyl 4-[7-(benzyloxy)-5-[(tert-butoxy)carbonyl]-8-methoxy-5H-pyrido[4,3-b]indol-1-yl]-1,2,3,6-tetrahydropyridine-1-carboxylate as a white foam. 166 mg; 62% yield.

Step 2

A mixture of tert-butyl 4-[7-(benzyloxy)-5-[(tert-butoxy)carbonyl]-8-methoxy-5H-pyrido[4,3-b]indol-1-yl]-1,2,3,6-tetrahydropyridine-1-carboxylate (50.00 mg; 0.09 mmol; 1.00 eq.) and palladium on carbon (0.91 mg; 0.01 mmol; 0.10 eq.) in methanol (0.85 mL) was stirred under an atmosphere of H₂ from a balloon. After overnight stirring the mixture was filtered with additional MeOH and concentrated. This material was taken on without further purification assuming 100% yield (40 mg).

Step 3

A mixture of tert-butyl 4-{5-[(tert-butoxy)carbonyl]-7-hydroxy-8-methoxy-5H-pyrido[4,3-b]indol-1-yl}-1,2,3,6-tetrahydropyridine-1-carboxylate (40.00 mg; 0.08 mmol; 1.00 eq.), 1-(3-chloropropyl)pyrrolidin-1-ium chloride (29.72 mg; 0.16 mmol; 2.00 eq.) and potassium carbonate (44.55 mg; 0.32 mmol; 4.00 eq.) in N,N-dimethylformamide (0.81 mL) was stirred at 100° C. The mixture was then cooled to ambient temperature, diluted with 1:1 PhMe/EtOAc, washed with water, dried over MgSO₄, filtered and concentrated to provide an orange oil.

The oil was taken up in DCM (1 mL) and treated with TFA (0.5 mL) at ambient temperature. After 2 h the mixture was concentrated in vacuo. The residue was taken up in 1.5 mL 1N HCl, filtered through a syringe filter and purified by Prep HPLC ((Phenomenex Luna C18, 21×250 mm, 0-70% acetonitrile/0.1% aqueous HCl gradient over 13 minutes, flow rate 22 ml/min) to provide 4-{8-methoxy-7-[3-(pyrrolidin-1-yl)propoxy]-5H-pyrido[4,3-b]indol-1-yl}-1,2,3,6- tetrahydropyridine bishydrochloride as a yellow solid, 20.2 mg. $^1$H NMR (400 MHz, DMSO-$d_6$) δ 13.11 (s, 1H), 10.49 (s, 1H), 9.76 (br s, 2H), 8.41 (d, J=6.7 Hz, 1H), 7.83 (s, 1H), 7.62 (s, 1H), 7.29 (s, 1H), 6.54 (s, 1H), 4.20 (t, J=6.0 Hz, 2H), 3.96-3-91 (m, 4H), 3.61-3.52 (m, 2H), 3.48-3.41 (m, 2H), 3.28-3.24 (m, 2H), 3.04-2.93 (m, 4H), 2.25-2.17 (m, 2H), 2.02-1.95 (m, 2H), 1.92-1.82 (m, 2H); MS (ESI, pos. ion) m/z: 407.3 (M+1).

Example 67

(3-{[8-methoxy-1-(propan-2-yl)-5H-pyrido[4,3-b]indol-7-yl]oxy}propyl)dimethylamine hydrochloride

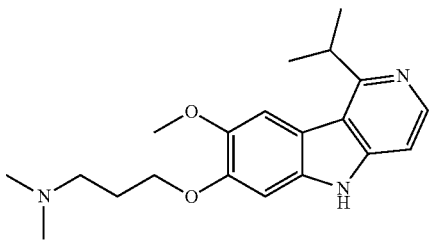 [SMILES: COc1cc2c(cc1OCCCN(C)C)[nH]c1ccnc(C(C)C)c12]

Step 1

To a mixture of tert-butyl 7-(benzyloxy)-1-chloro-8-methoxy-5H-pyrido[4,3-b]indole-5-carboxylate (Reference 5; 300 mg; 0.68 mmol; 1.00 eq.), and tris((3Z)-4-hydroxypent-3-en-2-one) iron (12 mg; 0.03 mmol; 0.05 eq.) in tetrahydrofuran (5 mL) and NMP (0.5 mL) at ambient temperature was added (isopropyl)magnesium bromide (0.8 mL; 1.00 mol/L; 0.82 mmol; 1.20 eq.) and the mixture was stirred at ambient temperature. After 0.5 h the mixture was diluted with EtOAc, washed with water, dried over MgSO$_4$, filtered and concentrated. The residue was purified by column chromatography (24 G ISCO Gold) eluting with 0-60% EtOAc in heptane to obtain NO SEPARATION of the product from the unreacted starting material. The semi-purified material was taken up in DMF and purified by Prep HPLC (Phenomenex Luna C18, 21×250 mm, 5-95% acetonitrile/0.1% aqueous HCl gradient over 13 minutes, flow rate 22 ml/min) to provide tert-butyl 7-(benzyloxy)-8-methoxy-1-(propan-2-yl)-5H-pyrido[4,3-b]indole-5-carboxylate as a white powder (60 mg. 19%)

Step 2

A mixture of tert-butyl 7-(benzyloxy)-8-methoxy-1-(propan-2-yl)-5H-pyrido[4,3-b]indole-5-carboxylate (60 mg; 0.13 mmol; 1.00 eq.) and palladium on carbon (2 mg; 0.01 mmol; 0.10 eq.) in methanol (3 mL) was stirred under an atmosphere of H$_2$ from a balloon. After 4 the mixture was filtered with additional MeOH and concentrated. The crude white solid was taken on to the next step without further purification assuming 100% yield.

Step 3

A mixture of tert-butyl 7-hydroxy-8-methoxy-1-(propan-2-yl)-5H-pyrido[4,3-b]indole-5-carboxylate (47 mg; 0.13 mmol; 1.00 eq.), (3-chloropropyl)dimethylamine (32 mg; 0.26 mmol; 2.00 eq.) and potassium carbonate (73 mg; 0.53 mmol; 4.00 eq.) in DMF (2 mL) was stirred at 100° C. After 2 h the mixture was cooled to ambient temperature, diluted with 1:1 PhMe/EtOAc, washed with water, dried over MgSO$_4$, filtered and concentrated to provide a colorless oil. The oil was taken up in DCM (1 mL) and treated with TFA (0.5 mL) at ambient temperature. After 1.5 h the mixture was concentrated in vacuo. The residue was taken up in 1.5 mL 1N HCl and purified by R-Phase HPLC (Phenomenex Luna C18, 21×250 mm, 0-60% acetonitrile/0.1% aqueous HCl gradient over 13 minutes, flow rate 22 ml/min) to provide (3-{[8-methoxy-1-(propan-2-yl)-5H-pyrido[4,3-b]indol-7-yl]oxy}propyl)dimethylamine hydrochloride as a white powder. $^1$H NMR (400 MHz, DMSO-$d_6$) δ 13.11 (s, 1H), 10.40 (s, 1H), 8.34 (d, J=6.7 Hz, 1H), 7.79 (d, J=6.7 Hz, 1H), 7.68 (s, 1H), 7.33 (s, 1H), 4.21 (dt, J=11.9, 6.4 Hz, 3H), 3.92 (s, 3H), 3.25-3.18 (m, 2H), 2.78 (s, 3H), 2.77 (s, 3H), 2.22 (p, J=6.2 Hz, 2H), 1.54 (s, 3H), 1.52 (s, 3H). MS (ESI, pos. ion) m/z: 342.4 (M+1).

Example 68

(3-{[8-methoxy-1-(oxan-4-yl)-5H-pyrido[4,3-b]indol-7-yl]oxy}propyl)dimethylamine hydrochloride

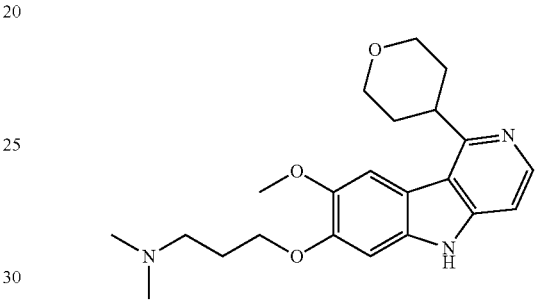

The title compound was prepared using the synthetic procedures described for Example 64 changing step 2 and 3 as follows:

Step 2

A mixture of tert-butyl 7-(benzyloxy)-1-(3,6-dihydro-2H-pyran-4-yl)-8-methoxy-5H-pyrido[4,3-b]indole-5-carboxylate (100.00 mg; 0.21 mmol; 1.00 eq.) and palladium on carbon (2.19 mg; 0.02 mmol; 0.10 eq.) in ethyl acetate (2.06 mL) was stirred under an atmosphere of H$_2$ from a balloon. After overnight the mixture was heated to 50° C. for 6 h. The mixture was then filtered with additional EtOAc and concentrated. The crude material was taken on to the next step without further purification assuming 100% yield.

Step 3

A mixture of tert-butyl 7-hydroxy-8-methoxy-1-(oxan-4-yl)-5H-pyrido[4,3-b]indole-5-carboxylate (80.00 mg; 0.20 mmol; 1.00 eq.), (3-chloropropyl)dimethylamine (48.83 mg; 0.40 mmol; 2.00 eq.) and potassium carbonate (110.83 mg; 0.80 mmol; 4.00 eq.) in N,N-dimethylformamide (2.01 mL) was stirred at 100° C. After 1.5 the mixture was cooled to ambient temperature, diluted with 1:1 PhMe/EtOAc, washed with water, dried over MgSO$_4$, filtered and concentrated to provide a yellow wax. The wax was taken up in DCM (1.5 mL) and treated with TFA (0.7 mL) at ambient temperature. After 1.5 h the mixture was concentrated in vacuo. The residue was taken up in 1.5 mL 1N HCl and purified by Prep HPLC (Phenomenex Luna C18, 21×250 mm, 0-60% acetonitrile/0.1% aqueous HCl gradient over 13 minutes, flow rate 22 ml/min) to provide (3-{[8-methoxy-1-(oxan-4-yl)-5H-pyrido[4,3-b]indol-7-yl]oxy}propyl)dimethylamine hydrochloride as a white powder. (39 mg)$^1$H NMR (400 MHz, DMSO-$d_6$) δ 14.28 (s, 1H), 13.17 (s, 1H), 10.46 (s, 1H), 8.35 (d, J=6.7 Hz, 1H), 7.81 (d, J=6.7 Hz, 1H), 7.64 (s, 1H), 7.34 (s, 1H), 4.20 (t, J=6.2 Hz, 2H), 4.06 (dd, J=11.4, 4.1 Hz, 3H), 3.93 (s, 3H), 3.73 (td, J=11.6, 1.8 Hz, 2H), 3.22

(s, 2H), 2.78 (s, 3H), 2.77 (s, 3H), 2.26-2.19 (m, 2H), 2.14 (td, J=12.4, 4.3 Hz, 1H), 1.97-1.90 (m, 2H). MS (ESI, pos. ion) m/z: 384.4 (M+1).

Example 69

[3-({1-cyclobutyl-8-methoxy-5H-pyrido[4,3-b]indol-7-yl}oxy)propyl]dimethylamine hydrochloride

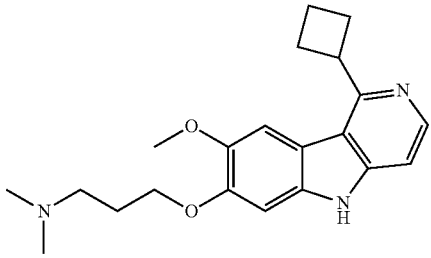 [SMILES: COc1cc2c(cc1OCCCN(C)C)[nH]c1ccnc(C3CCC3)c12]

The title compound was prepared using the synthetic procedures described for Example 67 changing step 1 as follows:

To a mixture of tert-butyl 7-(benzyloxy)-1-chloro-8-methoxy-5H-pyrido[4,3-b]indole-5-carboxylate (Reference 5; 300.00 g; 0.68 mol; 1.00 eq.) and 1,1'-bis(diphenylphosphino)ferrocene]dichloropalladium(II) (50.01 mg; 0.07 mmol; 0.10 eq.) in 1,4-dioxane (6.84 mL) at ambient temperature under Argon was added bromo(cyclobutyl)zinc (2.73 mL; 0.50 mol/L; 1.37 mmol; 2.00 eq.) drop-wise. After complete addition the mixture was heated to 80° C. under Argon. After 2 h the mixture was cooled to ambient temperature, water was added and the suspension was stirred vigorously for 10 minutes. The mixture was then extracted with EtOAc. The organic phase was washed once with brine and the combined aqueous phase back-extracted with EtOAc. The combined organic phase was dried over MgSO$_4$, filtered and concentrated. The residue was purified by column chromatography (24 G ISCO Gold) eluting with 0-50% EtOAc in heptane to obtain almost complete separation of tert-butyl 7-(benzyloxy)-1-cyclobutyl-8-methoxy-5H-pyrido[4,3-b]indole-5-carboxylate from the unreacted starting material. This material was taken on to the next step without further purification (95 mg; 30% yield).

After step 3 [3-({1-cyclobutyl-8-methoxy-5H-pyrido[4,3-b]indol-7-yl}oxy)propyl]dimethylamine hydrochloride was obtained as a white powder (54 mg). $^1$H NMR (400 MHz, DMSO-d$_6$) δ 14.25 (s, 1H), 13.09 (s, 1H), 10.45 (s, 1H), 8.34 (d, J=6.8 Hz, 1H), 7.79 (d, J=6.7 Hz, 1H), 7.67 (s, 1H), 7.31 (s, 1H), 4.73 (p, J=8.7 Hz, 1H), 4.19 (t, J=6.1 Hz, 2H), 3.94 (s, 3H), 3.22 (q, J=7.3, 5.7 Hz, 2H), 2.78 (s, 3H), 2.77 (s, 3H), 2.60 (td, J=8.8, 8.3, 5.7 Hz, 4H), 2.31-2.23 (m, 1H), 2.24-2.16 (m, 2H), 2.01-1.92 (m, 1H). MS (ESI, pos. ion) m/z: 354.4 (M+1).

Example 70

[2-({8-methoxy-5H-pyrido[4,3-b]indol-7-yl}oxy)ethyl]dimethylamine hydrochloride

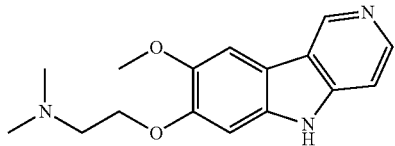 [SMILES: COc1cc2c(cc1OCCN(C)C)[nH]c1ccncc12]

Step 1

A mixture of tert-butyl 7-(benzyloxy)-1-chloro-8-methoxy-5H-pyrido[4,3-b]indole-5-carboxylate (Reference 5; 610.00 mg; 1.39 mmol; 1.00 eq.) and palladium on carbon (29.58 mg; 0.28 mmol; 0.20 eq.) in tetrahydrofuran (13.90 mL) was stirred under an atmosphere of H$_2$ from a balloon. After 24 h the mixture was filtered with additional MeOH and concentrated. The crude orange oil was taken on to the next step without further purification assuming 100% yield.

Step 2

A mixture of tert-butyl 7-hydroxy-8-methoxy-5H-pyrido[4,3-b]indole-5-carboxylate (100.00 mg; 0.32 mmol; 1.00 eq.), 2-(dimethylamino)ethanol (0.04 mL; 0.35 mmol; 1.10 eq.) and (tributylphosphoranylidene)acetonitrile (153.56 mg; 0.64 mmol; 2.00 eq.) in toluene (1.06 mL) was heated to 110° C. After 30 minutes, the mixture was cooled to ambient temperature and concentrated in vacuo. The residue was taken up in DMF and 1N HCl (total of 1.5 mL) and purified by Prep HPLC (Phenomenex Luna C18, 21×250 mm, 0-60% acetonitrile/0.1% aqueous HCl gradient over 13 minutes, flow rate 22 ml/min) to provide [2-({8-methoxy-5H-pyrido[4,3-b]indol-7-yl}oxy)ethyl]dimethylamine hydrochloride as a tan solid. 12.9 mg. $^1$H NMR (400 MHz, DMSO-d$_6$; containing 2 drops of D$_2$O) δ 9.53 (s, 1H), 8.47 (dd, J=6.7, 0.9 Hz, 1H), 8.04 (s, 1H), 7.90 (d, J=6.7 Hz, 1H), 7.38 (s, 1H), 4.46 (t, J=5.0 Hz, 2H), 3.87 (s, 3H), 3.57 (t, J=5.0 Hz, 2H), 2.88 (s, 6H). MS (ESI, pos. ion) m/z: 286.4 (M+1).

Example 71

1-[2-({8-methoxy-5H-pyrido[4,3-b]indol-7-yl}oxy)ethyl]pyrrolidine hydrochloride

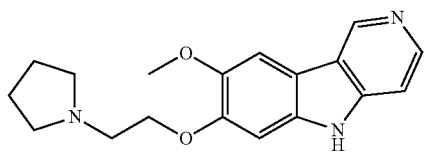 [SMILES: COc1cc2c(cc1OCCN1CCCC1)[nH]c1ccncc12]

The title compound was prepared using the synthetic procedures described for Example 70 changing step 2 as follows:

A mixture of tert-butyl 7-hydroxy-8-methoxy-5H-pyrido[4,3-b]indole-5-carboxylate (100.00 mg; 0.32 mmol; 1.00 eq.), 2-(1-pyrrolidinyl)ethanol (146.56 mg; 1.27 mmol; 4.00 eq.) and (tributylphosphoranylidene)acetonitrile (153.56 mg; 0.64 mmol; 2.00 eq.) in toluene (1.06 mL) was heated to 115° C. After 1 h the mixture was cooled to ambient temperature and concentrated in vacuo. The crude dark oil was taken up in DCM (1 mL) and treated with TFA (0.5 mL) at ambient temperature. After 3 h the mixture was concentrated in vacuo. The residue was taken up in 1N HCl (total of 1.5 mL) and purified by Prep HPLC (Phenomenex Luna C18, 21×250 mm, 0-40% acetonitrile/0.1% aqueous HCl gradient over 13 minutes, flow rate 22 ml/min) to provide 1-[2-({8-methoxy-5H-pyrido[4,3-b]indol-7-yl}oxy)ethyl]pyrrolidine hydrochloride as an off-white solid 28.9 mg. $^1$H NMR (400 MHz, DMSO-$d_6$) δ 13.09 (s, 1H), 11.19 (s, 1H), 9.60 (s, 1H), 8.51 (d, J=6.7 Hz, 1H), 8.10 (s, 1H), 7.91 (d, J=6.7 Hz, 1H), 7.36 (s, 1H), 4.50 (t, J=5.0 Hz, 2H), 3.89 (s, 3H), 3.68-3.57 (m, 4H), 3.13 (br s, 2H), 1.99 (br s, 2H), 1.88 (br s, 2H). MS (ESI, pos. ion) m/z: 312.3 (M+1).

Example 72

1-[3-({8-methoxy-5H-pyrido[4,3-b]indol-7-yl}oxy)propyl]azetidine hydrochloride

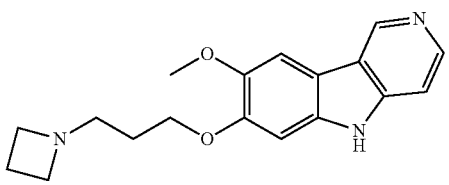 [SMILES: COc1cc2c(cc1OCCCN1CCC1)[nH]c1ccncc12]

The title compound was prepared using the synthetic procedures described for Example 70 changing step 2 as follows:

A mixture of tert-butyl 7-hydroxy-8-methoxy-5H-pyrido[4,3-b]indole-5-carboxylate (140.00 mg; 0.45 mmol; 1.00 eq.), 3-(azetidin-1-yl)propan-1-ol (205.19 mg; 1.78 mmol; 4.00 eq.) and (tributylphosphoranylidene)acetonitrile (214.99 mg; 0.89 mmol; 2.00 eq.) in toluene (1.48 mL) was heated to 115° C. After 0.5 h LC/MS the mixture was cooled to ambient temperature and concentrated in vacuo. The crude dark oil was taken up in DCM (1.5 mL) and treated with TFA (1.3 mL) at ambient temperature. After 2 h the mixture was concentrated in vacuo. The residue was taken up in 1N HCl (1.5 mL) and DMF (0.5 mL) and purified by Prep HPLC (Phenomenex Luna C18, 21×250 mm, 0-40% acetonitrile/0.1% aqueous HCl gradient over 13 minutes, flow rate 22 ml/min) to provide 1-[3-({8-methoxy-5H-pyrido[4,3-b]indol-7-yl}oxy)propyl]azetidine hydrochloride, 12.5 mg. $^1$H NMR (400 MHz, DMSO-$d_6$) δ 13.00 (s, 1H), 10.56 (s, 1H), 9.57 (s, 1H), 8.51 (d, J=6.7 Hz, 1H), 8.05 (s, 1H), 7.90 (d, J=6.7 Hz, 1H), 7.28 (s, 1H), 4.17 (t, J=6.1 Hz, 2H), 4.10 (dt, J=8.8, 5.5 Hz, 2H), 4.03-3.94 (m, 2H), 3.18-3.28 (m, 2H), 2.42-2.33 (m, 1H), 2.26 (ddd, J=10.7, 7.9, 4.4 Hz, 1H), 2.02 (p, J=6.5 Hz, 2H). MS (ESI, pos. ion) m/z: 312.3 (M+1).

Example 73

1-(3-{[8-methoxy-1-(oxan-4-yloxy)-5H-pyrido[4,3-b]indol-7-yl]oxy}propyl)pyrrolidine trifluoroacetate

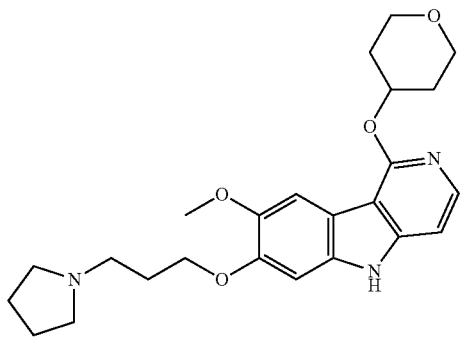 [SMILES: COc1cc2c(cc1OCCCN1CCCC1)[nH]c1ccnc(OC3CCOCC3)c12]

Step 1

Into a 100-mL round-bottom flask, was placed 3-bromopyridin-2-ol (4 g, 22.99 mmol, 1.00 eq.), tetrahydrofuran (40 mL), tetrahydro-2H-pyran-4-ol (2.34 g, 22.91 mmol, 1.00 eq.), PPh$_3$ (7.23 g, 27.56 mmol, 1.20 eq.), then added DEAD (4.8 g, 27.56 mmol, 1.20 eq.) by dropwise. The resulting solution was stirred for 1 h at 25° C. The resulting mixture was concentrated under vacuum. The residue was applied onto a silica gel column with ethyl acetate/petroleum ether (1:5). The collected fractions were combined and concentrated under vacuum. This resulted in 2.58 g (43%) of 3-bromo-2-((tetrahydro-2H-pyran-4-yl)oxy)pyridine as colorless oil. MS (ESI, pos. ion) m/z: 258.1 (M+1).

Step 2

Into a 100-mL round-bottom flask, was placed 2-[4-(benzyloxy)-5-methoxy-2-nitrophenyl]-4,4,5,5-tetramethyl-1,3,2-dioxaborolane (850 mg, 2.21 mmol, 1.00 eq.), dioxane (30 mL), water (10 mL), 3-bromo-2-((tetrahydro-2H-pyran-4-yl)oxy)pyridine (570 mg, 2.21 mmol, 1.00 eq.), Cs$_2$CO$_3$ (2158 mg, 6.62 mmol, 3.00 eq.), Pd(PPh$_3$)$_4$(255 mg, 0.22 mmol, 0.10 eq.). The resulting solution was stirred for 6 h at 100° C. The resulting mixture was concentrated under vacuum. The resulting solution was diluted with 50 mL of EA and washed with 2×30 mL of water. The residue was applied onto a silica gel column with ethyl acetate/petroleum ether (1:3). The collected fractions were combined and concentrated under vacuum. This resulted in 285 mg (30%) of 3-(4-(benzyloxy)-5-methoxy-2-nitrophenyl)-2-((tetrahydro-2H-pyran-4-yl)oxy)pyridine as yellow solid. MS (ESI, pos. ion) m/z: 437.2 (M+1).

Step 3

Into a 50-mL round-bottom flask, was placed 3-(4-(benzyloxy)-5-methoxy-2-nitrophenyl)-2-((tetrahydro-2H-pyran-4-yl)oxy)pyridine (285 mg, 0.65 mmol, 1.00 eq.), P(OEt)$_3$ (8 mL). The resulting solution was stirred for 24 h at 130° C. The resulting mixture was concentrated under vacuum. The residue was applied onto a silica gel column with ethyl acetate/petroleum ether (1:1). The collected fractions were combined and concentrated under vacuum. This resulted in 120 mg (45%) of 7-(benzyloxy)-8-methoxy-1-((tetrahydro-2H-pyran-4-yl)oxy)-5H-pyrido[4,3-b]indole as light yellow solid. MS (ESI, pos. ion) m/z: 405.2 (M+1).

Step 4

Into a 50-mL round-bottom flask, was placed 7-(benzyloxy)-8-methoxy-1-((tetrahydro-2H-pyran-4-yl)oxy)-5H-pyrido[4,3-b]indole (120 mg, 0.30 mmol, 1.00 eq.), tetrahydrofuran (10 mL), 4-dimethylaminopyridine (36 mg, 0.29 mmol, 1.00 eq.), Boc$_2$O (65 mg, 0.30 mmol, 1.00 eq.). The resulting solution was stirred for 6 h at 25° C. The resulting mixture was concentrated under vacuum. The residue was applied onto a silica gel column with ethyl acetate/petroleum ether (1:4). The collected fractions were combined and concentrated under vacuum. This resulted in 130 mg (87%) of tert-butyl 7-(benzyloxy)-8-methoxy-1-((tetrahydro-2H-pyran-4-yl)oxy)-5H-pyrido[4,3-b]indole-5-carboxylate as yellow solid. MS (ESI, pos. ion) m/z: 405.2 (M+1).

Step 5

To a solution of tert-butyl 7-(benzyloxy)-8-methoxy-1-((tetrahydro-2H-pyran-4-yl)oxy)-5H-pyrido[4,3-b]indole-5-carboxylate 120 mg, 0.24 mmol, 1.00 eq.) in MeOH (12 mL) was added 12 mg of 10% Pd/C (50% water moistened). The mixture was degassed and purged with hydrogen for three times. The resulting mixture was stirred for 4 h at room temperature under H$_2$ atmosphere. The solids were filtered out. The resulting mixture was concentrated under vacuum. This resulted in 80 mg (81%) of tert-butyl 7-hydroxy-8-methoxy-1-((tetrahydro-2H-pyran-4-yl)oxy)-5H-pyrido[4,3-b]indole-5-carboxylate as light yellow solid. MS (ESI, pos. ion) m/z: 405.2 (M+1).

Step 6

Into a 50-mL round-bottom flask, was placed tert-butyl 7-hydroxy-8-methoxy-1-(oxan-4-yloxy)-5H-pyrido[4,3-b]indole-5-carboxylate (80 mg, 0.19 mmol, 1.00 eq.), MeCN (6 mL), 1-(3-chloropropyl)pyrrolidine hydrochloride (36 mg, 0.20 mmol, 1.00 eq.), potassium carbonate (80 mg, 0.58 mmol, 3.00 eq.). The resulting solution was stirred for 3 h at 60° C. The reaction mixture was cooled to room temperature. The solids were filtered out. The resulting mixture was concentrated under vacuum. This resulted in 98 mg (97%) of tert-butyl 8-methoxy-7-(3-(pyrrolidin-1-yl)propoxy)-1-((tetrahydro-2H-pyran-4-yl)oxy)-5H-pyrido[4,3-b]indole-5-carboxylate as yellow solid. MS (ESI, pos. ion) m/z: 526.3 (M+1).

Step 7

Into a 50-mL round-bottom flask, was placed tert-butyl 8-methoxy-7-(3-(pyrrolidin-1-yl)propoxy)-1-((tetrahydro-2H-pyran-4-yl)oxy)-5H-pyrido[4,3-b]indole-5-carboxylate (88 mg, 0.17 mmol, 1.00 eq.), dichloromethane (5 mL), hydrogen chloride(g)/dioxane (1 mL, 2M). The resulting solution was stirred for 1 h at 25° C. The resulting mixture was concentrated under vacuum. The crude reaction mixture was filtered and subjected to reverse phase preparative HPLC (Waters SunFire column, 19×150 mm; gradient elution of 10% MeCN in water to 20% MeCN in water over a 10 min period, where both solvents contain 0.05% TFA) to provide the title compound as light yellow solid (18.4 mg, 20%). $^1$H NMR (300 MHz, DMSO-d$_6$): δ 11.60 (br, 1H), 9.50 (s, 1H), 7.90 (d, J=5.9 Hz, 1H), 7.62 (s, 1H), 7.21-7.07 (m, 2H), 5.54 (dq, J=8.2, 4.3, 3.8 Hz, 1H), 4.17 (t, J=5.9 Hz, 2H), 4.02-3.89 (m, 2H), 3.65 (qd, J=9.8, 7.9, 5.2 Hz, 4H), 3.37 (q, J=6.8 Hz, 2H), 3.08 (dq, J=13.9, 7.5 Hz, 2H), 2.27-1.87 (m, 10H). MS (ESI, pos. ion) m/z: 426.2 (M+1).

Example 74

3-({8-methoxy-7-[3-(pyrrolidin-1-yl)propoxy]-5H-pyrido[4,3-b]indol-1-yl}oxy)pyrrolidine bis(2,2,2-trifluoroacetate)

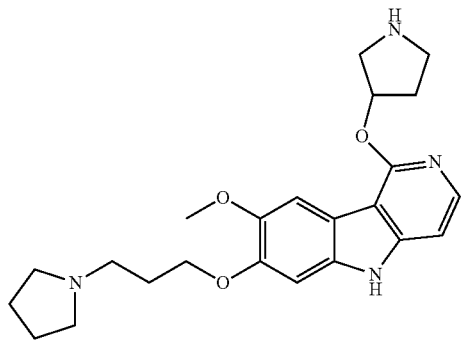 [SMILES: COc1cc2c(cc1OCCCN1CCCC1)[nH]c1ccnc(OC3CCNC3)c12]

The title compound was prepared as described in Example 73, Steps 1-7 above, but substituting tetrahydro-2H-pyran-4-ol with tert-butyl 3-hydroxypyrrolidine-1-carboxylate. $^1$H NMR (300 MHz, DMSO-d$_6$) δ 11.63 (s, 1H), 9.70 (br, 1H), 9.30 (br, 1H), 9.14 (br, 1H), 7.91 (d, J=5.7 Hz, 1H), 7.64 (s, 1H), 7.16-7.13 (m, 2H), 5.87 (d, J=3.6 Hz, 1H), 4.15 (t, J=5.9 Hz, 2H), 3.90 (s, 3H), 3.66-3.49 (m, 6H), 3.47-3.40 (m, 2H), 3.47-3.33 (m, 2H), 3.13-3.05 (m, 2H), 2.42-2.38 (m, 2H), 2.28-2.17 (m, 2H), 2.13-2.06 (m, 2H), 1.95-1.87 (m, 2H). MS (ESI, pos. ion) m/z: 411.2 (M+1).

Example 75

1-(3-{[8-methoxy-1-(propan-2-yloxy)-5H-pyrido[4,3-b]indol-7-yl]oxy}propyl)pyrrolidine trifluoroacetate

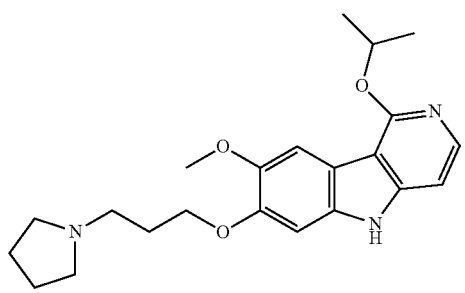 [SMILES: COc1cc2c(cc1OCCCN1CCCC1)[nH]c1ccnc(OC(C)C)c12]

The title compound was prepared as described in Example 73, Steps 1-7 above, but substituting tetrahydro-2H-pyran-4-ol with isopropanol. $^1$H NMR (300 MHz, DMSO-d$_6$) δ 11.60 (s, 1H), 9.48 (br, 1H), 7.90 (d, J=6.0 Hz, 1H), 7.59 (s, 1H), 7.14 (s, 1H), 7.10 (d, J=6.0 Hz, 1H), 5.54-5.46 (m, 1H), 4.16 (t, J=6.0 Hz, 2H), 3.88 (s, 3H), 3.67-3.65 (m, 2H), 3.41-3.34 (m, 2H), 3.11-3.05 (m, 2H), 2.22-2.17 (m, 2H), 2.07-1.93 (m, 2H), 1.95-1.89 (m, 2H), 1.46 (d, J=6.0 Hz, 3H) MS (ESI, pos. ion) m/z: 384.2 (M+1).

Example 76

1-{8-methoxy-7-[3-(pyrrolidin-1-yl)propoxy]-5H-pyrido[4,3-b]indol-1-yl}-1H-imidazole trifluoroacetate

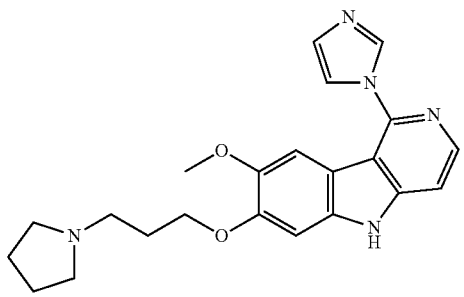 [SMILES: COc1cc2c(cc1OCCCN1CCCC1)[nH]c1ccnc(-n3ccnc3)c12]

Step 1

Into a 40-mL vial purged and maintained with an inert atmosphere of nitrogen, was placed a mixture of tert-butyl 7-(benzyloxy)-1-chloro-8-methoxy-5H-pyrido[4,3-b]indole-5-carboxylate, Reference 5 (1.0 g, 2.28 mmol, 1.00 eq.), DMSO (20 mL), imidazole (1.55 g, 22.77 mmol, 10.00 eq.), Cu$_2$O (33 mg, 0.23 mmol, 0.10 eq.), Ninhydrin (81 mg, 0.456 mmol, 0.20 eq.) and potassium hydroxide (255 mg, 4.54 mmol, 2.00 eq.). The resulting mixture was stirred for 24 hours at 150° C. under nitrogen atmosphere. The reaction mixture was cooled to room temperature. The resulting solution was poured into H$_2$O (200 mL), extracted with ethyl acetate (3×150 mL). The combined organic layers were washed with brine (150 mL), dried over anhydrous sodium sulfate and concentrated under vacuum. The residue was purified by flash column eluted with EtOAc/DCM (3/1). This resulted in 500 mg (59%) of the title compound as a brown solid. MS (ESI, pos. ion) m/z: 371.1 (M+1).

Step 2

Into a 40-mL vial, was placed a mixture of 1-[7-(benzyloxy)-8-methoxy-5H-pyrido[4,3-b]indol-1-yl]-1H-imidazole (500 mg, 1.35 mmol, 1.00 eq.), tetrahydrofuran (10 mL), Boc$_2$O (443 mg, 2.03 mmol, 1.50 eq.) and 4-dimethylaminopyridine (41 mg, 0.34 mmol, 0.25 eq.). The resulting solution was stirred for 1 hour at room temperature. The solution was concentrated under vacuum. The residue was triturated with MeOH (50 mL). The solids were collected by filtration. This resulted in 365 mg (57%) of tert-butyl 7-(benzyloxy)-1-(1H-imidazol-1-yl)-8-methoxy-5H-pyrido[4,3-b]indole-5-carboxylate. MS (ESI, pos. ion) m/z: 471.2 (M+1).

Step 3

Into a 50-mL round-bottom flask, was placed a solution of tert-butyl 7-(benzyloxy)-1-(1H-imidazol-1-yl)-8-methoxy-5H-pyrido[4,3-b]indole-5-carboxylate (350 mg, 0.74 mmol, 1.00 eq.) in methanol (20 mL). To which was added 10% palladium on carbon (105 mg, wet). The flask was evacuated and flushed three times with hydrogen. The mixture was stirred 16 hours at room temperature under an atmosphere of hydrogen (balloon). The solids were filtered out. The filter cake was washed with methanol (3×50 mL) and DCM/MeOH (V/V=10/1, 20 mL). The filtrate was concentrated under vacuum. This resulted in 215 mg (76%) of the tert-butyl 7-hydroxy-1-(1H-imidazol-1-yl)-8-methoxy-5H-pyrido[4,3-b]indole-5-carboxylate. MS (ESI, pos. ion) m/z: 381.1 (M+1).

Step 4

Into a 40-mL vial, was placed a mixture of tert-butyl 7-hydroxy-1-(1H-imidazol-1-yl)-8-methoxy-5H-pyrido[4,3-b]indole-5-carboxylate (100 mg, 0.26 mmol, 1.00 eq.), CH$_3$CN (15 mL), 1-(3-chloropropyl)pyrrolidine hydrochloride (73 mg, 0.39 mmol, 1.50 eq.), Cs$_2$CO$_3$ (257 mg, 3.00 eq.) and KI (66 mg, 0.39 mmol, 1.50 eq.). The resulting mixture was stirred for 16 hours at 80° C. The crude reaction mixture was filtered and subjected to reverse phase preparative HPLC (Waters SunFire column, 19×150 mm; gradient elution of 2% MeCN in water to 15% MeCN in water over a 10 min period, where both solvents contain 0.05% TFA). This resulted in 10.9 mg (11%) of the title compound as brown oil. $^1$H NMR (300 MHz, DMSO-d6, ppm): 12.17 (s, 1H), 9.97 (s, 1H), 8.46 (d, J=1.5 Hz, 1H), 8.33-8.29 (m, 2H), 8.18 (s, 1H), 7.67 (d, J=5.7 Hz, 1H), 7.10 (s, 1H), 6.91 (s, 1H), 4.44 (d, J=6.9 Hz, 2H), 3.75 (s, 3H), 2.53-2.50 (m, 2H), 2.48-2.44 (m, 4H), 2.18-2.09 (m, 2H), 1.70-1.63 (m, 4H). MS (ESI, pos. ion) m/z: 392.2 (M+1).

Example 77

1-[8-methoxy-7-[3-(pyrrolidin-1-yl)propoxy]-5H-pyrido[4,3-b]indol-1-yl]-1H-pyrazole trifluoroacetate

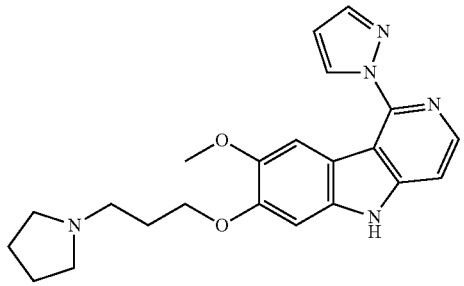 [SMILES: COc1cc2c(cc1OCCCN1CCCC1)[nH]c1ccnc(-n3cccn3)c12]

The title compound was prepared as described in Example 76, Steps 1-4 above, but substituting imidazole with pyrazole. $^1$H NMR (300 MHz, DMSO-d$_6$) δ 11.60 (s, 1H), 9.48 (br, 1H), 7.90 (d, J=6.0 Hz, 1H), 7.59 (s, 1H), 7.14 (s, 1H), 7.10 (d, J=6.0 Hz, 1H), 5.54-5.46 (m, 1H), 4.16 (t, J=6.0 Hz, 2H), 3.88 (s, 3H), 3.67-3.65 (m, 2H), 3.41-3.34 (m, 2H), 3.11-3.05 (m, 2H), 2.22-2.17 (m, 2H), 2.07-1.93 (m, 2H), 1.95-1.89 (m, 2H), 1.46 (d, J=6.0 Hz, 3H) MS (ESI, pos. ion) m/z: 384.2 (M+1).

Example 78

5-{8-methoxy-7-[3-(pyrrolidin-1-yl)propoxy]-5H-pyrido[4,3-b]indol-1-yl}-1,3-thiazole trifluoroacetate

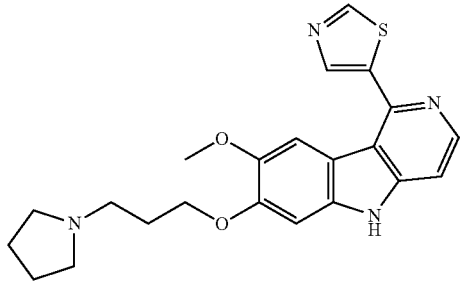 [SMILES: COc1cc2c(cc1OCCCN1CCCC1)[nH]c1ccnc(-c3cncs3)c12]

Step 1

Into a 25-mL round-bottom flask purged and maintained with an inert atmosphere of nitrogen, was placed a mixture of tert-butyl 7-(benzyloxy)-1-chloro-8-methoxy-5H-pyrido [4,3-b]indole-5-carboxylate (1.0 g, 2.28 mmol, 1.00 eq.), toluene (10 mL), 5-(tributylstannyl)-1,3-thiazole (1278 mg, 3.42 mmol, 1.50 eq.), Pd(PPh$_4$)$_3$(132 mg, 0.11 mmol, 0.05 eq.). The resulting solution was stirred for 16 h at 110° C. The reaction mixture was concentrated under vacuum. The residue was purified by a silica gel column eluted with ethyl acetate/petroleum ether (1:1) to provide tert-butyl 7-(benzyloxy)-8-methoxy-1-(1,3-thiazol-5-yl)-5H-pyrido[4,3-b] indole-5-carboxylate (610 mg, 55%) as a white solid. MS (ESI, pos. ion) m/z: 488.2 (M+1).

Step 2

Into a 10-mL round-bottom flask, was placed a solution of tert-butyl 7-(benzyloxy)-8-methoxy-1-(1,3-thiazol-5-yl)-5H-pyrido[4,3-b]indole-5-carboxylate (300 mg, 0.62 mmol, 1.00 eq.) in trifluoroacetic acid (5 mL). The resulting solution was stirred for 16 h at 50° C. The solution was concentrated under vacuum to provide 8-methoxy-1-(1,3-thiazol-5-yl)-5H-pyrido[4,3-b]indol-7-ol (400 mg, crude) as a yellow solid. MS (ESI, pos. ion) m/z: 298.1 (M+1).

Step 3

Into a 10-mL round-bottom flask purged and maintained with an inert atmosphere of nitrogen, was placed a mixture of 8-methoxy-1-(1,3-thiazol-5-yl)-5H-pyrido[4,3-b]indol-7-ol (300 mg, 1.01 mmol, 1.00 eq.), N,N-dimethylformamide (5 mL), 1-(3-chloropropyl)pyrrolidine hydrochloride (94 mg, 0.50 mmol, 0.50 eq.), Cs$_2$CO$_3$ (659 mg, 2.02 mmol, 2.00 eq.) and KI (17 mg, 0.10 mmol, 0.10 eq.). The resulting mixture was stirred for 16 h at 80° C. The crude reaction mixture was filtered and subjected to reverse phase preparative HPLC (Waters SunFire column, 19×150 mm; gradient elution of 15% MeCN in water to 29% MeCN in water over a 10 min period, where both solvents contain 0.05% TFA) to provide the title compound (36.9 mg, 9%) as a light yellow solid. $^1$H NMR (300 MHz, DMSO-d$_6$): δ 11.83 (s, 1H), 9.31 (s, 1H), 8.53 (s, 1H), 8.37 (d, J=5.4 Hz, 1H), 7.50 (s, 1H), 7.47 (d, J=5.7 Hz, H), 7.18 (s, 1H), 4.19 (t, J=6.0 Hz, 2H), 3.75 (s, 3H), 3.39-3.30 (m, 2H), 3.20-3.12 (m, 4H), 2.21-2.14 (m, 2H), 1.94-1.85 (m, 4H). MS (ESI, pos. ion) m/z: 409.1 (M+1).

Example 79

{8-methoxy-7-[3-(pyrrolidin-1-yl)propoxy]-5H-pyrido[4,3-b]indol-3-yl}methanol trifluoroacetate

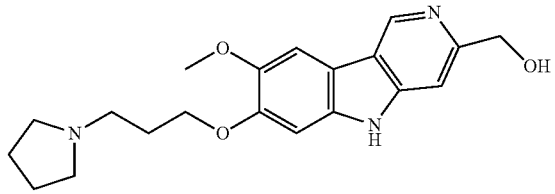 [SMILES: COc1cc2c(cc1OCCCN1CCCC1)[nH]c1cc(CO)ncc12]

Step 1

Into a 100-mL round-bottom flask, was placed a mixture of 1-(benzyloxy)-4-bromo-2-methoxy-5-nitrobenzene (2.0 g, 5.91 mmol, 1.00 eq.), dioxane (50 mL), water (10 mL), [6-(methoxycarbonyl)pyridin-3-yl]boronic acid (1.61 g, 8.90 mmol, 1.50 eq.), Cs$_2$CO$_3$ (5.78 g, 17.74 mmol, 3.00 eq.) and Pd(PPh$_3$)$_4$(0.34 g, 0.30 mmol, 0.05 eq.). The resulting mixture was stirred for 3 h at 80° C. under N2 and concentrated under vacuum. The residue was purified by a silica gel column eluted with ethyl acetate/petroleum ether (1/1) to provide methyl 5-(4-(benzyloxy)-5-methoxy-2-nitrophenyl) picolinate (1.47 g, 63%). MS (ESI, pos. ion) m/z: 395.1 (M+1).

Step 2

A solution of methyl 5-[4-(benzyloxy)-5-methoxy-2-nitrophenyl]pyridine-2-carboxylate (1.45 g, 3.68 mmol, 1.00 eq.) in P(OEt)$_3$ (20 mL) was stirred for 16 h at 130° C. The reaction mixture was concentrated under vacuum. The residue was dissolved in DMF (10 mL), filtered and subjected to reverse phase preparative HPLC (Waters SunFire column, 19×150 mm; gradient elution of 20% MeCN in water to 30% MeCN in water over a 10 min period, where both solvents contain 0.05% TFA) to provide methyl 7-(benzyloxy)-8-methoxy-5H-pyrido[4,3-b]indole-3-carboxylate (0.32 g, 24%). MS (ESI, pos. ion) m/z: 363.1 (M+1).

Step 3

Into a 25-mL round-bottom flask, was placed a solution of methyl 7-(benzyloxy)-8-methoxy-5H-pyrido[4,3-b]indole-3-carboxylate (500 mg, 1.38 mmol, 1.00 eq.), THF (10 mL), 4-dimethylaminopyridine (17 mg, 0.14 mmol, 0.10 eq.) and Boc$_2$O (602 mg, 2.76 mmol, 2.00 eq.). The resulting solution was stirred for 6 h at room temperature and concentrated under vacuum. The residue was purified by a silica gel column eluted with ethyl acetate/petroleum ether (1/1) to provide 5-(tert-butyl) 3-methyl 7-(benzyloxy)-8-methoxy-5H-pyrido[4,3-b]indole-3,5-dicarboxylate (140 mg, 22%). MS (ESI, pos. ion) m/z: 463.2 (M+1).

Step 4

To a mixture of 5-tert-butyl 3-methyl 7-(benzyloxy)-8-methoxy-5H-pyrido[4,3-b]indole-3,5-dicarboxylate (130 mg, 0.28 mmol, 1.00 eq.) in methanol (26 mL) was added 130 mg of 10% Pd/C (60% water moistened). The mixture was degassed and purged with hydrogen for three times. The resulting mixture was stirred for 6 h at room temperature under H$_2$ atmosphere. The solids were filtered out and the filtrate was concentrated under vacuum. This resulted in 100 mg (96%) of 5-(tert-butyl) 3-methyl 7-hydroxy-8-methoxy-5H-pyrido[4,3-b]indole-3,5-dicarboxylate. MS (ESI, pos. ion) m/z: 373.1 (M+1).

Step 5

Into a 25-mL round-bottom flask, was placed a mixture of 5-tert-butyl 3-methyl 7-hydroxy-8-methoxy-5H-pyrido[4,3-b]indole-3,5-dicarboxylate (100 mg, 0.27 mmol, 1.00 eq.), MeCN (10 mL), 1-(3-chloropropyl)pyrrolidine hydrochloride (49 mg, 0.27 mmol, 1.00 eq.) and potassium carbonate (111 mg, 0.80 mmol, 3.00 eq.). The resulting mixture was stirred for 6 h at 60° C. and concentrated under vacuum. The residue was purified by a silica gel column eluted with ethyl acetate/petroleum ether (1/1) to provide 5-(tert-butyl) 3-methyl 8-methoxy-7-(3-(pyrrolidin-1-yl)propoxy)-5H-pyrido[4,3-b]indole-3,5-dicarboxylate (98 mg, 75%). MS (ESI, pos. ion) m/z: 484.2 (M+1).

Step 6

To a mixture of 5-tert-butyl 3-methyl 8-methoxy-7-[3-(pyrrolidin-1-yl)propoxy]-5H-pyrido[4,3-b]indole-3,5-dicarboxylate (98 mg, 0.20 mmol, 1.00 eq.) in THF (10 mL) at 0° C. was added LiAlH$_4$ (15 mg, 0.40 mmol, 2.00 eq.) in portions. The resulting mixture was stirred for 1 h at 25° C. under N2. The reaction mixture was diluted with THF (10 mL), quenched by water (0.1 mL) and concentrated under vacuum. The residue was dissolved in DMF (5 mL), filtered and subjected to reverse phase preparative HPLC (Waters SunFire column, 19×150 mm; gradient elution of 15% MeCN in water to 25% MeCN in water over a 10 min period, where both solvents contain 0.05% TFA) to provide the title compound as a gray solid (19.1 mg, 16%). $^1$H NMR (300 MHz, DMSO-d$_6$) δ 14.46 (br, 1H), 12.76 (s, 1H), 9.62 (br, 1H), 9.54 (s, 1H), 8.09 (s, 1H), 7.83 (s, 1H), 7.28 (s, 1H), 6.20 (br, 1H), 4.91 (s, 2H), 4.21 (t, J=5.4 Hz, 2H), 3.91 (s, 3H), 3.75-3.65 (m, 2H), 3.37-3.31 (m, 2H), 3.12-3.05 (m, 2H), 2.24-2.14 (m, 2H), 2.06-1.96 (m, 2H), 1.94-1.88 (m, 2H). MS (ESI, pos. ion) m/z: 356.2 (M+1).

Example 80

8-methoxy-7-(3-(pyrrolidin-1-yl)propoxy)-5H-pyrido[4,3-b]indol-3-ol formate

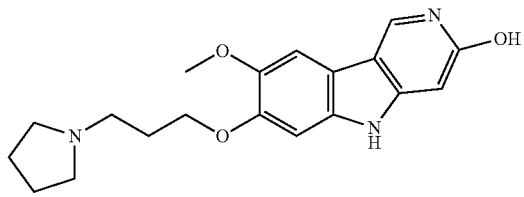 [SMILES: COc1cc2c(cc1OCCCN1CCCC1)[nH]c1cc(O)ncc12]

Step 1

Into a 250-mL round-bottom flask, was placed a mixture of 1-(benzyloxy)-4-bromo-2-methoxy-5-nitrobenzene, Reference 1 (2.0 g, 5.91 mmol, 1.00 eq.), dioxane (100 mL), water (20 mL), 2-methoxy-5-(tetramethyl-1,3,2-dioxaborolan-2-yl)pyridine (2.1 g, 8.93 mmol, 1.50 eq.), Cs$_2$CO$_3$ (5.78 g, 17.74 mmol, 3.00 eq.) and Pd(PPh$_3$)$_4$ (340 mg, 0.29 mmol, 0.05 eq.). The resulting mixture was stirred for 8 h at 80° C. under N2. The reaction mixture was cooled to room temperature and concentrated under vacuum. The residue was purified by a silica gel column eluted with ethyl acetate/petroleum ether (1/2) to provide 5-(4-(benzyloxy)-5-methoxy-2-nitrophenyl)-2-methoxypyridine (1.25 g, 58%). MS (ESI, pos. ion) m/z: 367.1 (M+1).

Step 2

A solution of 5-[4-(benzyloxy)-5-methoxy-2-nitrophenyl]-2-methoxypyridine (1.15 g, 3.14 mmol, 1.00 eq.) in P(OEt)$_3$ (20 mL) was stirred for 24 h at 130° C. The reaction solution was cooled to room temperature and concentrated under vacuum. The residue was purified by a silica gel column eluted with ethyl acetate/petroleum ether (1/1) to provide 7-(benzyloxy)-3,8-dimethoxy-5H-pyrido[4,3-b]indole (210 mg, 20%). MS (ESI, pos. ion) m/z: 335.1 (M+1).

Step 3

Into a 25-mL round-bottom flask, was placed a solution of 7-(benzyloxy)-3,8-dimethoxy-5H-pyrido[4,3-b]indole (210 mg, 0.63 mmol, 1.00 eq.), THF (10 mL), 4-dimethylaminopyridine (7 mg, 0.06 mmol, 0.10 eq.) and Boc$_2$O (270 mg, 1.24 mmol, 2.00 eq.). The resulting solution was stirred for 3 h at 25° C. and concentrated under vacuum. The residue was purified by a silica gel column eluted with ethyl acetate/petroleum ether (1/3) to provide tert-butyl 7-(benzyloxy)-3,8-dimethoxy-5H-pyrido[4,3-b]indole-5-carboxylate (230 mg, 84%). MS (ESI, pos. ion) m/z: 435.2 (M+1).

Step 4

To a mixture of tert-butyl 7-(benzyloxy)-3,8-dimethoxy-5H-pyrido[4,3-b]indole-5-carboxylate (220 mg, 0.51 mmol, 1.00 eq.) in MeOH (22 mL) was added 220 mg of 10% Pd/C (60% water moistened). The mixture was degassed and purged with hydrogen for three times. The resulting mixture was stirred for 6 h at room temperature under H$_2$ atmosphere. The solids were filtered out and the filtrate was concentrated under vacuum. This resulted in 156 mg (89%) of tert-butyl 7-hydroxy-3,8-dimethoxy-5H-pyrido[4,3-b]indole-5-carboxylate. MS (ESI, pos. ion) m/z: 345.1 (M+1).

Step 5

Into a 25-mL round-bottom flask, was placed a mixture of tert-butyl 7-hydroxy-3,8-dimethoxy-5H-pyrido[4,3-b]indole-5-carboxylate (150 mg, 0.44 mmol, 1.00 eq.), MeCN (10 mL), 1-(3-chloropropyl)pyrrolidine hydrochloride (80 mg, 0.43 mmol, 1.00 eq.) and potassium carbonate (181 mg, 1.31 mmol, 3.00 eq.). The resulting mixture was stirred for 6 h at 60° C. The reaction mixture was cooled to room temperature. The solids were filtered out and the filtrate was concentrated under vacuum. This resulted in 135 mg (68%) of tert-butyl 3,8-dimethoxy-7-(3-(pyrrolidin-1-yl)propoxy)-5H-pyrido[4,3-b]indole-5-carboxylate. MS (ESI, pos. ion) m/z: 456.2 (M+1).

Step 6

Into a 25-mL round-bottom flask, was placed a solution of tert-butyl 3,8-dimethoxy-7-[3-(pyrrolidin-1-yl)propoxy]-5H-pyrido[4,3-b]indole-5-carboxylate (125 mg, 0.27 mmol, 1.00 eq.), ethanol (5 mL) and conc. HCl (aq., 5 mL). The resulting solution was stirred for 16 h at 80° C. The reaction mixture was cooled to room temperature and concentrated under vacuum. The residue was dissolved in DMF (5 mL), filtered and subjected to reverse phase preparative HPLC (Waters SunFire column, 19×150 mm; gradient elution of 15% MeCN in water to 25% MeCN in water over a 10 min period, where both solvents contain 0.1% formic acid) to provide the title compound as a light yellow solid (42.6 mg, 40%). $^1$H NMR (300 MHz, DMSO-d$_6$) δ 11.0 (s, 1H), 8.69 (s, 1H), 8.15 (s, 1H), 7.45 (s, 1H), 6.98 (s, 1H), 6.62 (s, 1H), 4.11 (t, J=6.0 Hz, 2H), 3.88 (s, 3H), 3.14-3.03 (m, 6H), 2.11-2.06 (m, 2H), 1.90-1.85 (m, 4H). MS (ESI, pos. ion) m/z: 342.2 (M+1).

Example 81

4-[8-methoxy-7-[3-(pyrrolidin-1-yl)propoxy]-5H-pyrido[4,3-b]indol-1-yl]-1H-pyrazole hydrochloride

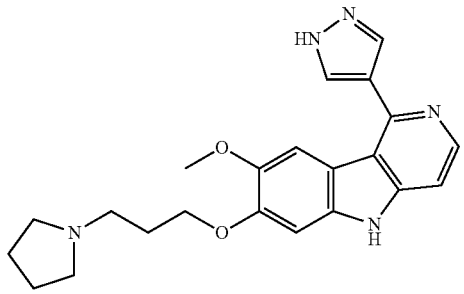 [SMILES: COc1cc2c(cc1OCCCN1CCCC1)[nH]c1ccnc(-c3cn[nH]c3)c12]

Step 1

To a solution of 7-(benzyloxy)-1-chloro-8-methoxy-5H-pyrido[4,3-b]indole (Reference 5, step 2) (3.2 g, 9.45 mmol, 1.00 eq.) in dichloromethane (50 mL) at 0° C. was added TEA (1.9 g, 18.90 mmol, 2.00 eq.) followed by TsCl (2.2 g, 11.34 mmol, 1.20 eq.) and 4-dimethylaminopyridine (116 mg, 0.95 mmol, 0.10 eq.). The resulting solution was stirred for 1 h at room temperature and concentrated under vacuum. The residue was purified by column chromatography on silica gel eluted with ethyl acetate/petroleum ether (1/1) to provide 7-(benzyloxy)-1-chloro-8-methoxy-5-[(4-methylbenzene)sulfonyl]-5H-pyrido[4,3-b]indole (3.8 g, 82%). MS (ESI, pos. ion) m/z: 493.2 (M+1).

Step 2

A solution of 7-(benzyloxy)-1-chloro-8-methoxy-5-[(4-methylbenzene)sulfonyl]-5H-pyrido[4,3-b]indole (3.8 g, 7.71 mmol, 1.00 eq.) in trifluoroacetic acid (30 mL) was stirred for 16 h at room temperature. The resulting solution was concentrated under vacuum. The residue was purified by column chromatography on silica gel eluted with dichloromethane/methanol (10/1) to provide methyl 1-chloro-8-methoxy-5-[(4-methylbenzene)sulfonyl]-5H-pyrido[4,3-b]indol-7-ol (4.03 g). MS (ESI, pos. ion) m/z: 403.1 (M+1).

Step 3

Into a 250-mL round-bottom flask, was placed a mixture of 1-chloro-8-methoxy-5-[(4-methylbenzene)sulfonyl]-5H-pyrido[4,3-b]indol-7-ol (4.3 g, 10.67 mmol, 1.00 eq.), $CH_3CN$ (150 mL), 1-(3-chloropropyl)pyrrolidine hydrochloride (2.15 g, 11.74 mmol, 1.10 eq.), $Cs_2CO_3$ (10.4 g, 32.01 mmol, 3.00 eq.) and KI (178 mg, 1.07 mmol, 0.10 eq.). The resulting mixture was stirred for 2 h at 85° C. under N2. The mixture was filtered and the filter cake was washed with $CH_3CN$ (2×50 mL). The combined filtrate was concentrated under vacuum. The residue was purified by column chromatography on silica gel eluted with dichloromethane/methanol (10/1) to provide 1-[3-([1-chloro-8-methoxy-5-[(4-methylbenzene)sulfonyl]-5H-pyrido[4,3-b]indol-7-yl]oxy)propyl]pyrrolidine (1.6 g, 29%). MS (ESI, pos. ion) m/z: 514.1 (M+1).

Step 4

Into a 40-mL vial, was placed a mixture of 1-[3-([1-chloro-8-methoxy-5-[(4-methylbenzene)sulfonyl]-5H-pyrido[4,3-b]indol-7-yl]oxy)propyl]pyrrolidine (300 mg, 0.58 mmol, 1.00 eq.), dioxane (20 mL), water (2 mL), 1-[(tert-butoxy)carbonyl]-1H-pyrazol-4-ylboronic acid (250 mg, 1.16 mmol, 2.00 eq.), $Cs_2CO_3$ (567 mg, 1.74 mmol, 3.00 eq.) and $Pd(PPh_3)_4$ (35 mg, 0.03 mmol, 0.05 eq.). The resulting mixture was stirred for 8 h at 80° C. under N2 and then concentrated under vacuum. The residue was purified by column chromatography on silica gel eluted with dichloromethane/methanol (5/1) to provide 4-[8-methoxy-5-[(4-methylbenzene)sulfonyl]-7-[3-(pyrrolidin-1-yl)propoxy]-5H-pyrido[4,3-b]indol-1-yl]-1H-pyrazole (310 mg, 97%). MS (ESI, pos. ion) m/z: 546.3 (M+1).

Step 5

Into a 40-mL vial, was placed a mixture of 4-[8-methoxy-5-[(4-methylbenzene)sulfonyl]-7-[3-(pyrrolidin-1-yl)propoxy]-5H-pyrido[4,3-b]indol-1-yl]-1H-pyrazole (350 mg, 0.64 mmol, 1.00 eq.), dioxane (10 mL), water (2 mL) and sodium hydroxide (76.8 mg, 1.92 mmol, 3.00 eq.). The resulting mixture was stirred for 16 h at 80° C. and then concentrated under vacuum. The residue was purified by column chromatography on silica gel eluted with dichloromethane/methanol (6/1) to afford the free title compound. To the obtained compound in DCM (5 mL) was added HCl/dioxane (4 M/dioxane, 1 mL) and stirred for 0.5 h. The solid was collected by filtration to provide the title compound as a yellow solid (125.7 mg, 46%). $^1$H NMR (300 MHz, DMSO-$d_6$) δ 14.96 (br, 1H), 13.46 (s, 1H), 11.20 (br, 1H), 8.50 (s, 1H), 8.48 (s, 1H), 8.40 (d, J=6.0 Hz, 1H), 7.84 (d, J=6.6 Hz, 1H), 7.43 (s, 1H), 7.33 (s, 1H), 4.24 (t, J=5.7 Hz, 2H), 3.76 (s, 3H), 3.59-3.54 (m, 2H), 3.39-3.27 (m, 2H), 3.07-2.99 (m, 2H), 2.32-2.23 (m, 2H), 2.05-1.81 (m, 4H). MS (ESI, pos. ion) m/z: 392.2 (M+1).

Example 82

8-methoxy-7-[3-(pyrrolidin-1-yl)propoxy]-5H-pyrido[4,3-b]indol-1-yl]methanol trifluoroacetate

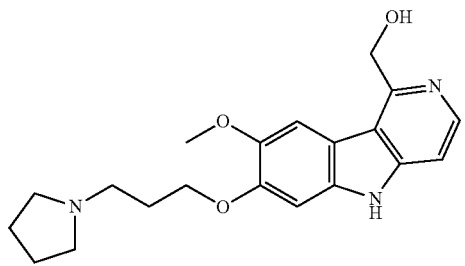 [SMILES: COc1cc2c(cc1OCCCN1CCCC1)[nH]c1ccnc(CO)c12]

Step 1

Into a 50-mL sealed tube, was placed a mixture of 1-[3-([1-chloro-8-methoxy-5-[(4-methylbenzene) sulfonyl]-5H-pyrido[4,3-b]indol-7-yl]oxy)propyl]pyrrolidine (Example 81, step 3) (320 mg, 0.62 mmol, 1.00 eq.), methanol (10 mL), TEA (182 mg, 1.80 mmol, 3.00 eq.) and Pd(dppf)$Cl_2$ (22 mg, 0.03 mmol, 0.05 eq.). The mixture was degassed and purged with CO for 3 times and then stirred for 16 h at 80° C. under CO (20 atm). The reaction mixture was concentrated under vacuum. The residue was purified by column chromatography on silica gel eluted with dichloromethane/methanol (10/1) to provide methyl 8-methoxy-5-[(4-methylbenzene)sulfonyl]-7-[3-(pyrrolidin-1-yl)propoxy]-5H-pyrido[4,3-b]indole-1-carboxylate (135 mg, 40%). MS (ESI, pos. ion) m/z: 538.1 (M+1).

Step 2

To a mixture of [8-methoxy-5-[(4-methylbenzene)sulfonyl]-7-[3-(pyrrolidin-1-yl)propoxy]-5H-pyrido[4,3-b]indol-1-yl]methanol (135 mg, 0.25 mmol, 1.00 eq.) in tetrahydrofuran (10 mL) cooled at 0° C. was added LAH (19 mg, 0.5 mmol, 2.0 eq.) with stirring. The resulting mixture was stirred for 1 h at room temperature. The reaction mixture was diluted with tetrahydrofuran (10 mL), quenched with water (0.02 mL), 15% aqueous solution of sodium hydroxide (0.02 mL) and water (0.06 mL). The mixture was filtered and the filtrate was concentrated under vacuum. The residue was diluted with DMF (5 mL) and subjected to reverse phase preparative HPLC (Waters SunFire column, 19×150 mm; gradient elution of 2% MeCN in water to 17% MeCN in water over a 10 min period, where both solvents contain 0.05% TFA) to provide the title compound as light yellow solid (30.4 mg, 17%). $^1$H NMR (300 MHz, DMSO-$d_6$) δ 14.18 (br, 1H), 13.06 (s, 1H), 9.76 (br, 1H), 8.39 (d, J=6.6 Hz, 1H), 7.88 (d, J=6.6 Hz, 1H), 7.62 (s, 1H), 7.36 (s, 1H), 5.47 (s, 2H), 4.23 (t, J=6.0 Hz, 2H), 3.96 (s, 3H), 3.69-3.65 (m, 2H), 3.37-3.35 (m, 2H), 3.10-3.03 (m, 2H), 2.27-2.25 (m, 2H), 2.10-2.06 (m, 2H), 1.96-1.90 (m, 2H). MS (ESI, pos. ion) m/z: 356.2 (M+1).

Example 83

3-[8-methoxy-7-[3-(pyrrolidin-1-yl)propoxy]-5H-pyrido[4,3-b]indol-1-yl]-4H-1,2,4-triazole formate

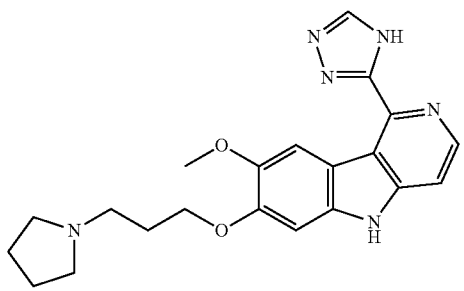 [SMILES: COc1cc2c(cc1OCCCN1CCCC1)[nH]c1ccnc(-c3nnc[nH]3)c12]

Step 1

Into a 40-mL vial, was placed a solution of methyl 8-methoxy-5-[(4-methylbenzene)sulfonyl]-7-[3-(pyrrolidin-1-yl)propoxy]-5H-pyrido[4,3-b]indole-1-carboxylate (Example 82, step 1) (350 mg, 0.65 mmol, 1.00 eq.), ethanol (10 mL) and $N_2H_4 \cdot H_2O$ (98%, 5 mL). The resulting solution was stirred for 16 h at 80° C. The reaction solution was concentrated under vacuum to provide the title compound as brown oil (320 mg crude). MS (ESI, pos. ion) m/z: 384.2 (M+1).

Step 2

Into a 40-mL vial, was placed a solution of 8-methoxy-7-[3-(pyrrolidin-1-yl)propoxy]-5H-pyrido[4,3-b]indole-1-carbohydrazide (320 mg, 0.83 mmol, 1.00 eq.), dichloromethane (10 mL) and DMFDMA (1 mL). The resulting solution was stirred for 3 h at 50° C. and then concentrated under vacuum. The residue was purified by column chromatography on silica gel eluted with dichloromethane/methanol (10/1) to provide N'-(8-methoxy-7-(3-(pyrrolidin-1-yl)propoxy)-5H-pyrido[4,3-b]indole-1-carbonyl)-N,N-dimethylformohydrazonamide (135 mg, 37%). MS (ESI, pos. ion) m/z: 439.3 (M+1).

Step 3

Into a 5-mL vial, was placed a solution of N'-(8-methoxy-7-(3-(pyrrolidin-1-yl)propoxy)-5H-pyrido[4,3-b]indole-1-carbonyl)-N,N-dimethylformohydrazonamide (135 mg, 0.31 mmol, 1.00 eq.), acetic acid amine (71.6 mg, 0.93 mmol, 3.00 eq.) and acetic acid (5 mL). The resulting solution was stirred for 16 h at 100° C. and then concentrated under vacuum. The residue was diluted with MeOH (5 mL), filtered and subjected to reverse phase preparative HPLC (Waters Xbridge column, 19×150 mm; gradient elution of 2% MeCN in water to 18% MeCN in water over a 6 min period, where both solvents contain 0.1% formic acid) to provide the title compound as light brown solid (22.5 mg, 17%). $^1H$ NMR (300 MHz, DMSO-$d_6$) δ 11.74 (br, 1H), 9.26 (s, 1H), 8.46 (d, J=5.4 Hz, 1H), 8.36 (s, 1H), 8.24 (s, 2H), 7.57 (d, J=5.4 Hz, 1H), 7.13 (s, 1H), 4.16 (t, J=6.0 Hz, 2H), 3.88 (s, 3H), 2.87-2.82 (m, 2H), 2.80-2.77 (m, 4H), 2.12-2.04 (m, 2H), 1.82-1.75 (m, 4H). MS (ESI, pos. ion) m/z: 393.2 (M+1).

Example 84

1-(1H-imidazol-5-yl)-8-methoxy-7-(3-(pyrrolidin-1-yl)propoxy)-5H-pyrido[4,3-b]indole trifluoroacetate

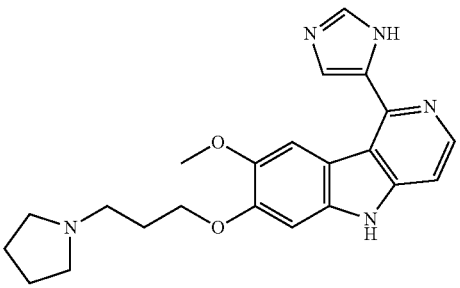 [SMILES: COc1cc2c(cc1OCCCN1CCCC1)[nH]c1ccnc(-c3cnc[nH]3)c12]

Step 1

Into a 50-mL round-bottom flask, was placed 1-(3-[[1-chloro-8-methoxy-5-(4-methylbenzenesulfonyl)-5H-pyrido[4,3-b]indol-7-yl]oxy]propyl)pyrrolidine (200 mg, 0.39 mmol, 1 eq.), dioxane (5 mL), water (1 mL), 1-(oxan-2-yl)-5-(4,4,5,5-tetramethyl-1,3,2-dioxaborolan-2-yl)-1H-imidazole (130 mg, 0.47 mmol, 1.20 eq.), $K_2CO_3$ (161 mg, 1.17 mmol, 3.00 eq.), Pd(PPh$_3$)$_4$ (23 mg, 0.02 mmol, 0.05 eq.). The resulting solution was stirred for 16 hr at 100° C. under N2. The reaction mixtures were combined and concentrated under vacuum. The product was subjected to reverse phase preparative HPLC (Waters SunFire column, 19×150 mm; gradient elution of 20% MeCN in water to 30% MeCN in water over a 10 min period, where both solvents contain 0.05% TFA) to provide 8-methoxy-7-(3-(pyrrolidin-1-yl)propoxy)-1-(1-(tetrahydro-2H-pyran-2-yl)-1H-imidazol-5-yl)-5-tosyl-5H-pyrido[4,3-b]indole (150 mg, 61%). MS (ESI, pos. ion) m/z: 630.3 (M+1).

Step 2

Into a 50-mL round-bottom flask, was placed 8-methoxy-7-(3-(pyrrolidin-1-yl)propoxy)-1-(1-(tetrahydro-2H-pyran-2-yl)-1H-imidazol-5-yl)-5-tosyl-5H-pyrido[4,3-b]indole (105 mg, 0.17 mmol, 1 eq.), water (5 mL), hydrogen chloride (12M, 1 mL). The resulting solution was stirred for 1 hr at 25° C. The resulting mixture was concentrated. This resulted in 100 mg (crude) of 1-(1H-imidazol-5-yl)-8-methoxy-7-(3-(pyrrolidin-1-yl)propoxy)-5-tosyl-5H-pyrido[4,3-b]indole as light yellow solid. MS (ESI, pos. ion) m/z: 546.2 (M+1).

Step 3

Into a 50-mL round-bottom flask, was placed 1-(1H-imidazol-5-yl)-8-methoxy-7-(3-(pyrrolidin-1-yl)propoxy)-5-tosyl-5H-pyrido[4,3-b]indole (100 mg, 0.18 mmol, 1 eq.), water (2 mL), dioxane (2 mL), NaOH (15 mg, 0.37 mmol, 2 eq.). The resulting solution was stirred for 8 hr at 80° C. The resulting mixture was concentrated under vacuum. The crude reaction mixture was filtered and subjected to reverse phase preparative HPLC (Waters SunFire column, 19×150 mm; gradient elution of 20% MeCN in water to 30% MeCN in water over a 10 min period, where both solvents contain 0.05% TFA) to provide the title compound as brown solid (20.1 mg, 22%). $^1H$ NMR (300 MHz, DMSO-$d_6$): δ13.09 (s, 1H), 9.80 (br, 1H), 8.84 (s, 1H), 8.42-8.40 (m, 1H), 8.34 (s, 1H), 8.27 (s, 1H), 7.82 (d, J=6.7 Hz, 1H), 7.31 (s, 1H), 4.23-4.17 (m, 2H), 3.88 (s, 3H), 3.65 (2, 3H), 3.35 (m, 2H), 3.08 (m, 2H), 2.23-1.90 (m, 6H). MS (ESI, pos. ion) m/z: 392.2 (M+1).

Example 85

N,N-diethyl-8-methoxy-7-[3-(pyrrolidin-1-yl)propoxy]-5H-pyrido[4,3-b]indol-1-amine bis formate

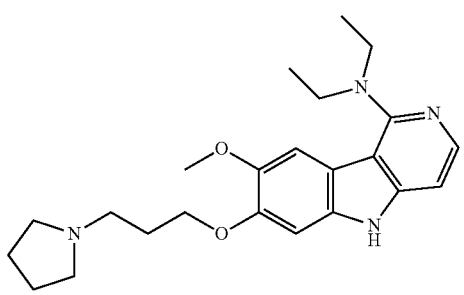 [SMILES: CCN(CC)c1nccc2[nH]c3cc(OCCCN4CCCC4)c(OC)cc3c12]

Step 1

In a microwave vial, a mixture of 7-(benzyloxy)-4-chloro-1-fluoro-8-methoxy-5H-pyrido[4,3-b]indole, Reference 6 (210 mg; 0.59 mmol; 1.00 eq.) and diethylamine (215 mg; 2.94 mmol; 5.00 eq.) in NMP (2 mL) was heated to 100° C. for 6 hours. The reaction mixture was concentrated under reduced pressure and purified by silica gel using 0% to 50% ethyl acetate in hexanes to afford 7-(benzyloxy)-4-chloro-N,N-diethyl-8-methoxy-5H-pyrido[4,3-b]indol-1-amine (200 mg; 82%). MS (ESI, pos. ion) m/z: 410.0 (M+1).

Step 2

In a 50 mL round bottom flask, di-tert-butyl dicarbonate (160 mg; 0.73 mmol; 1.50 eq.) was added to a mixture of 7-(benzyloxy)-4-chloro-N,N-diethyl-8-methoxy-5H-pyrido[4,3-b]indol-1-amine (200 mg; 0.49 mmol; 1.00 eq.) and DMAP (12 mg; 0.10 mmol; 0.20 eq.) in acetonitrile (5 mL). The reaction was stirred for 2 hours. The reaction mixture was concentrated under reduced pressure and purified by silica gel column using 0% to 30% ethyl acetate in hexanes to afford tert-butyl 7-(benzyloxy)-4-chloro-1-(diethylamino)-8-methoxy-5H-pyrido[4,3-b]indole-5-carboxylate (240 mg; 96%).

Step 3

In a 50 mL round bottom flask, a mixture of tert-butyl 7-(benzyloxy)-4-chloro-1-(diethylamino)-8-methoxy-5H-pyrido[4,3-b]indole-5-carboxylate (240 mg; 0.47 mmol; 1.00 eq.) and palladium on carbon (50 mg; 0.05 mmol; 0.10 eq.) in methanol (5 mL) was stirred for 2 hours under hydrogen gas via balloon. The reaction mixture was filtered thru a plug of Celite and concentrated under reduced pressure to afford tert-butyl 1-(diethylamino)-7-hydroxy-8-methoxy-5H-pyrido[4,3-b]indole-5-carboxylate (180 mg; 99%). MS (ESI, pos. ion) m/z: 329.9 (M-56).

Step 4

A mixture of tert-butyl 1-(diethylamino)-7-hydroxy-8-methoxy-5H-pyrido[4,3-b]indole-5-carboxylate (200 mg; 0.52 mmol; 1.00 eq.), 1-(3-chloropropyl)pyrrolidine (143 mg; 0.78 mmol; 1.50 eq.), and potassium carbonate (215 mg; 1.56 mmol; 3.00 eq.) in 10 mL of DMF was heated to 100° C. for 16 hours. The reaction mixture was cooled to rt. The reaction mixture was diluted with water. The aqueous layer was extracted with ethyl acetate. The combined organics were dried with MgSO$_4$, filtered, and concentrated under reduced pressure. The resulting residue was diluted with 1M HCl (4 mL) and heated to 50° C. for 1 hour. The aqueous layer was purified by Prep HPLC (Phenomenex Luna C18, 21×250 mm, 0-60% acetonitrile/0.1% aqueous formic acid gradient over 13 minutes, flow rate 22 ml/min) to afford the titled compound (42 mg; 20%). $^1$H NMR (400 MHz, Methanol-d4) δ 8.45 (s, 2H), 7.93 (d, J=6.3 Hz, 1H), 7.54 (s, 1H), 7.22 (d, J=6.3 Hz, 1H), 7.20 (s, 1H), 4.28 (t, J=5.5 Hz, 2H), 3.98 (s, 3H), 3.63 (q, J=7.1 Hz, 4H), 3.47 (t, J=7.0 Hz, 6H), 2.40-2.23 (m, 2H), 2.21-2.05 (m, 4H), 1.19 (t, J=7.1 Hz, 6H). MS (ESI, pos. ion) m/z: 392.2 (M+1).

Example 86

1-{4-chloro-8-methoxy-7-[3-(pyrrolidin-1-yl)propoxy]-5H-pyrido[4,3-b]indol-1-yl}pyrrolidine hydrochloride

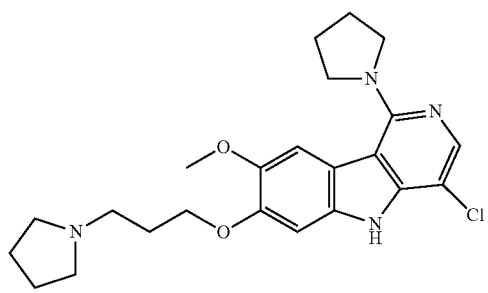 [SMILES: COc1cc2c(cc1OCCCN1CCCC1)[nH]c1c(Cl)cnc(N3CCCC3)c12]

Step 1

A mixture of 7-(benzyloxy)-4-chloro-1-fluoro-8-methoxy-5H-pyrido[4,3-b]indole, Reference 6 (810 mg; 2.27 mmol; 1.00 eq.) and pyrrolidine (807 mg; 11.35 mmol; 5.00 eq.) in NMP (8 mL) was heated in the microwave at 100° C. for 2 hours. The reaction mixture was diluted with water and extracted with ethyl acetate. The combined organics were dried with MgSO$_4$, filtered and concentrated under reduced pressure to afford crude 1-[7-(benzyloxy)-4-chloro-8-methoxy-5H-pyrido[4,3-b]indol-1-yl]pyrrolidine (926 mg; 99%).

Step 2

A mixture of 1-[7-(benzyloxy)-4-chloro-8-methoxy-5H-pyrido[4,3-b]indol-1-yl]pyrrolidine (310 mg; 0.76 mmol; 1.00 eq.) and rhodium (5% wt on alumina) (78 mg; 0.04 mmol; 0.05 eq.) in methanol (8 mL) was stirred under hydrogen pressure via balloon for 30 minutes. Reaction mixture was filtered thru a plug of Celite and concentrated under reduced pressure to afford crude 4-chloro-8-methoxy-1-(pyrrolidin-1-yl)-5H-pyrido[4,3-b]indol-7-ol (241 mg; 99%). MS (ESI, pos. ion) m/z: 317.7 (M+1).

Step 3

A mixture of 4-chloro-8-methoxy-1-(pyrrolidin-1-yl)-5H-pyrido[4,3-b]indol-7-ol (241 mg; 0.76 mmol; 1.00 eq.), 1-(3-chloropropyl)pyrrolidine (208 mg; 1.14 mmol; 1.50 eq.), and potassium carbonate (314 mg; 2.28 mmol; 3.00 eq.) in DMF (5 mL) was heated to 100° C. for 16 hours. The reaction mixture was cooled to rt. Filtered and purified by prep HPLC (Phenomenex Luna C18, 21×250 mm, 0-60% acetonitrile/0.1% aqueous formic acid gradient over 13 minutes, flow rate 22 ml/min) to afford the titled compound (12 mg; 4%). $^1$H NMR (400 MHz, Methanol-d4) δ 7.78 (s, 1H), 7.63 (s, 1H), 7.26 (s, 1H), 4.30 (t, J=5.6 Hz, 2H), 3.97 (s, 7H), 3.89-3.76 (m, 2H), 3.50 (t, J=7.1 Hz, 2H), 3.16 (ddt, J=11.3, 8.2, 4.4 Hz, 2H), 2.34 (t, J=6.2 Hz, 2H), 2.20 (h, J=3.4, 2.7 Hz, 6H), 2.07 (dq, J=10.8, 5.8, 4.7 Hz, 2H). MS (ESI, pos. ion) m/z: 429.2 (M+1).

Example 87

3-[({8-methoxy-5H-pyrido[4,3-b]indol-7-yl}oxy)methyl]piperidine hydrochloride

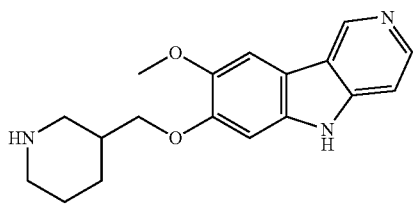 [SMILES: COc1cc2c(cc1OCC1CCCNC1)[nH]c1ccncc12]

A mixture of tert-butyl 7-hydroxy-8-methoxy-5H-pyrido[4,3-b]indole-5-carboxylate, Reference 7 (200.00 mg; 0.64 mmol; 1.00 eq.), tert-butyl 3-(bromomethyl)-1-piperidinecarboxylate (265.50 mg; 0.95 mmol; 1.50 eq.), and potassium carbonate (175.61 mg; 1.27 mmol; 2.00 eq.) in acetonitrile (7 mL) was heated to 85° C. for 4 hours. The reaction mixture was cooled to rt and filtered thru a plug of Celite. The reaction mixture was concentrated under reduced pressure and diluted with 5 mL of 1M HCl. The acidic solution was heated to 50° C. for 1 hour and purified by prep HPLC (Phenomenex Luna C18, 21×250 mm, 0-60% acetonitrile/0.1% aqueous HCl gradient over 13 minutes, flow rate 22 ml/min) to afford the titled compound (146.00 mg; 60%). $^1$H NMR (400 MHz, Methanol-d4) δ 9.40 (s, 1H), 8.41 (dd, J=6.7, 0.9 Hz, 1H), 7.91 (s, 1H), 7.87 (dd, J=6.8, 0.7 Hz, 1H), 7.30 (s, 1H), 4.18 (dd, J=9.6, 4.8 Hz, 1H), 4.06 (dd, J=9.6, 6.9 Hz, 1H), 3.97 (s, 3H), 3.62 (dd, J=12.6, 3.9 Hz, 1H), 3.44-3.33 (m, 1H), 3.00 (dd, J=13.3, 10.7 Hz, 2H), 2.41 (dq, J=7.9, 3.9 Hz, 1H), 2.13-1.97 (m, 2H), 1.93-1.73 (m, 1H), 1.67-1.50 (m, 1H). MS (ESI, pos. ion) m/z: 429.2 (M+1).

Example 88

[3-({8-methoxy-5H-pyrido[4,3-b]indol-7-yl}oxy)propyl]dimethylamine hydrochloride

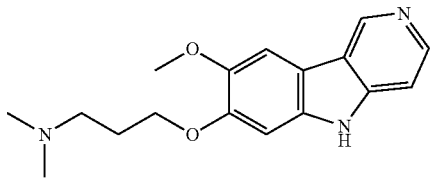 [SMILES: COc1cc2c(cc1OCCCN(C)C)[nH]c1ccncc12]

The title compound was synthesized from tert-butyl 7-hydroxy-8-methoxy-5H-pyrido[4,3-b]indole-5-carboxylate, Reference 7, following a synthetic sequence as described for Example 87, except that (3-chloropropyl)dimethylamine was used in place of tert-butyl 3-(bromomethyl)-1-piperidinecarboxylate. $^1$H NMR (400 MHz, Methanol-d4) δ 9.40 (s, 1H), 8.41 (dd, J=6.7, 0.9 Hz, 1H), 7.91 (s, 1H), 7.87 (dd, J=6.8, 0.7 Hz, 1H), 7.30 (s, 1H), 4.18 (dd, J=9.6, 4.8 Hz, 1H), 4.06 (dd, J=9.6, 6.9 Hz, 1H), 3.62 (dd, J=12.6, 3.9 Hz, 1H), 3.44-3.33 (m, 1H), 3.00 (dd, J=13.3, 10.7 Hz, 2H), 2.41 (dq, J=7.9, 3.9 Hz, 1H), 2.13-1.97 (m, 2H), 1.93-1.73 (m, 1H), 1.67-1.50 (m, 1H). MS (ESI, pos. ion) m/z: 300.1 (M+1).

Example 89

1-{8-methoxy-4-methyl-7-[3-(pyrrolidin-1-yl)propoxy]-5H-pyrido[4,3-b]indol-1-yl}pyrrolidine hydrochloride

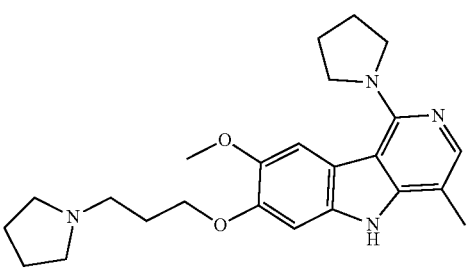 [SMILES: COc1cc2c(cc1OCCCN1CCCC1)[nH]c1c(C)cnc(N3CCCC3)c12]

Step 1

A mixture of 1-[7-(benzyloxy)-4-chloro-8-methoxy-5H-pyrido[4,3-b]indol-1-yl]pyrrolidine, Example 86, step 1 (1.50 g; 3.68 mmol; 1.00 eq.), di-tert-butyl dicarbonate (1.2 g; 5.52 mmol; 1.50 eq.), and N,N-dimethylaminopyridine (90 mg; 0.74 mmol; 0.20 eq.) in dichloromethane (20 mL) was stirred for overnight. The reaction mixture was concentrated under reduced pressure and purified by silica gel column using 0% to 40% ethyl acetate in hexanes to afford tert-butyl 7-(benzyloxy)-4-chloro-8-methoxy-1-(pyrrolidin-1-yl)-5H-pyrido[4,3-b]indole-5-carboxylate (1.45 g; 78%). MS (ESI, pos. ion) m/z: 508.2 (M+1).

Step 2

A mixture of tert-butyl 7-(benzyloxy)-4-chloro-8-methoxy-1-(pyrrolidin-1-yl)-5H-pyrido[4,3-b]indole-5-carboxylate (300 mg; 0.59 mmol; 1.00 eq.), tricyclohexylphosphine (17 mg; 0.06 mmol; 0.10 eq.), methylboronic acid (106 mg; 1.77 mmol; 3.00 eq.), diacetoxypalladium (13 mg; 0.06 mmol; 0.10 eq.), and potassium carbonate (245 mg; 1.77 mmol; 3.00 eq.) in DMF (3 mL) was heated in the microwave at 140° C. for 1 hour. The reaction mixture was diluted with water. The aqueous layer was extracted with ethyl acetate. The combined organics were dried with MgSO$_4$, filtered, concentrated and purified by silica gel column using 0% to 45% ethyl acetate in hexanes to afford tert-butyl 7-(benzyloxy)-8-methoxy-4-methyl-1-(pyrrolidin-1-yl)-5H-pyrido[4,3-b]indole-5-carboxylate (200 mg; 69%). MS (ESI, pos. ion) m/z: 488.0 (M+1).

Step 3

A mixture of tert-butyl 7-(benzyloxy)-8-methoxy-4-methyl-1-(pyrrolidin-1-yl)-5H-pyrido[4,3-b]indole-5-carboxylate (200 mg; 0.41 mmol; 1.00 eq.) and palladium on carbon (44 mg; 0.04 mmol; 0.10 eq.) in methanol (5 mL) was stirred under hydrogen pressure via balloon. The reaction mixture was stirred for 1 hour. The reaction mixture was filtered thru a plug of Celite and concentrated under reduced pressure to afford crude tert-butyl 7-hydroxy-8-methoxy-4-methyl-1-(pyrrolidin-1-yl)-5H-pyrido[4,3-b]indole-5-carboxylate (163.00 mg; 99%).

Step 4

A mixture of tert-butyl 7-hydroxy-8-methoxy-4-methyl-1-(pyrrolidin-1-yl)-5H-pyrido[4,3-b]indole-5-carboxylate (163 mg; 0.41 mmol; 1.00 eq.), 1-(3-chloropropyl)pyrrolidine (113 mg; 0.62 mmol; 1.50 eq.), and potassium carbonate (141 mg; 1.03 mmol; 2.50 eq.) in DMF (3 mL) was heated to 100° C. for 16 hours. The reaction mixture was cooled to rt, filtered thru a plug of Celite, and concentrated under reduced pressure. The resulting residue was diluted with 1M HCl (5 mL) and heated to 50° C. for 1 hour. The aqueous layer was purified by prep HPLC HPLC (Phenomenex Luna C18, 21×250 mm, 0-60% acetonitrile/0.1% aqueous HCl gradient over 13 minutes, flow rate 22 ml/min) to afford the titled compound (47 mg; 28%). $^1$H NMR (400 MHz, Methanol-d4) δ 7.65 (s, 1H), 7.49 (d, J=1.2 Hz, 1H), 7.24 (s, 1H), 4.29 (t, J=5.5 Hz, 2H), 3.97 (s, 3H), 3.96-3.90 (m, 4H), 3.83-3.81 (m, 2H), 3.50 (t, J=7.1 Hz, 2H), 3.16 (q, J=8.7, 7.9 Hz, 2H), 2.46 (d, J=1.1 Hz, 3H), 2.33 (p, J=6.5 Hz, 2H), 2.18 (p, J=3.2 Hz, 6H), 2.07 (dd, J=7.8, 4.9 Hz, 2H). MS (ESI, pos. ion) m/z: 408.9 (M+1).

Example 90

[3-({8-methoxy-1-methyl-5H-pyrido[4,3-b]indol-7-yl}oxy)propyl]dimethylamine hydrochloride

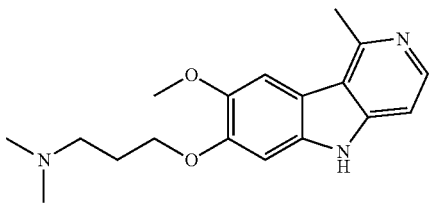 [SMILES: COc1cc2c(cc1OCCCN(C)C)[nH]c1ccnc(C)c12]

Step 1

A mixture of tert-butyl 7-(benzyloxy)-1-chloro-8-methoxy-5H-pyrido[4,3-b]indole-5-carboxylate (250 mg; 0.57 mmol; 1.00 eq.), methylboronic acid (68 mg; 1.14 mmol; 2.00 eq.), potassium carbonate (314 mg; 2.28 mmol; 4.00 eq.), and Pd(dppf)$_2$Cl$_2$.DCM (46 mg; 0.06 mmol; 0.10 eq.) in NMP (3 mL) were placed in a microwave vial. Heated the reaction to 120° C. for 1 hour in the microwave. Diluted reaction with water. Extracted aqueous layer with ethyl acetate, combined organics, dried with MgSO$_4$, filtered, and concentrated under reduced pressure. Resulting residue was purified by silica gel column using 0% to 50% ethyl acetate in hexanes to afford tert-butyl 7-(benzyloxy)-8-methoxy-1-methyl-5H-pyrido[4,3-b]indole-5-carboxylate (180 mg; 75%). MS (ESI, pos. ion) m/z: 363.0 (M-56).

Step 2

Combined tert-butyl 7-(benzyloxy)-8-methoxy-1-methyl-5H-pyrido[4,3-b]indole-5-carboxylate (180 mg; 0.43 mmol; 1.00 eq.), 10% palladium on carbon (45 mg; 0.04 mmol; 0.10 eq.), and methanol (5 mL). Stirred under hydrogen pressure for 3 hours via balloon. Filtered thru celite plug and concentrated under reduced pressure to afford tert-butyl 7-hydroxy-8-methoxy-1-methyl-5H-pyrido[4,3-b]indole-5-carboxylate (140 mg; 99%) as crude. MS (ESI, pos. ion) m/z: 273.0 (M-56).

Step 3

Combined tert-butyl 7-hydroxy-8-methoxy-1-methyl-5H-pyrido[4,3-b]indole-5-carboxylate (140 mg; 0.43 mmol; 1.00 eq.), (3-chloropropyl)dimethylamine (104 mg; 0.85 mmol; 2.00 eq.), and potassium carbonate (118 mg; 0.85 mmol; 2.00 eq.) in DMF (5 mL). The reaction was heated to 100° C. for 5 hours. Let the reaction cool to rt. Filtered thru a plug of Celite and concentrated under reduced pressure. Added 1M HCl to the resulting residue and heated to 50° C. for 1 hour. Purified residue by prep HPLC (Phenomenex Luna C18, 21×250 mm, 0-60% acetonitrile/0.1% aqueous HCl gradient over 13 minutes, flow rate 22 ml/min) to afford the titled compound (90.00 mg; 67%). $^1$H NMR (400 MHz, Methanol-d4) δ 8.26 (d, J=6.8 Hz, 1H), 7.74 (d, J=6.8 Hz, 1H), 7.72 (s, 1H), 7.35 (s, 1H), 4.32 (t, J=5.6 Hz, 2H), 4.04 (s, 3H), 3.45 (t, J=7.2 Hz, 2H), 3.20 (s, 3H), 3.01 (s, 6H), 2.43-2.28 (m, 2H). MS (ESI, pos. ion) m/z: 314.5 (M+1).

Example 91

[3-({1-ethyl-8-methoxy-5H-pyrido[4,3-b]indol-7-yl}oxy)propyl]dimethylamine hydrochloride

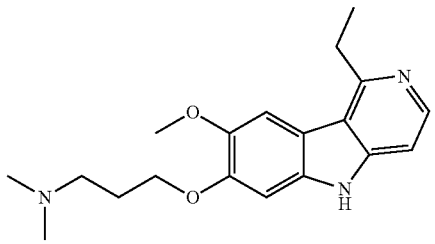 [SMILES: CCc1nccc2[nH]c3cc(OCCCN(C)C)c(OC)cc3c12]

The title compound was synthesized from tert-butyl 7-(benzyloxy)-1-chloro-8-methoxy-5H-pyrido[4,3-b]indole-5-carboxylate, Reference 5, following a synthetic sequence analogous to that described for Example 90, using ethylboronic acid in place of methylboronic acid. $^1$H NMR (400 MHz, Methanol-d4) δ 8.29 (d, J=6.8 Hz, 1H), 7.76 (d, J=6.8 Hz, 1H), 7.68 (s, 1H), 7.36 (s, 1H), 4.33 (t, J=5.6 Hz, 2H), 4.03 (s, 3H), 3.57 (q, J=7.6 Hz, 2H), 3.44 (q, J=7.5 Hz, 2H), 3.00 (s, 6H), 2.40-2.28 (m, 2H), 1.56 (t, J=7.6 Hz, 3H). MS (ESI, pos. ion) m/z: 328.1 (M+1).

Example 92

(3-{[8-methoxy-1-(pyrrolidin-1-yl)-5H-pyrido[4,3-b]indol-7-yl]oxy}propyl)dimethylamine hydrochloride

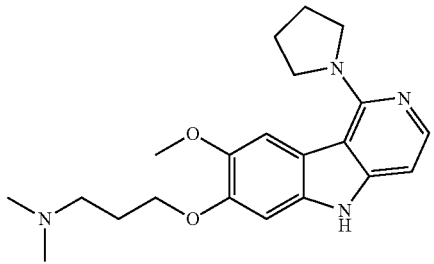 [SMILES: COc1cc2c(cc1OCCCN(C)C)[nH]c1ccnc(N3CCCC3)c12]

Step 1

A mixture of 7-(benzyloxy)-4-chloro-1-fluoro-8-methoxy-5H-pyrido[4,3-b]indole, Reference 6 (810 mg; 2.27 mmol; 1.00 eq.) and pyrrolidine (807 mg; 11.35 mmol; 5.00 eq.) in NMP (7.5 mL) was heated in the microwave at 100° C. for 2 hours. The reaction mixture was diluted with water and extracted with ethyl acetate. The combined organics were dried with MgSO$_4$, filtered and concentrated under reduced pressure to afford 1-[7-(benzyloxy)-4-chloro-8-methoxy-5H-pyrido[4,3-b]indol-1-yl]pyrrolidine (926 mg; 99%).

Step 2

A mixture of 1-[7-(benzyloxy)-4-chloro-8-methoxy-5H-pyrido[4,3-b]indol-1-yl]pyrrolidine (1.5 g; 3.68 mmol; 1.00 eq.), di-tert-butyl dicarbonate (1.2 g; 5.52 mmol; 1.50 eq.), and DMAP (90 mg; 0.74 mmol; 0.20 eq.) in dichloromethane (18 mL) was stirred for overnight. The reaction mixture was concentrated under reduced pressure and purified by silica gel column using 0% to 40% ethyl acetate in hexanes to afford tert-butyl 7-(benzyloxy)-4-chloro-8-methoxy-1-(pyrrolidin-1-yl)-5H-pyrido[4,3-b]indole-5-carboxylate (1.45 g; 78%). MS (ESI, pos. ion) m/z: 508.2 (M+1).

Step 3

In a 50 mL round bottom flask, tert-butyl 7-(benzyloxy)-4-chloro-8-methoxy-1-(pyrrolidin-1-yl)-5H-pyrido[4,3-b]indole-5-carboxylate (750 mg; 1.48 mmol; 1.00 eq.), 10% palladium on carbon (157 mg; 0.15 mmol; 0.10 eq.), and methanol (15 mL) were stirred under hydrogen pressure via balloon. The reaction was stirred for 3 hours. The reaction mixture was filtered thru a plug of celite and concentrated to obtain tert-butyl 7-hydroxy-8-methoxy-1-(pyrrolidin-1-yl)-5H-pyrido[4,3-b]indole-5-carboxylate (566 mg; 99%) as crude. MS (ESI, pos. ion) m/z: 327.8 (M-56).

Step 4

In a 10 mL scintillation vial, tert-butyl 7-hydroxy-8-methoxy-1-(pyrrolidin-1-yl)-5H-pyrido[4,3-b]indole-5-carboxylate (170 mg; 0.44 mmol; 1.00 eq.), (3-chloropropyl)dimethylamine (70 mg; 0.58 mmol; 1.30 eq.), and potassium carbonate (183 mg; 1.33 mmol; 3.00 eq.) in DMF (3 mL) were heated to 100° C. for 3 hours. The reaction mixture was cooled to rt. Filtered the reaction thru a plug of Celite and concentrated under reduced pressure. Added 1M HCl to the resulting residue and stirred at 50° C. for 1 hour. The resulting mixture was concentrated under reduced pressure and purified by prep HPLC (Phenomenex Luna C18, 21×250 mm, 0-60% acetonitrile/0.1% aqueous HCl gradient over 13 minutes, flow rate 22 ml/min) to afford the title compound (100 mg; 51%). $^1$H NMR (400 MHz, Methanol-d4) δ 7.65 (d, J=6.9 Hz, 1H), 7.60 (s, 1H), 7.21 (s, 1H), 7.10 (d, J=6.9 Hz, 1H), 4.28 (t, J=5.6 Hz, 2H), 3.96 (d, J=7.1 Hz, 7H), 3.44 (t, J=7.2 Hz, 2H), 3.00 (s, 6H), 2.33 (p, J=6.5 Hz, 2H), 2.25-2.09 (m, 4H). MS (ESI, pos. ion) m/z: 369.0 (M+1).

Example 93

7-[3-(dimethylamino)propoxy]-8-methoxy-N,N-dimethyl-5H-pyrido[4,3-b]indol-1-amine hydrochloride

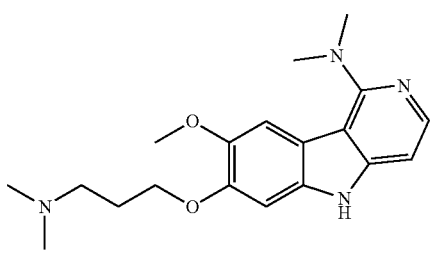 [SMILES: COc1cc2c(cc1OCCCN(C)C)[nH]c1ccnc(N(C)C)c12]

The title compound was prepared using the synthetic sequence described for Example 92, changing step 1 as follows:

In a capped microwave vial, 7-(benzyloxy)-4-chloro-1-fluoro-8-methoxy-5H-pyrido[4,3-b]indole Reference 6 (220 mg; 0.62 mmol; 1.00 eq.) and 2M sodium hydroxide (0.40 mL; 0.80 mmol; 1.30 eq.) in DMF (4 mL) were placed in a microwave reactor. Heated the reaction in the microwave for 1 hour at 160° C. Let the reaction cool to rt. Diluted reaction with water and extracted aqueous layer with ethyl acetate. Combined organics, dried with MgSO$_4$, filtered and concentrated to afford 7-(benzyloxy)-4-chloro-8-methoxy-N,N-dimethyl-5H-pyrido[4,3-b]indol-1-amine (235 mg; 99%) as a crude mixture.

The title compound was made from 7-(benzyloxy)-4-chloro-8-methoxy-N,N-dimethyl-5H-pyrido[4,3-b]indol-1-amine following procedures used to make Example 92, steps 2 thru 4. $^1$H NMR (400 MHz, Methanol-d4) δ 7.78 (d, J=6.8 Hz, 1H), 7.40 (s, 1H), 7.27 (d, J=6.9 Hz, 1H), 7.24 (s, 1H), 4.28 (t, J=5.6 Hz, 2H), 3.99 (s, 3H), 3.46 (t, J=7.2 Hz, 2H), 3.36 (s, 6H), 3.01 (s, 6H), 2.35 (t, J=6.5 Hz, 2H). MS (ESI, pos. ion) m/z: 343.3 (M+1).

Example 94

1-[3-({8-methoxy-5-methyl-5H-pyrido[4,3-b]indol-7-yl}oxy)propyl]pyrrolidine hydrochloride

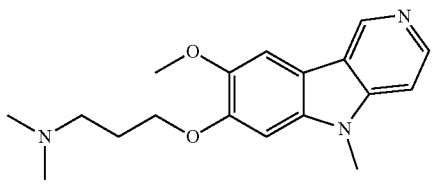 [SMILES: COc1cc2c3cnccc3n(C)c2cc1OCCCN(C)C]

A mixture of 1-[3-({8-methoxy-5H-pyrido[4,3-b]indol-7-yl}oxy)propyl]pyrrolidine, Example 88 (70 mg; 0.22 mmol; 1.00 eq.), dimethyl carbonate (39 mg; 0.43 mmol; 2.00 eq.), and potassium carbonate (59 mg; 0.43 mmol; 2.00 eq.) in DMF (2 mL) were placed in a microwave vial. Heated the reaction to 100° C. for 30 minutes in the microwave. The reaction mixture was filtered and purified by prep HPLC (Phenomenex Luna C18, 21×250 mm, 0-60% acetonitrile/0.1% aqueous HCl gradient over 13 minutes, flow rate 22 ml/min) to afford the title compound (10 mg; 11%). $^1$H NMR (400 MHz, Methanol-d4) δ 9.42 (s, 1H), 8.47 (dd, J=6.9, 0.9 Hz, 1H), 8.00 (d, J=8.3 Hz, 2H), 7.46 (s, 1H), 4.43-4.36 (m, 2H), 4.08 (s, 3H), 4.00 (s, 3H), 3.91-3.75 (m, 2H), 3.50 (q, J=6.4, 5.8 Hz, 2H), 3.17 (dt, J=13.3, 7.1 Hz, 2H), 2.36 (h, J=7.5, 7.0 Hz, 2H), 2.20 (d, J=7.6 Hz, 2H), 2.13-2.00 (m, 2H). MS (ESI, pos. ion) m/z: 340.1 (M+1).

Example 95

(3-{[8-methoxy-1-(methylsulfanyl)-5H-pyrido[4,3-b]indol-7-yl]oxy}propyl)dimethylamine hydrochloride

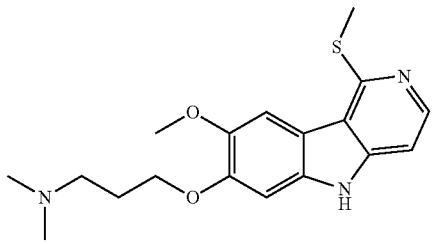 [SMILES: COc1cc2c(cc1OCCCN(C)C)[nH]c1ccnc(SC)c12]

Step 1

To a mixture of [3-(4-bromo-2-methoxy-5-nitrophenoxy)propyl]dimethylamine (300 mg; 0.90 mmol; 1.00 eq.) and 2-chloro-3-pyridinylboronic acid (240 mg; 1.53 mmol; 1.70 eq.) in DMF (5 mL) was added potassium carbonate (0.90 mL; 2.00 mol/L; 1.80 mmol; 2.00 eq.) followed by Pd(dppf)$_2$ Cl$_2$.DCM (37 mg; 0.05 mmol; 0.05 eq.) in a microwave vial. The reaction was heated to 120° C. for 30 minutes. The reaction was diluted with water and extracted with ethyl acetate. The combined organics were dried with MgSO$_4$, filtered, and concentrated to afford {3-[4-(2-chloropyridin-3-yl)-2-methoxy-5-nitrophenoxy]propyl}dimethylamine (250 mg; 76%) as crude. MS (ESI, pos. ion) m/z: 366.2 (M+1).

Step 2

Sodium methanethiolate (144 mg; 2.05 mmol; 3.00 eq.) was added to a solution containing {3-[4-(2-chloropyridin-3-yl)-2-methoxy-5-nitrophenoxy]propyl}dimethylamine (250 mg; 0.68 mmol; 1.00 eq.) in DMSO (3 mL) in a microwave vial. Heated the reaction to 100° C. for 40 minutes in the microwave. Diluted reaction with 1M HCl (10 mL) and washed with ethyl acetate. Collected acidic aqueous layer and purified product by prep HPLC (Phenomenex Luna C18, 21×250 mm, 0-60% acetonitrile/0.1% aqueous HCl gradient over 13 minutes, flow rate 22 ml/min) to afford (3-{2-methoxy-4-[2-(methylsulfanyl)pyridin-3-yl]-5-nitrophenoxy}propyl)dimethylamine (50 mg; 19%). MS (ESI, pos. ion) m/z: 378.1 (M+1).

Step 3

In a capped 20 L scintillation vial, a solution of (3-{2-methoxy-4-[2-(methylsulfanyl)pyridin-3-yl]-5-nitrophenoxy}propyl)dimethylamine (50 mg; 0.13 mmol; 1.00 eq.) in triethyl phosphite (2 mL) was heated to 120° C. for 18 hours. The reaction was cooled to rt and concentrated under reduced pressure. The resulting residue was diluted with 1M HCl and purified by prep HPLC (Phenomenex Luna C18, 21×250 mm, 0-60% acetonitrile/0.1% aqueous HCl gradient over 13 minutes, flow rate 22 ml/min) to afford the title compound (4 mg; 7%). $^1$H NMR (400 MHz, Methanol-d4) δ 8.27 (d, J=6.8 Hz, 1H), 7.87 (s, 1H), 7.69 (d, J=6.8 Hz, 1H), 7.35 (s, 1H), 4.32 (t, J=5.6 Hz, 2H), 4.02 (s, 3H), 3.44 (t, J=7.1 Hz, 2H), 3.01 (s, 3H), 3.00 (s, 6H), 2.35 (ddd, J=12.7, 7.0, 5.5 Hz, 2H). MS (ESI, pos. ion) m/z: 346.2 (M+1).

Example 96

1-(3-{[8-methoxy-1-(2-methoxyethoxy)-5H-pyrido[4,3-b]indol-7-yl]oxy}propyl)pyrrolidine trifluoroacetate Step 1

Combined 1-[3-(4-bromo-2-methoxy-5-nitrophenoxy)propyl]pyrrolidine, Reference 3 (800 mg; 2.23 mmol; 1.00 eq.), 2-fluoro-3-pyridinylboronic acid (627 mg; 4.45 mmol; 2.00 eq.), Potassium Carbonate (3.3 mL; 2.00 mol/L; 6.68 mmol; 3.00 eq.) and Pd(dppf)$_2$Cl$_2$.DCM (182 mg; 0.22 mmol; 0.10 eq.) in DMF (8 mL) in a microwave vial. Heated the reaction to 130° C. for 1 hour in the microwave reactor. The reaction was filtered thru a plug of Celite, diluted filtrate with water and washed aqueous layer with ethyl acetate. Combined organics, dried with MgSO$_4$, filtered, and concentrated under reduced pressure. The resulting residue was purified with silica gel using 0% to 20% methanol in DCM to afford 2-fluoro-3-{5-methoxy-2-nitro-4-[3-(pyrrolidin-1-yl)propoxy]phenyl}pyridine (316.00 mg; 38%).

Step 2

Into a 50-mL round-bottom flask, was placed 2-fluoro-3-[5-methoxy-2-nitro-4-[3-(pyrrolidin-1-yl)propoxy]phenyl]pyridine (300 mg, 0.80 mmol, 1.00 eq.), N,N-dimethylformamide (10 mL), 2-methoxyethan-1-ol (91.2 mg, 1.20 mmol, 1.50 eq.), Cs$_2$CO$_3$ (782 mg, 2.40 mmol, 3.00 eq.). The resulting solution was stirred for 3 h at 100° C. The crude reaction mixture was filtered and subjected to reverse phase preparative MPLC (Prep-C18, 120 g, Tianjin Bonna-Agela Technologies; gradient elution of 10% MeCN in water to 20% MeCN in water over a 10 min period, where both solvents contain 0.1% formic acid) to provide 3-(5-methoxy-2-nitro-4-(3-(pyrrolidin-1-yl)propoxy)phenyl)-2-(2-methoxyethoxy)pyridine as yellow solid (0.18 g, 52%). MS (ESI, pos. ion) m/z: 432.2 (M+1).

Step 3

Into a 50-mL round-bottom flask, was placed 3-(5-methoxy-2-nitro-4-(3-(pyrrolidin-1-yl)propoxy)phenyl)-2-(2-methoxyethoxy)pyridine (150 mg, 0.35 mmol, 1.00 eq.), P(OEt)$_3$ (8 mL). The resulting solution was stirred for 16 h at 120° C. The mixture was concentrated under vacuum. The crude reaction mixture was filtered and subjected to reverse phase preparative HPLC (Prep-C18, Waters SunFire column, 19×150 mm; gradient elution of 20% MeCN in water to 30% MeCN in water over a 10 min period, where both solvents contain 0.05% TFA) to provide the title compound as light yellow semi-solid (15.9 mg, 8.9%) $^1$HNMR (300 MHz, DMSO-d6) δ11.58 (s, 1H), 9.59 (br, 1H), 7.89 (d, J=5.9 Hz, 1H), 7.60 (s, 1H), 7.16-7.07 (m, 2H), 4.62 (dd, J=5.8, 3.7 Hz, 2H), 4.15 (t, J=5.8 Hz, 2H), 3.83 (d, J=4.4 Hz, 1H), 3.66 (dt, J=11.1, 6.0 Hz, 2H), 3.39 (d, J=10.5 Hz, 6H), 3.07 (dq, J=14.3, 7.5 Hz, 2H), 2.19 (dq, J=12.4, 6.4 Hz, 2H), 2.04 (q, J=6.9, 5.9 Hz, 2H), 1.89 (p, J=5.3 Hz, 2H). MS (ESI, pos. ion) m/z: 400.2 (M+1).

Example 97

8-methoxy-7-(3-(pyrrolidin-1-yl)propoxy)-5H-pyrido[4,3-b]indol-1-ol trifluoroacetate

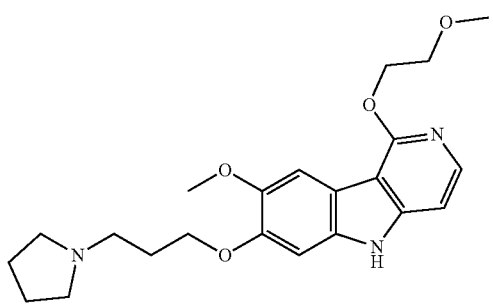 [SMILES: COCCOc1nccc2[nH]c3cc(OCCCN4CCCC4)c(OC)cc3c12]

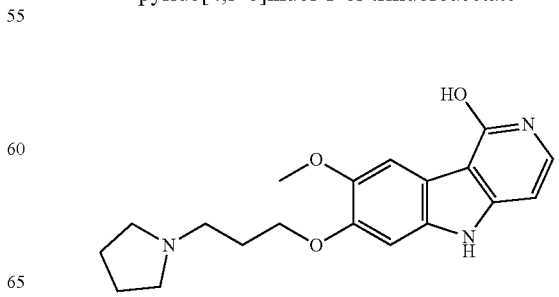

Step 1

Into a 50-mL round-bottom flask, was placed 7-(benzyloxy)-1-chloro-8-methoxy-5H-pyrido[4,3-b]indole, Reference 5 (400 mg, 1.18 mmol, 1.00 eq.), sodium methylate-MeOH (30%, 10 mL). The resulting solution was stirred for 48 h at 120° C. The resulting mixture was concentrated under vacuum. The residue was applied onto a silica gel column with ethyl acetate/petroleum ether (1:1). This resulted in 285 mg (72%) of 7-(benzyloxy)-1,8-dimethoxy-5H-pyrido[4,3-b]indole as yellow solid. MS (ESI, pos. ion) m/z: 335.1 (M+1).

Step 2

Into a 50-mL round-bottom flask, was placed 7-(benzyloxy)-1,8-dimethoxy-5H-pyrido[4,3-b]indole (275 mg, 0.82 mmol, 1.00 eq.), tetrahydrofuran (10 mL), 4-dimethylaminopyridine (100 mg, 0.82 mmol, 1.00 eq.), Boc$_2$O (180 mg, 0.82 mmol, 1.00 eq.). The resulting solution was stirred for 4 h at 25° C. The resulting mixture was concentrated under vacuum. The residue was applied onto a silica gel column with ethyl acetate/petroleum ether (1:3). This resulted in 260 mg (73%) of tert-butyl 7-(benzyloxy)-1,8-dimethoxy-5H-pyrido[4,3-b]indole-5-carboxylate as yellow solid. MS (ESI, pos. ion) m/z: 435.2 (M+1).

Step 3

To a solution of tert-butyl 7-(benzyloxy)-1,8-dimethoxy-5H-pyrido[4,3-b]indole-5-carboxylate (250 mg, 0.58 mmol, 1.00 eq.) in MeOH (25 mL) was added 25 mg of 10% Pd/C (50% water moistened). The mixture was degassed and purged with hydrogen for three times. The resulting mixture was stirred for 6 h at room temperature under H$_2$ atmosphere. The solid was filtered out. The filtration was concentrated under vacuum. This resulted in 200 mg (crude) of tert-butyl 1,7-dihydroxy-8-methoxy-5H-pyrido[4,3-b]indole-5-carboxylate as light yellow solid. MS (ESI, pos. ion) m/z: 331.1 (M+1).

Step 4

Into a 50-mL round-bottom flask, was placed tert-butyl 1,7-dihydroxy-8-methoxy-5H-pyrido[4,3-b]indole-5-carboxylate (190 mg, 0.55 mmol, 1.00 eq.), MeCN (8 mL), potassium carbonate (229 mg, 1.66 mmol, 3.00 eq.), 1-(3-chloropropyl)pyrrolidine hydrochloride (101.5 mg, 0.55 mmol, 1.00 eq.). The resulting solution was stirred for 3 h at 60° C. The solid was filtered out. The filtration was concentrated under vacuum. This resulted in 120 mg (48%) of tert-butyl 1,8-dimethoxy-7-(3-(pyrrolidin-1-yl)propoxy)-5H-pyrido[4,3-b]indole-5-carboxylate as light yellow solid. MS (ESI, pos. ion) m/z: 456.2 (M+1).

Step 5

Into a 50-mL round-bottom flask, was placed tert-butyl 1,8-dimethoxy-7-(3-(pyrrolidin-1-yl)propoxy)-5H-pyrido[4,3-b]indole-5-carboxylate (110 mg, 0.24 mmol, 1.00 eq.), ethanol (3 mL), hydrogen chloride (3 mL). The resulting solution was stirred for 24 h at 100° C. The resulting mixture was concentrated under vacuum. The crude reaction mixture was filtered and subjected to reverse phase preparative HPLC (Prep-C18, Waters SunFire column, 19×150 mm; gradient elution of 20% MeCN in water to 30% MeCN in water over a 10 min period, where both solvents contain 0.05% TFA) to provide the title compound as off-white solid (39.1 mg, 28%). $^1$H NMR (300 MHz, DMSO-d6) δ 11.48 (s, 1H), 11.01 (d, J=5.8 Hz, 1H), 9.53 (br, 1H), 7.62 (s, 1H), 7.20 (t, J=6.5 Hz, 1H), 7.08 (s, 1H), 6.48 (d, J=7.1 Hz, 1H), 4.12 (t, J=5.8 Hz, 2H), 3.85 (s, 3H), 3.65 (s, 2H), 3.36 (q, J=7.0 Hz, 2H), 3.03-3.12 (m, 2H), 2.15-2.20 (m, 2H), 2.06-2.10 (m, 2H), 1.87-1.96 (m, 2H). MS (ESI, pos. ion) m/z: 342.2 (M+1).

Example 98

3-[3-({8-methoxy-5H-pyrido[4,3-b]indol-7-yl}oxy)propyl]-3-azabicyclo[3.1.1]heptane hydrochloride

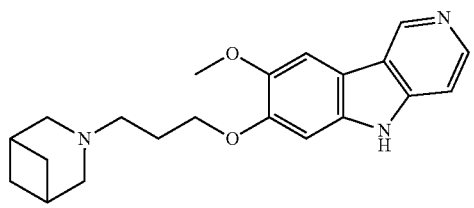 [SMILES: COc1cc2c(cc1OCCCN1CC3CC(C3)C1)[nH]c1ccncc12]

Step 1

Tert-butyl 7-hydroxy-8-methoxy-5H-pyrido[4,3-b]indole-5-carboxylate, Reference 7 (65.00 mg; 0.21 mmol; 1.00 eq.) was suspended in acetonitrile (3 mL). 1-Chloro-3-iodopropane (44 µL; 0.41 mmol; 2.00 eq.) and then potassium carbonate (37 mg; 0.268 mmol; 1.28 eq.) were added. The reaction was stirred in a heat block at 80° C. After 6 h the reaction was cooled, filtered, rinsed with warm acetonitrile and evaporated. The mixture was purified by silica gel chromatography (methanol/dichloromethane gradient) to give some tert-butyl 7-(3-chloropropoxy)-8-methoxy-5H-pyrido[4,3-b]indole-5-carboxylate (9 mg, 11%). MS (ESI, pos. ion) m/z: 391.2 (M+1).

Step 2

Tert-butyl 7-(3-chloropropoxy)-8-methoxy-5H-pyrido[4,3-b]indole-5-carboxylate (38.00 mg; 0.10 mmol; 1.00 eq.) was dissolved in DMF (1 mL). 3-Azabicyclo[3.1.1]heptane hydrochloride (19.49 mg; 0.15 mmol; 1.50 eq.) dissolved in N,N-dimethylformamide (0.5 mL), potassium iodide (16.14 mg; 0.10 mmol; 1.00 eq.) and potassium carbonate (33.54 mg; 0.24 mmol; 2.50 eq.) were added. The reaction was stirred in a heat block at 80° C. After 14 h, the reaction was evaporated. The residue was taken up in heptanes, evaporated again and placed under vacuum. Purification by reverse phase chromatography (Waters XSelect CSH C18 column. 19×250 mm, 0-60% acetonitrile/0.1% aqueous HCl gradient) gave the title compound (5.6 mg, 13%). $^1$H NMR (400 MHz, Methanol-d$_4$) δ 9.58 (s, 1H), 8.53 (d, J=6.9 Hz, 1H), 7.89-7.81 (m, 2H), 7.13 (s, 1H), 4.75 (t, J=7.3 Hz, 2H), 4.03 (s, 3H), 3.91-3.86 (m, 2H), 3.42-3.36 (m, 4H), 2.64-2.59 (m, 2H), 2.55-2.52 (m, 2H), 2.42-2.37 (m, 1H), 2.33-2.27 (m, 1H), 2.02-1.98 (m, 1H), 1.58-1.51 (m, 1H). MS (ESI, pos. ion) m/z: 352.3 (M+1).

Example 99

1-[3-({8-methoxy-3-methyl-5H-pyrido[4,3-b]indol-7-yl}oxy)propyl]pyrrolidine hydrochloride

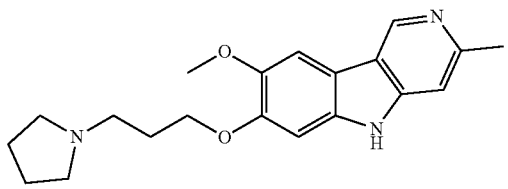 [SMILES: COc1cc2c(cc1OCCCN1CCCC1)[nH]c1cc(C)ncc12]

The title compound was prepared using the synthetic procedures described for Example 29 changing step 1 as follows:

A mixture of 1-(benzyloxy)-4-bromo-2-methoxy-5-nitrobenzene (Reference 1; 500.00 mg; 1.48 mmol; 1.00 eq.), 6-methyl-3-pyridinylboronic acid (222.74 mg; 1.63 mmol; 1.10 eq.), sodium carbonate (235.07 g; 2.22 mol; 1.50 eq.) and 1,1'-Bis(diphenylphosphino)ferrocene]dichloropalladium(II) (54.10 mg; 0.07 mmol; 0.05 eq.) in 1,4-dioxane (14.79 mL) and water (1.10 mL) was subjected to three cycles of evacuation/back-filling with argon then it was heated under an argon atmosphere to 85° C. After 36 h the mixture was cooled to ambient temperature and concentrated. The residue was taken up in EtOAc, washed with water and brine, dried over MgSO$_4$, filtered and concentrated to obtain a dark oil. This material was absorbed onto a plug of silica gel and purified by column chromatography (24 G ISCO Gold) eluting with 0-70% EtOAc in heptane to provide 5-[4-(benzyloxy)-5-methoxy-2-nitrophenyl]-2-methylpyridine (219 mg; 42%).

After step 5, the title compound was obtained as a colorless free flowing powder (8.2 mg; 50%). $^1$H NMR (400 MHz, DMSO-d$_6$) δ 12.65 (s, 1H), 9.99 (s, 1H), 9.40 (s, 1H), 7.97 (s, 1H), 7.69 (s, 1H), 7.22 (s, 1H), 4.18 (t, J=6.0 Hz, 2H), 3.87 (s, 3H), 3.59 (br. s, 2H), 3.36-3.30 (m, 2H), 3.02 (br. s, 2H), 2.71 (s, 3H), 2.19 (p, J=7.4 Hz, 2H), 2.02 (br. s, 2H), 1.86 (br. s, 2H). MS (ESI, pos. ion) m/z: 340.3 (M+1).

Example 100

1-[3-({1,8-dimethoxy-5H-pyrido[4,3-b]indol-7-yl}oxy)propyl]pyrrolidine hydrochloride

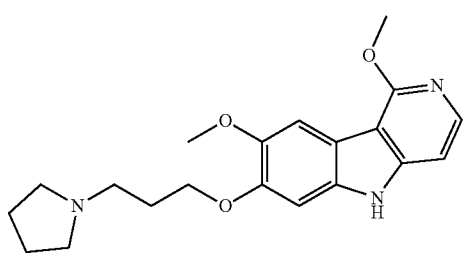 [SMILES: COc1cc2c(cc1OCCCN1CCCC1)[nH]c1ccnc(OC)c12]

The title compound was prepared using the synthetic procedures described for Example 29 changing step 1 as follows:

A mixture of 1-(benzyloxy)-4-bromo-2-methoxy-5-nitrobenzene (Reference 1; 488.00 mg; 1.44 mmol; 1.00 eq.), (RSM from previous reactions) 2-methoxy-3-pyridinylboronic acid (242.79 mg; 1.59 mmol; 1.10 eq.), sodium carbonate (229.43 mg; 2.16 mmol; 1.50 eq.) and 1,1'-Bis(diphenylphosphino)ferrocene]dichloropalladium(II) (52.80 mg; 0.07 mmol; 0.05 eq.) in 1,4-dioxane (14.43 mL) and water (1.07 mL) was subjected to three cycles of evacuation/back-filling with argon then it was heated under an argon atmosphere to 85° C. After 17 h the mixture was cooled to ambient temperature and concentrated. The residue was taken up in EtOAc, washed with water and brine, dried over MgSO$_4$, filtered and concentrated to obtain a dark oil. This material was absorbed onto a plug of silica gel and purified by column chromatography (24 G ISCO Gold) eluting with 0-40% EtOAc in heptane to provide 3-[4-(benzyloxy)-5-methoxy-2-nitrophenyl]-2-methoxypyridine (200 mg; 38%).

After step 5, the title compound was obtained as a colorless free flowing powder (75.2 mg; 71%). MS (ESI, pos. ion) m/z: 356.4 (M+1).

Example 101

1-[3-({3-cyclopropyl-8-methoxy-5H-pyrido[4,3-b]indol-7-yl}oxy)propyl]pyrrolidine hydrochloride

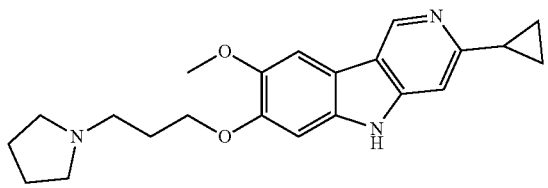 [SMILES: COc1cc2c(cc1OCCCN1CCCC1)[nH]c1cc(C3CC3)ncc12]

The title compound was prepared using the synthetic procedures described for Example 29 changing step 1 and adding step 4A (between steps 4 and 5) as described below:

Step 1

A mixture of 1-(benzyloxy)-4-bromo-2-methoxy-5-nitrobenzene (Reference 1; 600.00 mg; 1.77 mmol; 1.00 eq.), 6-chloro-3-pyridinylboronic acid (307.14 mg; 1.95 mmol; 1.10 eq.), sodium carbonate (282.09 g; 2.66 mol; 1.50 eq.) and 1,1'-Bis(diphenylphosphino)ferrocene]dichloropalladium(II) (64.91 mg; 0.09 mmol; 0.05 eq.) in 1,4-dioxane (17.74 mL) and water (1.31 mL) was subjected to three cycles of evacuation/back-filling with argon then it was heated under an argon atmosphere to 85° C. After 17 h the mixture was cooled to ambient temperature and concentrated. The residue was taken up in EtOAc, washed with water and brine, dried over MgSO$_4$, filtered and concentrated to obtain a dark oil. This material was absorbed onto a plug of silica gel and purified by column chromatography (40 G ISCO Gold) eluting with 0-50% EtOAc in hexanes to provide 5-[4-(benzyloxy)-5-methoxy-2-nitrophenyl]-2-chloropyridine (462 mg; 70%)

Step 4A

A mixture of tert-butyl 7-(benzyloxy)-3-chloro-8-methoxy-5H-pyrido[4,3-b]indole-5-carboxylate (71.00 mg; 0.16 mmol; 1.00 eq.), cyclopropylboronic acid (48.63 mg; 0.57 mmol; 3.50 eq.), tricyclohexylphosphane (4.54 mg; 0.02 mmol; 0.10 eq.) and potassium phosphate, tribasic (68.68 mg; 0.32 mmol; 2.00 eq.) in toluene (0.81 mL) and water (0.04 mL) was sparged with nitrogen for 10 minutes. Palladium acetate (3.63 mg; 0.02 mmol; 0.10 eq.) was then added and the sealed vial was heated to 100° C. overnight. The mixture was then cooled to ambient temperature, diluted with EtOAc and washed with water and brine. The organic layer was dried over MgSO$_4$, filtered and concentrated.

The residue was purified by column chromatography (4 G ISCO Gold) eluting with 0-40% EtOAc in heptane to obtain tert-butyl 7-(benzyloxy)-3-cyclopropyl-8-methoxy-5H-pyrido[4,3-b]indole-5-carboxylate as a white solid.

After step 5, the title compound was obtained as a colorless free flowing powder (75.2 mg; 71%). $^1$H NMR (400 MHz, DMSO-d$_6$) δ 12.58 (s, 1H), 10.33 (s, 1H), 9.34 (s, 1H), 8.00 (s, 1H), 7.45 (s, 1H), 7.21 (s, 1H), 4.17 (t, J=6.0 Hz, 2H), 3.86 (s, 3H), 3.62-3.52 (m, 2H), 3.32-3.29 (m, 2H), 3.06-2.95 (m, 2H), 2.40 (dq, J=8.7, 5.2, 4.4 Hz, 1H), 2.20 (p, J=6.2 Hz, 2H), 2.05-1.95 (m, 2H), 1.92-1.81 (m, 2H), 1.26-1.19 (d, J=8.1 Hz, 2H), 1.14-1.08 (m, 2H). MS (ESI, pos. ion) m/z: 366.4 (M+1).

Example 102

[3-({1-cyclopropyl-8-methoxy-5H-pyrido[4,3-b]indol-7-yl}oxy)propyl]diethylamine hydrochloride

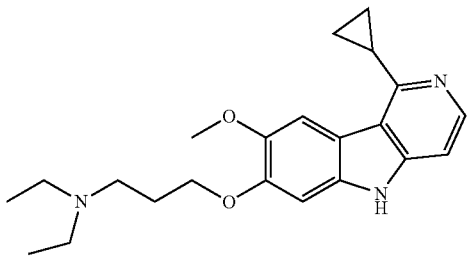 [SMILES: CCN(CC)CCCOc1cc2[nH]c3ccnc(C4CC4)c3c2cc1OC]

The title compound was prepared using the synthetic sequence described for Example 29, changing step 4 as follows:

A mixture of tert-butyl 7-(3-chloropropoxy)-1-cyclopropyl-8-methoxy-5H-pyrido[4,3-b]indole-5-carboxylate (40.00 mg; 0.09 mmol; 1.00 eq.), potassium iodide (1.54 mg; 0.01 mmol; 0.10 eq.) and N-ethylethanamine (0.06 mL; 0.60 mmol; 6.50 eq.) in N,N-dimethylformamide (0.46 mL) was heated to 70° C. After 3 h the mixture was cooled to ambient temperature, diluted with 1:1 PhMe/EtOAc, washed with water, dried over MgSO$_4$, filtered and concentrated.

The crude oil was dissolved in DCM (1.5 mL) and treated with TFA (0.7 mL) at ambient temperature. After 3 h the mixture was concentrated in vacuo. The oily residue was taken up in 1N HCl (~1.5 mL) and purified by prep HPLC (Phenomenex Luna C18, 21×250 mm, 0-70% acetonitrile/0.1% aqueous HCl gradient over 13 minutes, flow rate 22 ml/min) to provide the title compound (18 mg; 53%). $^1$H NMR (400 MHz, DMSO-d$_6$) δ 13.95 (s, 1H), 12.96 (s, 1H), 10.05 (s, 1H), 8.21 (d, J=6.7 Hz, 1H), 7.85 (s, 1H), 7.73 (d, J=6.7 Hz, 1H), 7.32 (s, 1H), 4.21 (t, J=6.0 Hz, 2H), 3.91 (s, 3H), 3.22 (p, J=5.0 Hz, 2H), 3.14 (td, J=7.3, 4.8 Hz, 4H), 3.02 (ddd, J=13.8, 8.6, 5.3 Hz, 1H), 2.20 (q, J=7.4, 6.7 Hz, 2H), 1.46-1.39 (m, 2H), 1.35-1.30 (m, 2H), 1.22 (t, J=7.2 Hz, 6H). MS (ESI, pos. ion) m/z: 368.4 (M+1).

Biological Examples

Example 1

Determination of G9a Enzymatic Activity Assay

The G9a AlphaLISA assay was used to detect the methyl modifications of a biotinylated histone H3 peptide by the compounds. These modifications are done by the histone methyl transferase activity of the G9a enzyme. The assay consists of reading a chemiluminescent signal at 615 nm; this signal is generated by a laser excitation at 680 nm that transfers a reactive singlet oxygen between the donor beads and acceptor beads. Donor beads are streptavidin conjugated and bind to the biotin on the peptide. Acceptor beads are conjugated with an antibody that recognizes the specific G9a methyl mark on the peptide. If there is a methyl mark on the peptide, the acceptor beads will bind to the peptide. Upon binding, the acceptor beads will be in close proximity (<200 nm) of the donor beads and when the donor beads are excited, the transfer of the oxygen can occur and a strong signal will be generated. If there is no methyl mark, the interaction between beads will not occur and signal will be at background levels.

For the assay, the following buffer was used to set up reactions: 50 mM Tris-HCl pH9, 50 mM NaCl, 0.01% Tween-20 and 1 mM DTT (added fresh prior to starting the reactions). The assay is set up by adding a final concentration of 0.15 nM G9a, 10 uM S-adenosyl-methionine and, 100 nM biotinylated histone 3 peptide (1-21). The reaction is incubated at room temperature for 1 h, and subsequently quenched by the addition of the acceptor beads (anti-H3k9me2 AlphaLISA acceptor beads, Perkin-Elmer #AL117) at a final concentration of 20 ug/mL. The acceptor beads are incubated for 1 h. After 1 h, the donor beads are added at a final concentration of 20 ug/mL (Alpha Streptavidin donor beads, PerkinElmer #6760002). Donor beads are incubated for 0.5 h. Both donor and acceptor beads are resuspended in AlphaLISA 5× Epigenetics Buffer 1 Kit (PerkinElmer #AL008) prior to addition to the reaction. All manipulations and incubations with the donor and acceptor beads are done in subdued light. Signal is detected in an EnVision plate reader in Alpha mode (See ACS Med Chem Lett. 2014 Jan. 2; 5(2):205-9)

Percent inhibition was calculated for each compound dilution and the concentration that produced 50% inhibition was calculated. This value is presented as the IC$_{50}$. The IC$_{50}$ values IC$_{50}$ values (nM) for a representative number of compounds of the disclosure are provided below.

TABLE B

| Table 1 Compound # | G9a IC50 (nM) |
|---|---|
| 1 | 250 |
| 2 | 150 |
| 3 | 60 |
| 4 | 170 |
| 5 | 1.2 |
| 6 | 3.2 |
| 7 | 280 |
| 8 | 5.3 |
| 9 | 590 |
| 10 | 4.5 |
| 11 | 8.2 |
| 12 | 1-3 |
| 13 | 34 |
| 14 | 6.5 |
| 15 | 3.3 |
| 16 | 61 |
| 17 | 370 |
| 18 | 12 |
| 19 | 300 |
| 20 | 7 |
| 21 | 3.3 |
| 22 | 570 |
| 23 | 100 |
| 24 | 93 |
| 25 | 140 |
| 26 | 250 |
| 27 | 150 |
| 28 | 60 |
| 29 | 1.2 |
| 30 | 280 |
| 31 | 3.6 |
| 32 | 5.3 |
| 33 | 320 |
| 34 | 590 |
| 35 | 4.5 |
| 36 | 8.2 |
| 37 | 34 |
| 38 | 6.5 |

TABLE B-continued

| Table 1 Compound # | G9a IC50 (nM) |
|---|---|
| 39 | 5.7 |
| 40 | 61 |
| 41 | 370 |
| 42 | 12 |
| 43 | 1.3 |
| 44 | 170 |
| 45 | 56 |
| 46 | 24 |
| 47 | 9.4 |
| 48 | 1300 |
| 49 | 45 |
| 50 | 690 |
| 51 | 470 |
| 52 | 100 |
| 53 | 62 |
| 55 | 18 |
| 56 | 15 |
| 57 | 61 |
| 58 | 86 |
| 59 | 160 |
| 60 | 51 |
| 61 | 480 |
| 62 | 53 |
| 63 | 130 |
| 64 | 12 |
| 65 | 8.2 |
| 66 | 5.6 |
| 67 | 9.5 |
| 68 | 26 |
| 69 | 30 |
| 70 | 400 |
| 71 | 52 |
| 72 | 9.1 |
| 73 | 960 |
| 74 | 6.7 |
| 75 | 1000 |
| 76 | 960 |
| 77 | 2500 |
| 78 | 260 |
| 79 | 140 |
| 80 | >10000 |
| 81 | 22 |
| 82 | 4.5 |
| 83 | N/A |
| 84 | 17 |
| 85 | 17 |
| 86 | 180 |
| 87 | 240 |
| 88 | 12 |
| 89 | 12 |
| 90 | 7.1 |
| 91 | 6.7 |
| 92 | 51 |
| 93 | 61 |
| 94 | 54 |
| 95 | 560 |
| 96 | 3300 |
| 97 | 68 |
| 98 | 2800 |
| 99 | 16 |
| 100 | 380 |
| 101 | 120 |
| 102 | 140 |

Example 2

Fetal Hemoglobin Induction Assay

Cryopreserved bone marrow CD34+ hematopoietic cells obtained from healthy adult human donors were used for all studies. A 21 day ex vivo serum free culture system was utilized that consists of two phases. In culture phase I (culture days 1-7), CD34+ cells were placed in media containing StemPro-34 complete media (1-glutamine, pen-strep and StemPro-34 nutrient supplement) (Invitrogen, Carlsbad, Calif.) supplemented with 50 ng/mL SCF (HumanZyme, Chicago, Ill.), 50 ng/mL FLT3-Ligand (HumanZyme) and 10 ng/mL IL-3 (HumanZyme). During the first phase of culture (days 0-7), the CD34+ cells differentiate into progenitor cell populations that include erythroblasts. After 7 days, the cells were transferred to erythropoietin (EPO; Stemcell) supplemented medium (phase 2; culture days 7-21) which is comprised of the following: StemPro-34 complete medium, 4 U/mL EPO, 3 µM mifepristone (Sigma Aldrich, St. Louis, Mo.), 10 µg/mL insulin (Sigma Aldrich), 3 U/mL heparin (Sigma Aldrich) and 0.8 mg/mL holo transferrin (Sigma Aldrich). The Compounds are added during phase 2; days 7-21 to test fetal hemoglobin production (See Blood. 2015 Jul. 30; 126(5):665-72).

Expression levels of α-, β- and γ-globin genes are assessed by quantitative PCR analyses. HbF protein levels are assessed by the human Hemoglobin F enzyme-linked immunosorbent assay (ELISA) Quantitation Kit (Bethyl Laboratory, Montgomery, Tex., USA). Percentages of cells expressing HbF are assessed by flow cytometry analysis. In brief, RNA samples were prepared and complementary DNA was synthesized, according to the manufacturer's instructions (Qiagen, Germany). The qRT-PCR analysis of human globin genes was performed using the TaqMan Gene Expression Master.

TABLE C

| Table 1 Compound # | Compound Conc. | Fold Induction |
|---|---|---|
| 29 (n = 1) | 0.3 | 3.8 |
| 31 (n = 1) | 0.3 | 4.8 |
| 35 (n = 2) | 0.3 | 4.3 |
| 36 (n = 2) | 0.3 | 3.0 |
| 38 (n = 1) | 0.3 | 3.3 |
| 39 (n = 1) | 0.3 | 2.8 |
| 43 (n = 1) | 0.3 | 2.0 |
| 46 (n = 1) | 0.3 | 2.6 |
| 47 (n = 4) | 0.4 | 4.7 |
| 55 (n = 1) | 0.3 | 2.6 |
| 56 (n = 1) | 0.3 | 3.8 |
| 65 (n = 1) | 0.3 | 6.3 |
| 66 (n = 1) | 0.3 | 1.3 |
| 67 (n = 5) | 0.3 | 3.9 |
| 69 (n = 1) | 0.3 | 2.9 |
| 88 (n = 2) | 0.3 | 3.5 |
| 89 (n = 2) | 0.3 | 3.2 |
| 90 (n = 1) | 0.3 | 2.4 |
| 91 (n = 5) | 0.3 | 4. |
| 92 (n = 1) | 0.3 | 2.3 |
| 99 (n = 1) | 0.3 | 3.6 |

Formulation Examples

The following are representative pharmaceutical formulations containing a compound of the present disclosure.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |

185

-continued

| Ingredient | Quantity per tablet mg |
|---|---|
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 g/mL

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 µL of spray for each application.

186

What is claimed:

1. A compound of Formula (I):

wherein:

X is $CR^1$;

Y is $CR^2$;

Q is N and P, T, and U are independently CH or C (when $R^4$ or $R^5$ is attached);

Z is $NR^6$, wherein $R^6$ is hydrogen, alkyl, or cycloalkyl;

one of $R^1$ and $R^2$ is hydrogen and the other is selected from the group consisting of alkyl, alkoxy, halo, haloalkyl, haloalkoxy, and cycloalkyl;

$R^3$ is —W-alkylene-$R^7$, wherein:
—W-alkylene- is —O—$(CH_2)_{1-3}$* or —O—$(CH_2)_2$—O—$(CH_2)_2$—*, wherein * indicates the point of attachment to $R^7$;

$R^7$ is —$NR^aNR^b$, wherein $R^a$ and $R^b$ are alkyl; or $R^a$ and $R^b$ together with the nitrogen to which they are attached form pyrrolidinyl, wherein said pyrrolidinyl is optionally substituted with one or two substituents independently selected from alkyl, halo, haloalkyl, hydroxy, alkoxy, and haloalkoxy;

$R^4$ and $R^5$ are independently alkyl, alkenyl, alkynyl, cycloalkyl, cycloalkenyl, halo, hydroxy, haloalkoxy, alkoxy, cyano, $NH_2$, $NR^cR^d$, alkoxyalkylamino, hydroxyalkylamino, aminoalkylamino, hydroxyalkyl, alkoxyalkyl, alkylthio, alkoxyalkyloxy, or phenyl, wherein the phenyl or the cycloalkyl, either alone or as part of another group are optionally substituted with one, two, or three substituents independently selected from alkyl, halo, haloalkyl, haloalkoxy, hydroxy, hydroxyalkyl, alkoxy, $NH_2$, alkylamino, dialkylamino, carboxy, carboxyalkyl, and alkoxycarbonyl, and wherein the alkyl of $R^4$ and $R^5$ is optionally substituted with cycloalkyl, and the alkenyl and the alkynyl of $R^4$ and $R^5$ are independently optionally substituted with hydroxy or cycloalkyl;

$R^c$ is hydrogen, alkyl, or cycloalkyl;

$R^d$ is alkyl or cycloalkyl; and v and w are independently 0 or 1;

or a pharmaceutically acceptable salt thereof.

2. The compound of claim 1, or a pharmaceutically acceptable salt thereof, wherein one of $R^1$ and $R^2$ is hydrogen and the other is alkoxy.

3. The compound of claim 1, or a pharmaceutically acceptable salt thereof, wherein $R^7$ is —$NR^aNR^b$, wherein $R^a$ and $R^b$ are alkyl.

4. The compound of claim 1, or a pharmaceutically acceptable salt thereof, wherein $R^a$ and $R^b$ are independently methyl, ethyl, n-propyl or isopropyl.

5. The compound of claim 1, or a pharmaceutically acceptable salt thereof, wherein $R^5$ is $NH_2$, halo, alkyl, hydroxy, alkoxy, cycloalkyl, or hydroxyalkyl.

6. The compound of claim 1, or a pharmaceutically acceptable salt thereof, wherein $R^4$ is cycloalkyl selected from the group consisting of cyclopropyl, cyclobutyl, or cyclopentyl, wherein the cyclopropyl, the cyclobutyl, and the cyclopentyl are optionally substituted with one, two, or three substituents independently selected from alkyl, halo, haloalkyl, haloalkoxy, hydroxy, alkoxy, NH₂, alkylamino, dialkylamino, carboxy, carboxyalkyl, and alkoxycarbonyl.

7. The compound of claim 1, or a pharmaceutically acceptable salt thereof, wherein R⁴ is NH₂, NR^c NR^d, alkoxyalkylamino, hydroxyalkylamino or aminoalkylamino; R^c is hydrogen, alkyl, or cycloalkyl; and R^d is alkyl or cycloalkyl.

8. The compound of claim 1, or a pharmaceutically acceptable salt thereof, wherein R⁴ is methyl, ethyl, n-propyl, isopropyl, n-butyl, iso-butyl, or tert-butyl.

9. The compound of claim 1, or a pharmaceutically acceptable salt thereof, wherein the compound of Formula (I) is selected from the group consisting of:

| Cmpd No. | Structure |
|---|---|
| 5 | 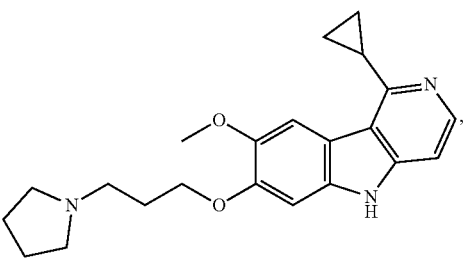 |
| 6 | 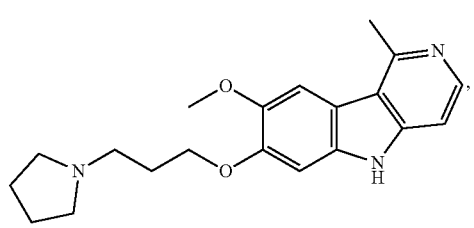 [SMILES: COc1cc2c(cc1OCCCN1CCCC1)[nH]c1ccnc(C)c12] |
| 8 | 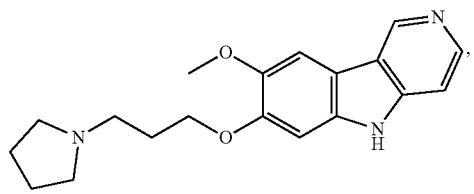 [SMILES: COc1cc2c(cc1OCCCN1CCCC1)[nH]c1ccncc12] |
| 9 | 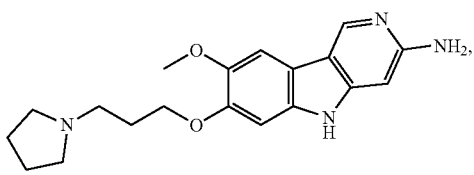 [SMILES: COc1cc2c(cc1OCCCN1CCCC1)[nH]c1cc(N)ncc12] |
| 10 | 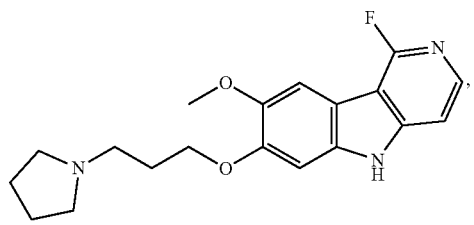 [SMILES: COc1cc2c(cc1OCCCN1CCCC1)[nH]c1ccnc(F)c12] |

-continued

| Cmpd No. | Structure |
|---|---|
| 12 | 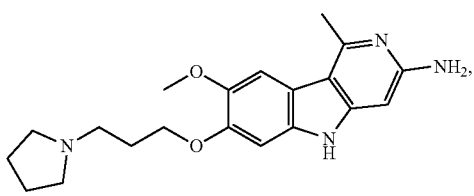 [SMILES: COc1cc2c(cc1OCCCN1CCCC1)[nH]c1cc(N)nc(C)c12] |
| 14 | 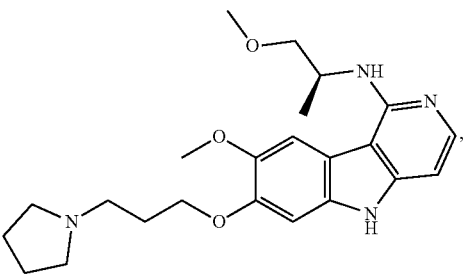 [SMILES: COC[C@H](C)Nc1nccc2[nH]c3cc(OCCCN4CCCC4)c(OC)cc3c12] |
| 20 | 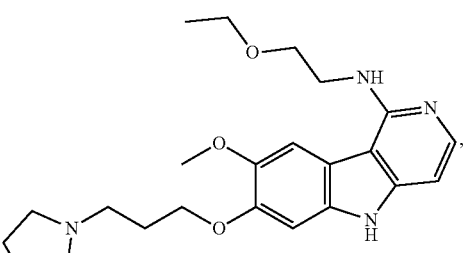 |
| 21 | 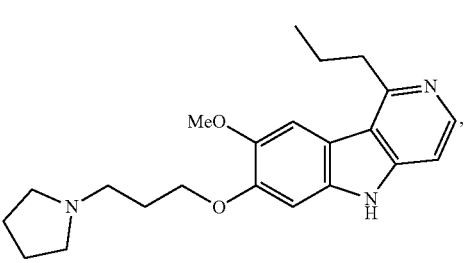 [SMILES: CCCc1nccc2[nH]c3cc(OCCCN4CCCC4)c(OC)cc3c12] |
| 29 | 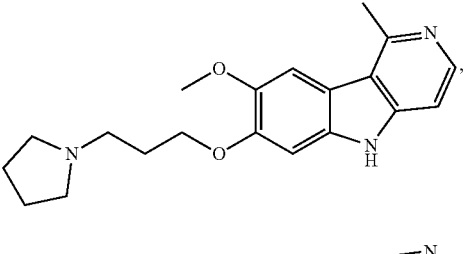 |
| 31 | 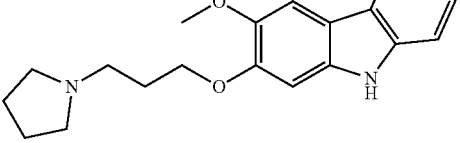 |

| Cmpd No. | Structure |
|---|---|
| 32 | (structure) |
| 34 | (structure) |
| 35 | (structure) |
| 38 | (structure) |
| 43 | (structure) |
| 45 | (structure) |

| Cmpd No. | Structure |
|---|---|
| 46 | (structure) |
| 47 | (structure) |
| 48 | (structure) |
| 49 | (structure) |
| 50 | (structure) |

| Cmpd No. | Structure |
|---|---|
| 51 | 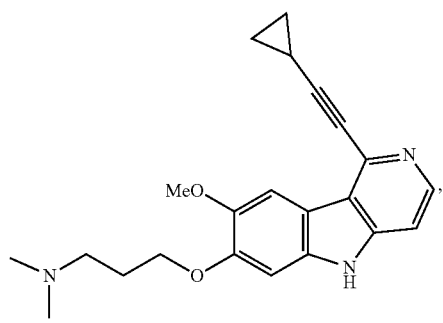 [SMILES: COc1cc2c(cc1OCCCN(C)C)[nH]c1ccnc(C#CC3CC3)c12] |
| 52 | 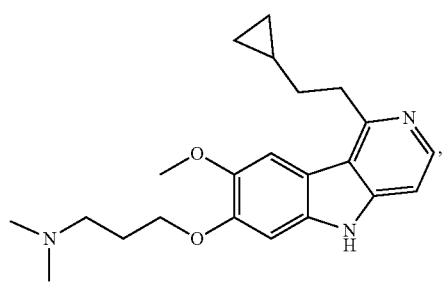 [SMILES: COc1cc2c(cc1OCCCN(C)C)[nH]c1ccnc(CCC3CC3)c12] |
| 52 | 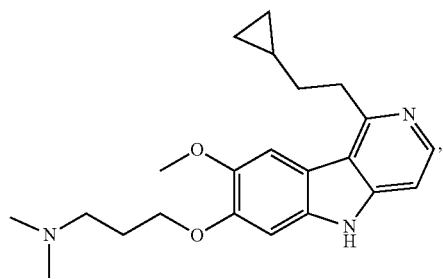 [SMILES: COc1cc2c(cc1OCCCN(C)C)[nH]c1ccnc(CCC3CC3)c12] |
| 53 | 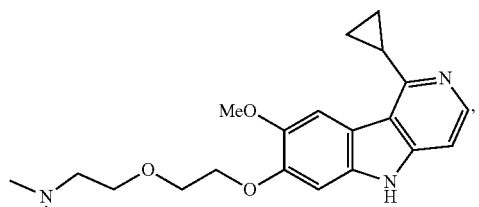 |
| 55 | 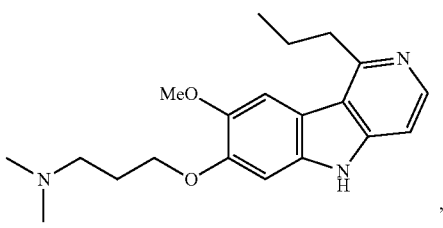 [SMILES: CCCc1nccc2[nH]c3cc(OCCCN(C)C)c(OC)cc3c12] |
| Cmpd No. | Structure |
|---|---|
| 56 | 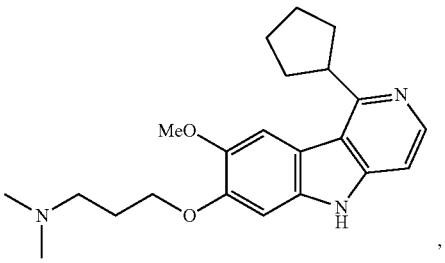 [SMILES: COc1cc2c(cc1OCCCN(C)C)[nH]c1ccnc(C3CCCC3)c12] |
| 57 | 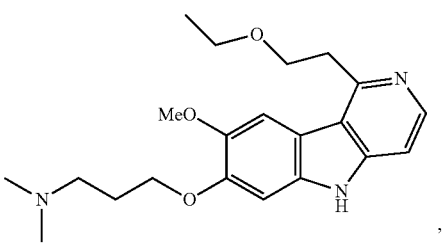 [SMILES: CCOCCc1nccc2[nH]c3cc(OCCCN(C)C)c(OC)cc3c12] |
| 58 | 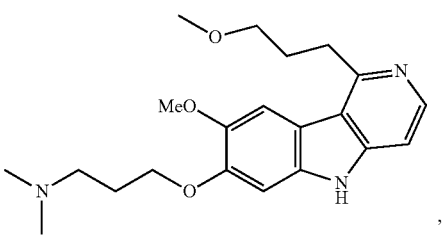 [SMILES: COCCCc1nccc2[nH]c3cc(OCCCN(C)C)c(OC)cc3c12] |
| 59 | 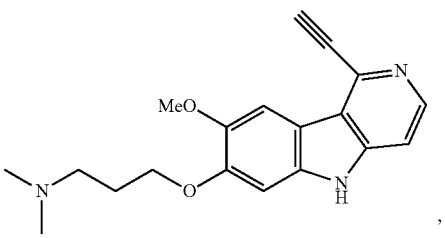 [SMILES: C#Cc1nccc2[nH]c3cc(OCCCN(C)C)c(OC)cc3c12] |
| 60 | 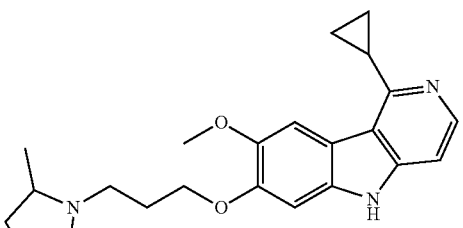 |
| 61 | 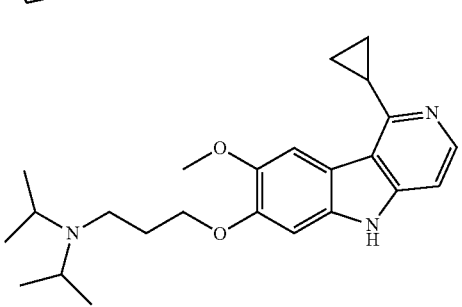 |

| Cmpd No. | Structure |
|---|---|
| 62 | 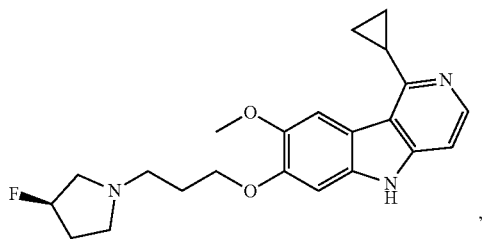 [SMILES: COc1cc2c(cc1OCCCN1CC[C@@H](F)C1)[nH]c1ccnc(C3CC3)c12] |
| 63 | 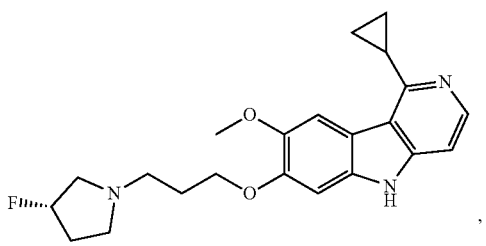 [SMILES: COc1cc2c(cc1OCCCN1CC[C@H](F)C1)[nH]c1ccnc(C3CC3)c12] |
| 67 | 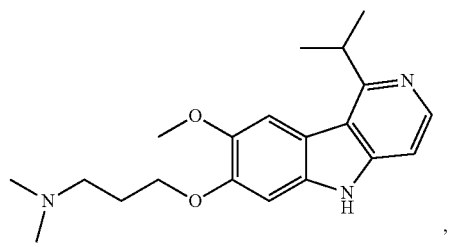 [SMILES: COc1cc2c(cc1OCCCN(C)C)[nH]c1ccnc(C(C)C)c12] |
| 69 | 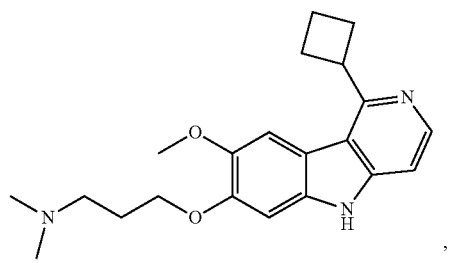 [SMILES: COc1cc2c(cc1OCCCN(C)C)[nH]c1ccnc(C3CCC3)c12] |
| 70 | 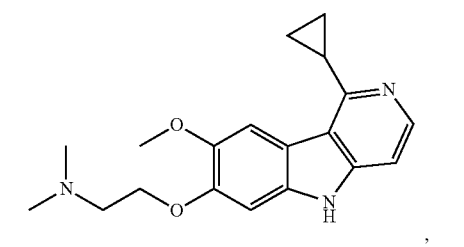 [SMILES: COc1cc2c(cc1OCCN(C)C)[nH]c1ccnc(C3CC3)c12] |
| 71 | 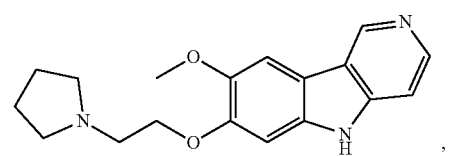 [SMILES: COc1cc2c(cc1OCCN1CCCC1)[nH]c1ccncc12] |
| Cmpd No. | Structure |
|---|---|
| 75 | 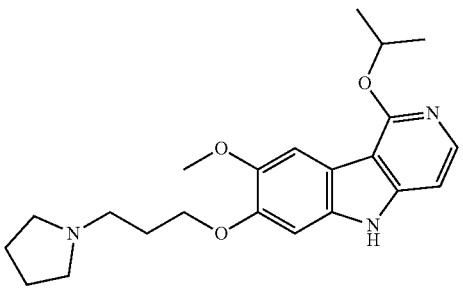 |
| 79 | 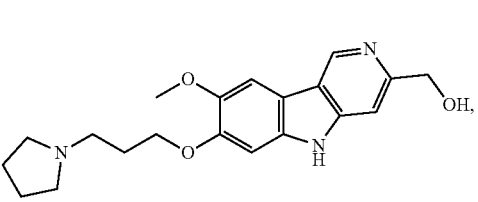 [SMILES: COc1cc2c(cc1OCCCN1CCCC1)[nH]c1cc(CO)ncc12] |
| 80 | 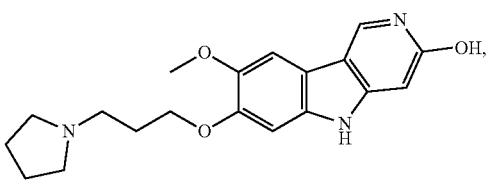 [SMILES: COc1cc2c(cc1OCCCN1CCCC1)[nH]c1cc(O)ncc12] |
| 82 | 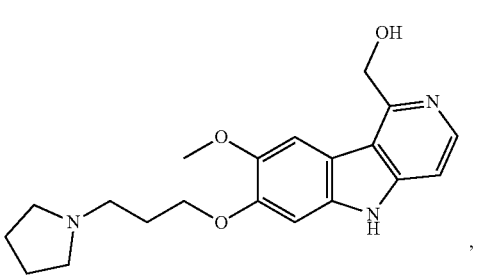 [SMILES: COc1cc2c(cc1OCCCN1CCCC1)[nH]c1ccnc(CO)c12] |
| 85 | 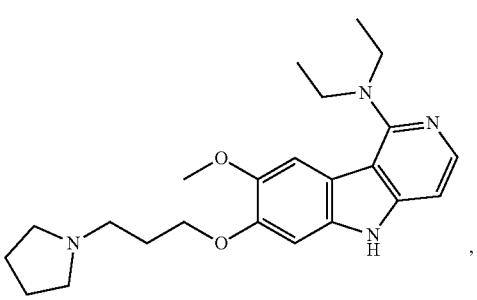 [SMILES: CCN(CC)c1nccc2[nH]c3cc(OCCCN4CCCC4)c(OC)cc3c12] |
| 88 | 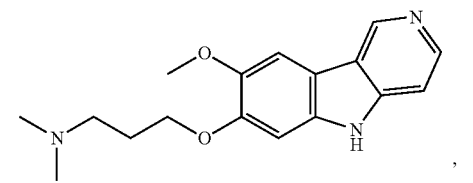 [SMILES: COc1cc2c(cc1OCCCN(C)C)[nH]c1ccncc12] |

195
-continued

| Cmpd No. | Structure |
|---|---|
| 90 | 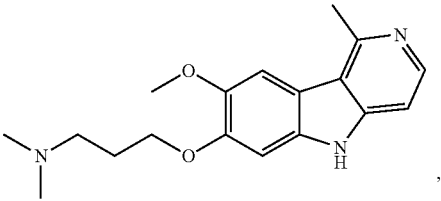 [SMILES: COc1cc2c(cc1OCCCN(C)C)[nH]c1ccnc(C)c12] , |
| 91 | 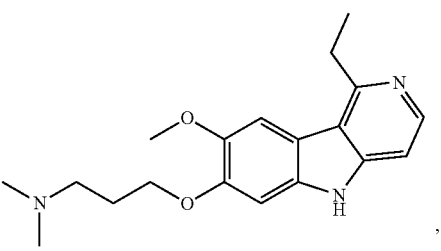 , |
| 93 | 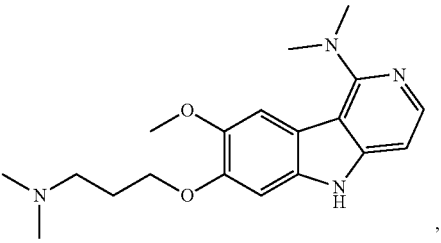 [SMILES: COc1cc2c(cc1OCCCN(C)C)[nH]c1ccnc(N(C)C)c12] , |
| 94 | 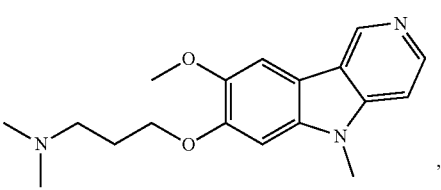 [SMILES: COc1cc2c3cnccc3n(C)c2cc1OCCCN(C)C] , |
| 95 | 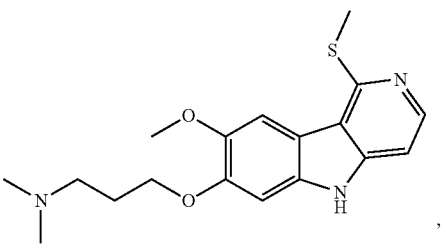 [SMILES: COc1cc2c(cc1OCCCN(C)C)[nH]c1ccnc(SC)c12] , |
| 96 | 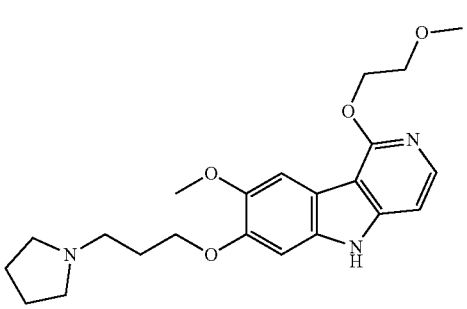 , |

196
-continued

| Cmpd No. | Structure |
|---|---|
| 97 | 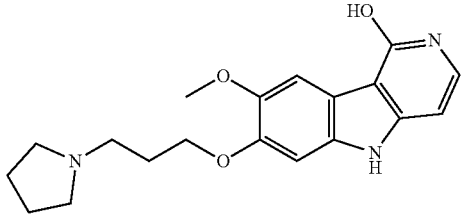 , |
| 99 | 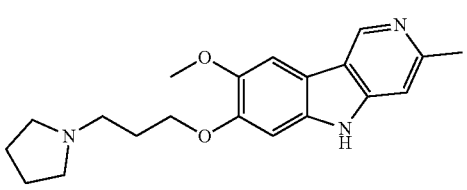 , |
| 100 | 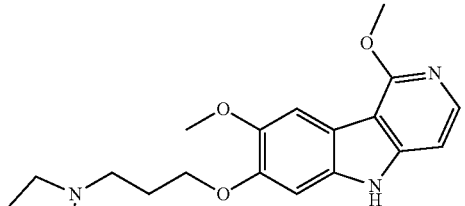 , |
| 101 | 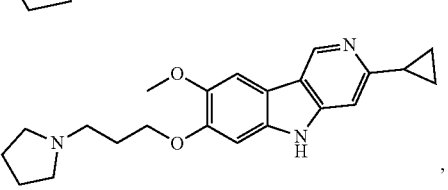 , and |
| 102 | 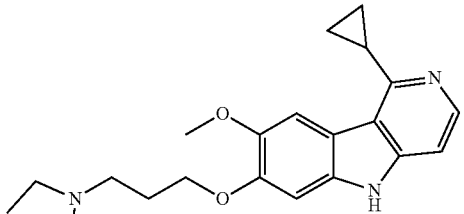 , | or a parent compound of a salt as shown above, or a pharmaceutically acceptable salt of the parent compound.

10. A pharmaceutical composition comprising a compound of claim 1, or a pharmaceutically acceptable salt thereof and a pharmaceutically acceptable excipient.

11. A method of inhibiting the activity of G9a comprising contacting a cell that contains G9a with an effective amount of a compound of claim 1, or a pharmaceutically acceptable salt thereof, and thereby inhibiting the activity of the G9a.

12. A method of ameliorating or treating a hemoglobinopathy, wherein the hemoglobinopathy is sickle cell disease or beta-thalassemia, comprising administering an effective amount of a compound of claim 1, or a pharmaceutically acceptable salt thereof, or the pharmaceutical composition of claim 10 to a subject in need thereof.

13. The compound of claim 1, or a pharmaceutically acceptable salt thereof, wherein $R^7$ is —$NR^aR^b$, wherein $R^a$ and $R^b$ together with the nitrogen to which they are attached form pyrrolidin-1-yl, optionally substituted with methyl or fluoro.

14. The compound of claim 1, or a pharmaceutically acceptable salt thereof, wherein —W-alkylene- is —O—$(CH_2)_3$—*, wherein the * indicates the point of attachment to $R^7$.

15. The compound of claim 1, or a pharmaceutically acceptable salt thereof, wherein $R^6$ is H.

16. The compound of claim 5, or a pharmaceutically acceptable salt thereof, wherein $R^5$ is $NH_2$, fluoro, chloro, methyl, ethyl, hydroxy, methoxy, cyclopropyl, cyclopentyl, or hydroxymethyl.

17. The compound of claim 2, or a pharmaceutically acceptable salt thereof, wherein $R^1$ is methoxy and $R^2$ is hydrogen.

18. The compound of claim 1, or a pharmaceutically acceptable salt thereof, wherein $R^4$ is methyl, ethyl, n-propyl, isopropyl, or cyclopropyl.

19. The compound of claim 1, or a pharmaceutically acceptable salt thereof, wherein v is 1 and w is 0.

20. The compound of claim 1, or a pharmaceutically acceptable salt thereof, wherein v is 0 and w is 0.

* * * * *